United States Patent
Lee et al.

(10) Patent No.: US 9,680,106 B2
(45) Date of Patent: Jun. 13, 2017

(54) PYRENE-BASED COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Eun-Young Lee, Yongin (KR); Kwang-Hyun Kim, Yongin (KR); Young-Kook Kim, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 408 days.

(21) Appl. No.: 14/290,310

(22) Filed: May 29, 2014

(65) Prior Publication Data
US 2015/0090967 A1    Apr. 2, 2015

(30) Foreign Application Priority Data
Oct. 1, 2013    (KR) ........................ 10-2013-0117585

(51) Int. Cl.
*H01L 51/00* (2006.01)
*H01L 51/50* (2006.01)
(Continued)

(52) U.S. Cl.
CPC ........ *H01L 51/0054* (2013.01); *C07D 209/56* (2013.01); *C07D 401/10* (2013.01);
(Continued)

(58) Field of Classification Search
None
See application file for complete search history.

(56) References Cited

U.S. PATENT DOCUMENTS

| 5,645,948 A | 7/1997 | Shi et al. |
| 2003/0165715 A1 | 9/2003 | Yoon et al. |

(Continued)

FOREIGN PATENT DOCUMENTS

| JP | 10-017860 | 1/1998 |
| JP | 11-087067 | 3/1999 |

(Continued)

OTHER PUBLICATIONS

Sakamoto et al. Synthesis, Characterization and Electron-Transport, etc., J. Am. Chem. Soc., 2000, 122, pp. 1832-1833.

(Continued)

*Primary Examiner* — J. L. Yang
(74) *Attorney, Agent, or Firm* — Lee & Morse, P.C.

(57) ABSTRACT

A pyrene-based compound is represented by Formula 1:

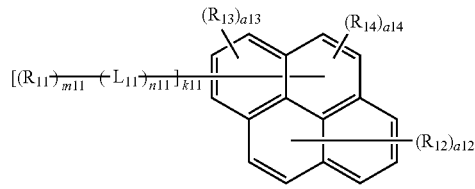

<Formula 1> where $R_{11}$ to $R_{14}$, $L_{11}$, m11, n11, k11, a12, a13, and a14 are as defined in the specification.

20 Claims, 1 Drawing Sheet

10

| 190 |
|---|
| 150 |
| 110 |

(51) Int. Cl.
*C07D 401/14* (2006.01)
*C07D 401/10* (2006.01)
*C07D 403/10* (2006.01)
*C07D 209/56* (2006.01)

(52) U.S. Cl.
CPC ......... *C07D 401/14* (2013.01); *C07D 403/10* (2013.01); *H01L 51/0058* (2013.01); *H01L 51/0067* (2013.01); *H01L 51/0072* (2013.01); *H01L 51/006* (2013.01); *H01L 51/0059* (2013.01); *H01L 51/5072* (2013.01)

(56) References Cited

U.S. PATENT DOCUMENTS

| | | | |
|---|---|---|---|
| 2004/0053069 A1 | 3/2004 | Sotoyama et al. | |
| 2004/0137270 A1 | 7/2004 | Seo et al. | |
| 2012/0256172 A1 | 10/2012 | Ito et al. | |
| 2015/0014656 A1* | 1/2015 | Lim | C07B 59/002 257/40 |

FOREIGN PATENT DOCUMENTS

| | | |
|---|---|---|
| JP | 4060669 | 12/2007 |
| JP | 2010-195708 | 9/2010 |
| KR | 10-00525408 | 10/2005 |
| KR | 10-0691543 | 2/2007 |
| KR | 10-2012-0051598 A | 5/2012 |
| KR | 10-2012-0104087 | 9/2012 |

OTHER PUBLICATIONS

Johansson et al. Solid-State Amplified Spontaneous Emission, etc., Adv. Mater. 1998, 10 No. 14, pp. 1136-1141.

Tao, et al. Sharp Green Electroluminescence From 1H-pyrazolo[3,4-b]Quinoline-Based Light-Emitting Diodes, Applied Physics Letters, vol. 77, No. 11, Sep. 11, 2000, pp. 1574-1577.

Tang et al., Organic Electroluminescent Diodes, Applied Physics Letters, vol. 12, Sep. 21, 1987, pp. 912-915.

Adachi et al. Confinement of Charge Carriers and Molecular Excitons, etc., Applied Physics Letters, vol. 57, Aug. 6, 1990, pp. 530-533.

Yamaguchi et al. Diphenylamino-Substituted 2,5-Diarylsiololes etc., The Chemical Society of Japan, Chemistry Letters 2001, pp. 98-99.

2009 Fall Assembly and Symposium, vol. 34, No. 2, A Novel Conjugated Polymer Based on 4H-benzo[def]carbazole backbone for OLED.

* cited by examiner

10

| 190 |
|-----|
| 150 |
| 110 |

PYRENE-BASED COMPOUND AND ORGANIC LIGHT-EMITTING DEVICE INCLUDING THE SAME

CROSS-REFERENCE TO RELATED APPLICATION

Korean Patent Application No. 10-2013-0117585, filed on Oct. 1, 2013, in the Korean Intellectual Property Office, and entitled: "Pyrene-Based Compound And Organic Light-Emitting Device Including The Same," is incorporated by reference herein in its entirety.

BACKGROUND

1. Field

One or more embodiments relate to a pyrene-based compound and an organic light-emitting device including the same.

2. Description of the Related Art

Organic light-emitting devices (OLEDs) are self-emitting devices that have advantages, such as wide viewing angles, excellent contrast, quick response, high brightness, and excellent driving voltage characteristics, and that can provide multicolored images.

An OLED may have a structure including a first electrode disposed on a substrate, and a hole transport region, an emission layer, an electron transport region, and a second electrode sequentially formed on the first electrode. Holes injected from the first electrode are transported to the emission layer through the hole transport region, and electrons injected from the second electrode are transported to the emission layer through the electron transport region. Carriers, such as the holes and electrons, recombine in the emission layer to generate excitons. When the excitons drop from an excited state to a ground state, light is emitted.

SUMMARY

Embodiments are directed to a pyrene-based compound represented by Formula 1:

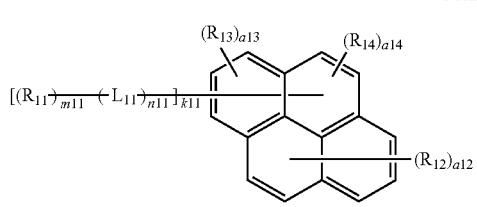

<Formula 1> wherein, in Formula 1, $L_{11}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, and a substituted or unsubstituted non-aromatic condensed polycycle;

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, and substituted non-aromatic condensed polycyclic group is selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group and a non-aromatic condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group and a non-aromatic condensed polycycle; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group and a non-aromatic condensed polycycle, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group and a non-aromatic condensed polycyclic group;

n11 is an integer of 0 to 3;

$R_{11}$ is represented by one of Formulae 2-1 and 2-2;

k11 is an integer of 1 to 4;

$R_{12}$ to $R_{14}$ are each independently selected from:

a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_1$-$C_{60}$ heteroaryl group and a non-aromatic condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group and a non-aromatic condensed polycycle; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group and a non-aromatic condensed polycycle, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group and a non-aromatic condensed polycyclic group;

a12 is an integer of 1 to 5;

a13 and a14 are each independently an integer of 1 to 3;

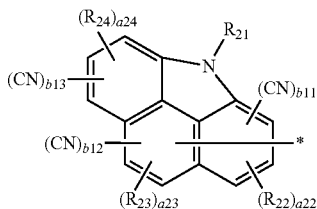

<Formula 2-1>

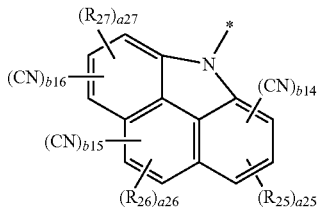

<Formula 2-2> wherein, in Formulae 2-1 and 2-2, $R_{21}$ to $R_{27}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group and a non-aromatic condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group and a non-aromatic condensed polycyclic group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group and a non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group and a non-aromatic condensed polycyclic group;

a22 to a27 are each independently an integer of 0 to 3;

b11 to b16 are each independently an integer of 0 to 2;

the sum of b11, b12, and b13 is 1 or greater, and the sum of b14, b15, and b16 is 1 or greater; and

* is a binding site with $L_{11}$ or a pyrene ring in Formula 1.

Embodiments are also directed to an organic light-emitting device (OLED) that includes a first electrode; a second electrode facing the first electrode; and an organic layer between the first electrode and the second electrode, the organic layer including an emission layer, the organic layer including the pyrene-based compound.

BRIEF DESCRIPTION OF THE DRAWINGS

Features will become apparent to those of skill in the art by describing in detail exemplary embodiments with reference to the attached drawings in which:

FIG. 1 illustrates a schematic diagram depicting an organic light-emitting device (OLED) according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present.

A pyrene-based compound is represented by Formula 1:

<Formula 1>

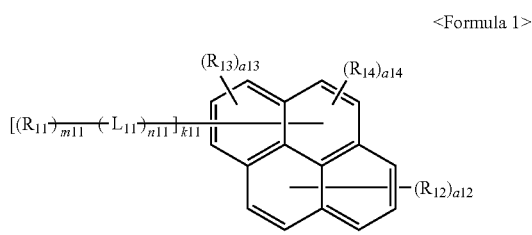

In Formula 1, $L_{11}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, and a substituted or unsubstituted non-aromatic condensed polycyclic group;

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, and substituted non-aromatic condensed polycyclic group may be selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$7C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycycle; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycycle, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group.

According to an embodiment, in Formula 1, $L_{11}$ may be selected from, for example, a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothienylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thienylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothienylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolyene group, a dibenzocarbazolyene group, and a dibenzosilolylene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thienyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothienyl group, a benzosilolyl group, an isobenzothiazolyl group, a benzoxazolyl group, an isobenzoxazolyl group, a triazolyl group, a tetrazole group, an oxadiazolyl group, a triazinyl group, a dibenzofuranyl group, a dibenzothienyl group, a benzocarbazolyl group, a dibenzocarbazolyl group, and a dibenzosilolyl group.

According to another embodiment, in Formula 1, $L_{11}$ may be represented by one of Formulae 3-1 to 3-32 below, as examples:

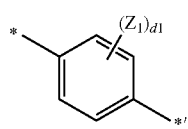

3-1

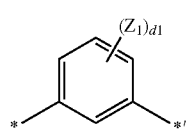

3-2

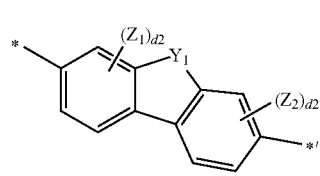

3-3

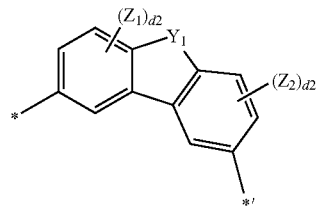

3-4

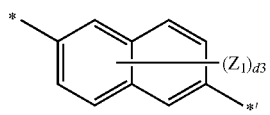

3-5

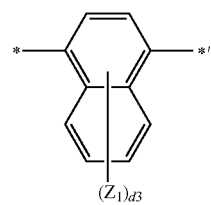

3-6

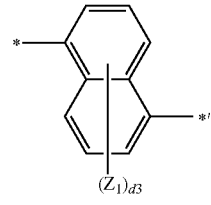

3-7

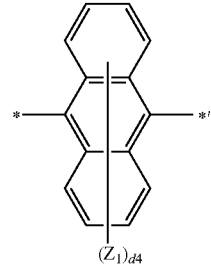

3-8

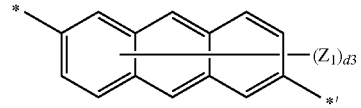

3-9

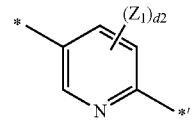

3-10

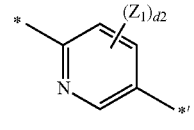

3-11

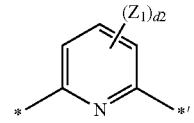

3-12

| | |
|---|---|
| 3-13 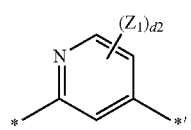 | 3-24 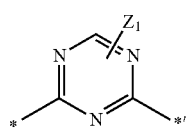 |
| 3-14 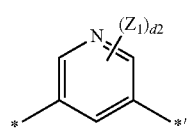 | 3-25 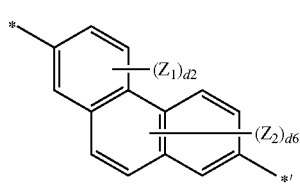 |
| 3-15 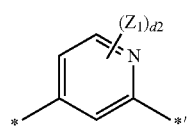 | 3-26 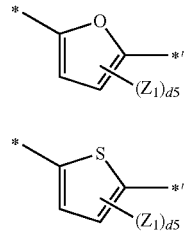 |
| 3-16 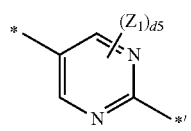 | 3-27 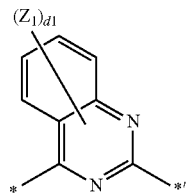 |
| 3-17 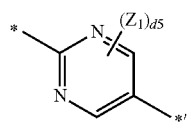 | 3-28 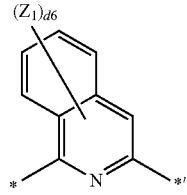 |
| 3-18 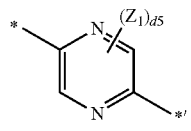 | 3-29 |
| 3-19 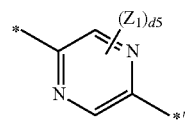 | 3-30 |
| 3-20 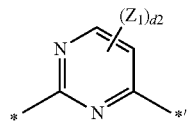 | 3-31 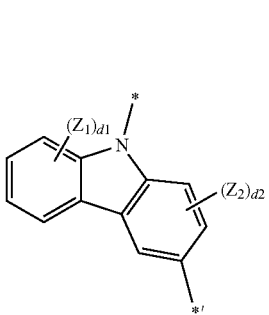 |
| 3-21 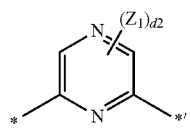 | |
| 3-22 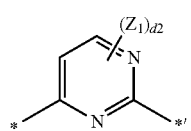 | |
| 3-23 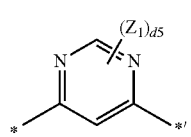 | |

-continued 3-32

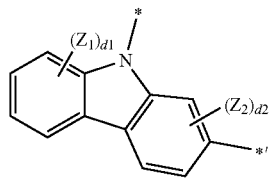

In Formulae 3-1 to 3-32, $Y_1$ is selected from $C(Q_{31})(Q_{32})$, $N(Q_{33})$, an oxygen atom, a sulfur atom, and $Si(Q_{34})(Q_{35})$;

$Q_{31}$ to $Q_{35}$ are each independently selected from a hydrogen atom, a deuterium atom, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$Z_1$ and $Z_2$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 is an integer of 1 to 4;
d2 is an integer of 1 to 3;
d3 is an integer of 1 to 6;
d4 is an integer of 1 to 8;
d5 is an integer of 1 or 2;
d6 is an integer of 1 to 5; and
* and *' represent a binding site with the pyrene ring, $R_{11}$ or another $L_{11}$.

According to another embodiment, in Formula 1, $L_{11}$ may be represented by one of Formula 4-1 to 4-23 below, as examples:

4-1

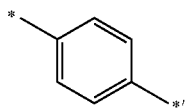

4-2

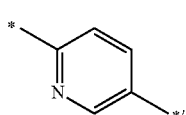

4-3

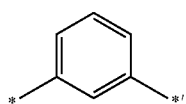

-continued 4-4

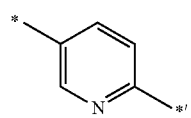

4-5

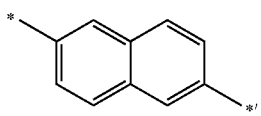

4-6

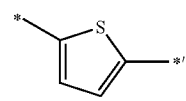

4-7

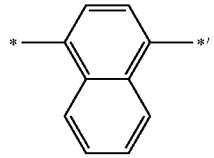

4-8

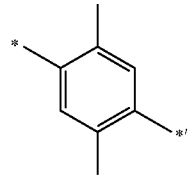

4-9

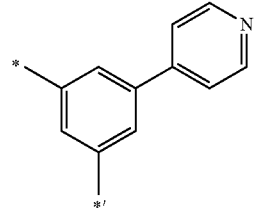

4-10

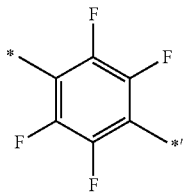

4-11

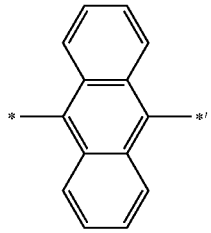

4-12

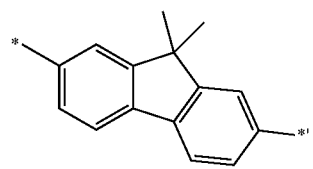

-continued 4-13 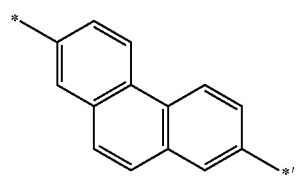

4-14 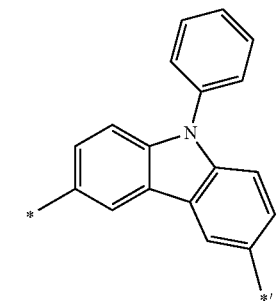

4-15 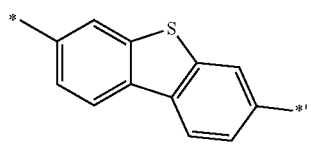

4-16 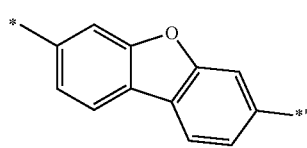

4-17 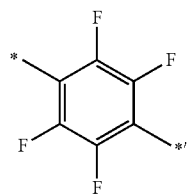

4-18 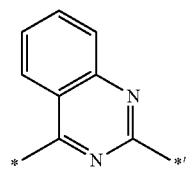

4-19 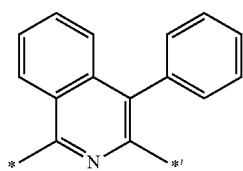

4-20 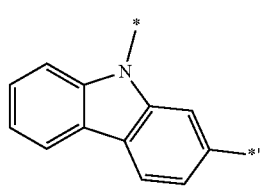

4-21 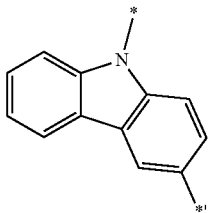

4-22 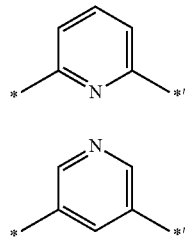

4-23 where * and *' represent a binding site with the pyrene ring, $R_{11}$ or another $L_{11}$.

In Formula 1, n11 denotes the number of $L_{11}$, and n11 is an integer of 0, 1, 2, or 3. For example, in Formula 1, n11 may be an integer of 0 or 1. In Formula 1, when n11 is 0, $-(L_{11})_{n11}-$ denotes a single bond. When n11 is 2 or greater, a plurality of $L_{11}$ s may be identical to or different from each other.

In Formula 1, $R_{11}$ may be represented by one of Formulae 2-1 and 2-2:

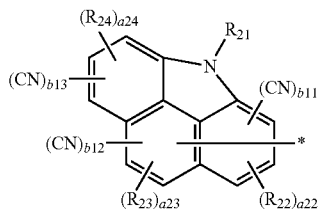  <Formula 2-1>

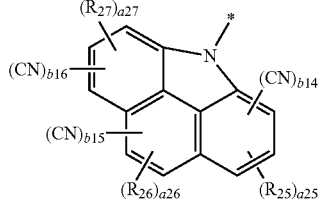  <Formula 2-2>

In Formulae 2-1 and 2-2, $R_{21}$ to $R_{27}$ are each independently selected from:

a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a22 to a27 are each independently an integer of 0 to 3;
b11 to b16 are each independently an integer of 0 to 2;
the sum of b11, b12, and b13 is 1 or greater, and the sum of b14, b15, and b16 is 1 or greater; and
\* is a binding site with $L_{11}$ or a pyrene ring in Formula 1.

In some embodiments, in Formula 1, $R_{11}$ may be represented by one of Formulae 2-1a and 2-2a:

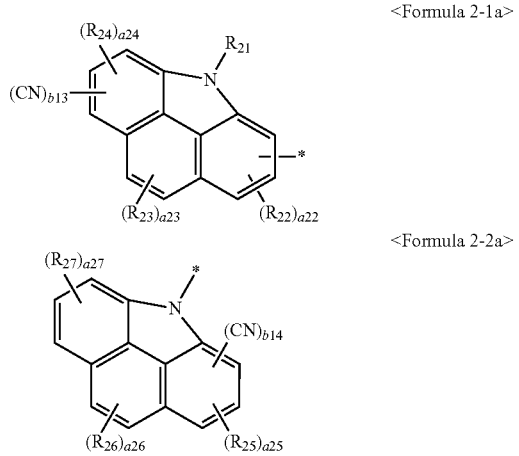

<Formula 2-1a>

<Formula 2-2a>

In Formulae 2-1a and 2-2a,
$R_{21}$ to $R_{27}$ are each independently selected from:
a hydrogen atom, a deuterium atom, a halogen atom, a hydroxyl group, a cyano group, a nitro group, a $C_1$-$C_{60}$ alkyl group, and a $C_1$-$C_{60}$ alkoxy group;
a $C_1$-$C_{60}$ alkyl group and a $C_1$-$C_{60}$ alkoxy group, each substituted with at least one of a deuterium atom, a halogen atom, a hydroxyl group, a cyano group, a nitro group, a $C_6$-$C_{60}$ aryl group, a $C_2$-$C_{60}$ heteroaryl group, and a non-aromatic condensed polycyclic group;

a $C_6$-$C_{60}$ aryl group, a $C_2$-$C_{60}$ heteroaryl group, and a non-aromatic condensed polycyclic group; and a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group;

a22 to a27 are each independently an integer of 0 to 3;
b13 to b14 are each independently an integer of 1 or 2; and
\* is a binding site with $L_{11}$ or a pyrene ring in Formula 1.

In some embodiments, in Formula 1, $R_{11}$ may be represented by Formula 2-1b:

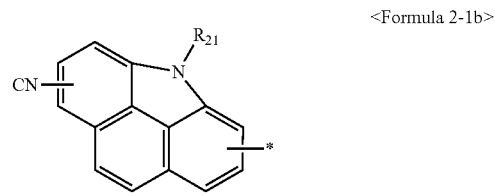

<Formula 2-1b>

In Formula 2-1 b,
$R_{21}$ may be selected from:
a $C_6$-$C_{60}$ aryl group, a $C_2$-$C_{60}$ heteroaryl group, and a non-aromatic condensed polycyclic group; and a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group; and \* is a binding site with $L_{11}$ or a pyrene ring in Formula 1.

For example, in Formulae 2-1, 2-2, 2-1a, and 2-2a, $R_{21}$ may be selected from:
a hydrogen atom, a deuterium atom, a methyl group, an ethyl group, a tert-butyl group, a methoxy group, an ethoxy group, and a tert-butoxy group;

a methyl group, an ethyl group, a tert-butyl group, a methoxy group, an ethoxy group, and a tert-butoxy group, each substituted with at least one of a deuterium atom, a halogen atom, a cyano group, a nitro group, a phenyl group, a naphthyl group, a pyridinyl group, a fluorenyl group, and a carbazolyl group;

a phenyl, a naphthyl group, a pyridinyl group, a fluorenyl group, a benzofluorenyl group, and a carbazolyl group; and a phenyl group, a naphthyl group, a pyridinyl group, a fluorenyl group, and a carbazolyl group, each substituted with at least one of a deuterium atom, a halogen atom, a cyano group, a nitro group, a methyl group, an ethyl group, a tert-butyl group, a methoxy group, an ethoxy group, a tert-butoxy group, a phenyl group, a naphthyl group, a pyridinyl group, a fluorenyl group, and a carbazolyl group.

For example, in Formulae 2-1, 2-2, 2-1a, and 2-2a, $R_{21}$ may be selected from:
a phenyl, a naphthyl group, a pyridinyl group, a fluorenyl group, a benzofluorenyl group, and a carbazolyl group; and a phenyl group, a naphthyl group, a pyridinyl group, a fluorenyl group, and a carbazolyl group, each substituted with at least one of a deuterium atom, a halogen atom, a cyano group, a nitro group, a methyl group, an ethyl group, a tert-butyl group, a methoxy group, an ethoxy group, a tert-butoxy group, a phenyl group, a naphthyl group, a pyridinyl group, a fluorenyl group, and a carbazolyl group.

For example, in Formulae 2-1, 2-2, 2-1a, and 2-2a, $R_{22}$ to $R_{27}$ may be each independently selected from:

a hydrogen atom, a deuterium atom, a halogen atom, a cyano group, a nitro group, a methyl group, an ethyl group, a tert-butyl group, a methoxy group, an ethoxy group, and a tert-butoxy group;

a methyl group, an ethyl group, a tert-butyl group, a methoxy group, an ethoxy group, and a tert-butoxy group, each substituted with at least one of a deuterium atom, a halogen atom, a cyano group, a nitro group, a phenyl group, a naphthyl group, a pyridinyl group, a fluorenyl group, and a carbazolyl group;

a phenyl, a naphthyl group, a pyridinyl group, a fluorenyl group, a benzofluorenyl group, and a carbazolyl group; and a phenyl group, a naphthyl group, a pyridinyl group, a fluorenyl group, and a carbazolyl group, each substituted with at least one of a deuterium atom, a halogen atom, a cyano group, a nitro group, a methyl group, an ethyl group, a tert-butyl group, a methoxy group, an ethoxy group, a tert-butoxy group, a phenyl group, a naphthyl group, a pyridinyl group, a fluorenyl group, and a carbazolyl group.

In Formula 1, m11 denotes the number of $R_{11}$, and m11 may be an integer of 1 to 3. For example, m11 may be an integer of 1, but is not limited thereto. When m11 is an integer of 2 or greater, a plurality of $R_{11}$ s are identical to or different from each other.

In Formula 1, k11 may be an integer of 1 to 4. For example, k11 may be an integer of 1, but is not limited thereto.

In Formula 1, $R_{12}$ to $R_{14}$ may be each independently selected from:

a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycycle; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycycle, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group.

In some embodiments, in Formula 1, $R_{12}$ to $R_{14}$ may be each independently selected from, for example:

a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In some embodiments, in Formula 1, $R_{12}$ to $R_{14}$ may be each independently selected from, for example:

a hydrogen atom, a deuterium atom, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, and a tert-butoxy group;

a phenyl group, a naphthyl group, a fluorenyl group, a benzofluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, and a triazinyl group; and a phenyl group, a naphthyl group, a fluorenyl group, a benzofluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, and a triazinyl group, each substituted with at least one of a deuterium atom, a halogen atom, a cyano group, a nitro group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

Also, in some embodiments, in Formula 1, $R_{12}$ may be selected from, for example, a hydrogen atom, a deuterium atom, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, a tert-butoxy group, and groups represented by Formulae 5-1 to 5-34:

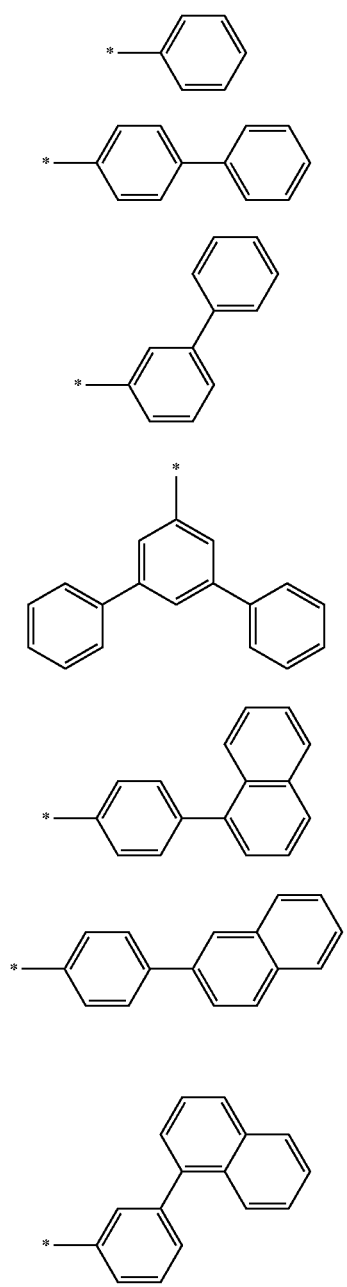

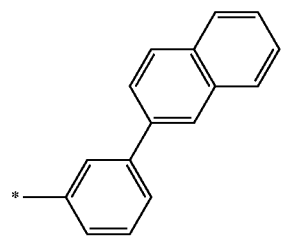

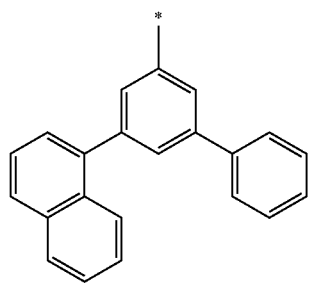

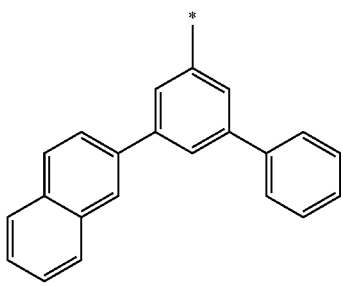

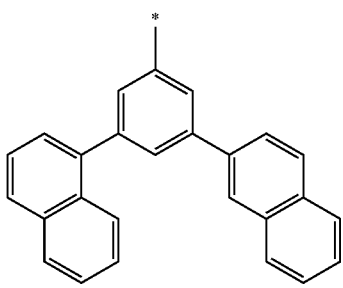

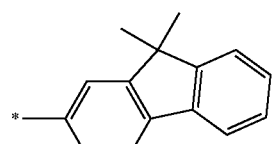

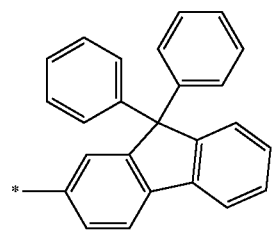

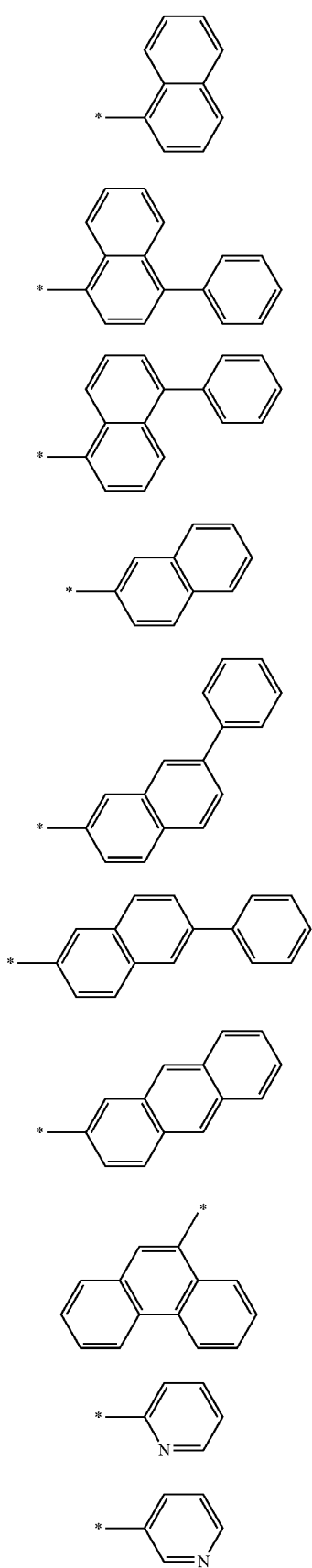

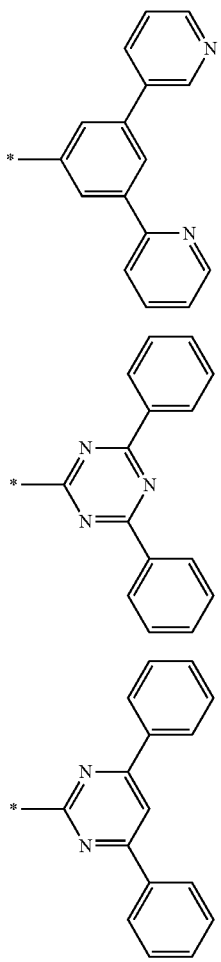

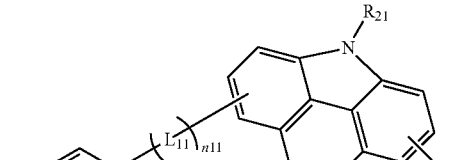

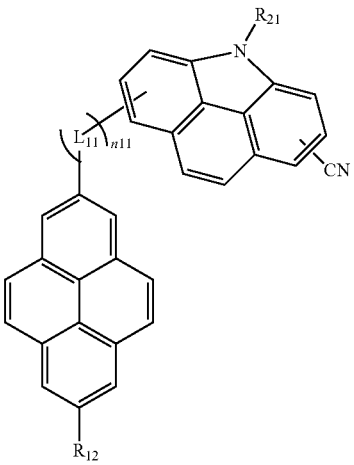

In Formulae 1-1 and 1-2, descriptions of $L_{11}$, n11, $R_{12}$, and $R_{21}$ are as stated above in the present specification.

In some embodiments, in Formula 1, the pyrene-based compound represented by Formula 1 may be represented by one of Formulae 1-1 and 1-2, and $L_{11}$ in Formulae 1-1 and 1-2 may be represented by one of Formulae 4-1 to 4-23.

In some embodiments, in Formula 1, the pyrene-based compound represented by Formula 1 may be represented by one of Formulae 1-1 and 1-2, and n11 in Formulae 1-1 and 1-2 may be an integer of 0 or 1.

In some embodiments, in Formula 1, the pyrene-based compound represented by Formula 1 may be represented by one of Formulae 1-1 and 1-2, and $R_{12}$ in Formulae 1-1 and 1-2 may be selected from a hydrogen atom, a deuterium atom, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, a tert-butoxy group, and compounds of Formulae 5-1 to 5-34.

In some embodiments, the pyrene-based compound represented by Formula 1 may be represented by one of Formulae 1-1 and 1-2, and $R_{21}$ in Formulae 1-1 and 1-2 may be selected from:

a $C_6$-$C_{60}$ aryl group, a $C_2$-$C_{60}$ heteroaryl group, and a non-aromatic condensed polycyclic group; and a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl Also, in some embodiments, in Formula 1, $R_{13}$ and $R_{14}$ may be selected from, for example, a hydrogen atom, a deuterium atom, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, and a tert-butoxy group.

In Formula 1, a12 denotes the number of $R_{12}$, a12 may be an integer of 0 to 3. When a12 is an integer of 2 or greater, a plurality of $R_{12}$s may be identical to or different from each other.

In Formula 1, a13 denotes the number of $R_{13}$, a13 may be an integer of 0 to 3. When a13 is an integer of 2 or greater, a plurality of $R_{13}$s may be identical to or different from each other.

In Formula 1, a14 denotes the number of $R_{14}$, a14 may be an integer of 0 to 3. When a14 is an integer of 2 or greater, a plurality of $R_{14}$s may be identical to or different from each other.

For example, a pyrene-based compound represented by Formula 1 may be represented by one of Formulae 1-1 and 1-2:

group, a $C_1$-$C_{60}$ alkoxy group, a $C_6$-$C_{60}$ aryl group, a $C_2$-$C_{60}$ heteroaryl group, and a non-aromatic condensed polycyclic group.
The pyrene-based compound represented by Formula 1 may be one of Compounds 1 to 133 below, as examples:
1
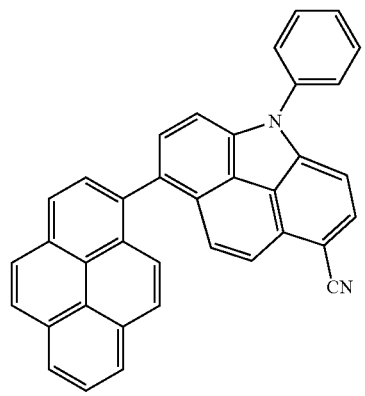
2
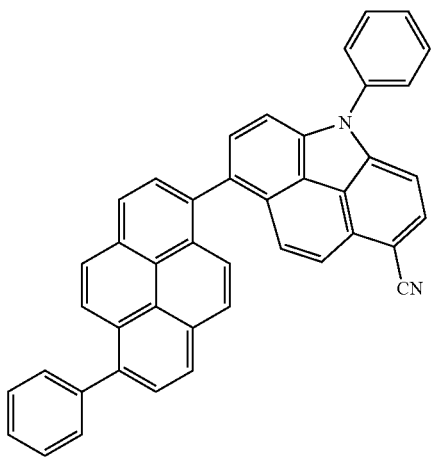
3
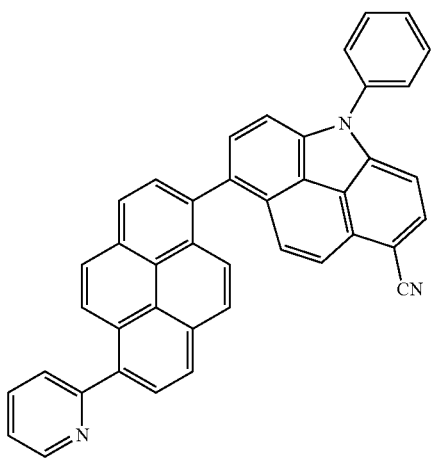
-continued
4
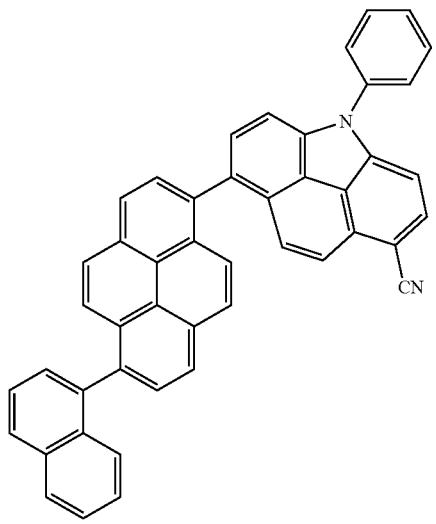
5
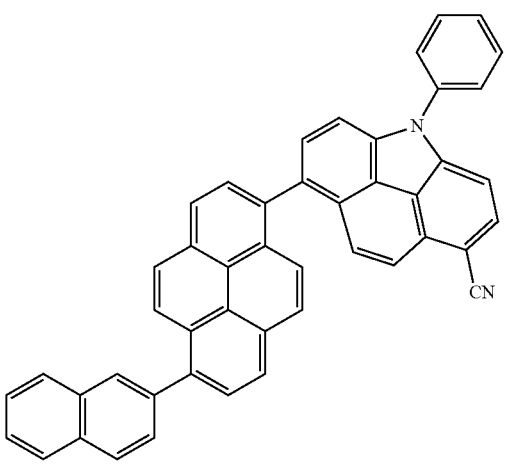
6
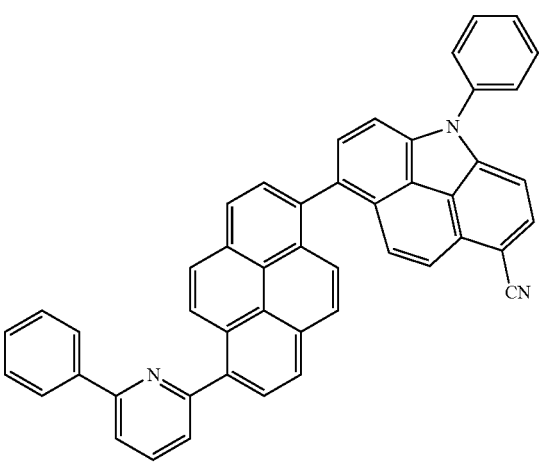

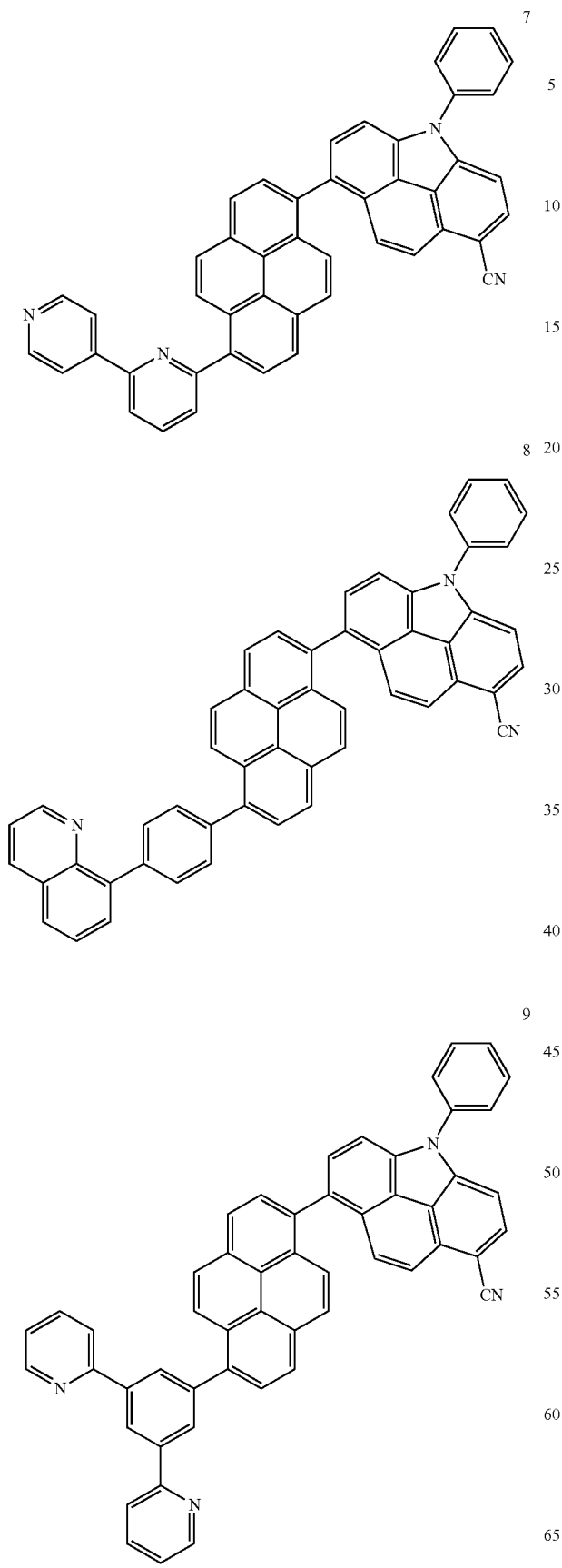
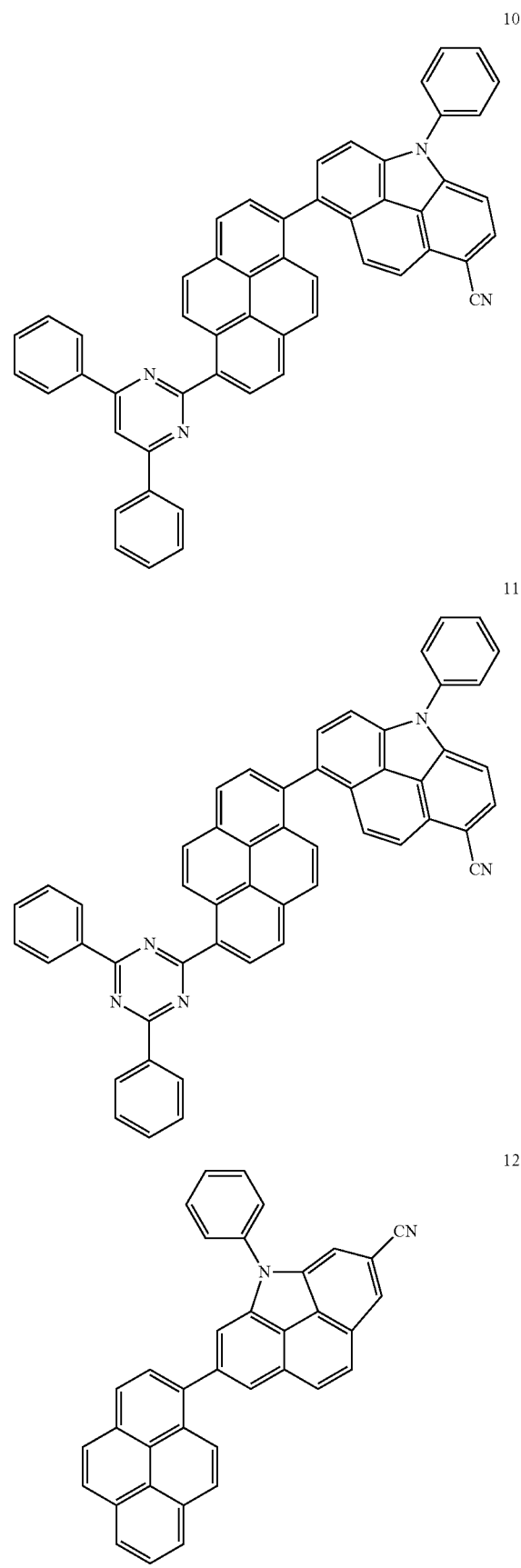

13
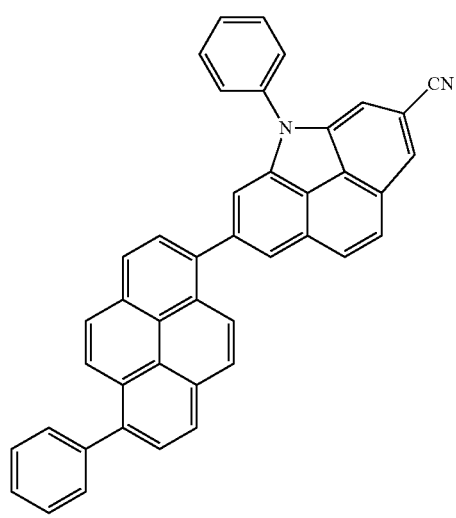
14
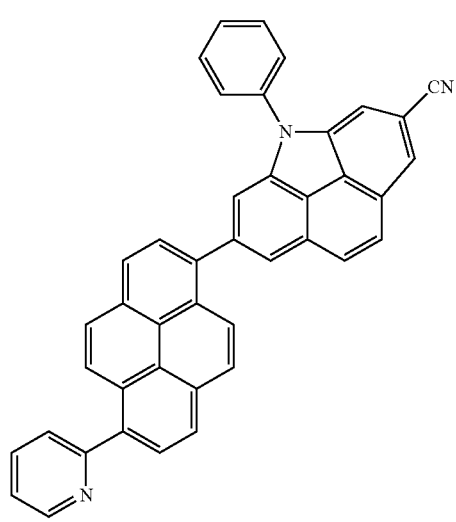
15
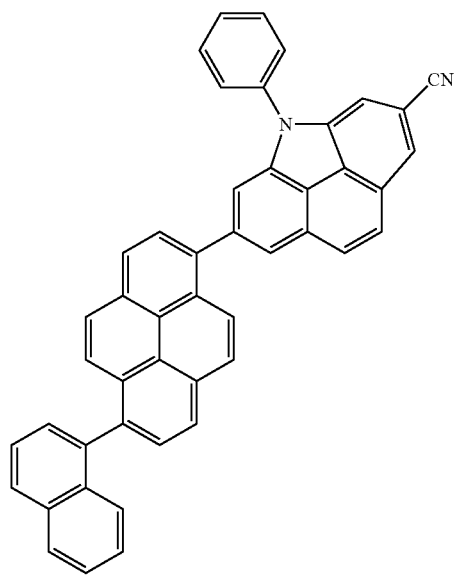
16
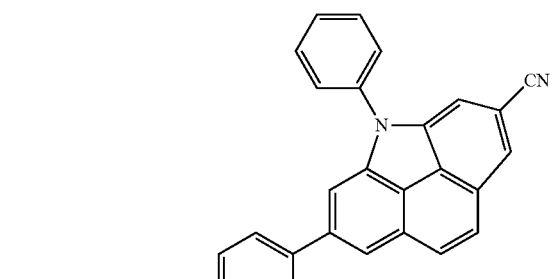
17
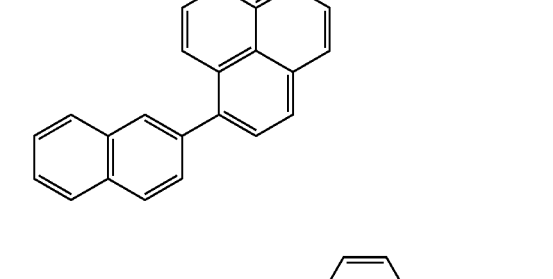
18
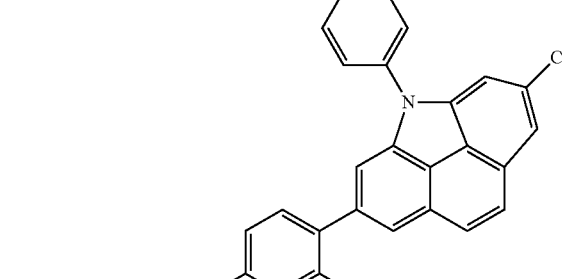

19
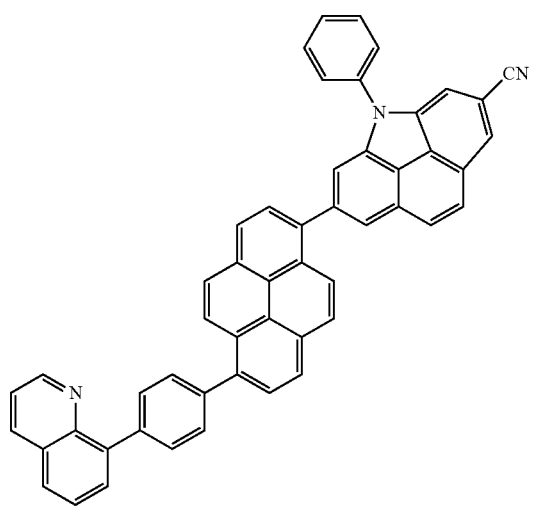
20
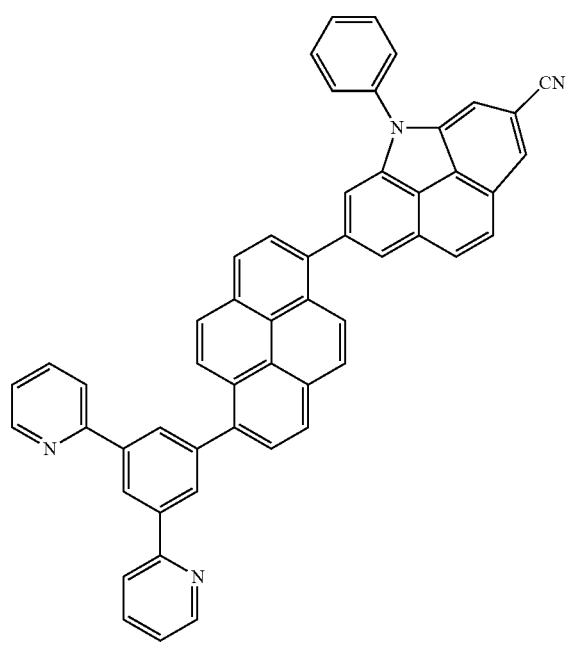
21
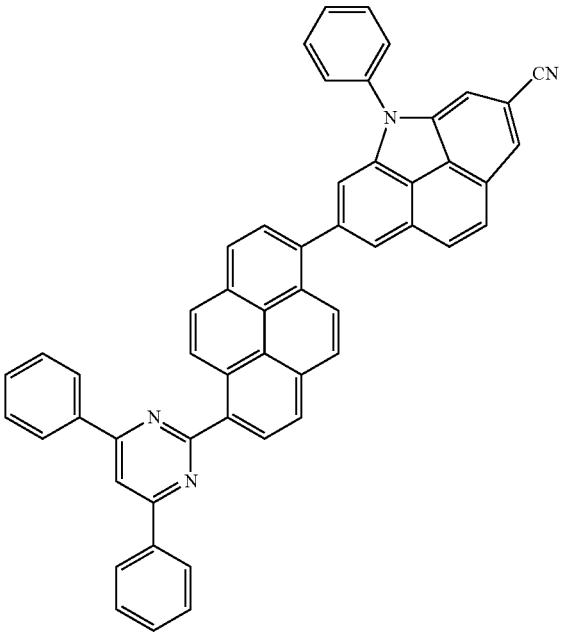
22
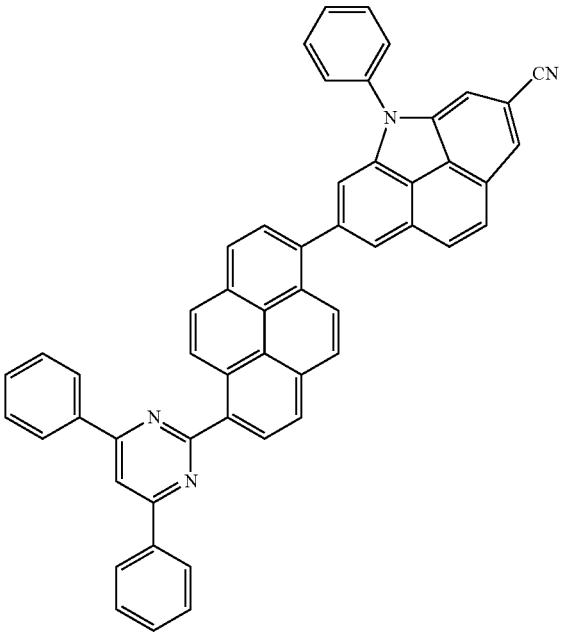

23
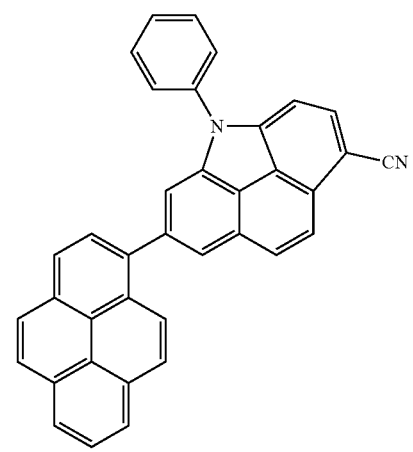
24
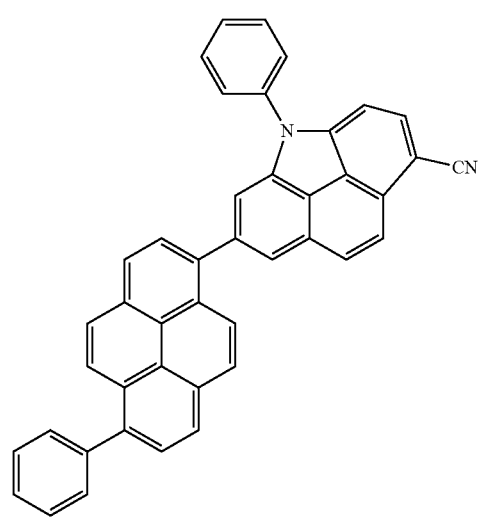
25
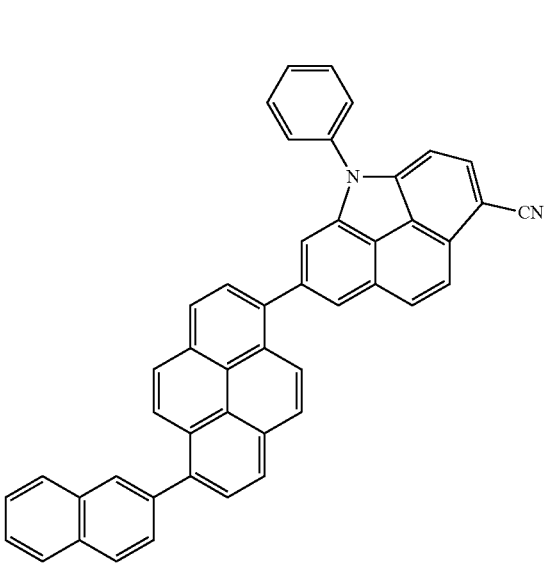
26
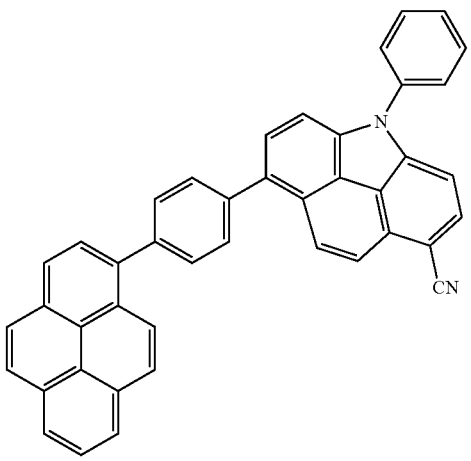
27
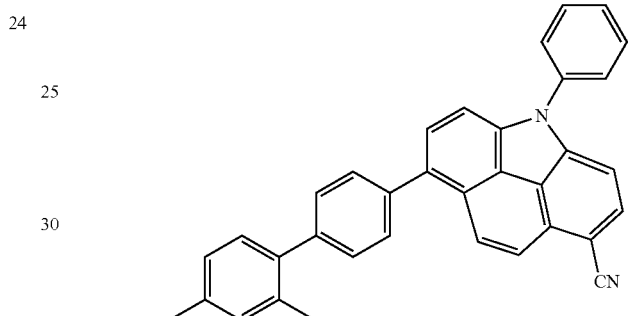
28
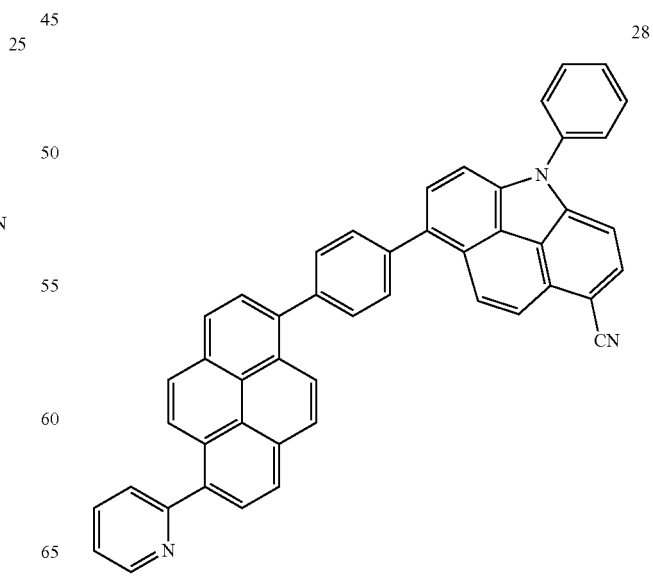

29
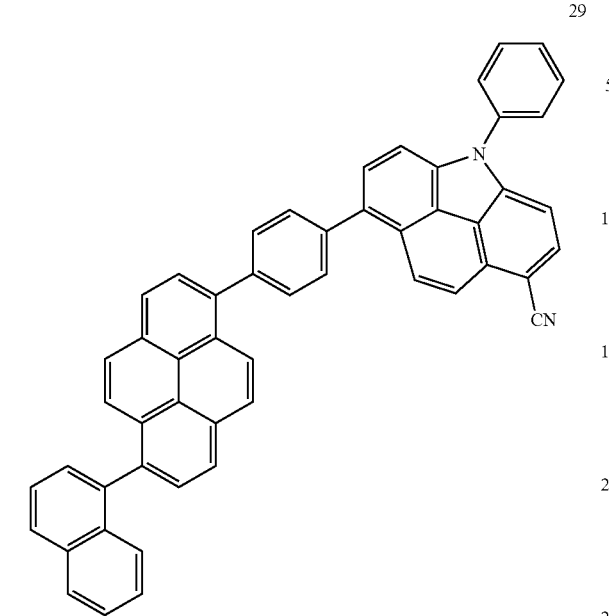
30
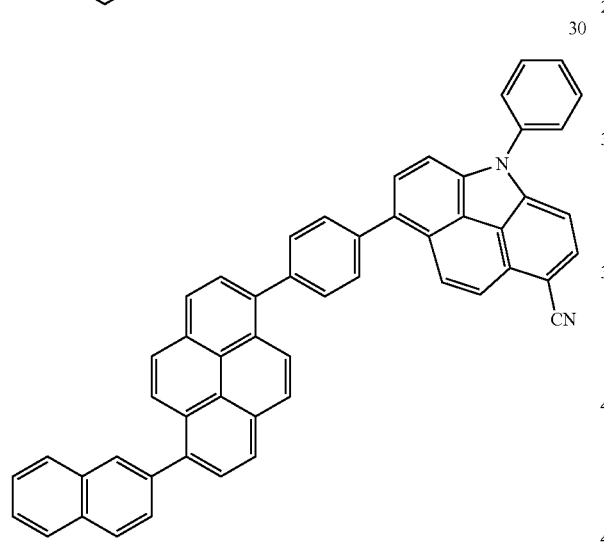
31
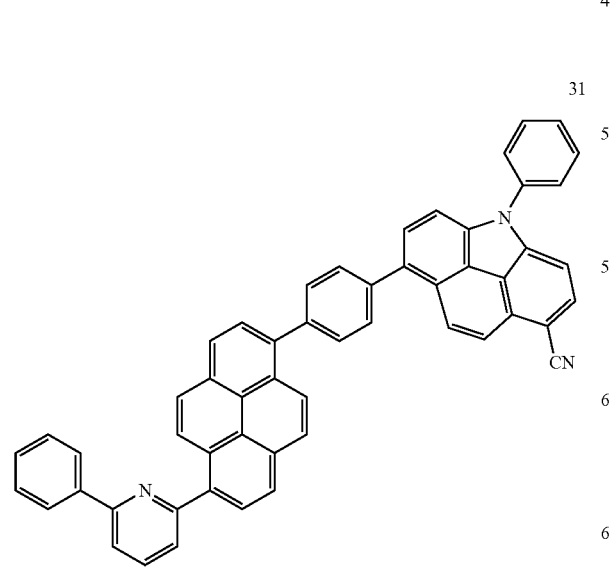
32
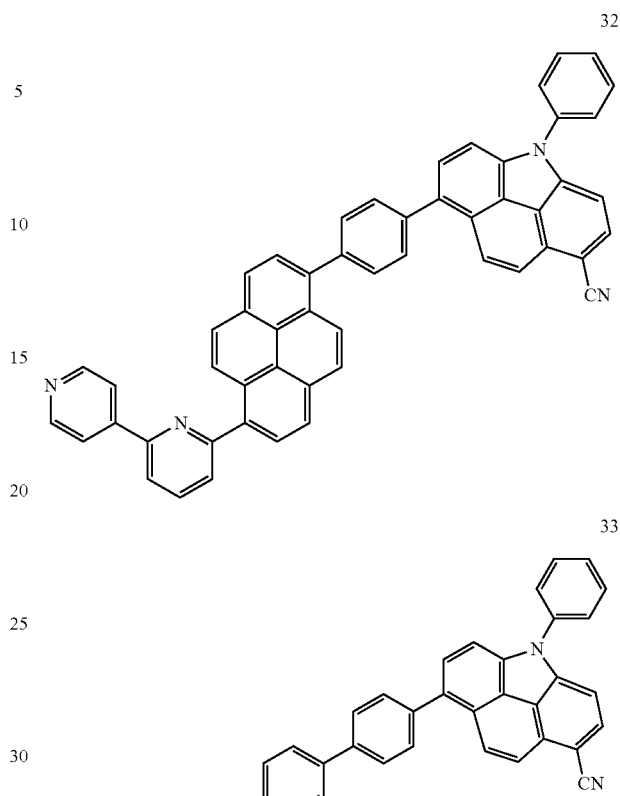
33
34
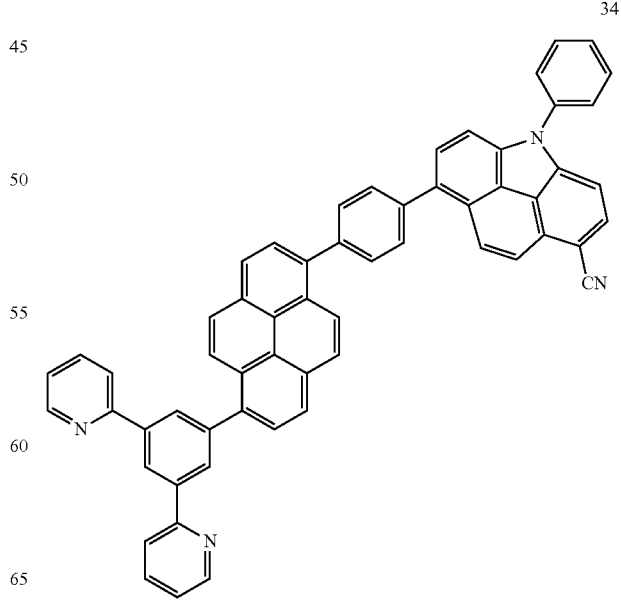

35
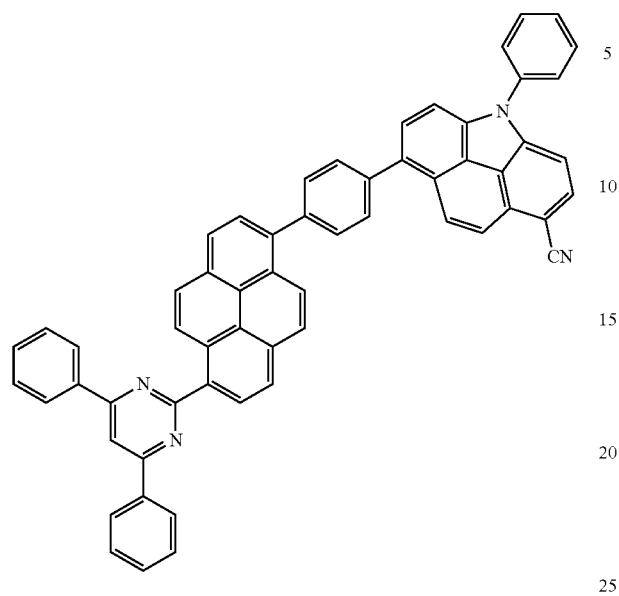
37
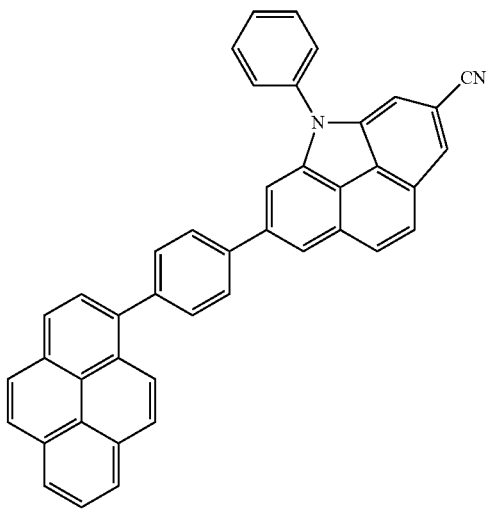
36
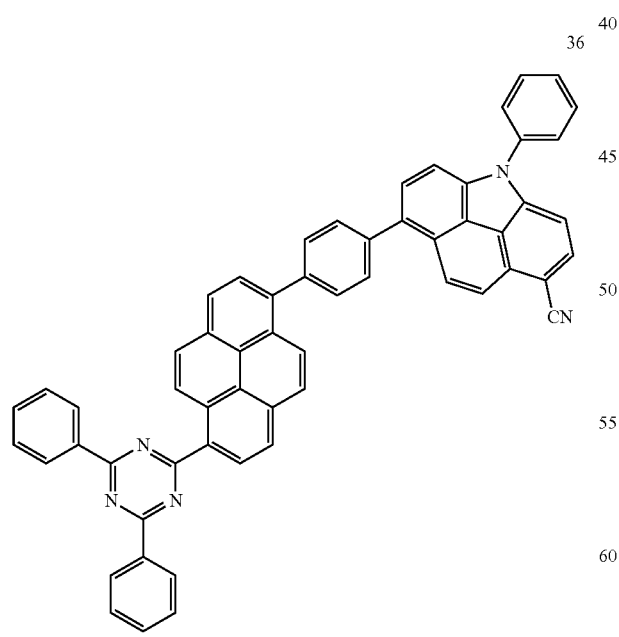
38

-continued
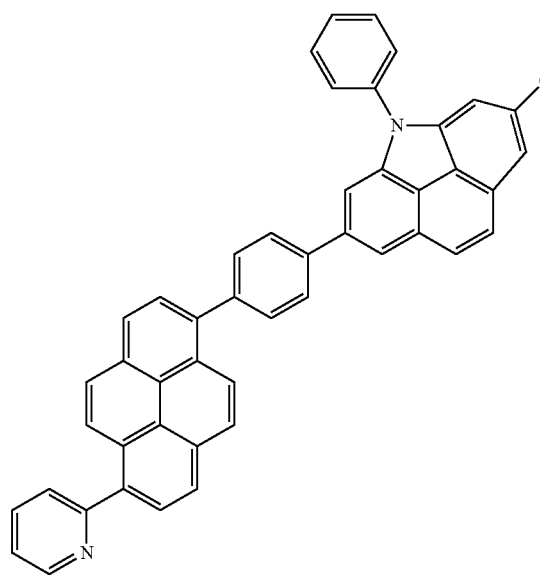
39
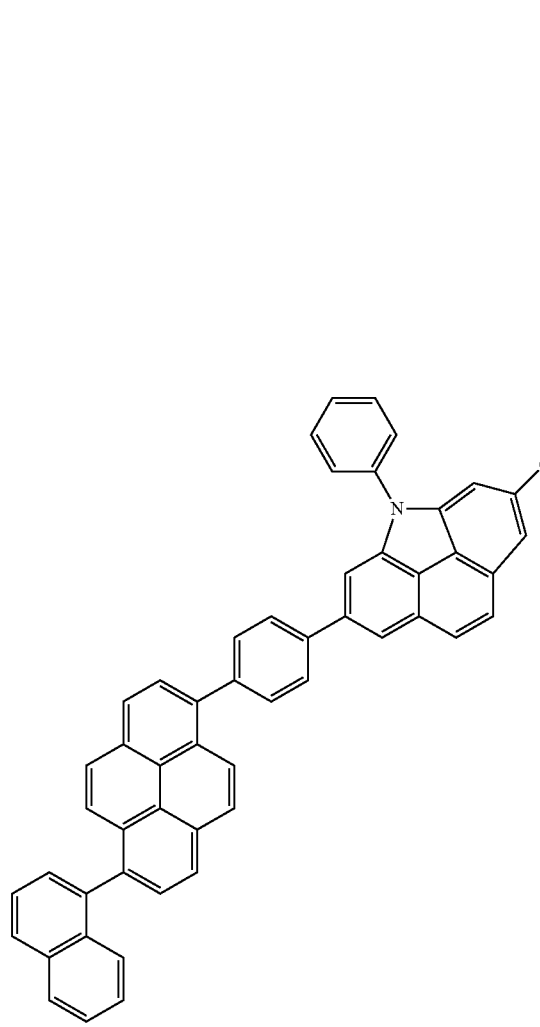
40
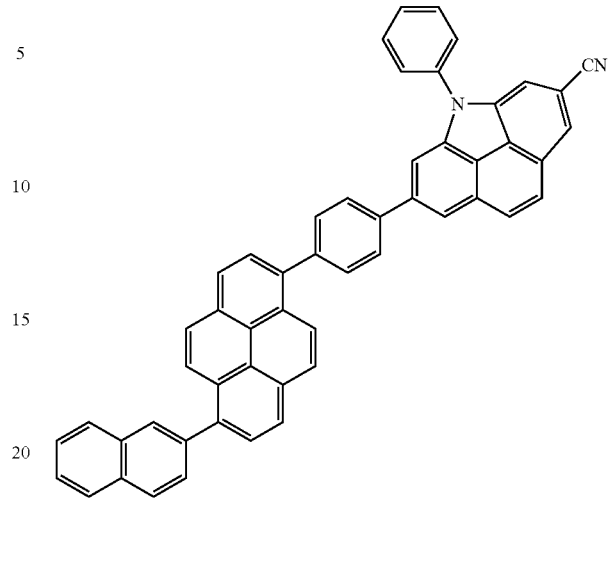
41
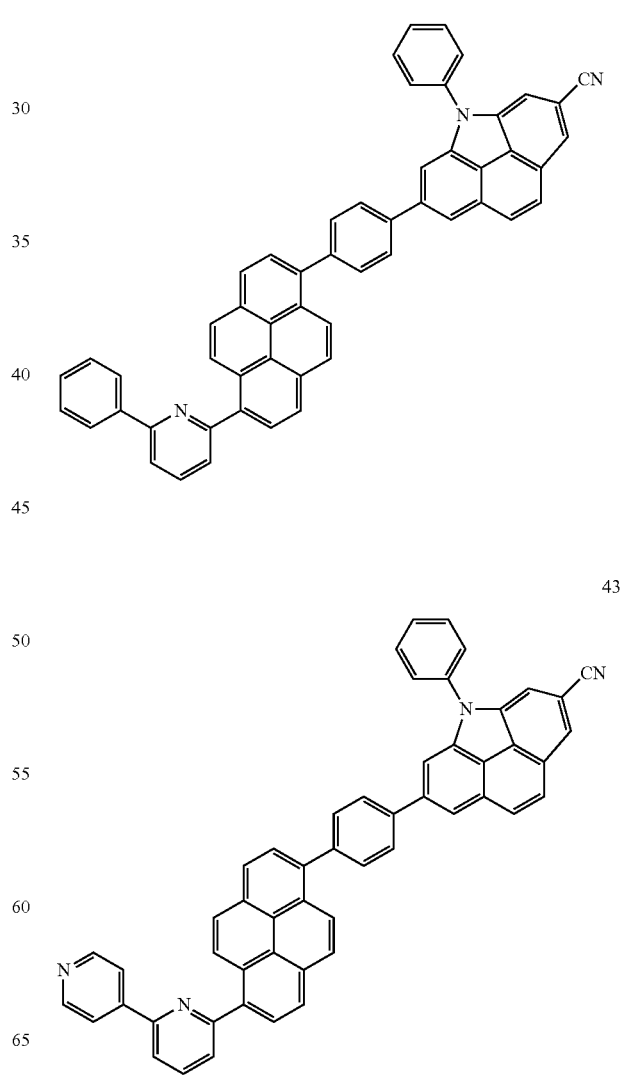
42
43

44
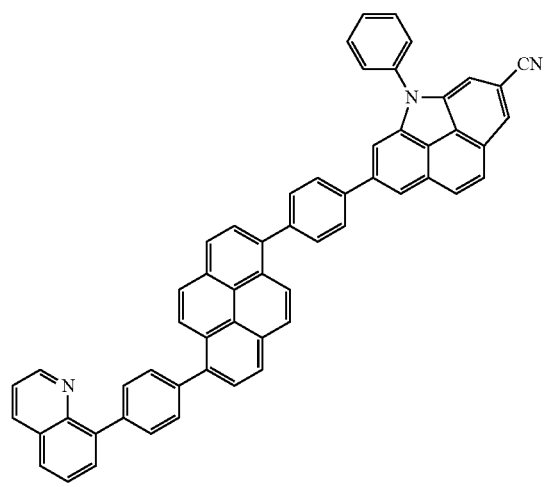
45
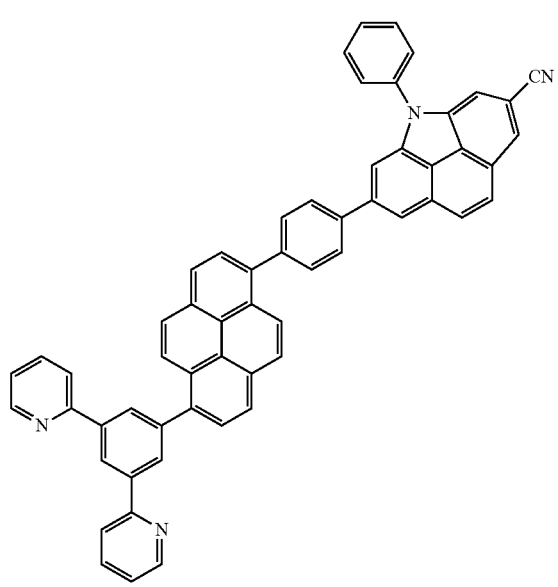
46
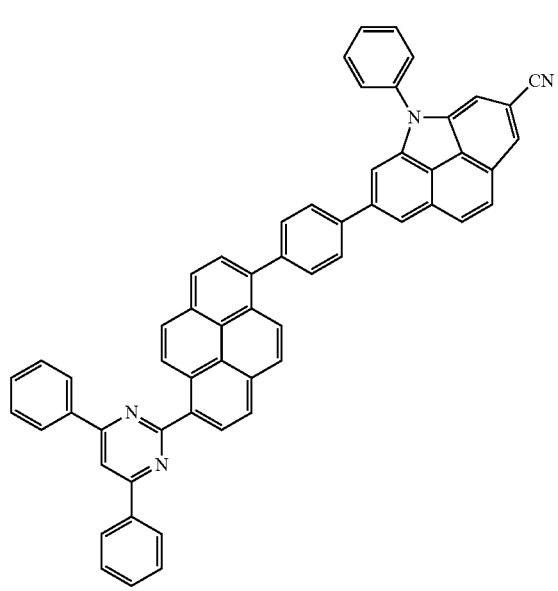
47
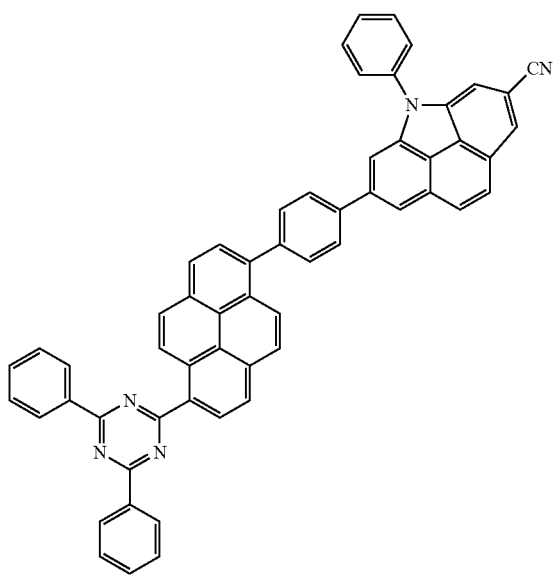
48
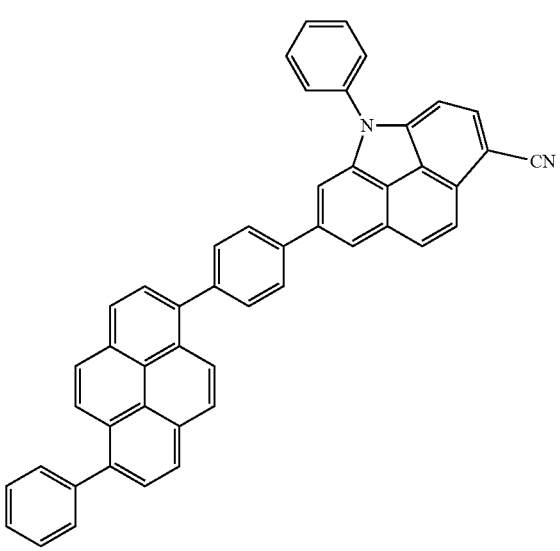
49
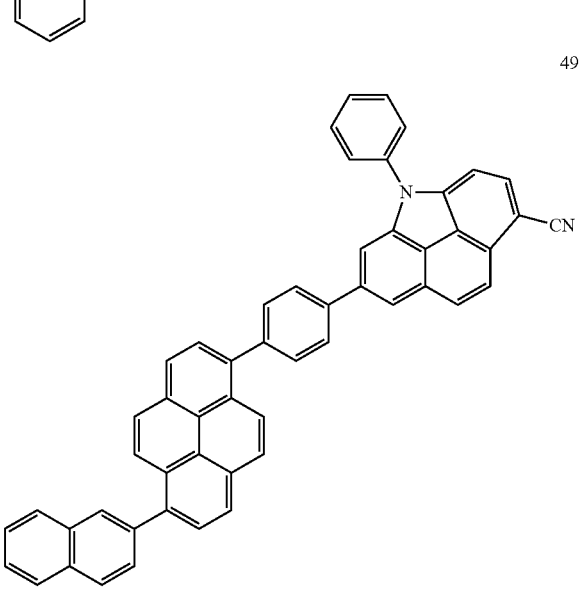

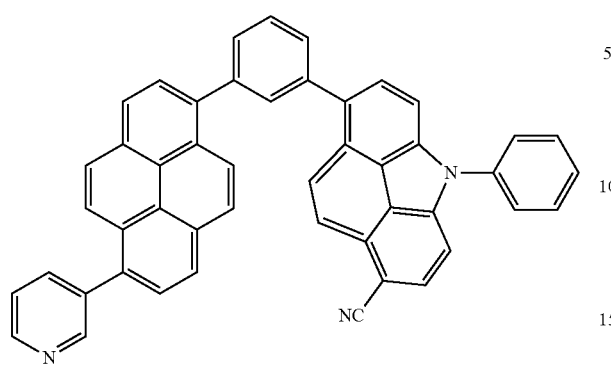
50
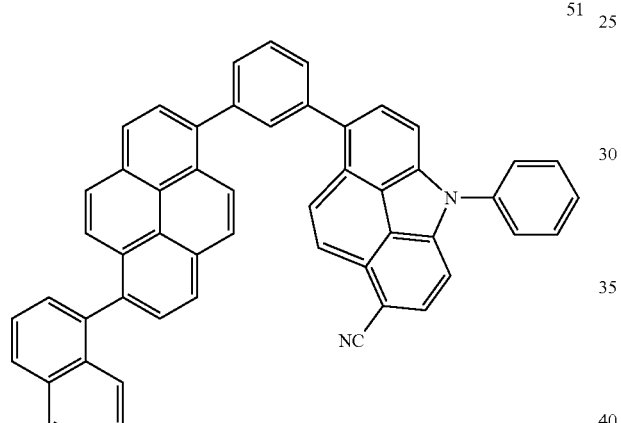
51
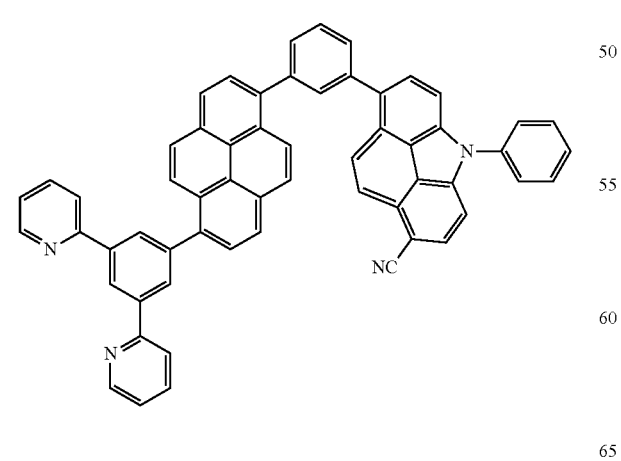
52
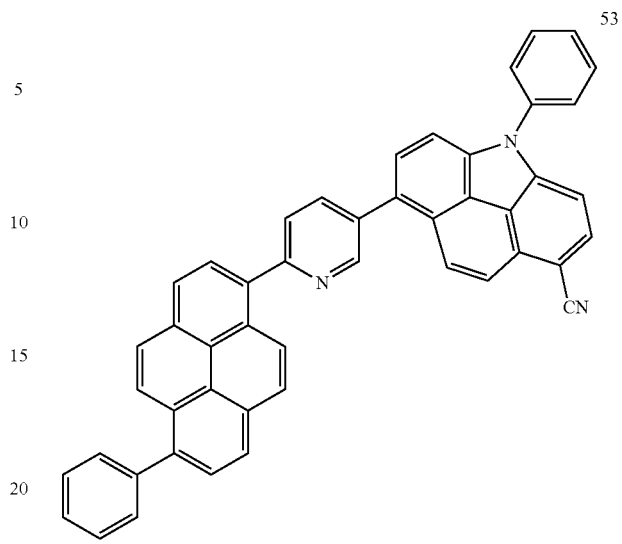
53
54
55

-continued
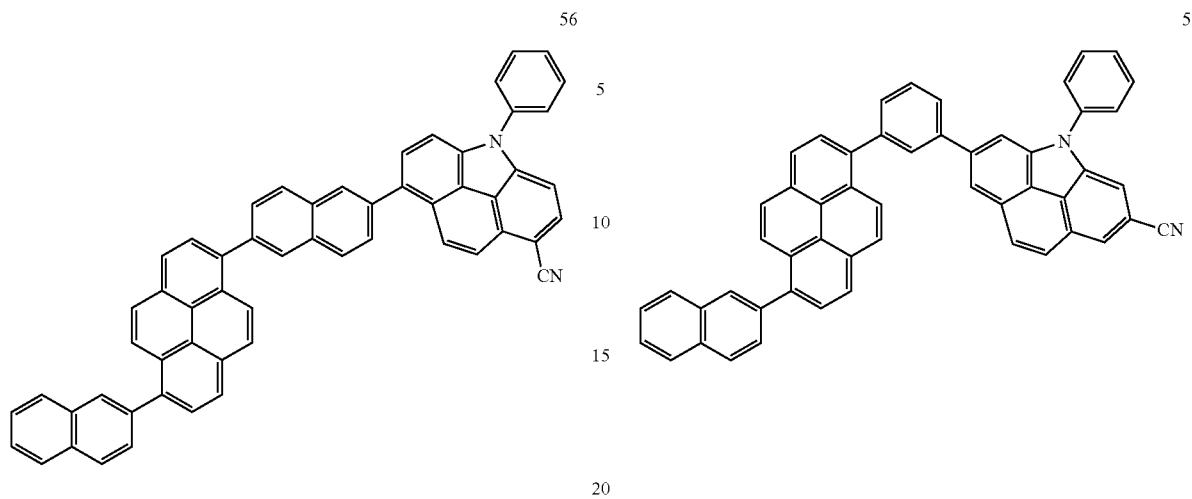
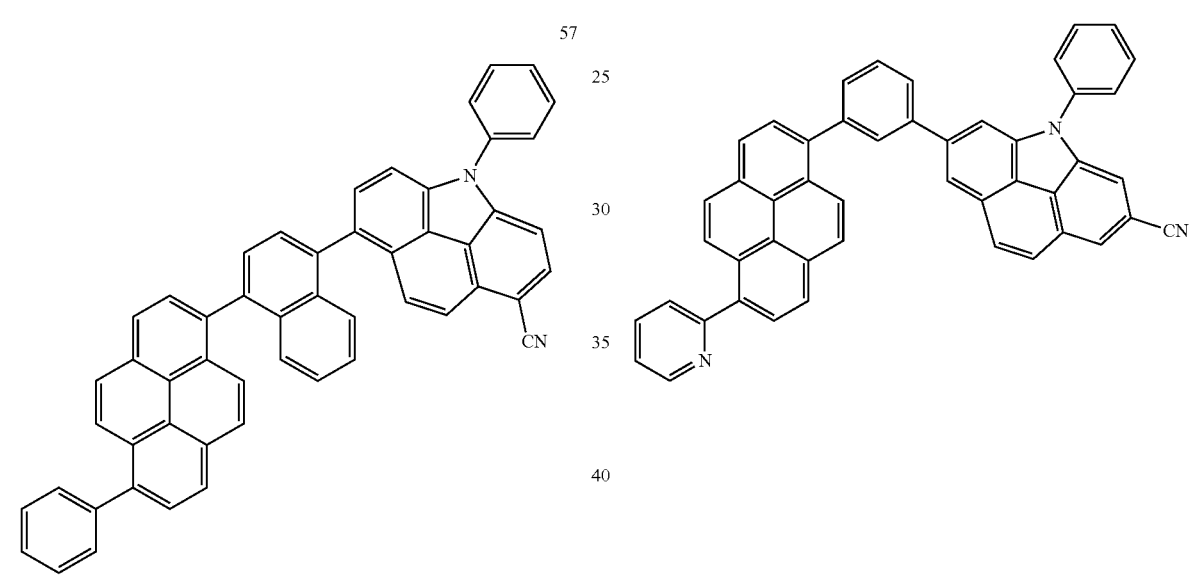
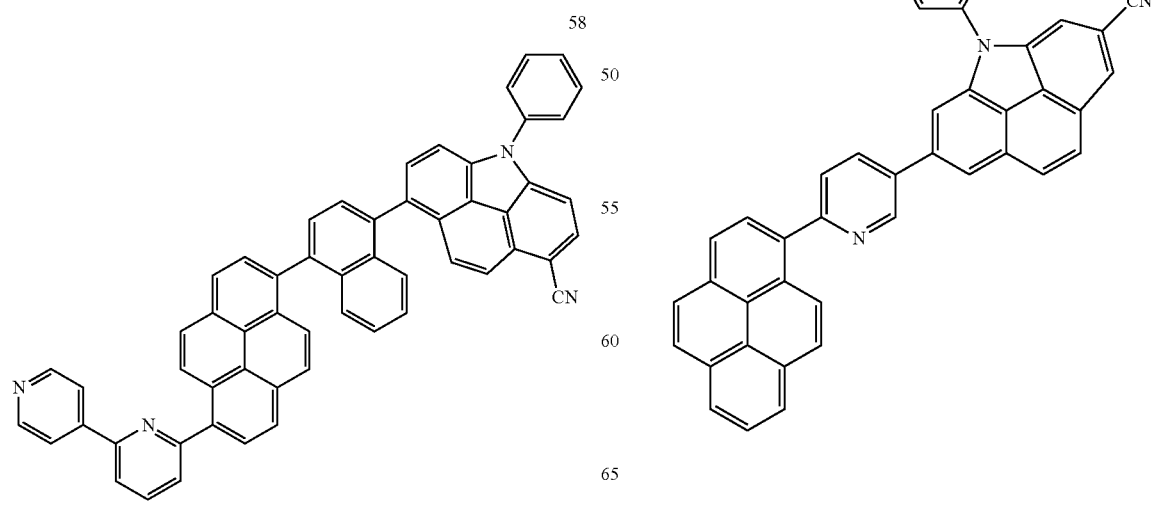

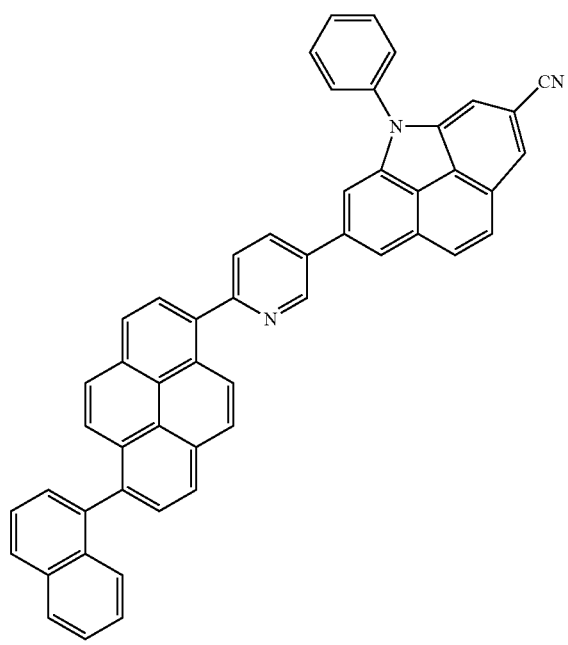
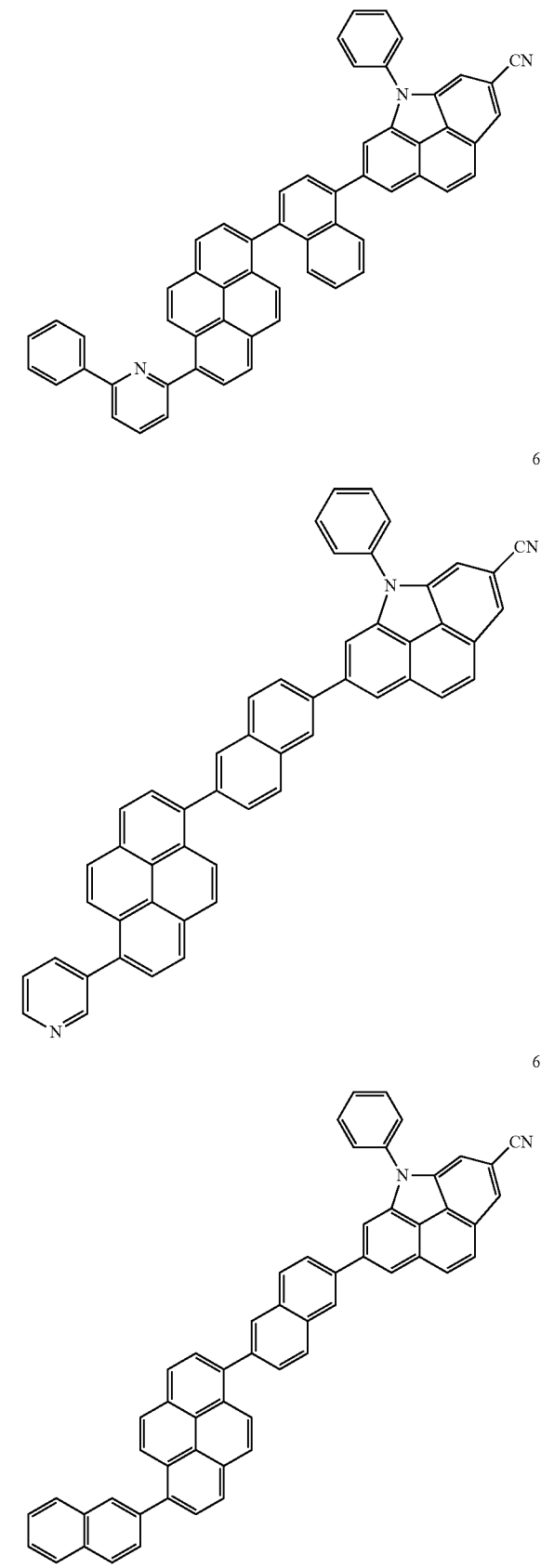

-continued
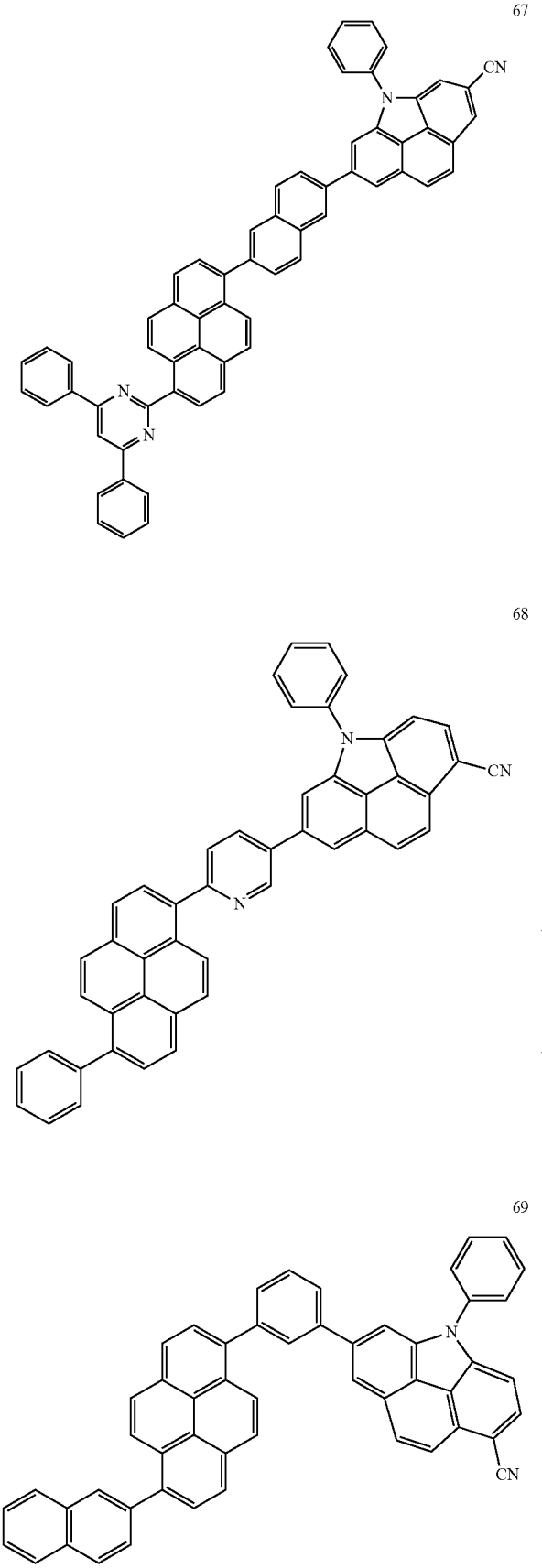
-continued
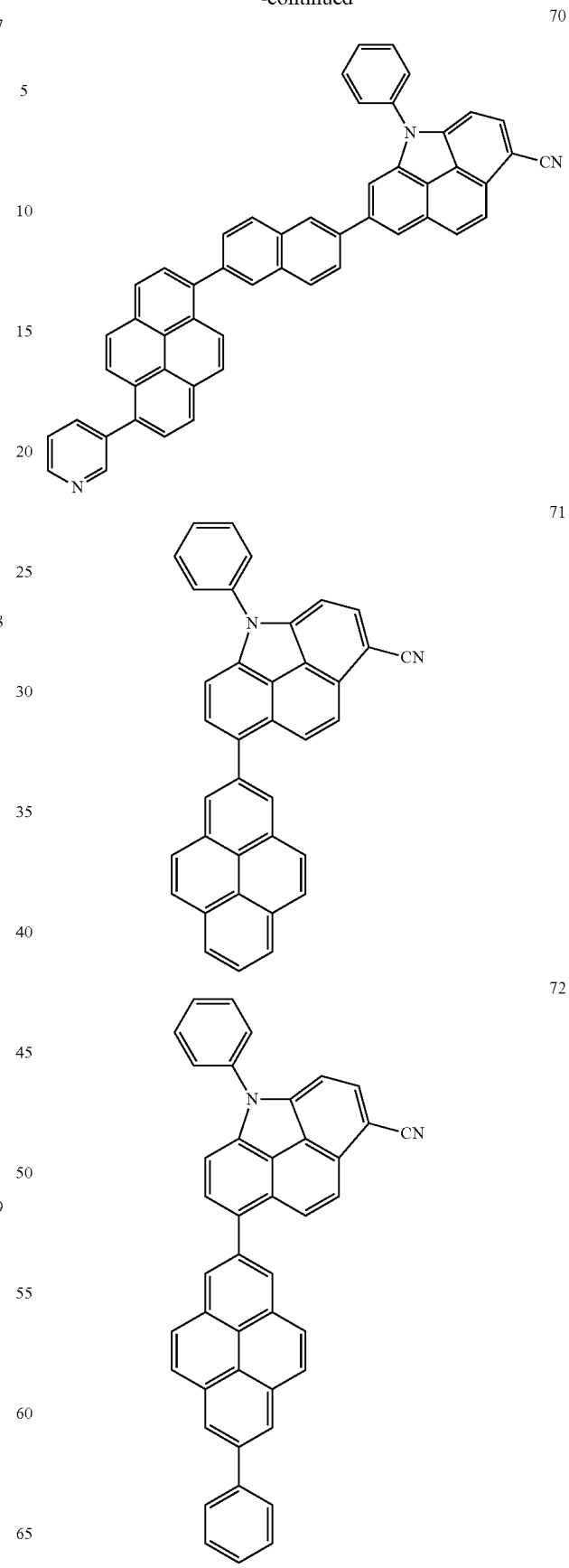

73
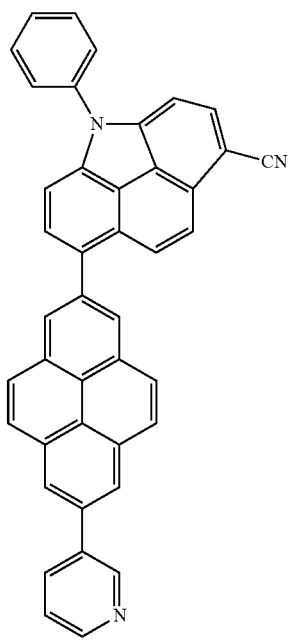
75
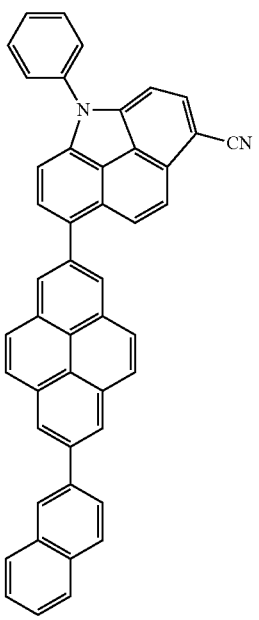
74
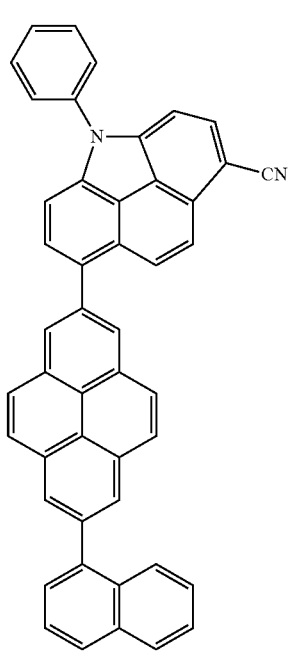
76
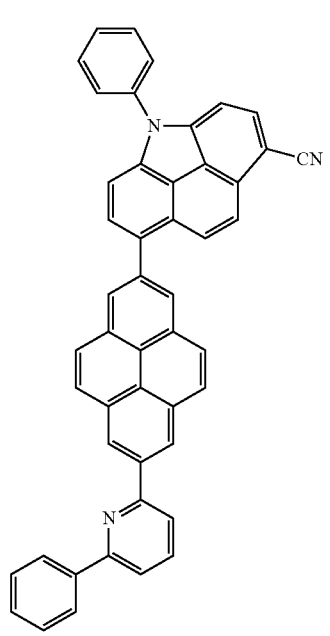

77
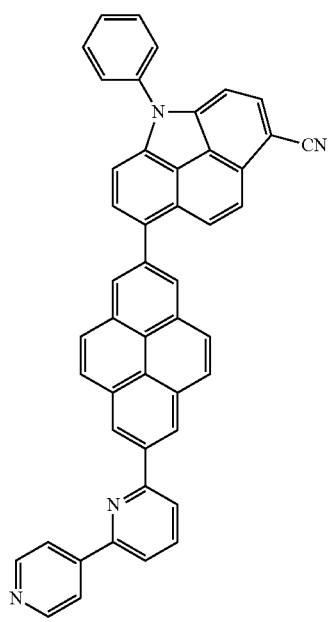
79
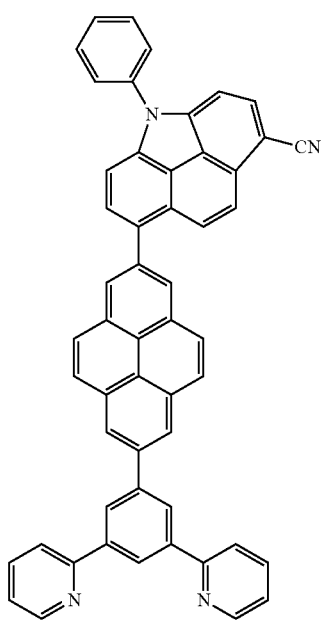
78
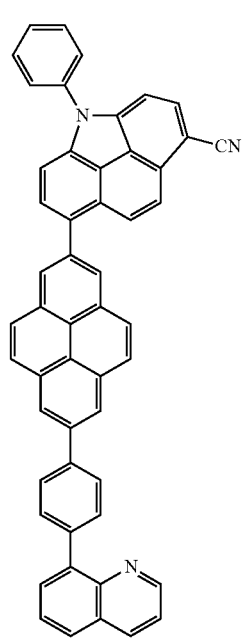
80
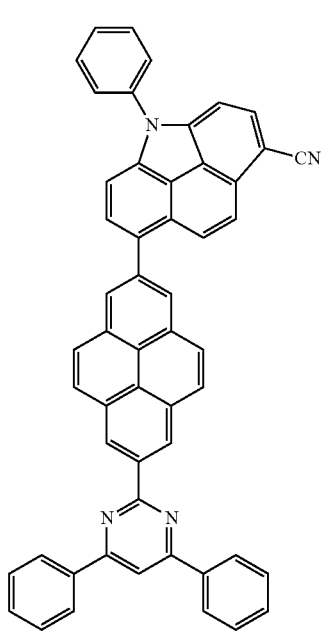

81
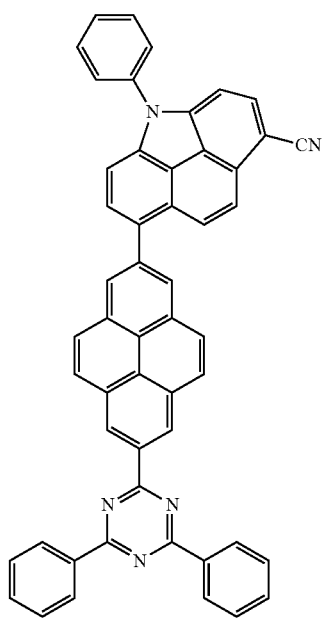
82
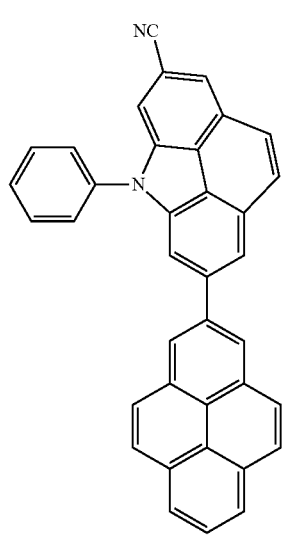
83
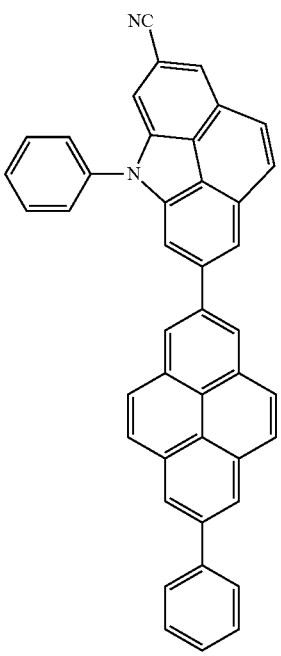
84
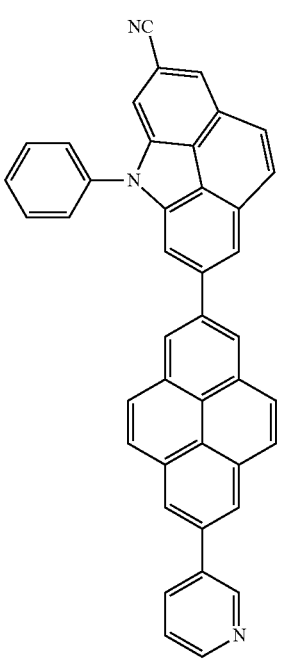

85
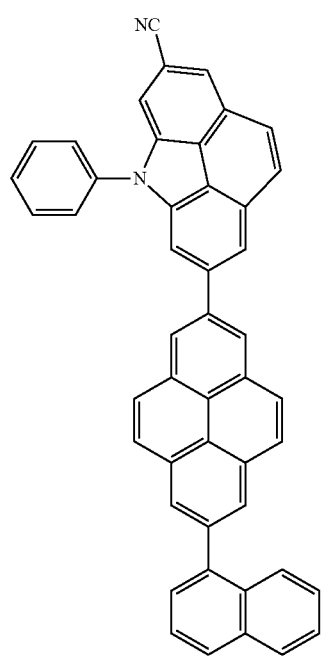
87
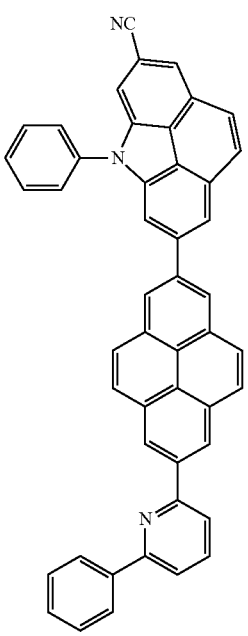
86
88

89
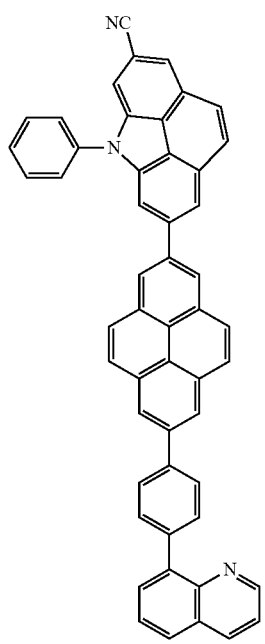
90
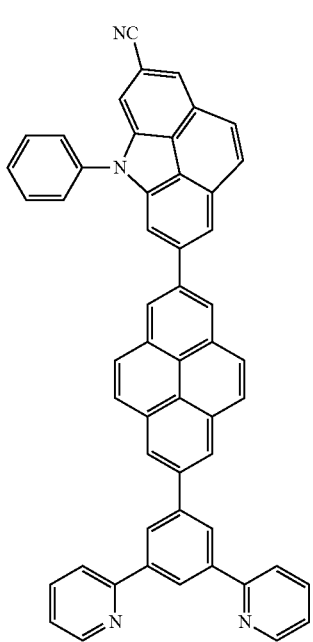
91
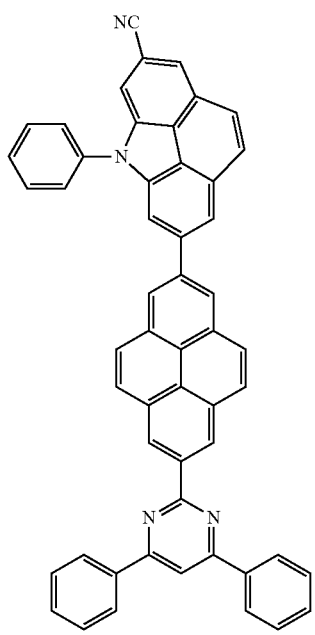
92
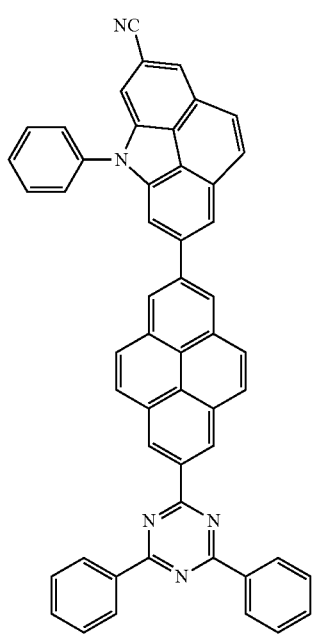

61
-continued
93
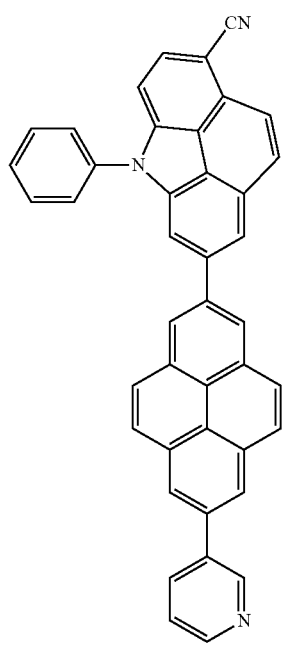
62
-continued
95
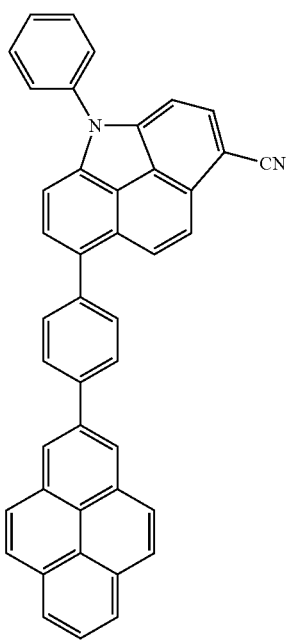
94
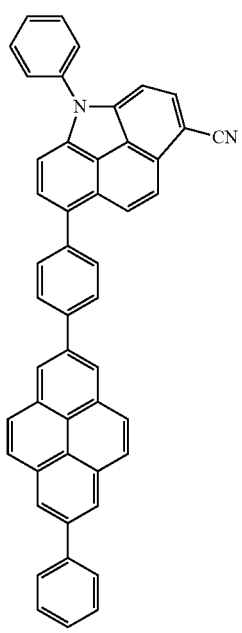
96

97
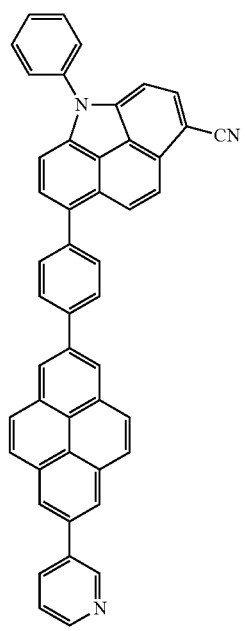
98
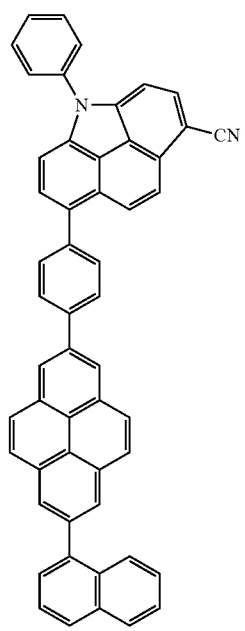
99
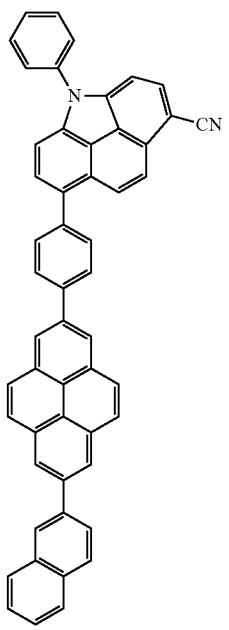
100
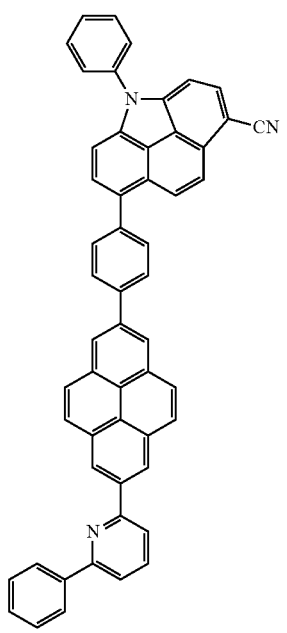

101 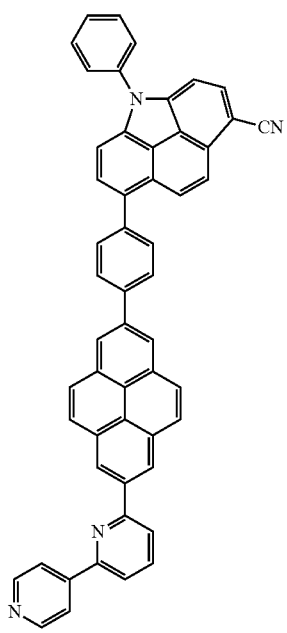
102 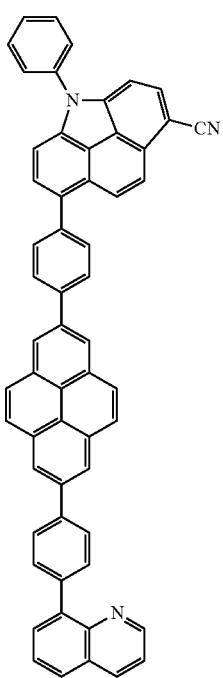
103 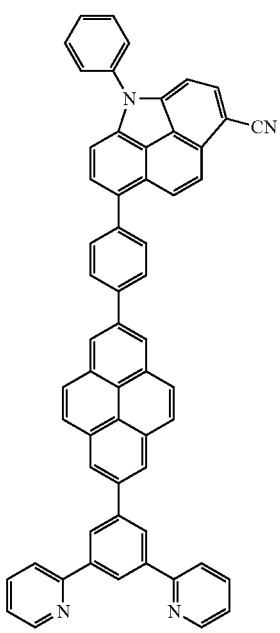
104 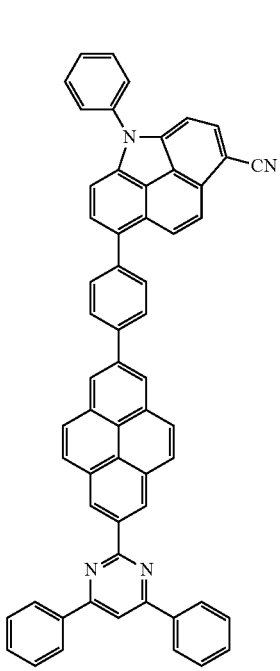

67
105
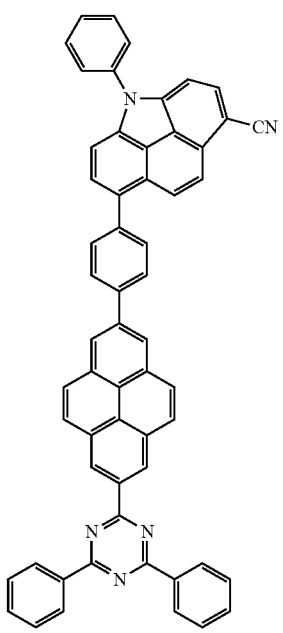
106
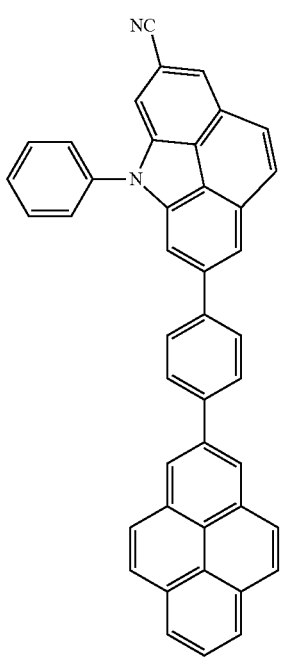
68
107
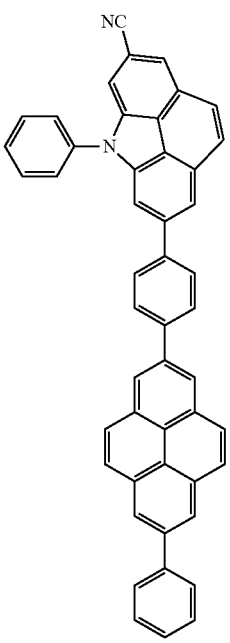
108
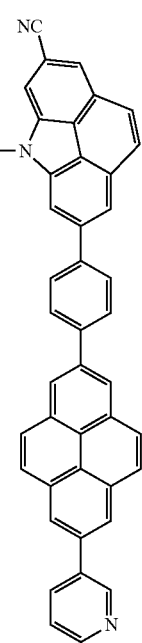

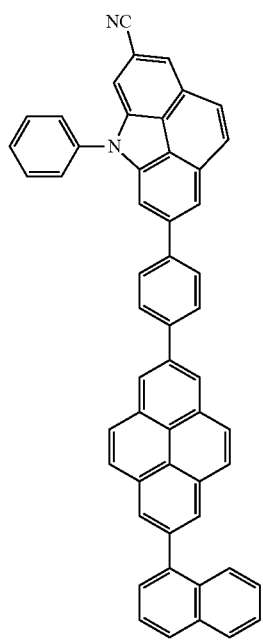
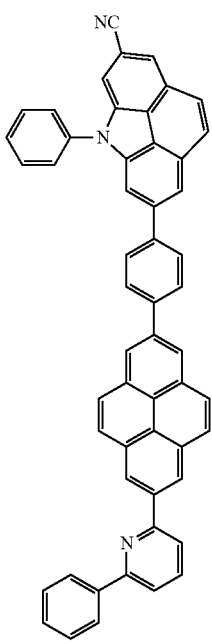

71
-continued
113
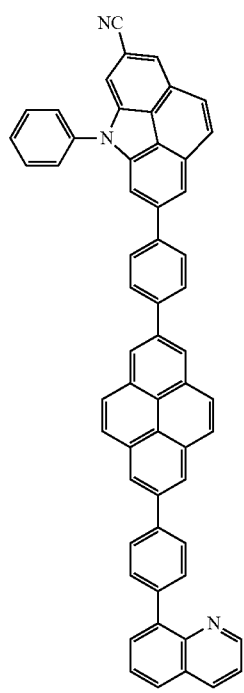
72
-continued
115
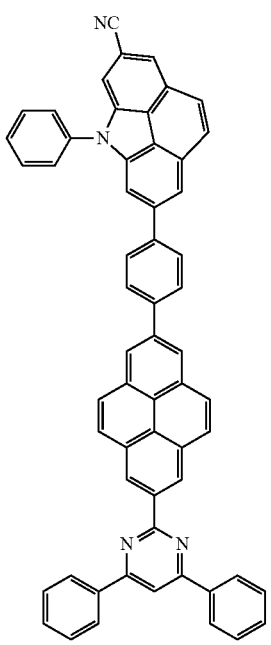
114
116
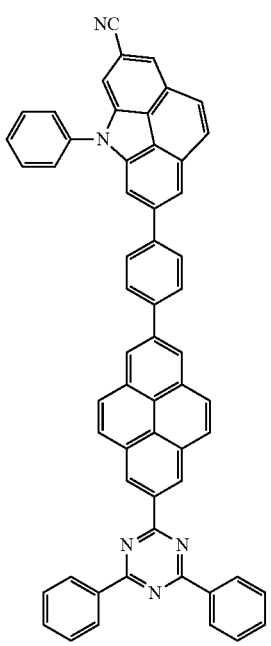

-continued
117
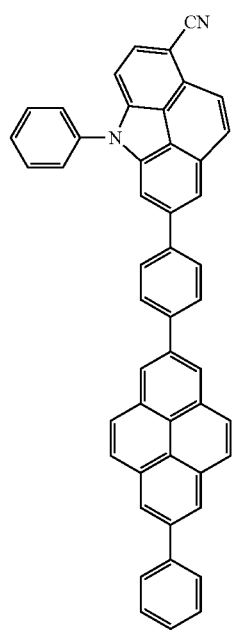
118
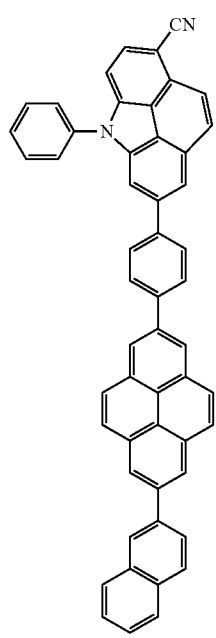
-continued
119
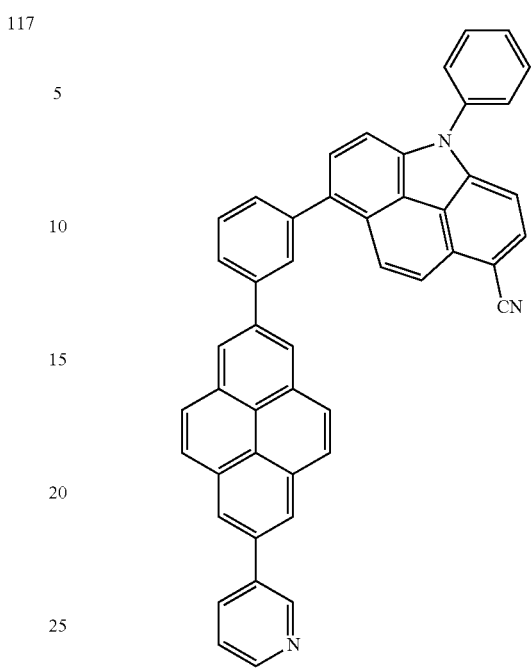
120
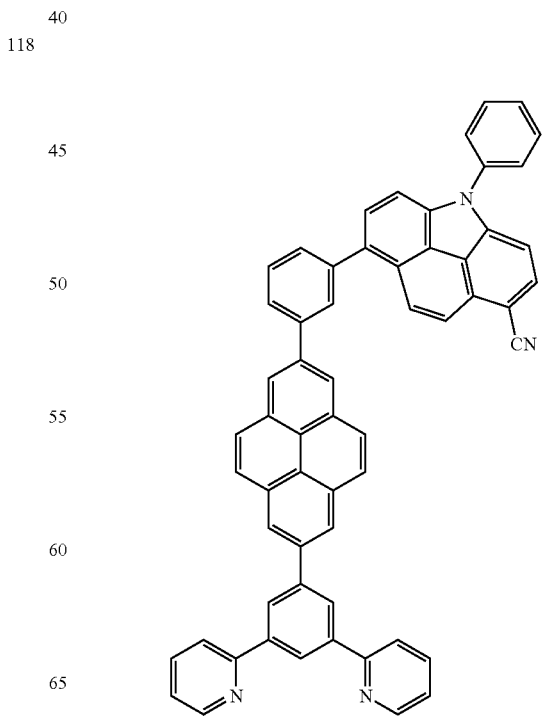

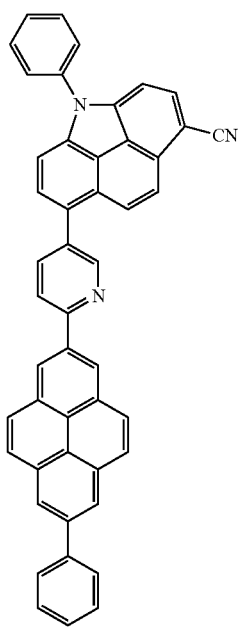
121
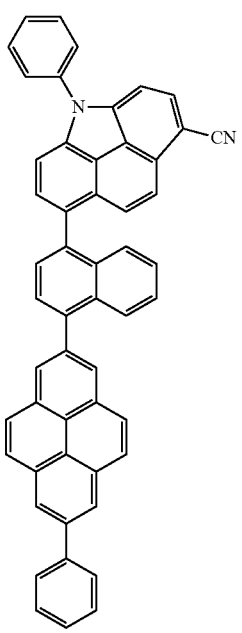
123
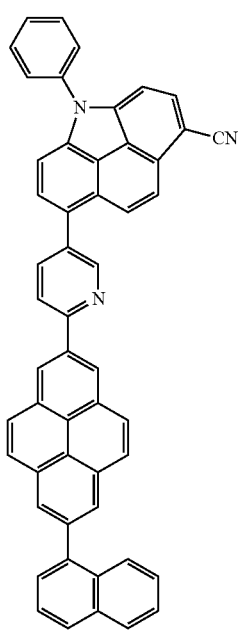
122
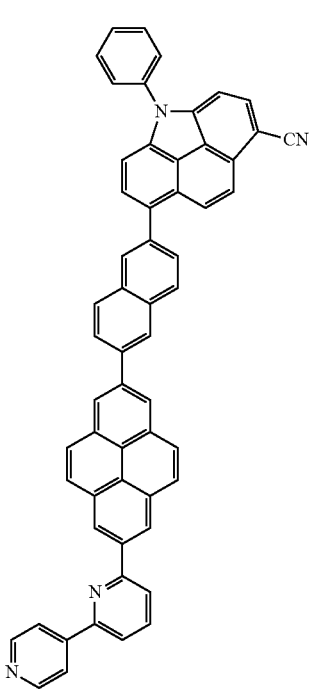
124

77
-continued
125
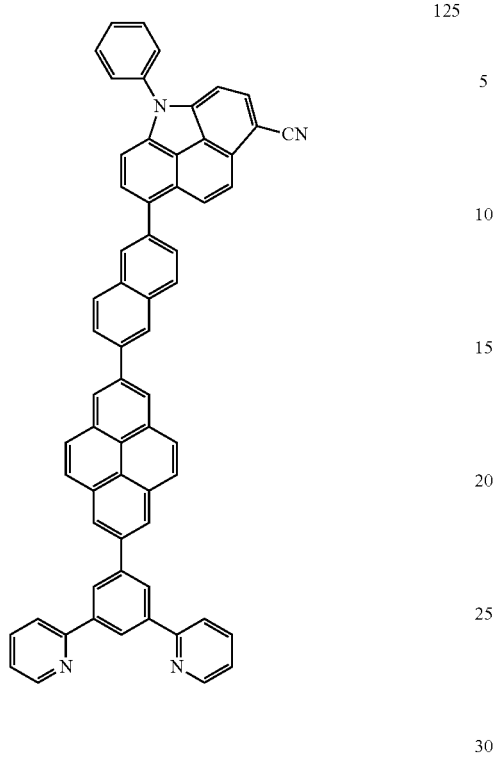
126
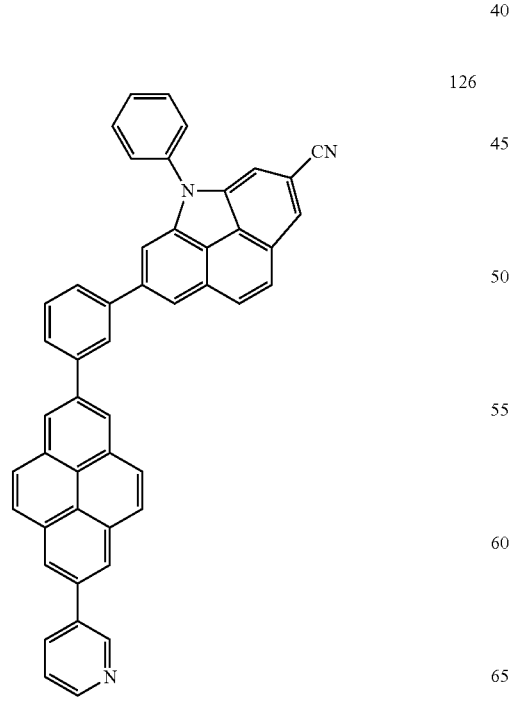
78
-continued
127
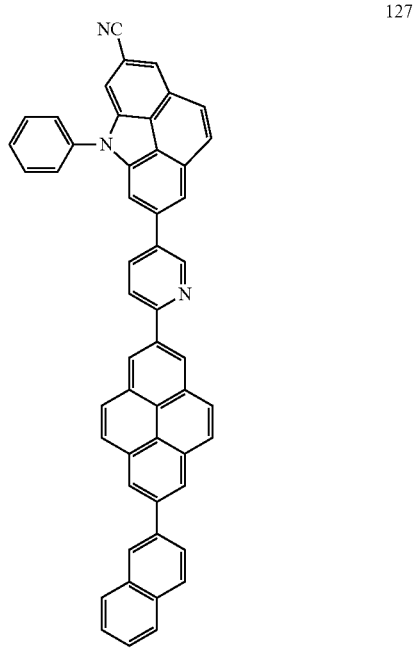
128
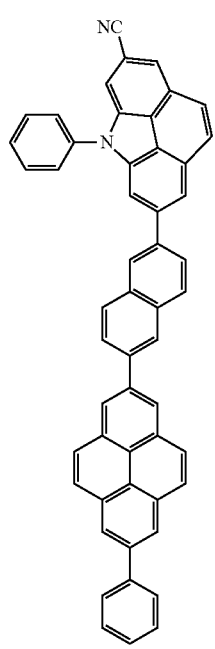

129
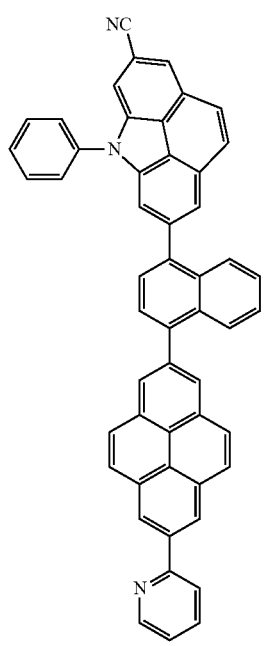
130
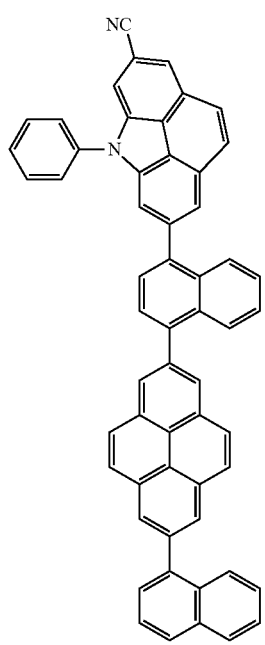
131
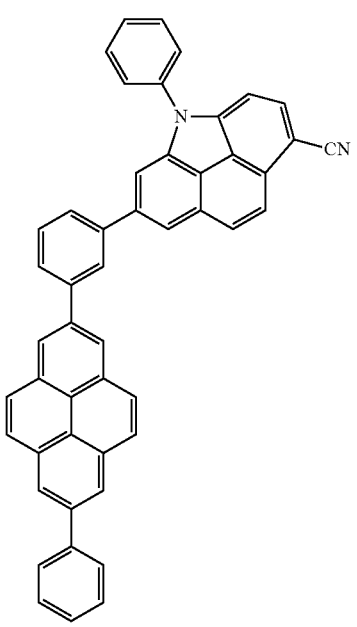
132
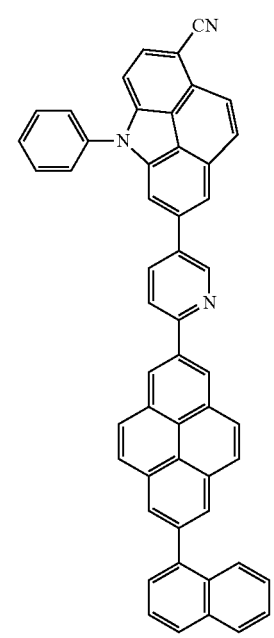

-continued

133

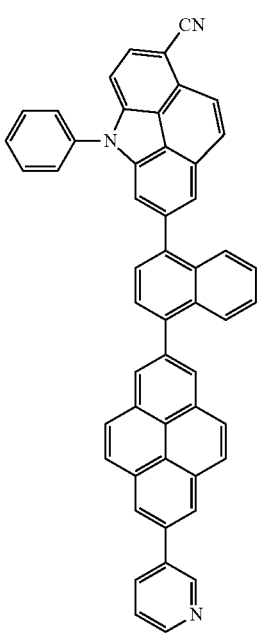

The pyrene compound may be a compound represented by Formula 1':

<Formula 1'>

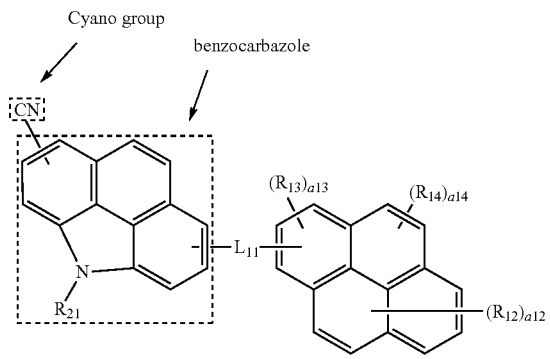

As represented by Formula 1', the pyrene-based compound represented by Formula 1 may include a benzocarbazole group and thus may have more electrons and a greater molecular weight (e.g., have more electrons and a greater molecular weight than a compound including only a carbazole group). Therefore, the pyrene-based compound represented by Formula 1 may have a high polarity having both hole and electron transporting abilities and thus may decrease a driving voltage and increase an efficiency of an OLED. Also, the pyrene-based compound represented by Formula 1 may have a high thermal stability, and thus, a glass transition temperature (Tg) of the compound may be high, and a lifespan of the OLED including the compound may be increased.

The pyrene-based compound represented by Formula 1 may include —CN and a benzocarbazole group together. Thus, a Tg of the compound may be high. When the pyrene-based compound represented by Formula 1 is applied to the OLED, a thin film stability of the OLED may increase and a lifespan of the OLED may be increased.

The OLED including the pyrene-based compound represented by Formula 1 may have a low driving voltage, a high efficiency, and a long lifespan.

The pyrene-based compound represented by Formula 1 may be synthesized by using a suitable organic synthesis method. The synthesis method for synthesizing the pyrene-based compound may be understood by one of ordinary skill in the art by referring to examples described below.

The pyrene-based compound represented by Formula 1 may be included between a pair of electrodes of an OLED. In some embodiments, the pyrene-based compound may be included in the electron transport region, for example, the ETL. Thus, an OLED may include a first electrode, a second electrode facing the first electrode, and an organic layer that is disposed between the first electrode and the second electrode and includes an emission layer (EML), wherein the organic layer includes at least one of pyrene-based compound represented by Formula 1.

As used herein, the expression "(the organic layer) may include at least one pyrene-based compound of Formula 1" may be understood as "(the organic layer) may include one pyrene-based compound represented by Formula 1 or at least two different compounds selected from pyrene-based compounds represented by Formula 1".

In some embodiments, the organic layer may only include Compound 1 as the pyrene-based compound. Here, Compound 1 may be included in the electron transport region of the OLED. In other implementations, the organic layer may include Compound 1 and Compound 2 as the pyrene-based compound. Compound 1 and Compound 2 may be included in the same layer (e.g., both Compound 1 and Compound 2 in an electron transport region) or respectively included in two different layers (e.g., Compound 1 in an EML and Compound 2 in an electron transport region).

The organic layer may further include a hole transport region disposed between the first electrode and the EML. The hole transport region may include at least one of a hole injection layer (HIL), a hole transport layer (HTL), a buffer layer, and an electron blocking layer (EBL).

The organic layer may further include an electron transport region disposed between the EML and the second electrode. The electron transport region may include at least one of a hole blocking layer (HBL), an electron transport layer (ETL), and an electron injection layer (EIL).

The electron transport region may include the pyrene-based compound represented by Formula 1. For example, the electron transport region may include the ETL, and the ELT may include the pyrene-based compound represented by Formula 1.

As used herein, the expression "organic layer" refers to a single layer and/or multiple layers disposed between a first electrode and a second electrode of an OLED. The "organic layer" may include other materials besides an organic material.

FIG. 1 illustrates a schematic cross-sectional view of an OLED 10 according to an embodiment. The OLED 10 may include a first electrode 110, an organic layer 150, and a second electrode 190.

Hereinafter, a structure and a manufacturing method of an OLED according to an embodiment will be described in more detail with reference to FIG. 1.

A substrate may be additionally disposed on a lower part of the first electrode 110 or on an upper part of the second electrode 190 of FIG. 1. The substrate may be a glass substrate or a transparent plastic substrate having excellent mechanical strength, thermal stability, transparency, surface smoothness, ease of handling, and waterproofness.

The first electrode 110 may be formed by applying a first electrode material on the substrate by deposition or sputtering. When the first electrode 110 is an anode, the first electrode material may be selected from materials having a high work function to facilitate hole injection. The first electrode 110 may be a reflective electrode or a transparent electrode. Examples of the first electrode material may include indium-tin oxide (ITO), Indium-zinc-oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), or magnesium-silver (Mg—Ag) is used as the first electrode material, the first electrode 110 may be formed as a reflective electrode.

The first electrode 110 may be formed as a single layer or have a multi-layered structure having at least two layers. For example, the first electrode 110 may have a three-layered structure, e.g., ITO/Ag/ITO.

The organic layer 150 may be formed on the first electrode 110. The organic layer 150 may include an EML.

The organic layer 150 may further include a hole transport region disposed between the first electrode and the EML. The organic layer 150 may further include an electron transport region disposed between the EML and the second electrode.

The hole transport region may include at least one of a HIL, a HTL, a buffer layer, and an EBL, and the electron transport region may include at least one of a HBL, an ETL, and an EIL.

The hole transport region may have a structure of a single layer formed of one material, a single layer formed of multiple different materials, or multiple layers formed of multiple different materials.

For example, the hole transport region may have a structure of a single layer formed of multiple different materials or a structure of HIL/HTL, HIL/HTL/buffer layer, HIL/buffer layer, HTL/buffer layer, or HIL/HTL/EBL sequentially stacked on the first electrode 110.

When the hole transport region includes the HIL, the HIL may be formed on the first electrode 110 by using various methods such as vacuum deposition, spin coating, casting, Langmuir-Blodgett (LB) deposition, inkjet printing, laser printing, or laser induced thermal imaging (LITI).

When the HIL is formed by vacuum deposition, the deposition conditions may be selected from ranges of, for example, a deposition temperature of about 100 to about 500° C., a degree of vacuum of about $10^{-8}$ to about $10^{-3}$ torr, and a deposition speed of about 0.01 to about 100 Å/sec in consideration of a desired compound for an HIL and a desired structure of the HIL.

When the HIL is formed by spin coating, the deposition conditions may be selected from ranges of, for example, a coating speed of about 2,000 rpm to about 5,000 rpm and a heat treatment temperature of about 80° C. to about 200° C. in consideration of a desired compound for an HIL and a desired structure of the HIL.

When the hole transport region includes the HTL, the HTL may be formed on the first electrode 110 or the HIL by using various methods such as vacuum deposition, spin coating, casting, LB deposition, inkjet printing, laser printing, or LITI. When the HTL is formed by vacuum deposition and spin coating, the deposition conditions and the coating conditions of the HTL may be referred to the de deposition conditions and the coating conditions of the HIL.

The hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine) (TCTA), polyaniline/Dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline)/poly(4-styrenesulfonate (PANI/PSS), a compound represented by Formula 201, a compound represented by Formula 202:

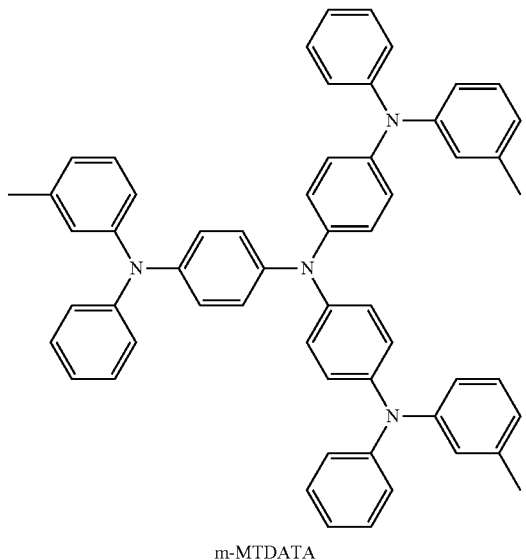

m-MTDATA

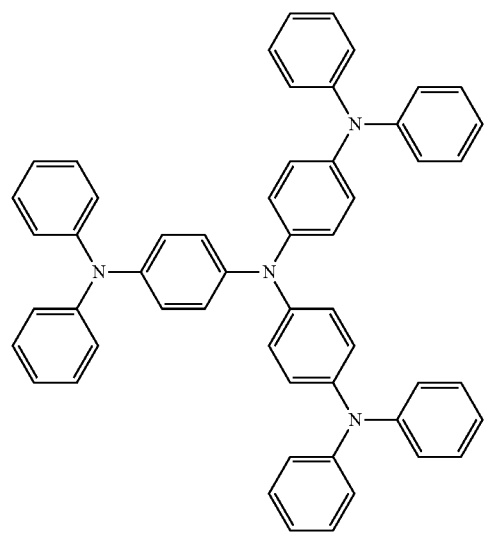

TDATA

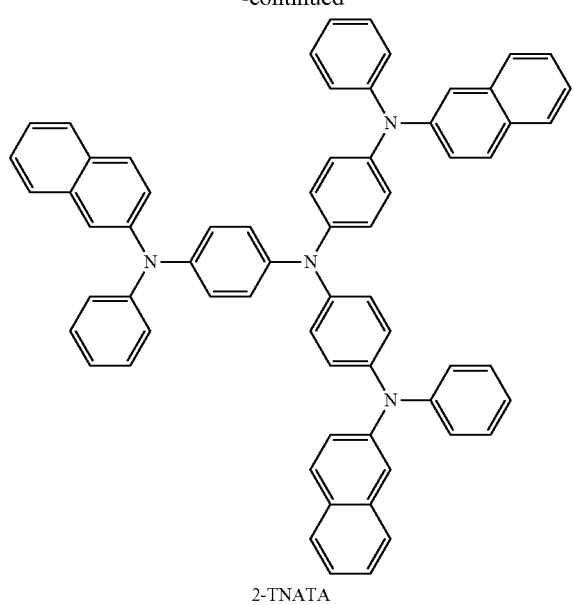
2-TNATA
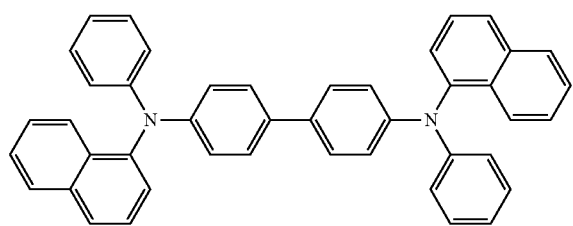
NPD
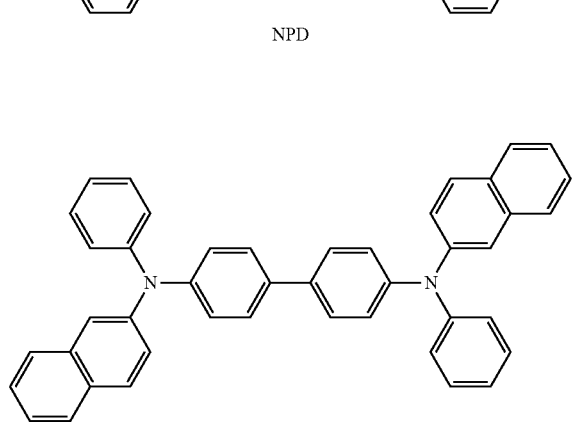
β-NPB
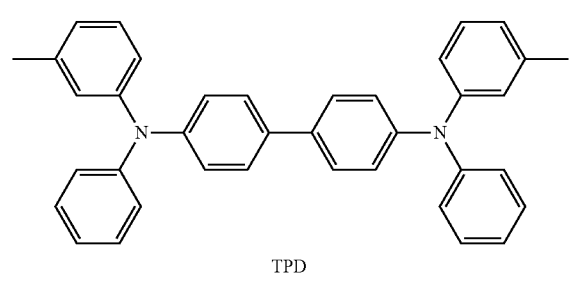
TPD
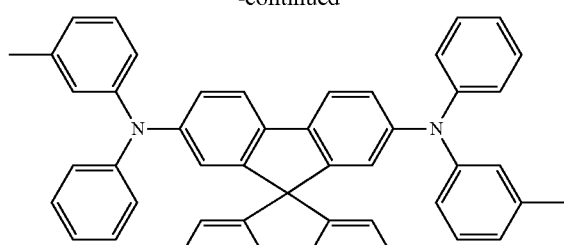
Spiro-TPD
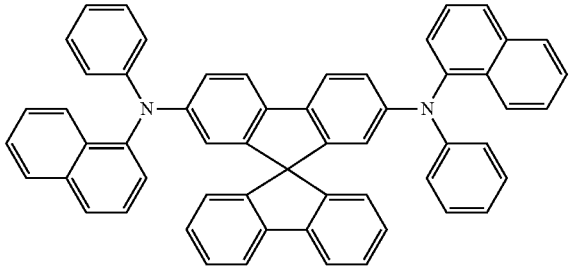
Spiro-NPD
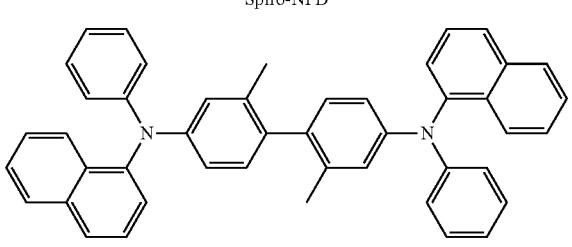
α-NPD
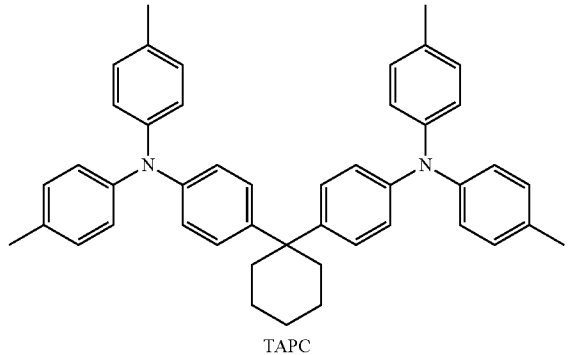
TAPC
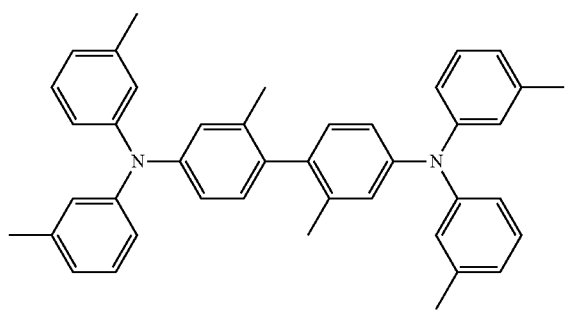
HMTPD
<Formula 201>
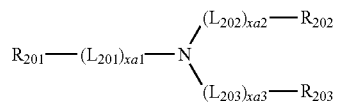

<Formula 202>

$$R_{201}-(L_{201})_{xa1} \quad (L_{203})_{xa3}-R_{203}$$
$$\phantom{R_{201}-(L_{201})_{xa1}}N-(L_{205})_{xa5}-N$$
$$R_{202}-(L_{202})_{xa2} \quad (L_{204})_{xa4}-R_{204}$$

In Formulae 201 and 202, $L_{201}$ to $L_{205}$ are each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, and a substituted or unsubstituted divalent non-aromatic condensed polycyclic group;

at least one substituent of the substituted $C_3$-$C_{10}$ cycloalkylene group, substituted $C_3$-$C_{10}$ heterocycloalkylene group, substituted $C_3$-$C_{10}$ cycloalkenylene group, substituted $C_3$-$C_{10}$ heterocycloalkenylene group, substituted $C_6$-$C_{60}$ arylene group, substituted $C_2$-$C_{60}$ heteroarylene group, and substituted divalent non-aromatic condensed polycyclic group is selected from:

a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a non-aromatic condensed polycyclic group, —N($Q_{201}$)($Q_{202}$), —Si($Q_{203}$)($Q_{204}$)($Q_{205}$), and —B($Q_{206}$)($Q_{207}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a non-aromatic condensed polycyclic group, —N($Q_{211}$)($Q_{212}$), —Si($Q_{213}$)($Q_{214}$)($Q_{215}$), and —B($Q_{216}$)($Q_{217}$); and —N($Q_{221}$)($Q_{222}$), —Si($Q_{223}$)($Q_{224}$)($Q_{225}$), and —B($Q_{226}$)($Q_{227}$);

xa1 to xa4 each denotes an integer of 0, 1, 2, or 3;

xa5 denotes an integer of 1, 2, 3, 4, or 5;

$R_{201}$ to $R_{205}$ are each independently selected from:

a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, non-aromatic condensed polycyclic group, —N($Q_{231}$)$Q_{232}$), —Si($Q_{233}$)($Q_{234}$)($Q_{235}$), and —B($Q_{236}$)($Q_{237}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, non-aromatic condensed polycyclic group, —N($Q_{241}$)($Q_{242}$), —Si($Q_{243}$)($Q_{244}$)($Q_{245}$), and —B($Q_{246}$)($Q_{247}$);

$Q_{201}$ to $Q_{207}$, $Q_{211}$ to $Q_{217}$, $Q_{221}$ to $Q_{227}$, $Q_{231}$ to $Q_{237}$, and $Q_{241}$ to $Q_{247}$ are each independently selected from:

a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group.

For examples of $L_{201}$ to $L_{205}$ in Formulae 201 and 202 the description of $L_{11}$ in the specification may be referred to, and for examples of $R_{201}$ to $R_{205}$ the description of $R_{11}$ in the specification may be referred to.

For example, in Formulae 201 and 202, $L_{201}$ to $L_{205}$ may be each independently selected from:

a phenylene group, a naphthylene group, a fluorenylene group, a spiro-fluorenylene group, a benzofluorenene group, a dibenzofluorenene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 each denotes an integer of 0, 1, or 2;

xa5 denotes an integer of 1, 2, or 3;

$R_{201}$ to $R_{205}$ are each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

The compound represented by Formula 201 may be represented by Formula 201A:

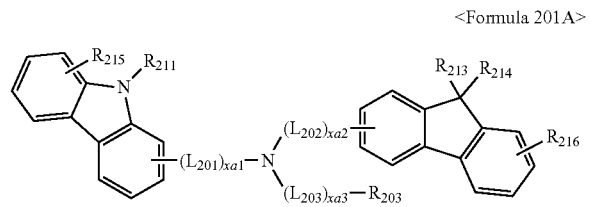

<Formula 201A>

The compound represented by Formula 201 may be represented by Formula 201A-1:

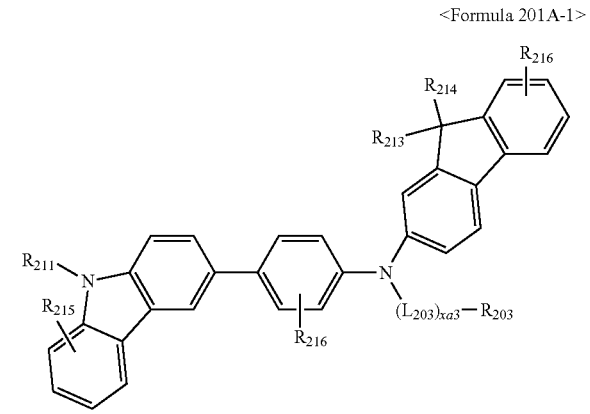

<Formula 201A-1>

The compound represented by Formula 202 may be represented by Formula 202A:

<Formula 202A>

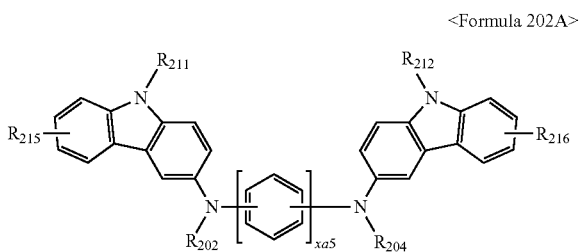

In Formulae 201A, 201A-1, and 202A, descriptions of $L_{201}$ to $L_{203}$, xa1 to xa3, xa5, and $R_{202}$ to $R_{204}$ may be referred to the descriptions stated in the specification, descriptions of $R_{211}$ may be referred to the description of $R_{203}$ stated in the specification, and $R_{213}$ to $R_{216}$ may be selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group.

For example, in 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 each independently denotes an integer of 0 or 1;

$R_{203}$, $R_{211}$, and $R_{212}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ are each independently selected from:

a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 denotes an integer of 1 or 2.

In Formulae 201A and 201A-1, $R_{213}$ and $R_{214}$ may link to each other and form a saturated or unsaturated ring.

The compound represented by Formula 201 and the compound represented by Formula 202 may include Compounds HT1 to HT16 below, as examples:

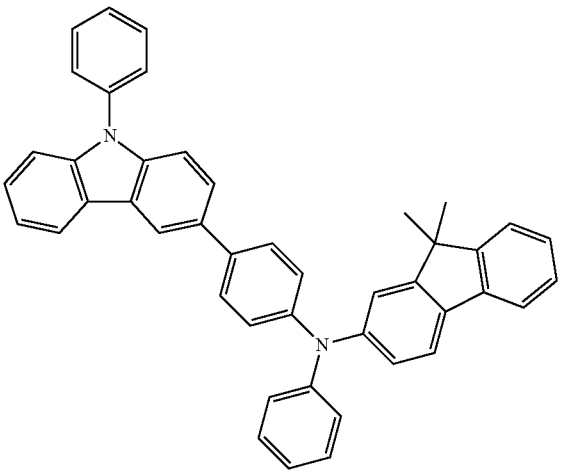

HT1

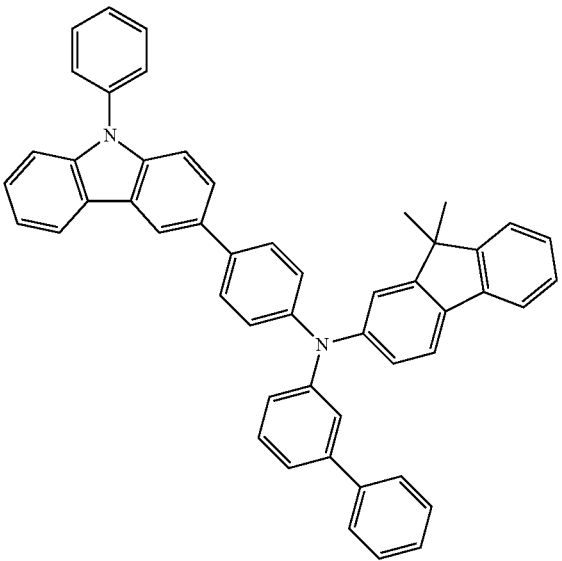

HT2

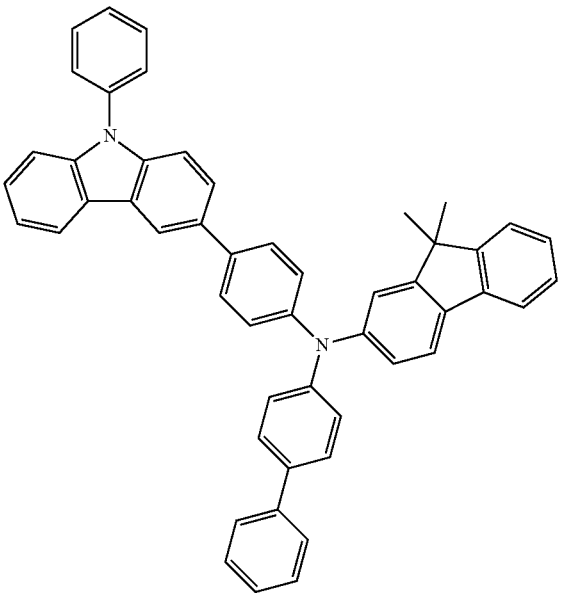

HT3

HT4
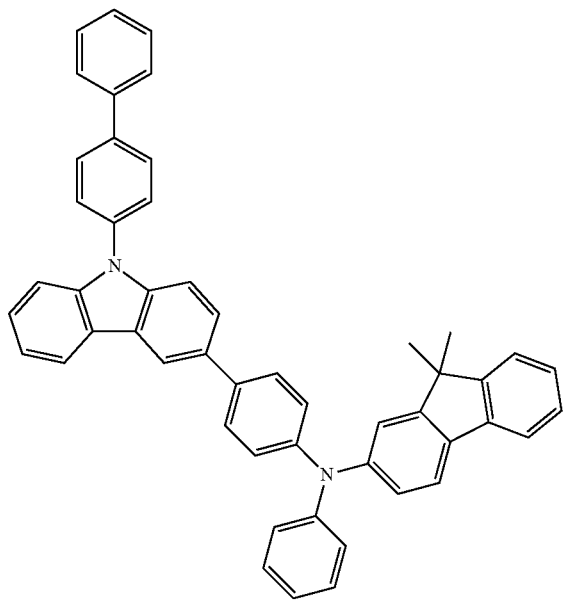
HT5
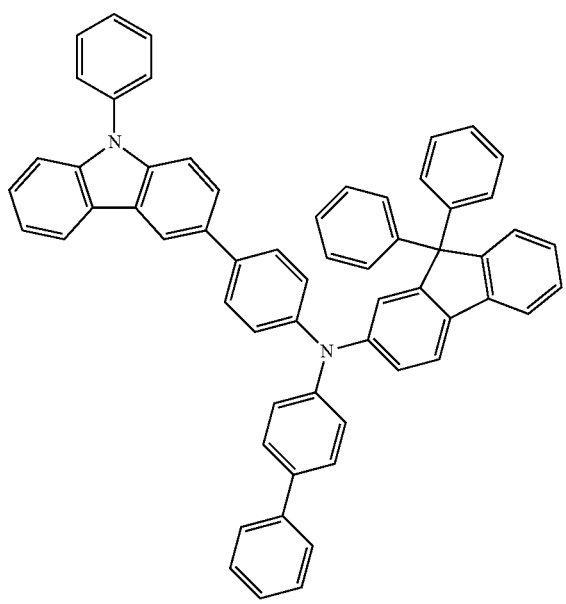
HT6
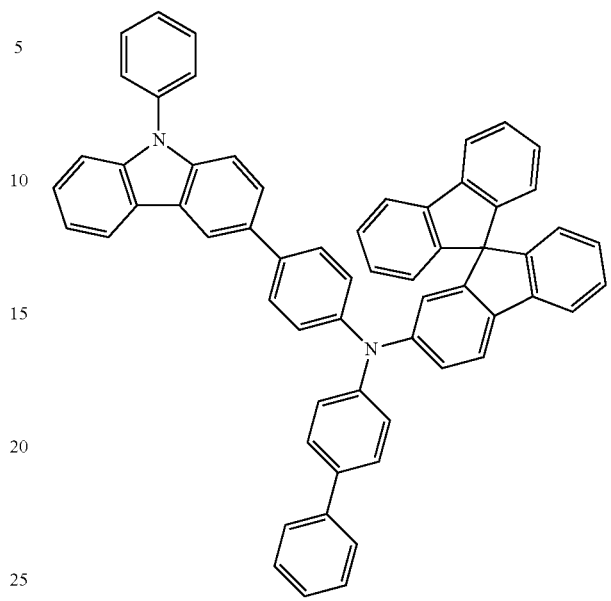
HT7
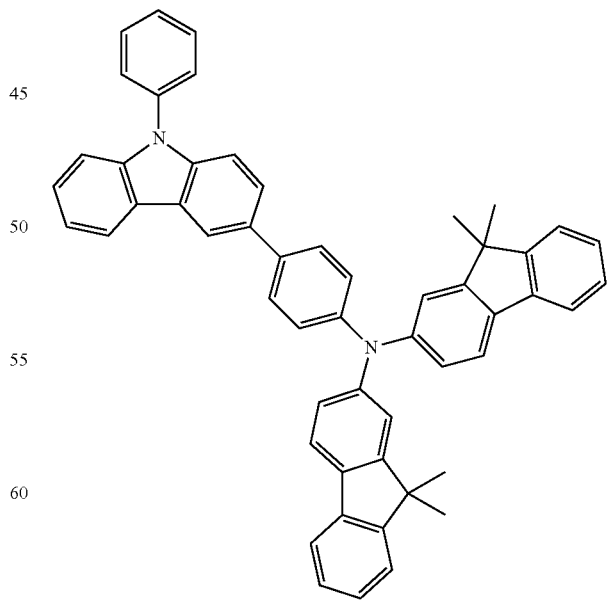

HT8
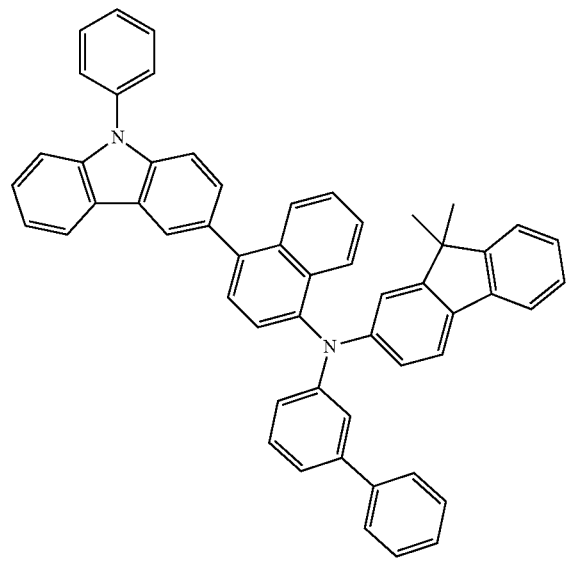
HT10
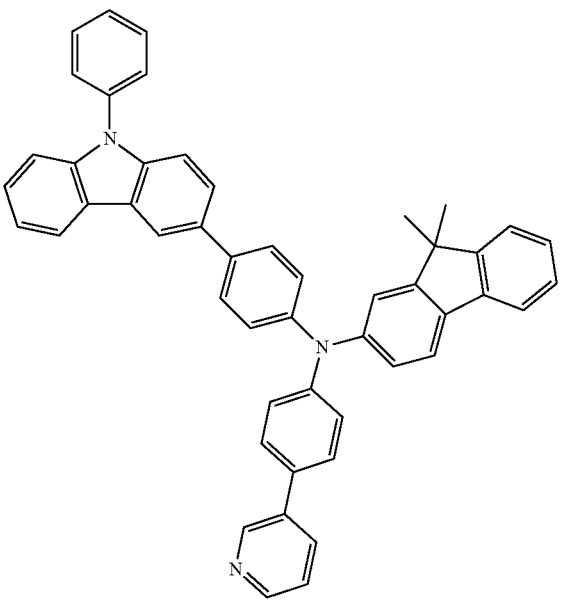
HT9
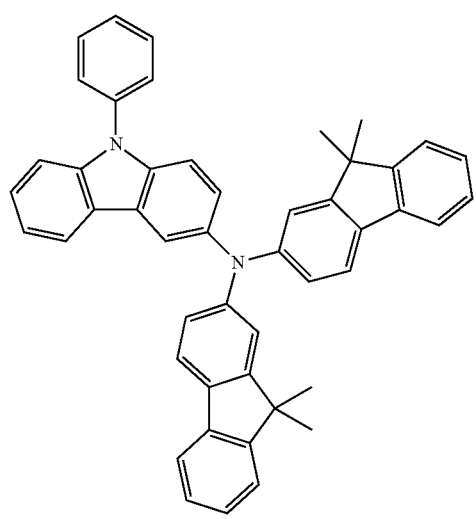
HT11
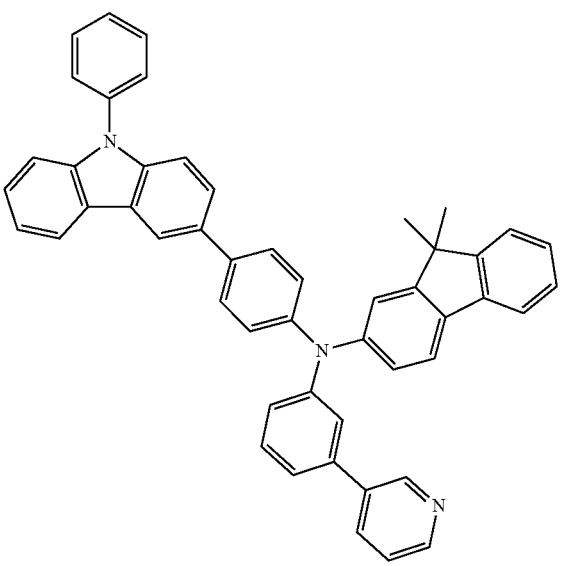

HT12
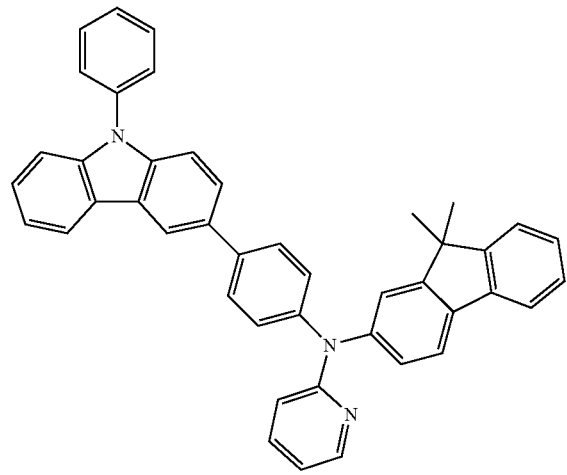
HT16
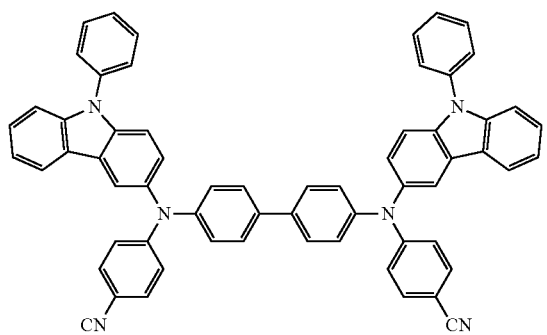
HT13
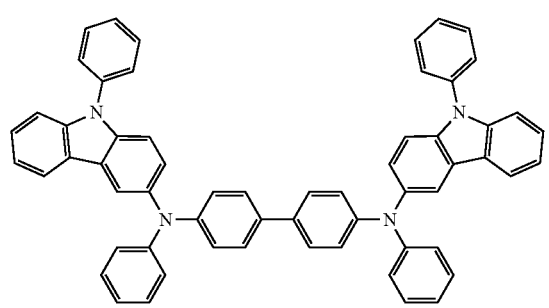
HT17
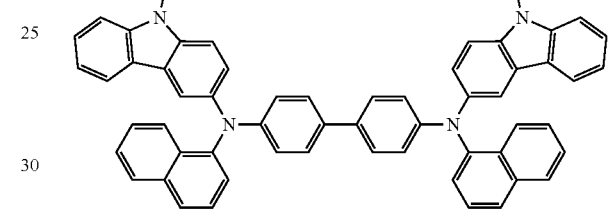
HT14
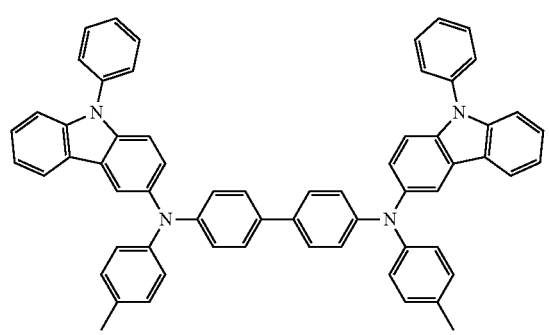
HT18
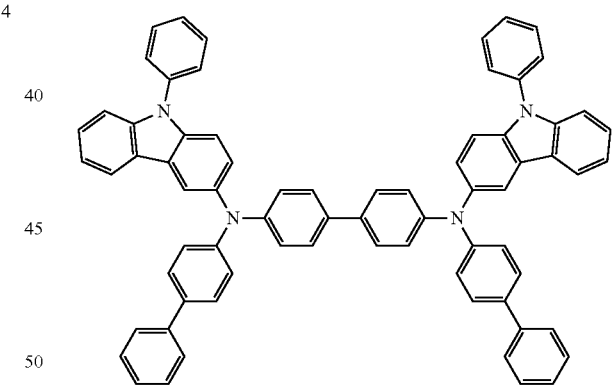
HT15
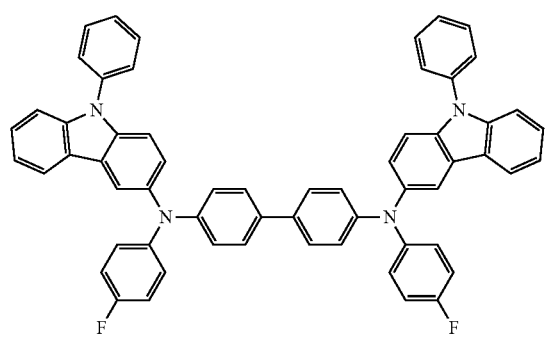
HT19
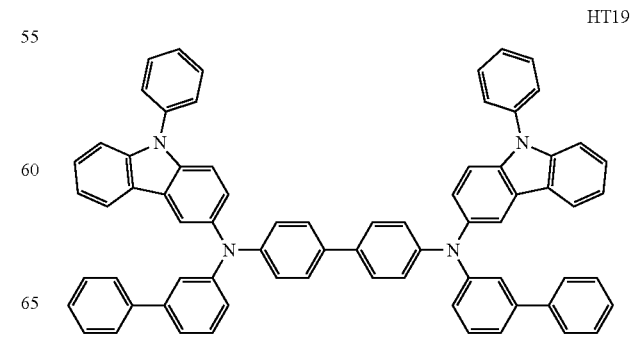

HT20

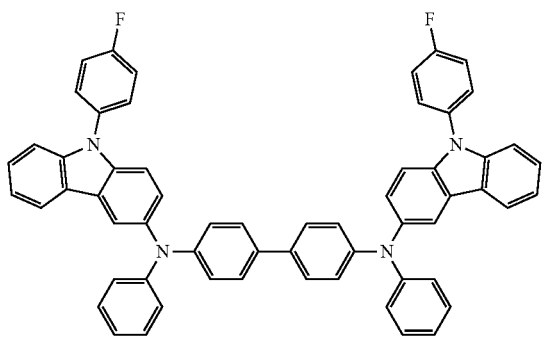

A thickness of the hole transport region may be in a range of about 100 Å to about 10,000 Å, for example, about 100 Å to about 1,000 Å. When the hole transport region includes both the HIL and the HTL, a thickness of the HIL may be in a range of about 100 Å to about 10,000 Å, for example, about 100 Å to about 1,000 Å, and a thickness of the HTL may be in a range of about 50 Å to about 2,000 Å, for example, about 100 Å to about 1,500 Å. When thicknesses of the hole transport region, the HIL, and the HTL are within these ranges, satisfactory hole transporting properties may be obtained without substantial increase in driving voltage.

The hole transport region may further include a charge-generating material in addition to the materials above to improve conductivity. The charge-generating material may be homogenously or non-homogenously dispersed in the hole transport region.

The charge-generating material may be, for example, a p-dopant. The p-dopant may be one of a quinone derivative, a metal oxide, and a cyano group-containing compounds, as examples. Examples of the p-dopant may include quinone derivative, such as a tetracyanoquinonedimethane (TCNQ) and 2,3,5,6-tetrafluoro-tetracyano-1,4-benzoquinondimethane (F4-TCNQ); metal oxides, such as a tungsten oxide and a molybdenum oxide; and Compound HT-D1 below, as examples:

<Compound HT-D1>

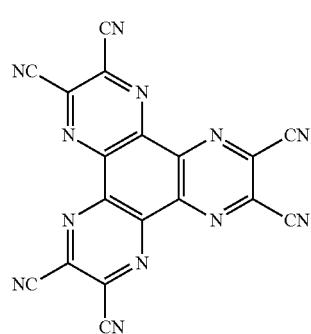

<F4-TCNQ>

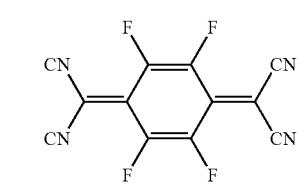

The hole transport region may further include at least one of a buffer layer or an EBL in addition to the HIL and the HTL. The buffer layer may increase light-emitting efficiency by compensating an optical resonance distance according the wavelength of light emitted from the EML. The buffer layer may include a material that may be included in the hole transport region. The EBL may block injection of electrons from the electron transport region.

The EML may be formed on the first electrode 110 or the hole transport region by using various methods such as vacuum deposition, spin coating, casting, LB deposition, inkjet printing, laser printing, or LITI. When the EML is formed by vacuum deposition and spin coating, the deposition conditions and the coating conditions for forming the HIL, as described above, may be referred to in determining suitable deposition conditions and coating conditions of the EML.

When the OLED 10 is a full-color OLED, the EML may be patterned as a red EML, a green EML, and a blue EML depending on a red pixel, a green pixel, and a blue pixel. In other implementations, the EML may have a multiple-layered structure, in which a red EML, a green EML, and a blue EML are stacked or a single-layered structure including all of a red light-emitting material, a green light-emitting material, and a blue light-emitting material mixed therein so as to emit white light. In other implementations, the EML may be a white light EML, and the OLED 10 may further include a color converting layer that converts the white light into light of desired color or a color filter.

The EML may include a host or a dopant.

The host may include at least one of TPBi, TBADN, ADN, a CBP, a CDBP, and TCP below:

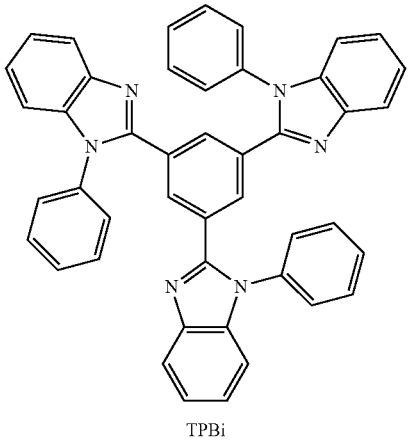

TPBi

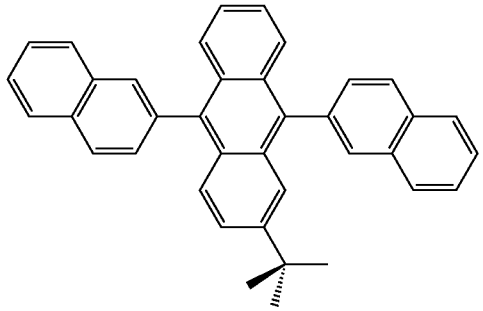

TBADN

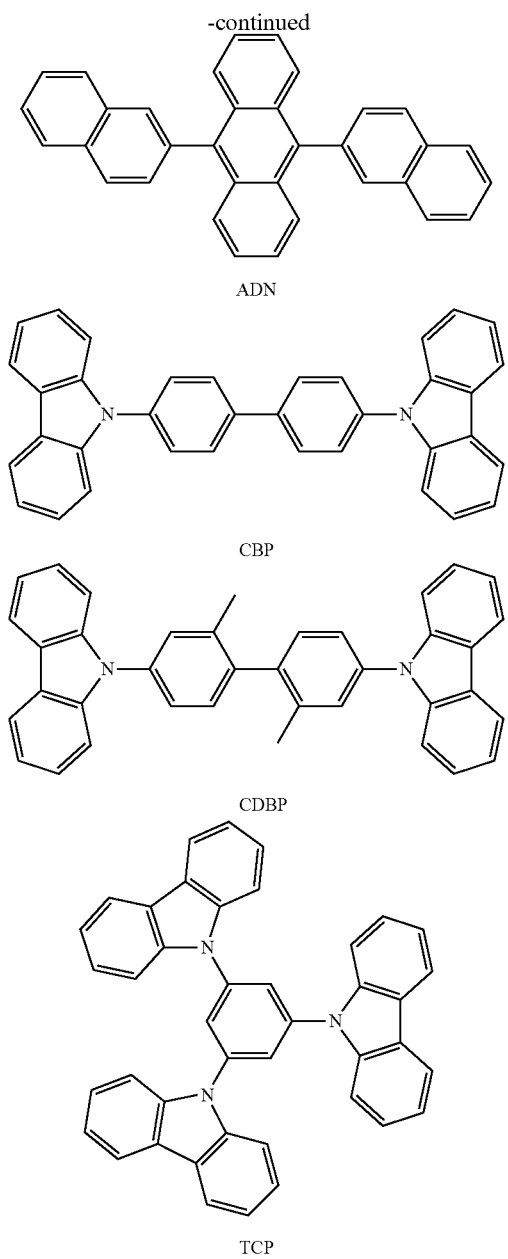

ADN

CBP

CDBP

TCP

The host may include a compound represented by Formula 301.

Ar$_{301}$-[(L$_{301}$)$_{xb1}$-R$_{301}$]$_{xb2}$  <Formula 301>

In Formula 301,

Ar$_{301}$ may be selected from:

a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group;

a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, pyrene, a chrysene group, a naphthacene group, a picene group, a perylene group, a pentaphene group, and an indenoanthracene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, non-aromatic condensed polycyclic group, and —Si(Q$_{301}$)(Q$_{302}$)(Q$_{303}$) (here, Q$_{301}$ to Q$_{303}$ are each independently selected from a hydrogen atom, a $C_1$-$C_{60}$ alkyl group, a $C_2$-$C_{60}$ alkenyl group, a $C_6$-$C_{60}$ aryl group, and a $C_2$-$C_{60}$ heteroaryl group);

the description of L$_{301}$ may be the same with the description of L$_{201}$ in the specification;

R$_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 is an integer of 0, 1, 2 or 3; and xb2 is an integer of 1, 2, 3 or 4.

For example, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

The compound represented by Formula 301 may include at least one of Compounds H1 to H42 below, but is not limited thereto:

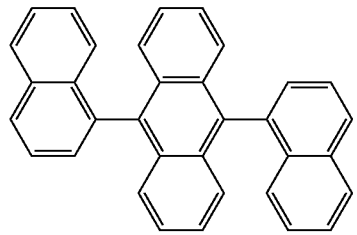
H1

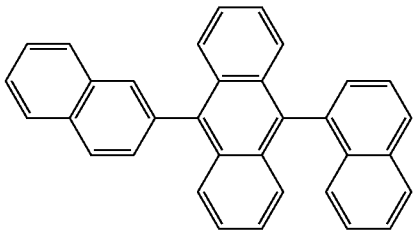
H2

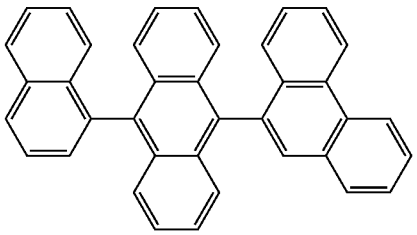
H3

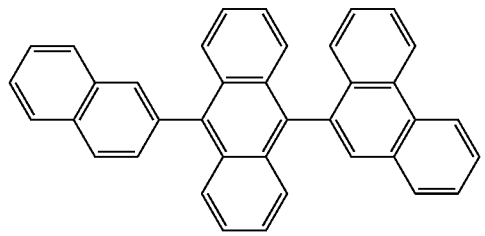
H4

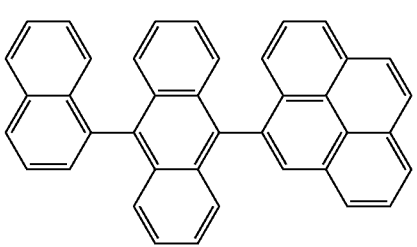
H5

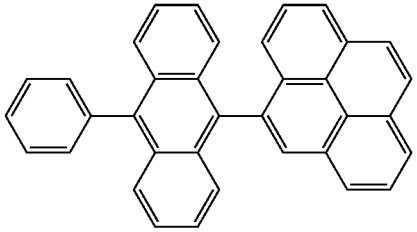
H6

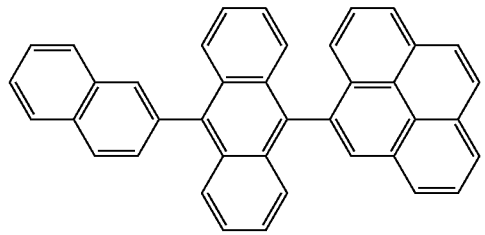
H7

H8
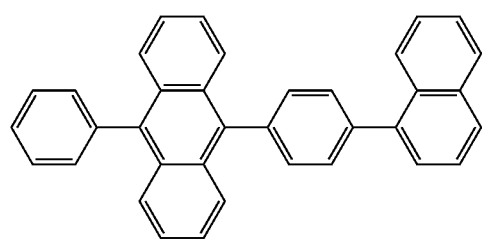
H9
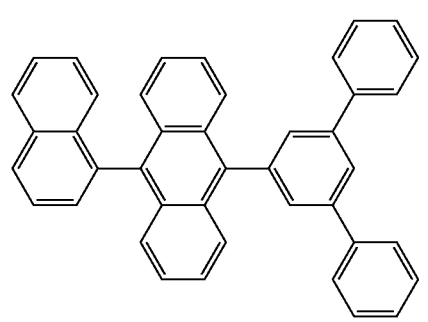
H10
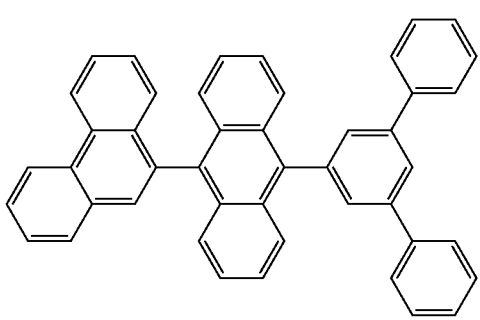
H11
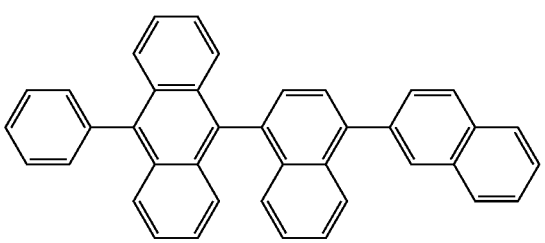
H12
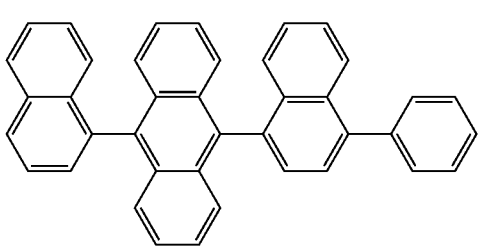
H13
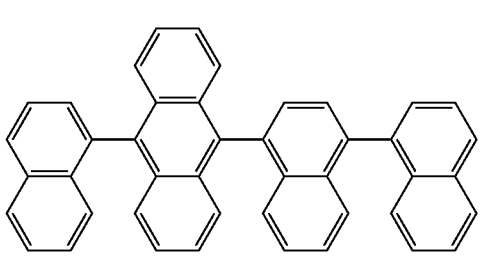
H14
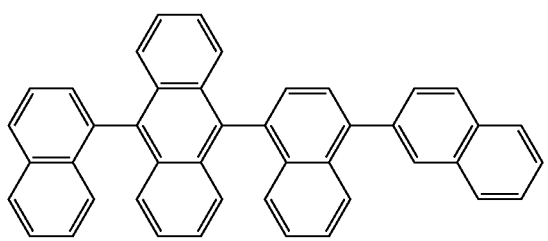
H15
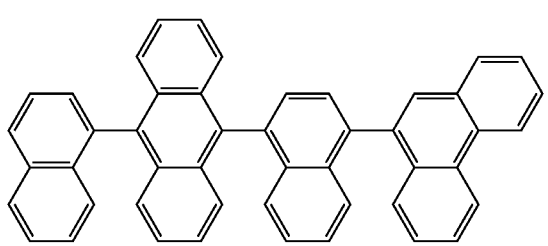
H16
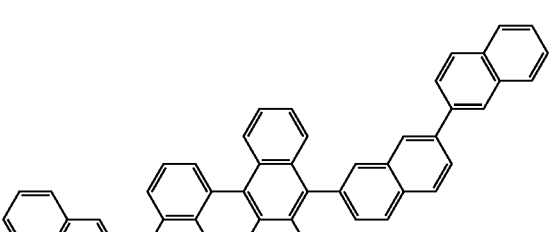
H17
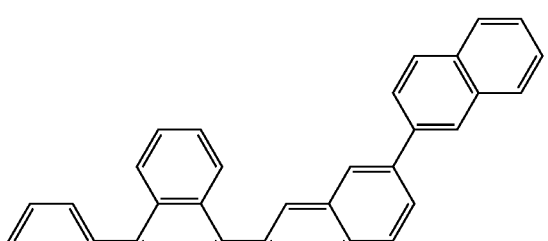
H18
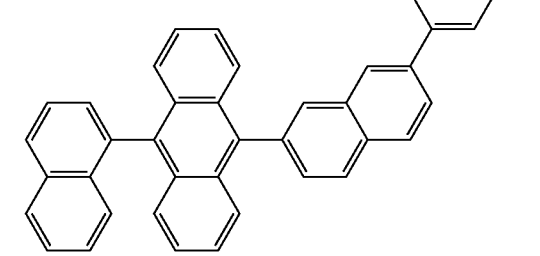

H19
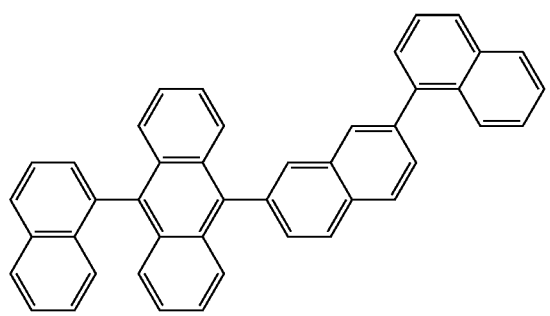
H20
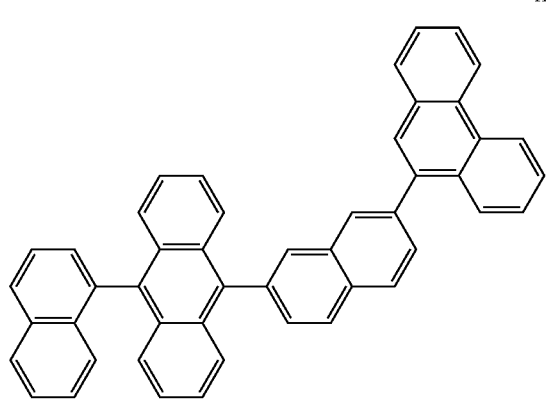
H21
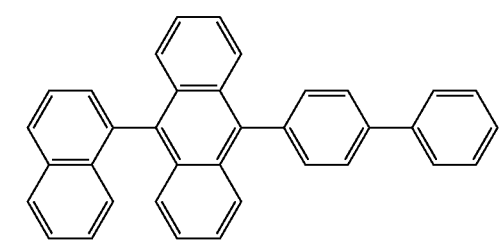
H22
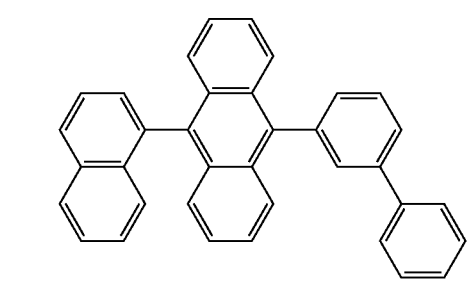
H23
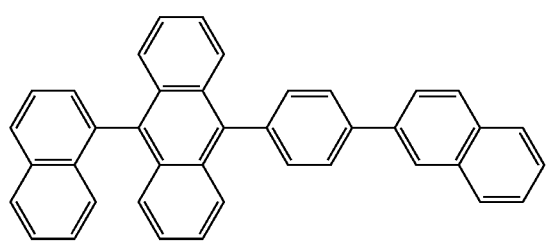
H24
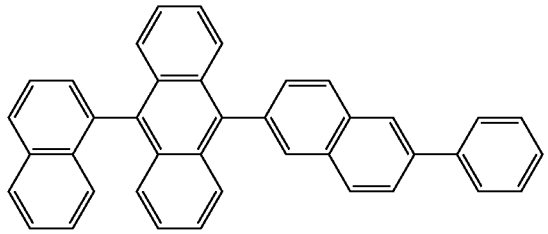
H25
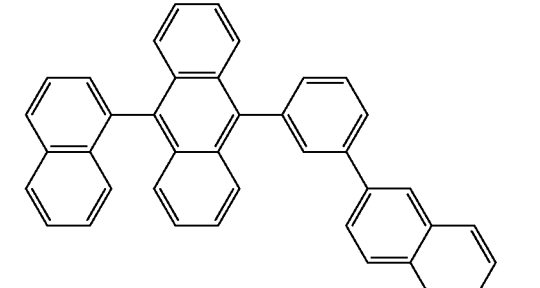
H26
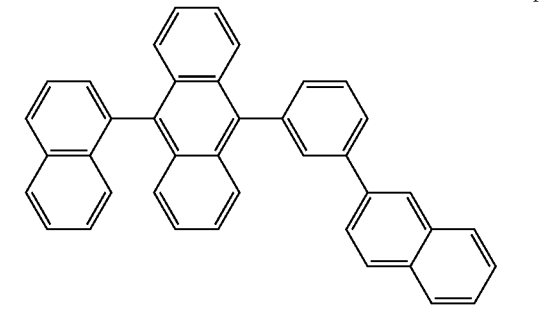
H27
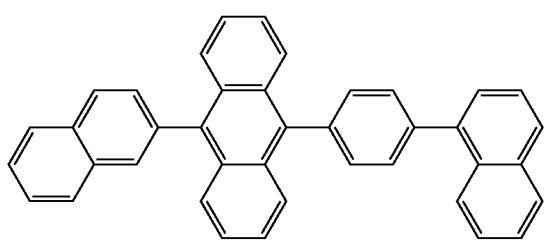
H28
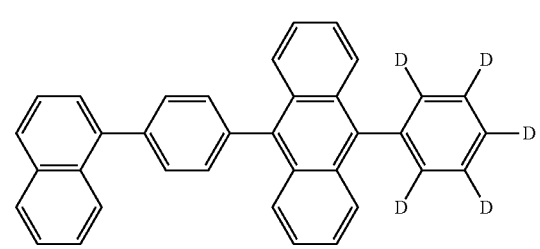
H29
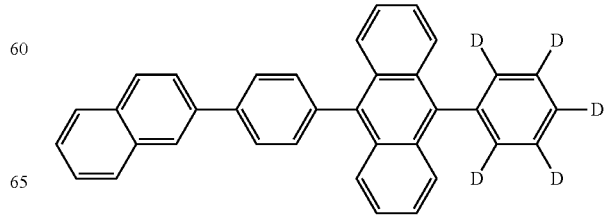

111
-continued
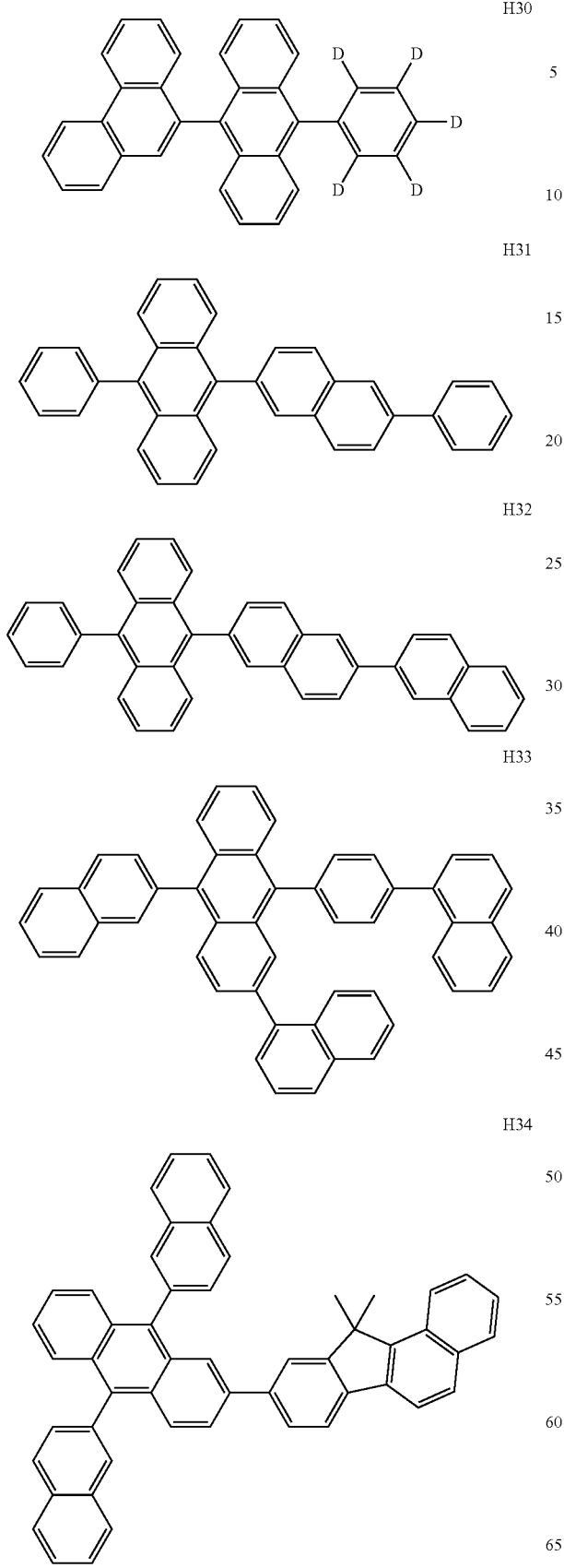
112
-continued
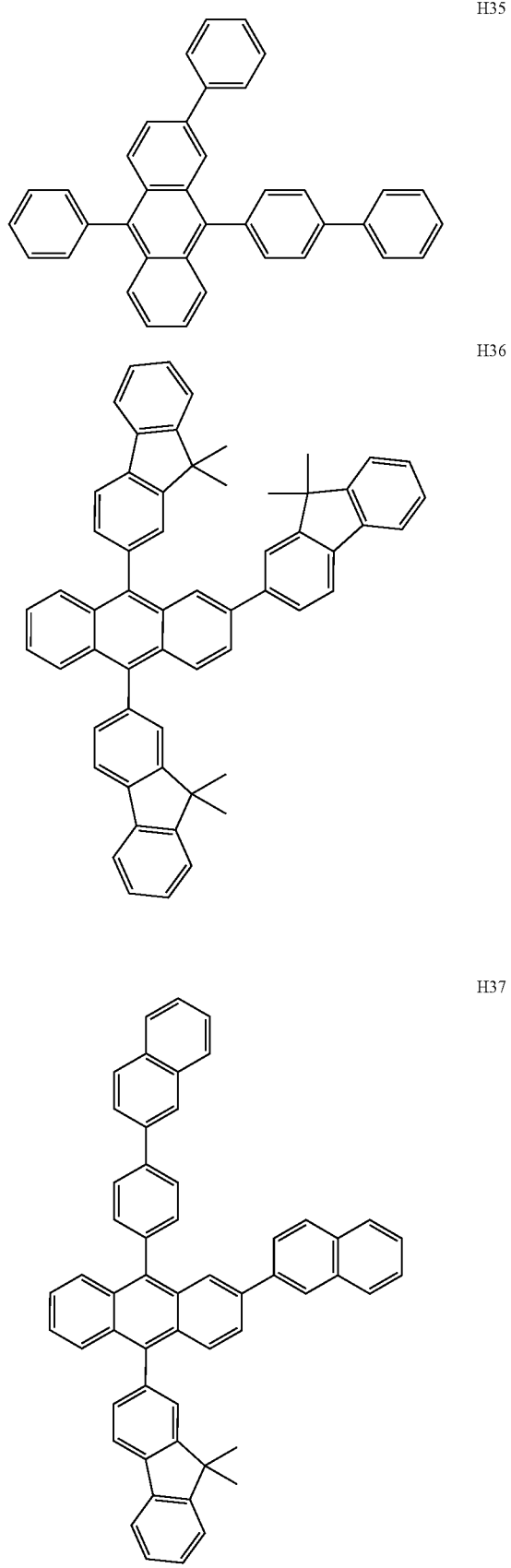

H38
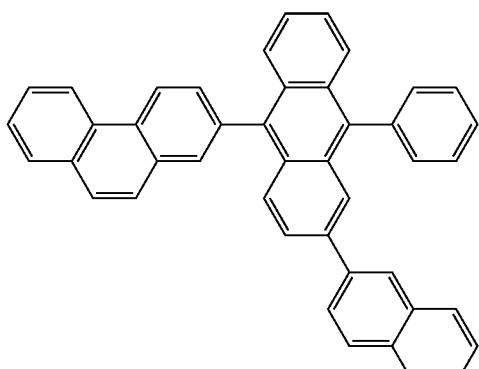
H39
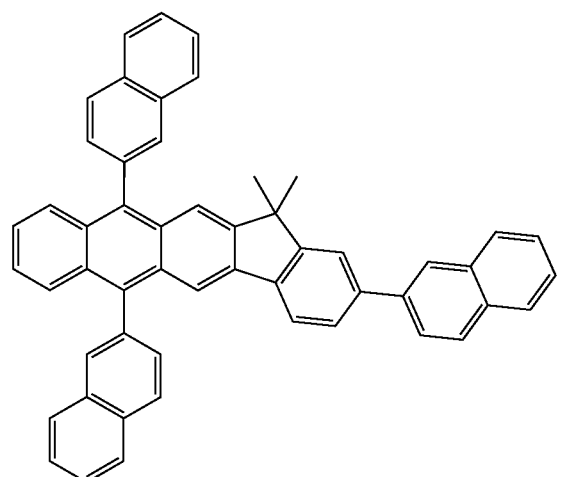
H40
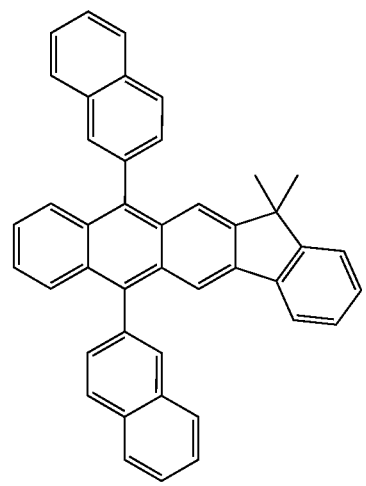
H41
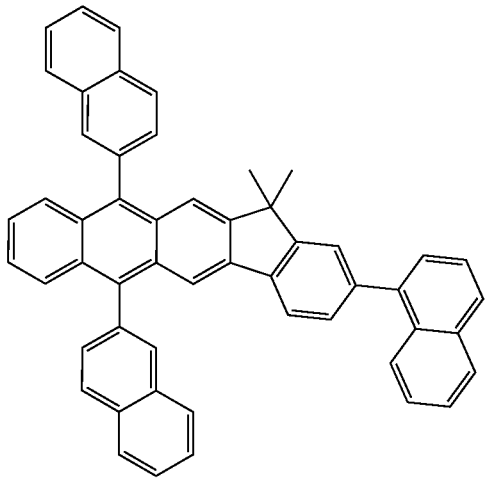
H42
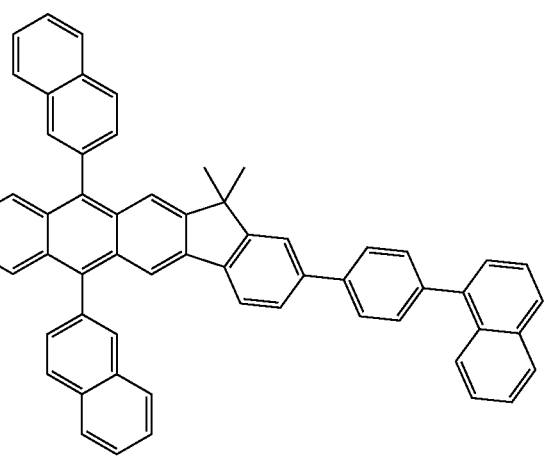
Also, the host may include at least one of Compounds H43 to H49 below, as examples:
H43
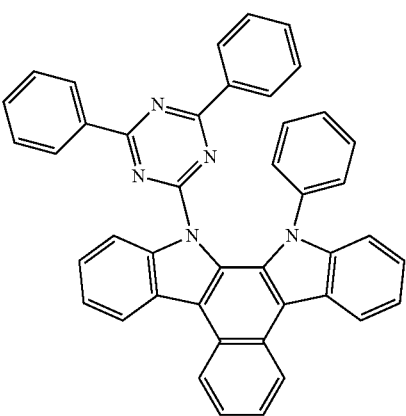

H44
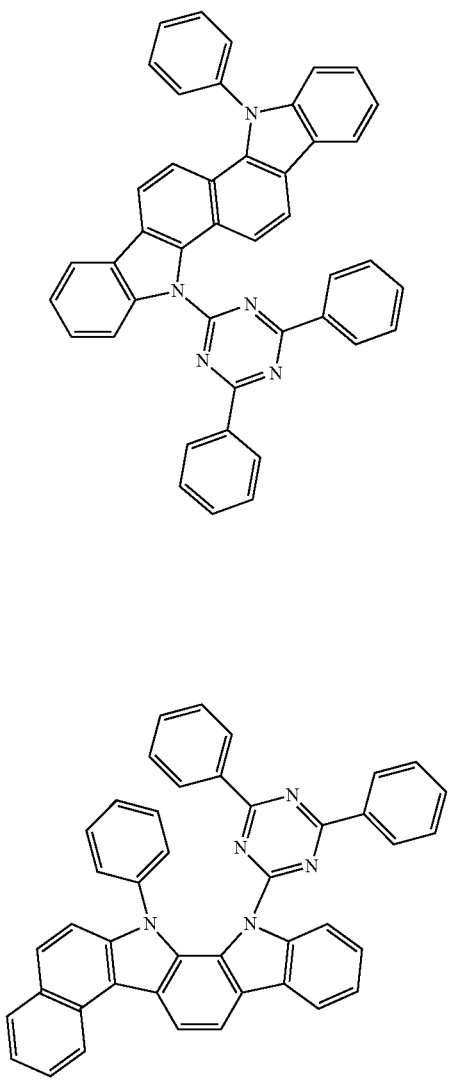
H45
H46
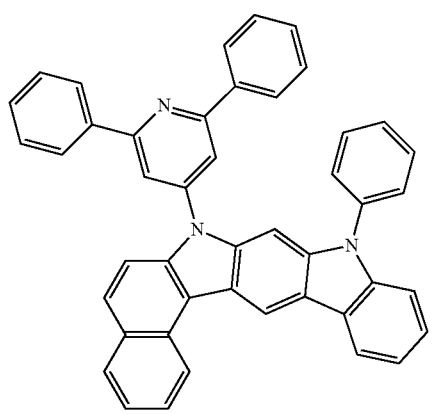
H47
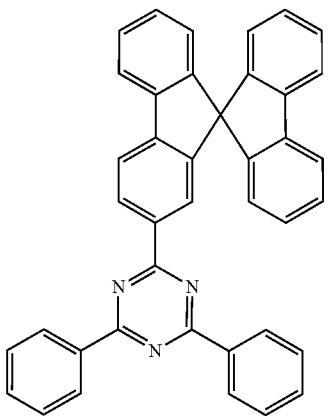
H48
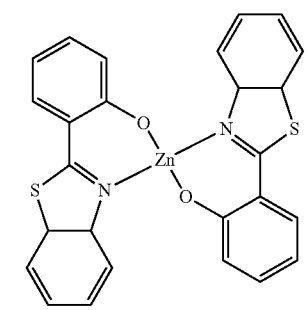
H49
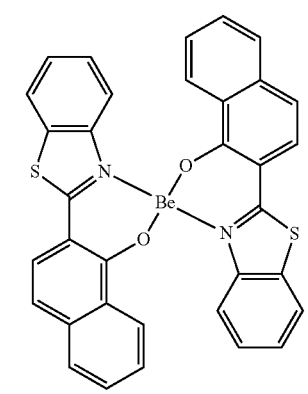
The dopant may include at least one of a fluorescent dopant and a phosphorescent dopant.
The phosphorescent dopant may include an organic metal complex represented by Formula 401:
<Formula 401>
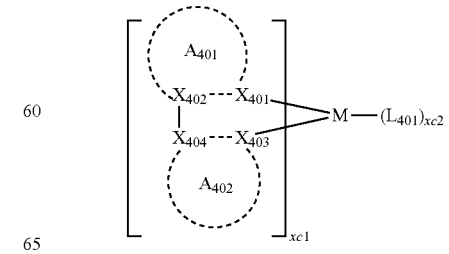

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen or carbon;

rings $A_{401}$ and $A_{402}$ are each independently selected from a substituted or unsubstituted benzene group, a substituted or unsubstituted naphthalene group, a substituted or unsubstituted fluorenene group, a substituted or unsubstituted spiro-fluorenene group, a substituted or unsubstituted indene group, a substituted or unsubstituted pyrrole group, a substituted or unsubstituted thiophene group, a substituted or unsubstituted furan group, a substituted or unsubstituted imidazole group, a substituted or unsubstituted pyrazole group, a substituted or unsubstituted thiazole group, a substituted or unsubstituted isothiazole group, a substituted or unsubstituted oxazole group, a substituted or unsubstituted isooxazole group, a substituted or unsubstituted pyridine group, a substituted or unsubstituted pyrazine group, a substituted or unsubstituted pyrimidine group, a substituted or unsubstituted pyridazine group, a substituted or unsubstituted quinoline group, a substituted or unsubstituted isoquinoline group, a substituted or unsubstituted benzoquinoline group, a substituted or unsubstituted quinoxaline group, a substituted or unsubstituted quinazoline group, a substituted or unsubstituted carbazole group, a substituted or unsubstituted benzoimidazole group, a substituted or unsubstituted benzofuran group, a substituted or unsubstituted benzothiophene group, a substituted or unsubstituted isobenzothiophene group, a substituted or unsubstituted benzoxazole group, a substituted or unsubstituted isobenzoxazole group, a substituted or unsubstituted triazole group, a substituted or unsubstituted oxadiazole group, a substituted or unsubstituted triazine group, a substituted or unsubstituted dibenzofuran group, and a substituted or unsubstituted dibenzothiophene group;

at least one substituent of the substituted benzene group, substituted naphthalene group, substituted fluorenene group, substituted spiro-fluorenene group, substituted indene group, substituted pyrrole group, substituted thiophene group, substituted furan group, substituted imidazole group, substituted pyrazole group, substituted thiazole group, substituted isothiazole group, substituted oxazole group, substituted isooxazole group, substituted pyridine group, substituted pyrazine group, substituted pyrimidine group, substituted pyridazine group, substituted quinoline group, substituted isoquinoline group, substituted benzoquinoline group, substituted quinoxaline group, substituted quinazoline group, substituted a carbazole group, substituted benzoimidazole group, substituted benzofuran group, substituted benzothiophene group, substituted isobenzothiophene group, substituted benzoxazole group, substituted isobenzoxazole group, substituted triazole group, substituted oxadiazole group, substituted triazine group, substituted dibenzofuran group, and substituted dibenzothiophene group is selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_2$-$C_{60}$ heteroaryl group, non-aromatic condensed polycyclic group(non-aromatic condensed polycyclic group), —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, non-aromatic condensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be an integer of 1, 2, or 3; and xc2 may be an integer of 0, 1, 2, or 3;

$L_{401}$ is a monovalent, divalent, or trivalent organic ligand. For example, $L_{401}$ may be selected from a halogen ligand (e.g., Cl or F), a diketone ligand (e.g., acetylacetonate, 1,3-diphenyl-1,3-propanedionate, 2,2,6,6-tetramethyl-3,5-heptanedionate, or hexafluoroacetonate), a carboxylic acid ligand (e.g., picolinate, dimethyl-3-pyrazolecarboxylate, or benzoate), a carbon monoxide ligand, an isonitrile ligand, a cyano ligand, and a phosphorus ligand (e.g., phosphine or phosphaite), but is not limited thereto.

In Formula 401, when $A_{401}$ has at least two substituents, the at least two substituents of $A_{401}$ may link to each other and form a saturated or unsaturated ring.

In Formula 401, when $A_{402}$ has at least two substituents, the at least two substituents of $A_{402}$ may link to each other and form a saturated or unsaturated ring.

In Formula 401, when xc1 is 2 or greater, a plurality of ligands,

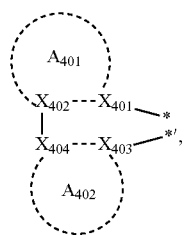

are identical to or different from each other. In Formula 401, when xc1 is 2 or greater, $A_{401}$ and $A_{402}$ may be linked to each other by directly linking to another neighboring ligand of $A_{401}$ and $A_{402}$ or with a connection group (e.g., a $C_1$-$C_5$ alkylene group or —N(R')— (here, R' is $C_1$-$C_{10}$ alkyl group or a $C_6$-$C_{20}$ aryl group) therebetween.

The phosphorescent dopant may include at least one of Compounds PD1 to PD74 below, as examples:

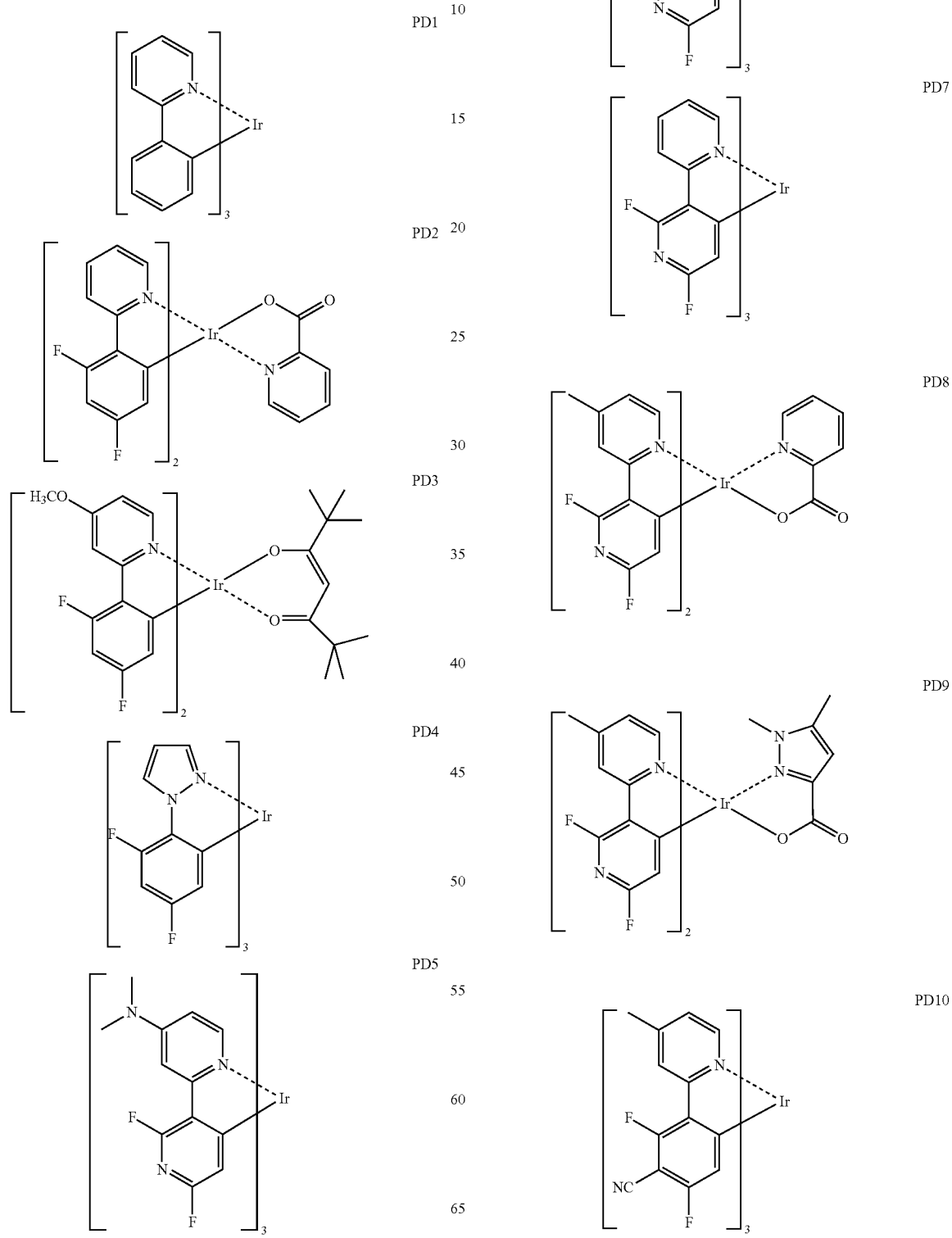

PD11 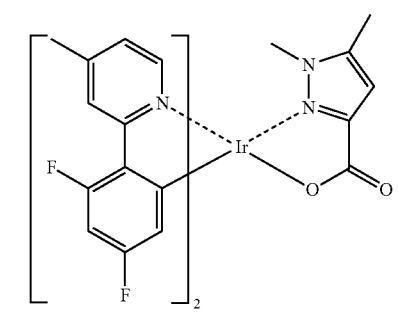
PD12 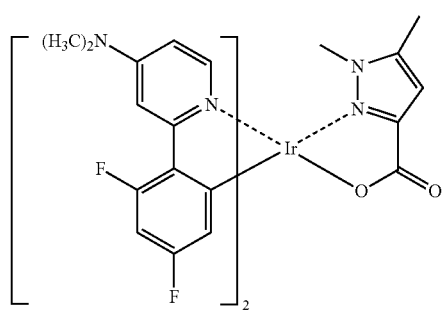
PD13 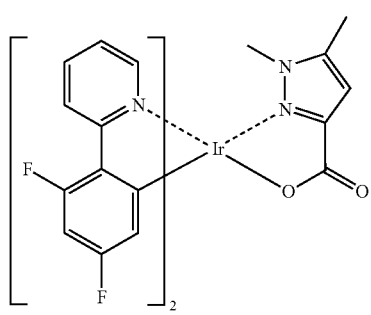
PD14 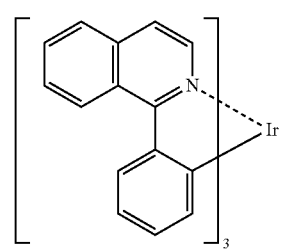
PD15 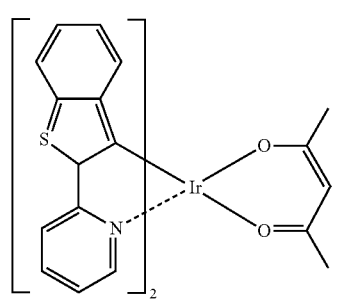
PD16 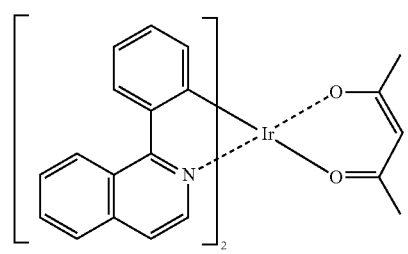
PD17 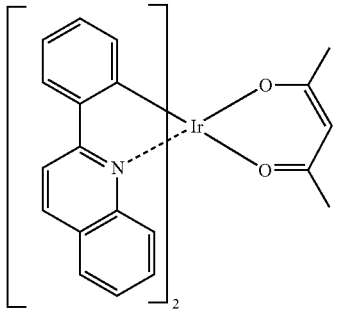
PD18 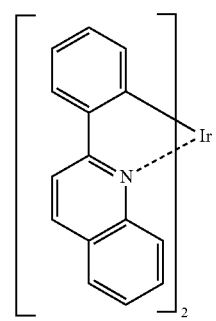
PD19 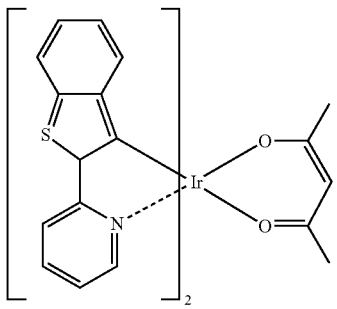
PD20 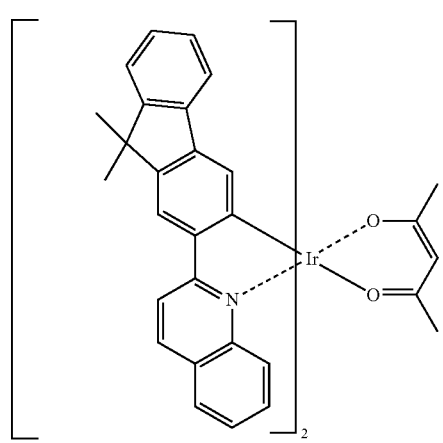

PD21 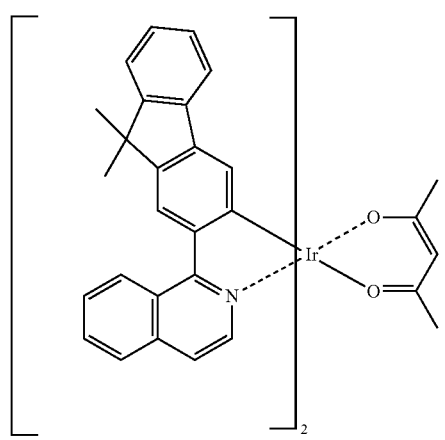
PD22 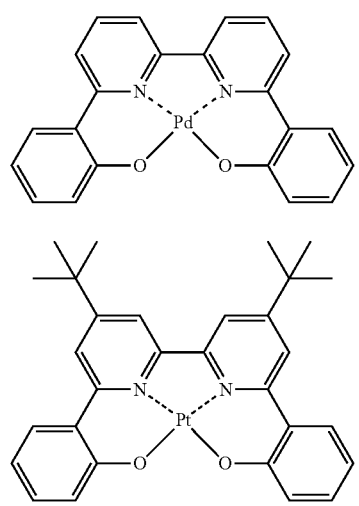
PD23 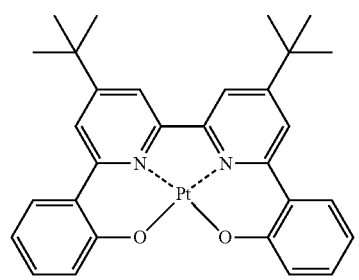
PD24 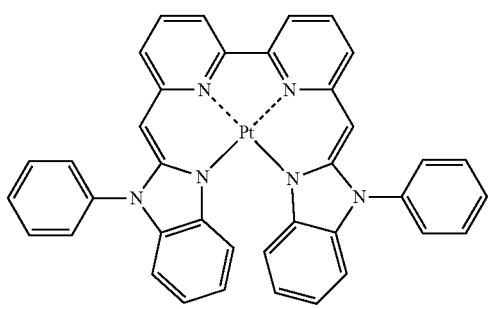
PD25 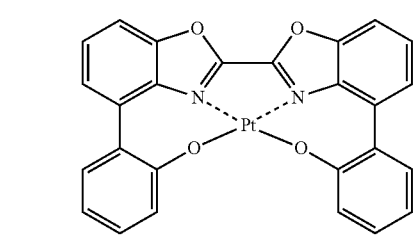
PD26 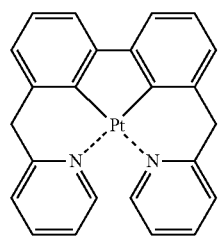
PD27 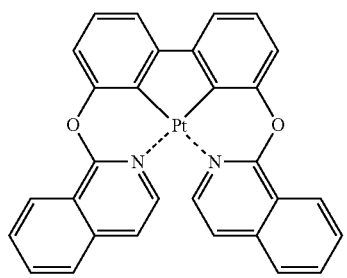
PD28 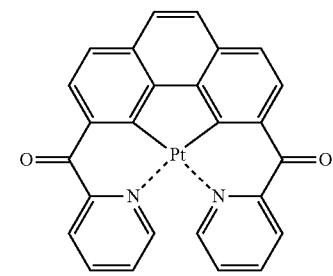
PD29 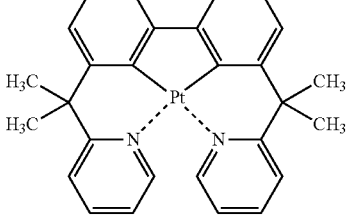
PD30 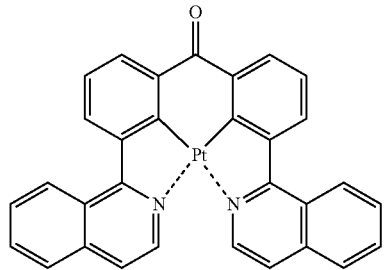
PD31 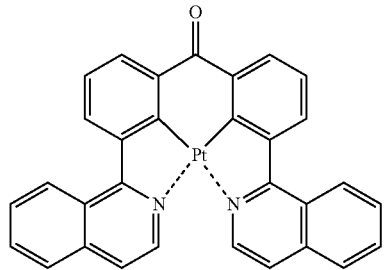

PD32
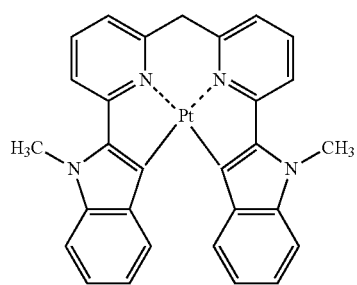
PD33
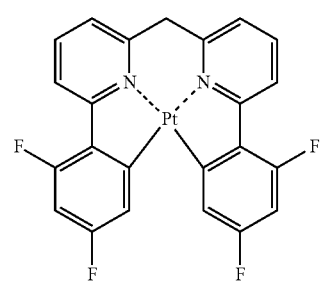
PD34
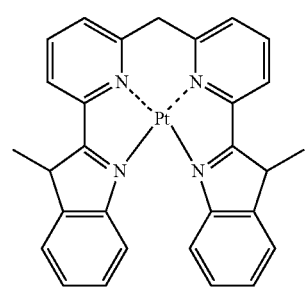
PD35
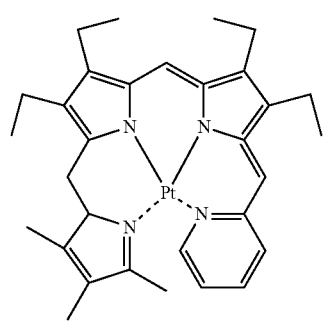
PD36
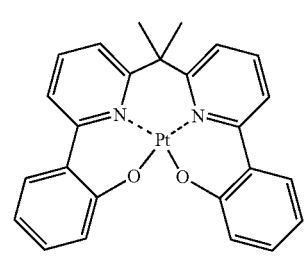
PD37
PD38
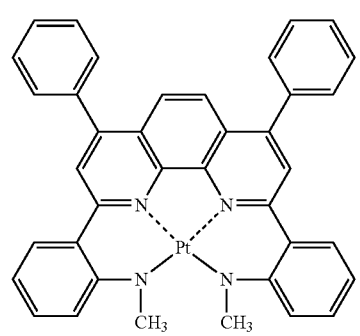
PD39
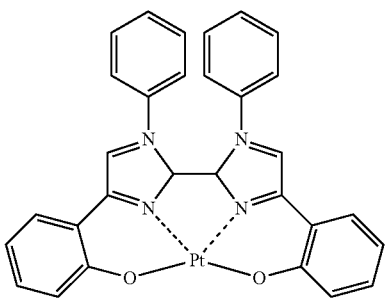
PD40
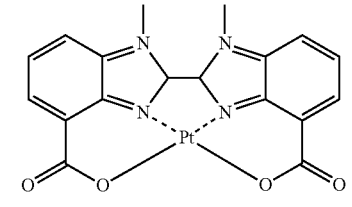
PD41
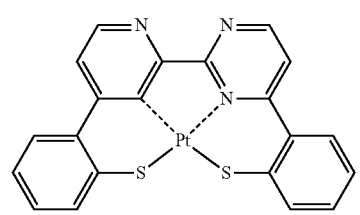

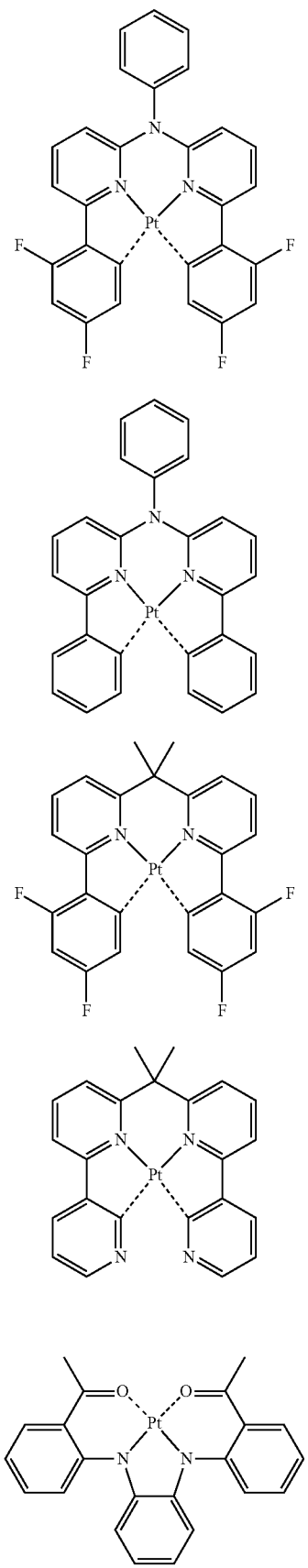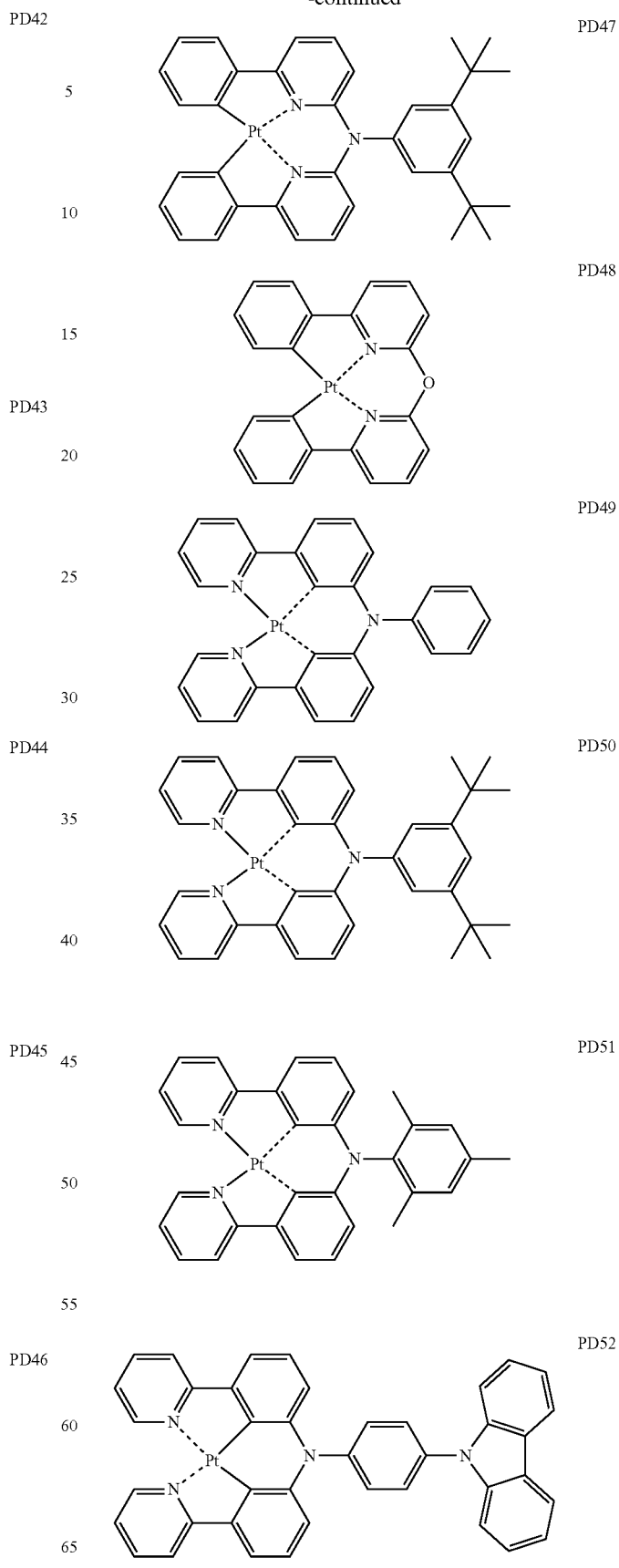

PD53
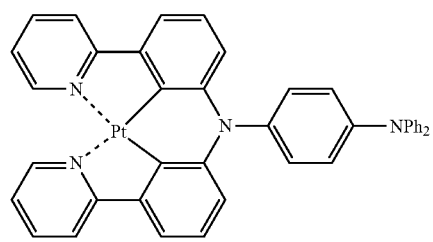
PD54
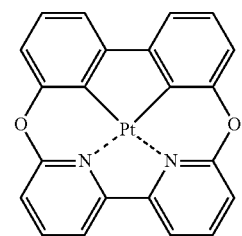
PD55
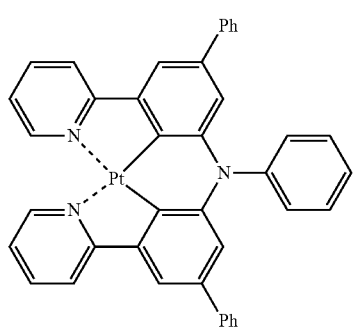
PD56
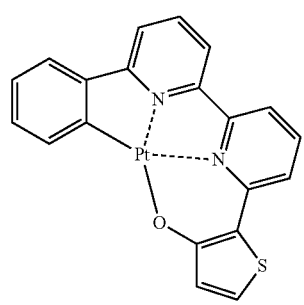
PD57
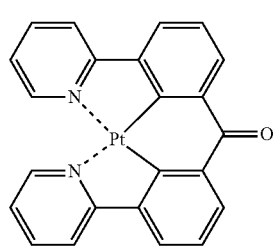
PD58
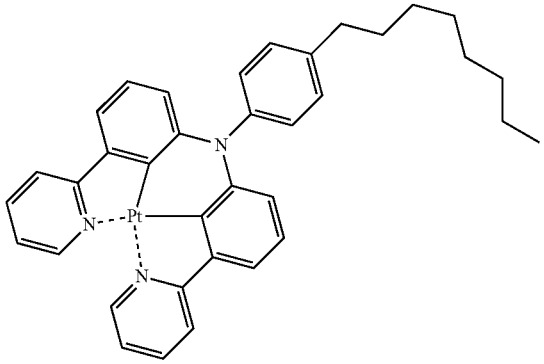
PD59
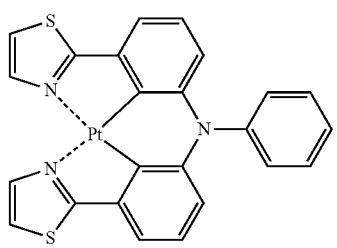
PD60
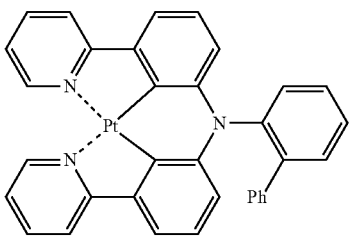
PD61
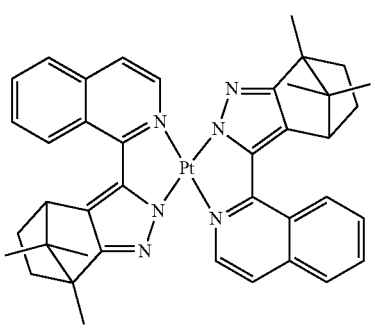
PD62
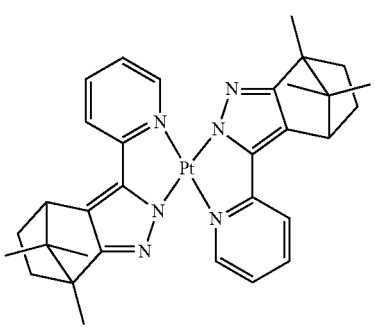

-continued
PD63 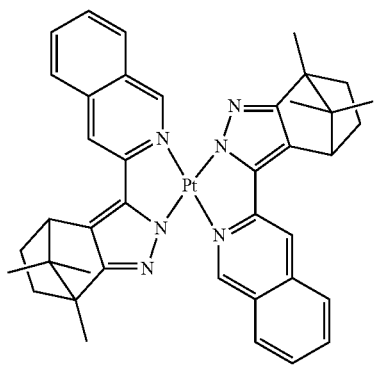
PD64 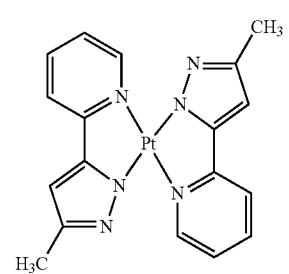
PD65 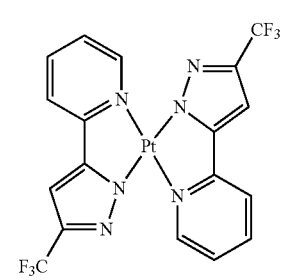
PD66 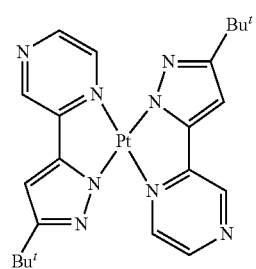
PD67 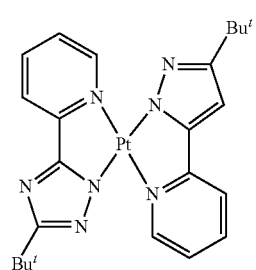
-continued
PD68 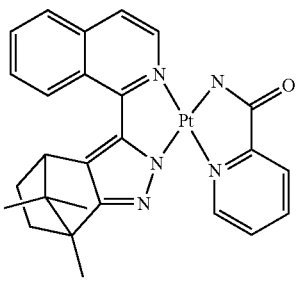
PD69 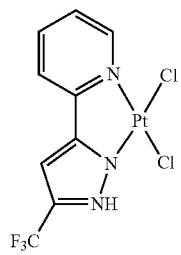
PD70 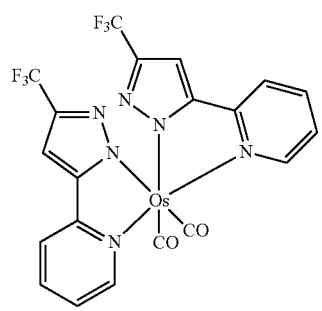
PF71
PD72 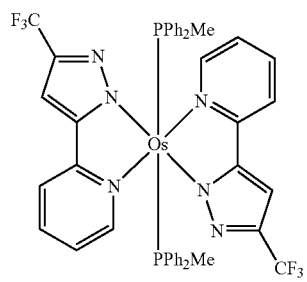

-continued
PD73
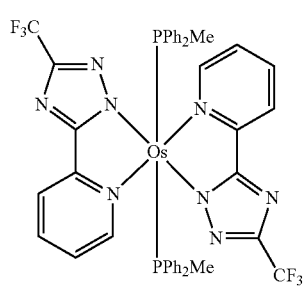
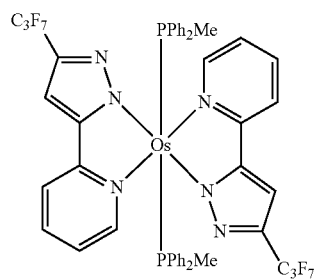
Also, the phosphorescent dopant may include PtOEP below:
PD74
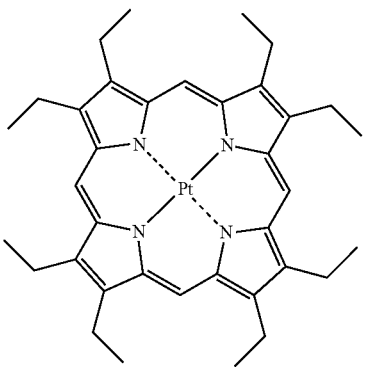
PtOEP
The fluorescent dopant may include at least one of DPAVBi, BDAVBi, TBPe, DCM, DCJTB, Coumarin 6, and a C545T below:
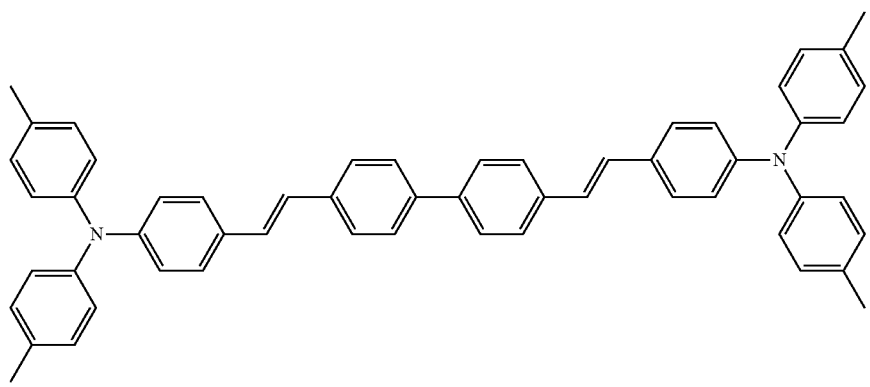
DPAVBi
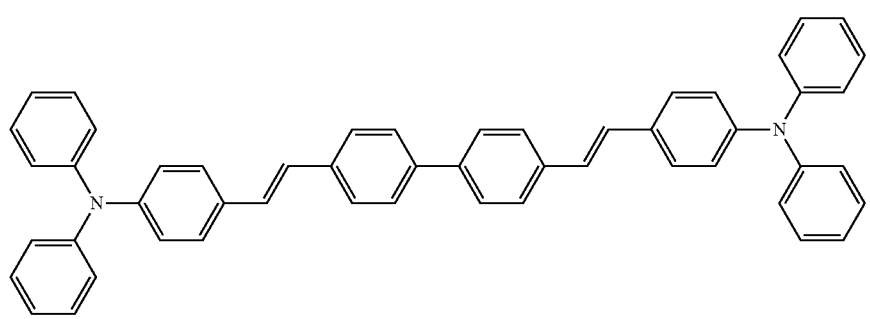
BDAVBi -continued

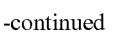
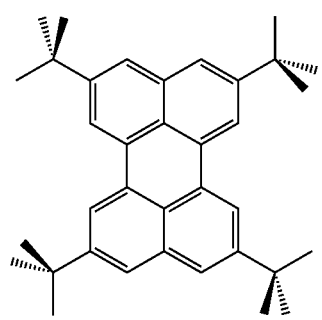
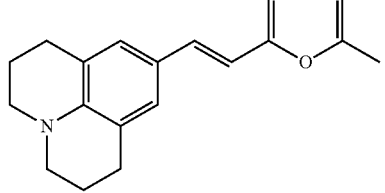
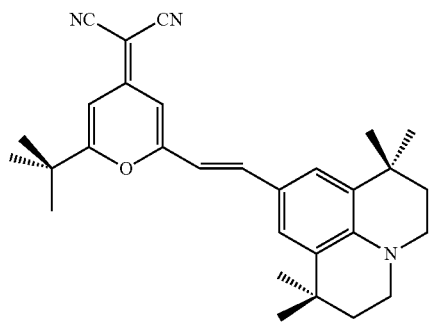

TBPe    DCM    DCJTB

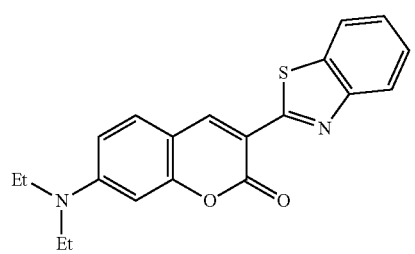
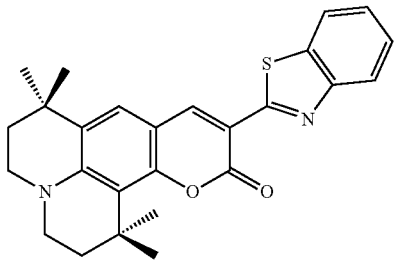

Coumarin 6    C545T

Also, the fluorescent dopant may include a compound represented by Formula 501:

a.

<Formula 501>

$$Ar_{501}\left[(L_{503})_{xd3}-N\begin{matrix}(L_{501})_{xd1}-R_{501}\\(L_{502})_{xd2}-R_{502}\end{matrix}\right]_{xd4}$$

In Formula 501, $Ar_{501}$ may be selected from:

a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorenene group, a spiro-fluorenene group, a benzofluorenene group, a dibenzofluorenene group, a phenalene group, a phenanthrene group, an anthracene group, a fluoranthene group, a triphenylene group, pyrene, a chrysene group, a naphthacene group, a picene group, a perylene group, a pentaphene group, and an indenoanthracene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, non-aromatic condensed polycyclic group, and —Si($Q_{501}$)($Q_{502}$)($Q_{503}$) (here $Q_{501}$ to $Q_{503}$ are each independently selected from a hydrogen atom, a $C_1$-$C_{60}$ alkyl group, a $C_2$-$C_{60}$ alkenyl group, a $C_6$-$C_{60}$ aryl group, and a $C_2$-$C_{60}$ heteroaryl group);

descriptions of $L_{501}$ to $L_{503}$ are the same with the description of $L_{201}$ of the specification;

$R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group, and a dibenzothiophenyl, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 are each independently an integer of 0, 1, 2, or 3; and xb4 is an integer of 1, 2, 3, or 4.

The fluorescent host may include at least one of Compounds FD1 to FD8 below:
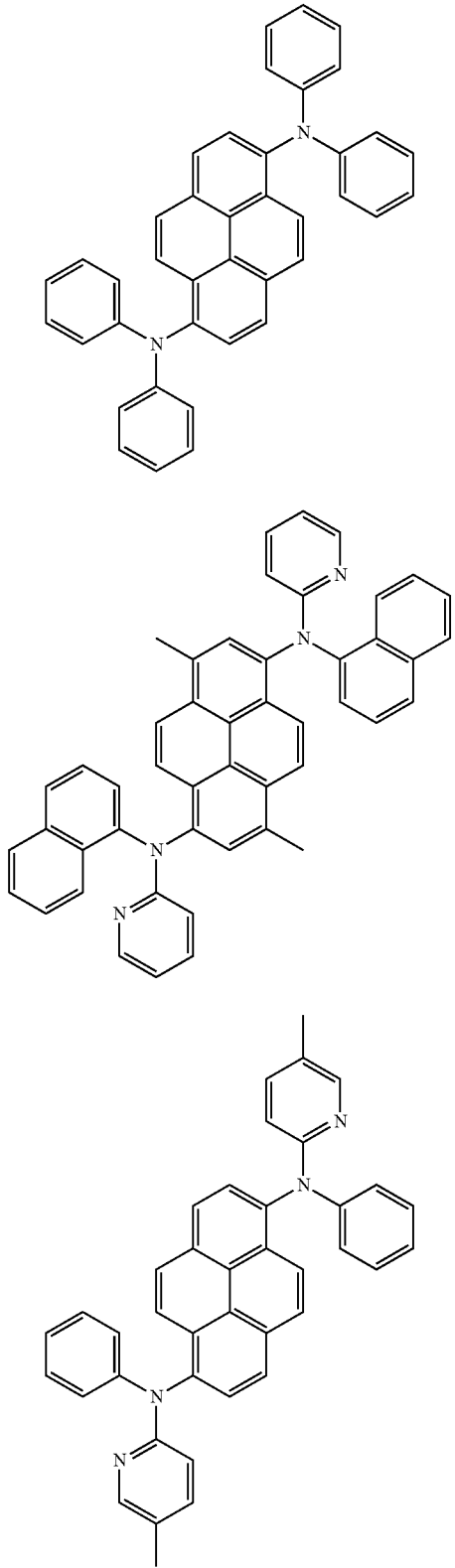
FD1
FD2
FD3
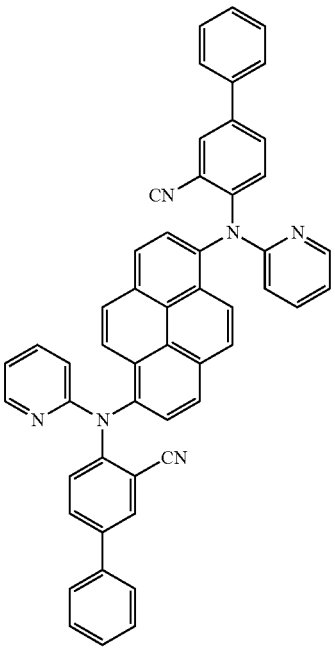
FD4
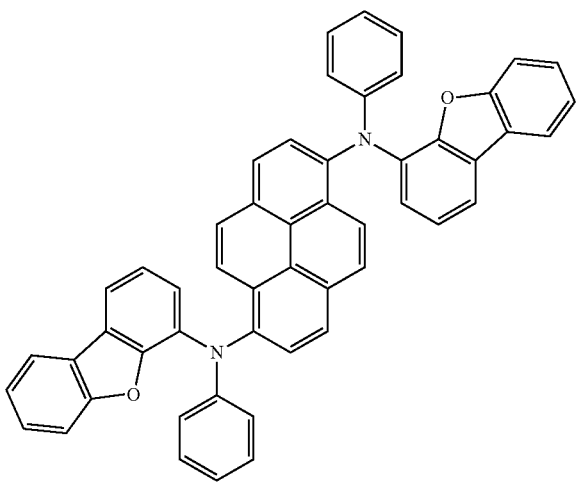
FD5
FD6

FD7

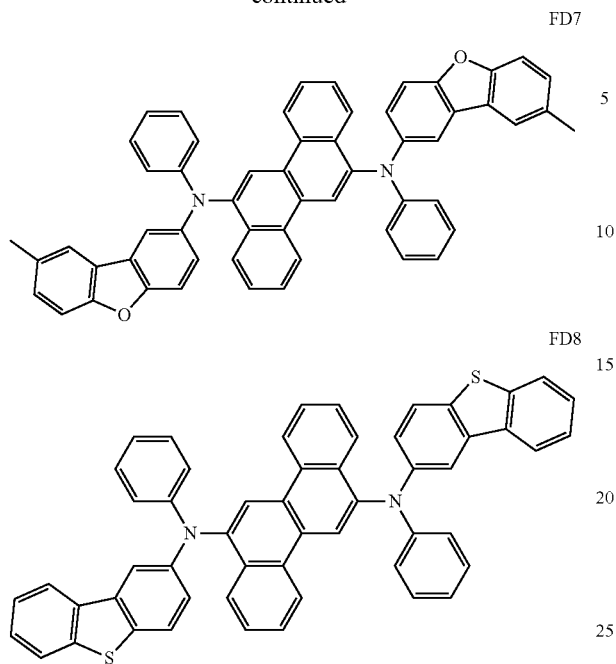

FD8

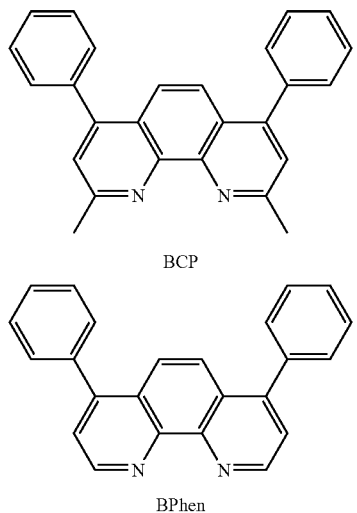

BCP

BPhen

An amount of a dopant in the EML may be generally in a range of about 0.01 part to about 15 parts by weight based on about 100 parts by weight of a host, but is not limited thereto.

A thickness of the EML may be in a range of about 100 Å to about 1,000 Å, for example, about 200 Å to about 600 Å. When a thickness of the EML is within this range, excellent light-emitting properties may be obtained without substantial increase in driving voltage.

Next, an electron transport region may be formed on the EML.

The electron transport region may include at least one of a HBL, an ETL, and an EIL, as examples.

For example, the electron transport region may have a structure of ETL/EIL or EBL/ETL/EIL sequentially stacked on the EML.

In some embodiments, the organic layer 150 of the OLED 10 may include the electron transport region disposed between the EML and the second electrode 190, and the pyrene-based compound represented by Formula 1 may be included in the electron transport region.

The electron transport region may include the HBL. The HBL may be formed to prevent triplet excitons or holes from being diffused to the ETL.

When the electron transport region includes the HBL, the HBL may be formed on the EML by using various methods such as vacuum deposition, spin coating, casting, LB deposition, inkjet printing, laser printing, or LITI. When the HBL is formed by as vacuum deposition and spin coating, the deposition conditions and the coating conditions described with respect to the HIL may be referred to for suitable deposition conditions and coating conditions of the HBL.

The HBL may include, for example, at least one of BCP and Bphen below.

A thickness of the HBL may be in a range of about 20 Å to about 1,000 Å, for example, about 30 Å to about 300 Å. When a thickness of the HBL is within this range, excellent hole blocking properties may be obtained without substantial increase in driving voltage.

The electron transport region may include the ETL. The ETL may be formed on the EML or the HBL by using various methods such as vacuum deposition, spin coating, casting, LB deposition, inkjet printing, laser printing, or LITI. When ETL is formed by vacuum deposition and spin coating, the deposition conditions and the coating conditions described with respect to the HIL may be referred to for suitable deposition conditions and coating conditions of the ETL.

In some embodiments, the organic layer 150 of the OLED 10 may include the electron transport region disposed between the EML and the second electrode 190. The electron transport region may include the ETL, and the pyrene-based compound represented by Formula 1 may be included in the ETL.

The ETL may further include at least one of BCP and Bphen above and $Alq_3$, Balq, TAZ, and NTAZ below in addition to the pyrene-based compound represented by Formula 1:

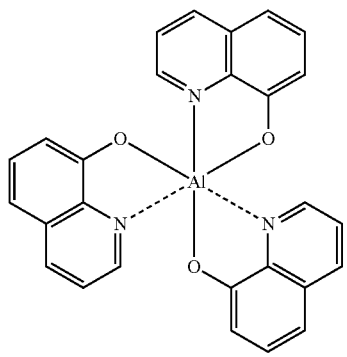

$Alq_3$

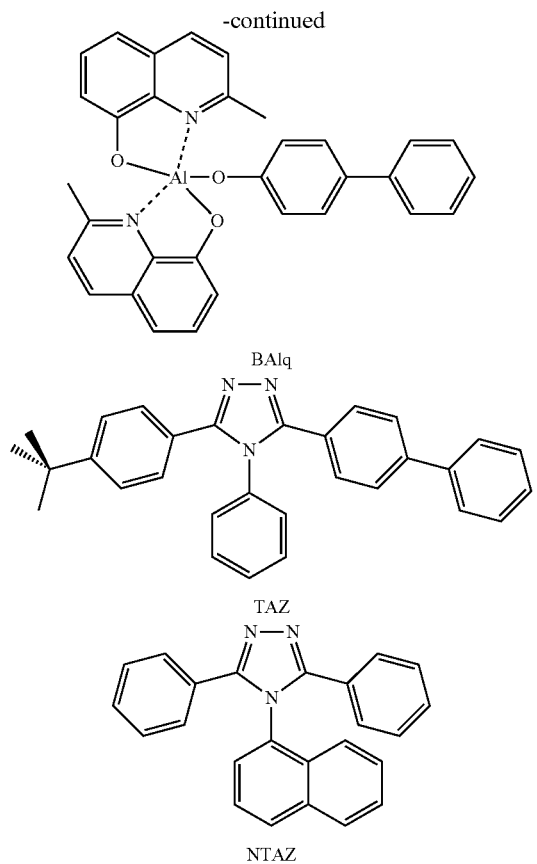

BAlq

TAZ

NTAZ

Also, the ETL may include at least one compound represented by Formula 601 in addition to the pyrene-based compound represented by Formula 1:

$Ar_{601}-[(L_{601})_{xe1}-E_{601}]_{xe2}$ <Formula 601>

In Formula 601, $Ar_{601}$ may be selected from a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, pyrene, a chrysene group, a naphthacene group, a picene group, a perylene group, a pentaphene group, and an indenoanthracene group; and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, pyrene, a chrysene group, a naphthacene group, a picene group, a perylene group, a pentaphene group, and an indenoanthracene group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, non-aromatic condensed polycyclic group, and —Si($Q_{301}$)($Q_{302}$)($Q_{303}$) (here, $Q_{301}$ to $Q_{303}$ are each independently selected from a hydrogen atom, a $C_1$-$C_{60}$ alkyl group, a $C_2$-$C_{60}$ alkenyl group, a $C_6$-$C_{60}$ aryl group, and a $C_2$-$C_{60}$ heteroaryl group);

a description of $L_{601}$ may be the same as the description of $L_{201}$ above;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl, a benzocarbazolyl group, and a dibenzocarbazolyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl, a benzocarbazolyl group, and a dibenzocarbazolyl group;

xe1 is an integer of 0, 1, 2, or 3; and xe2 is an integer of 1, 2, 3, or 4.

The ETL may include at least one compound represented by Formula 602 in addition to the pyrene-based compound represented by Formula 1:

<Formula 602>

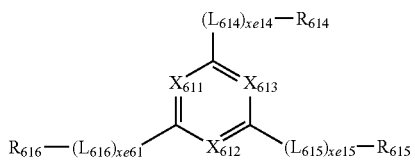

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, and at least one of $X_{611}$ to $X_{613}$ may be N;

a description of each of $L_{611}$ to $L_{616}$ may be the same as the description of $L_{201}$ above;

$R_{611}$ to $R_{616}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently an integer of 0, 1, 2, or 3.

The compound represented by Formula 601 and the compound represented by Formula 602 may include at least one of Compounds ET1 to ET15:

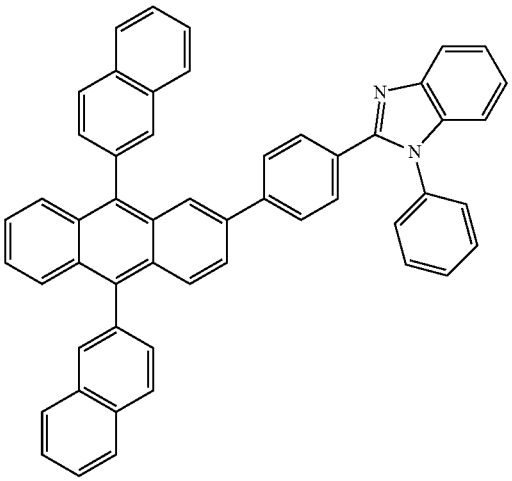

ET1

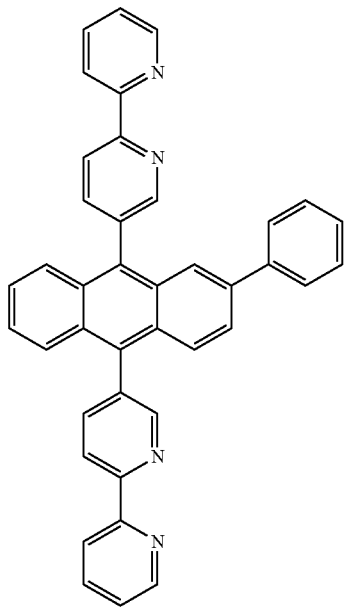

ET2

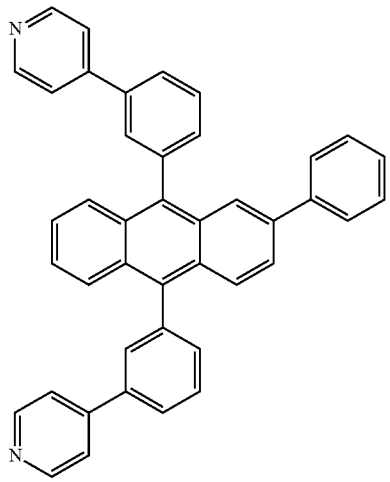

ET3

ET4
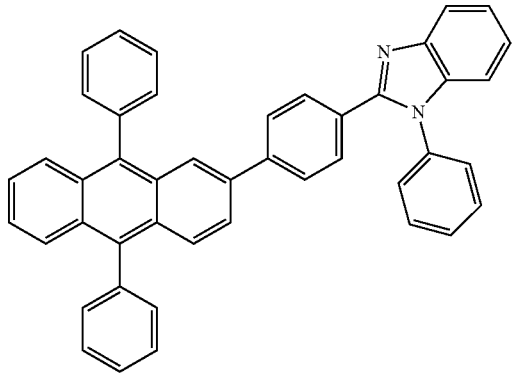
ET5
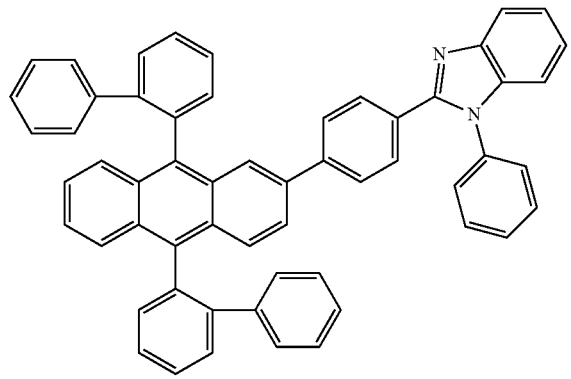
ET6
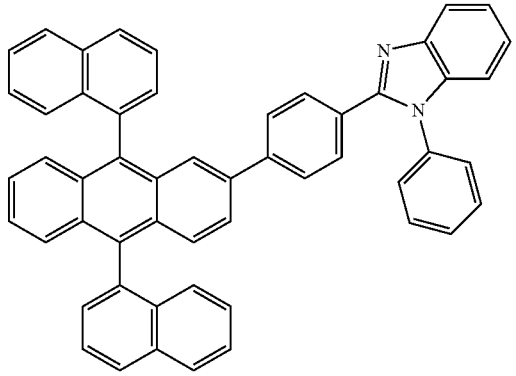
ET7
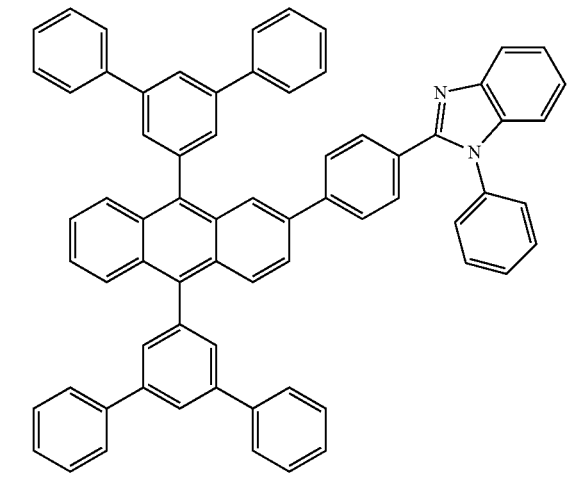
ET8
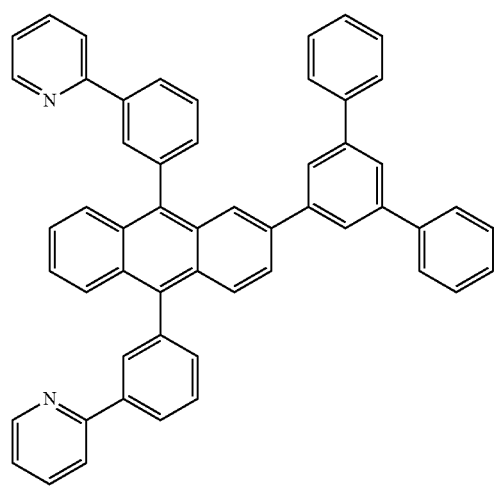
ET9
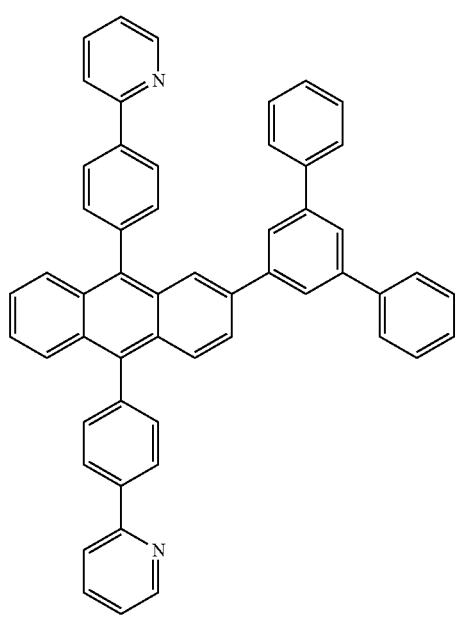

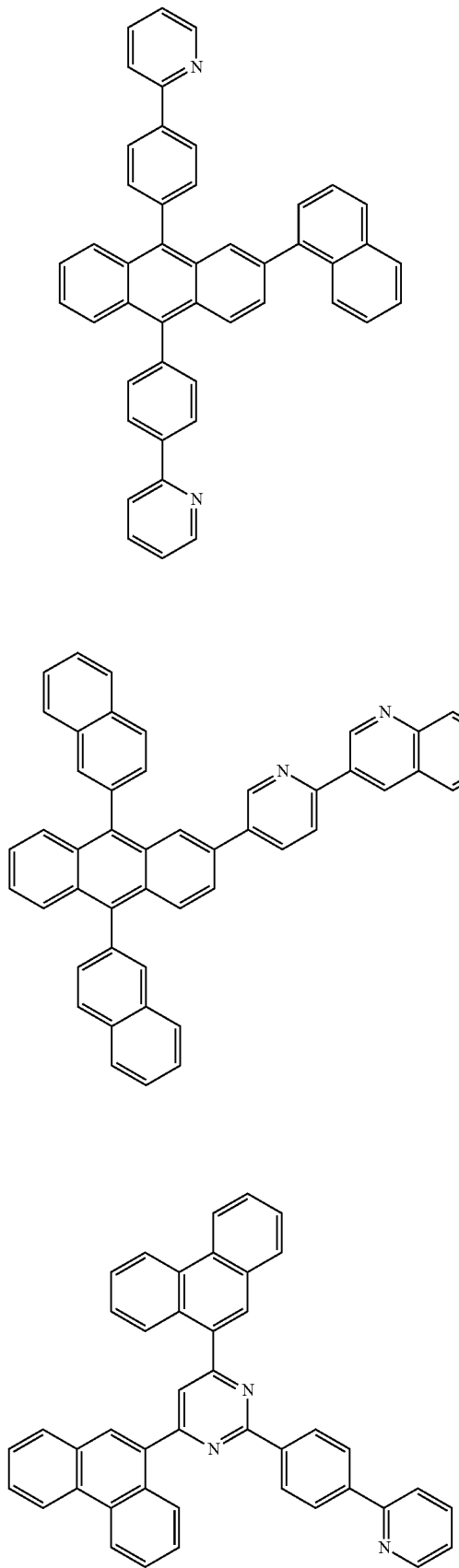
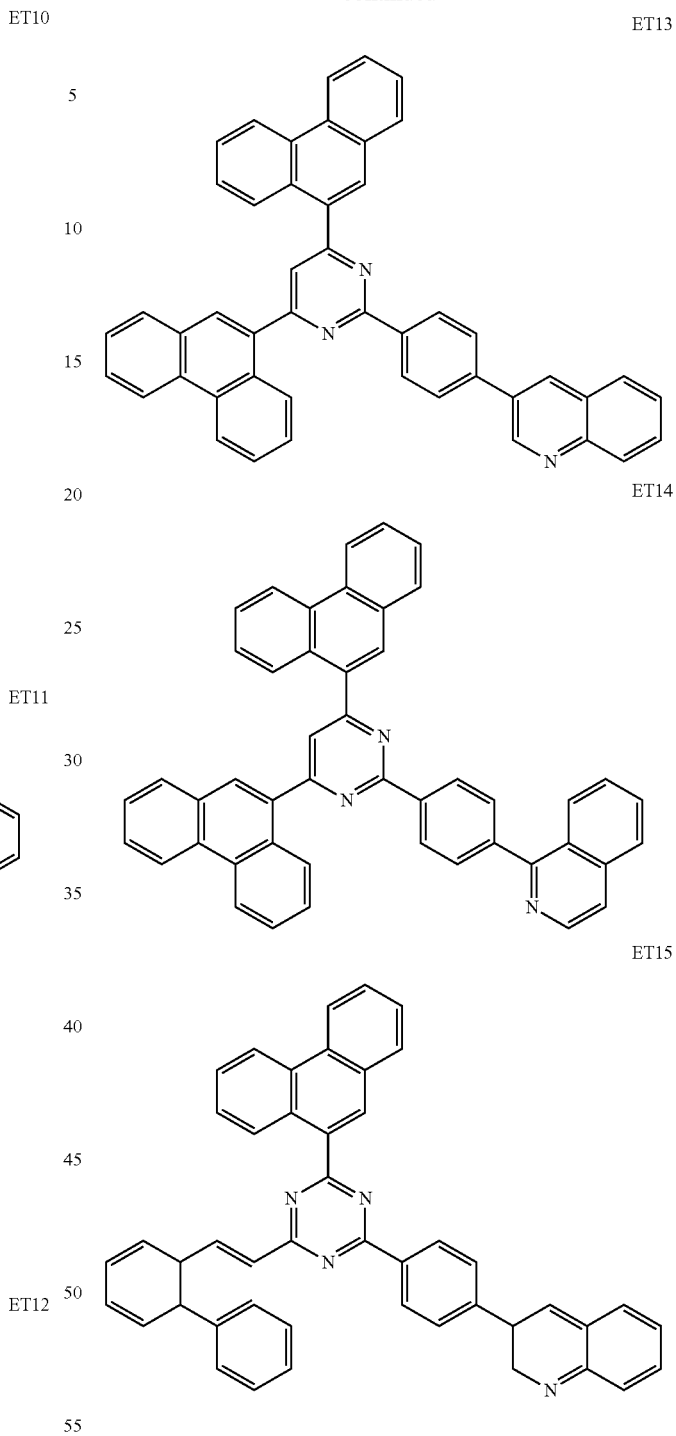

A thickness of the ETL may be in a range of about 100 Å to about 1,000 Å, for example, about 150 Å to about 500 Å. When a thickness of the ETL is within this range, excellent electron transporting properties may be obtained without substantial increase in driving voltage.

The ETL may further include a metal-containing material in addition to the materials above.

The metal-containing material may include a Li-complex. The Li-complex may include, for example, Compound ET-D1(lithium quinolate (LiQ)) or ET-D2:

ET-D1

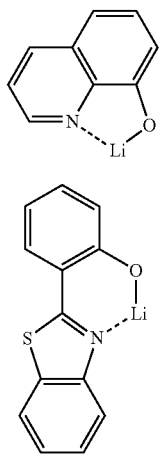

ET-D2

The electron transport region may include the EIL that facilitates injection of electrons from the second electrode 190.

The EIL may be formed on the ETL by using various methods such as vacuum deposition, spin coating, casting, LB deposition, inkjet printing, laser printing, or LITI. When EIL is formed by vacuum deposition and spin coating, the deposition conditions and the coating conditions described with respect to the HIL may be referred to for suitable deposition conditions and coating conditions of the EIL.

The EIL may include at least one selected from LiF, NaCl, a CsF, $Li_2O$, BaO, and LiQ.

A thickness of the EIL may be in a range of about 1 Å to about 100 Å, for example, about 3 Å to about 90 Å. When a thickness of the EIL is within this range, excellent electron injecting properties may be obtained without a substantial increase in driving voltage.

The second electrode 190 may be disposed on the organic layer 150. The second electrode 190 may be a cathode, which is an electron injection electrode. In this regard, a metal for forming the second electrode 190 may include a metal, an alloy, an electric conducting compound, and a mixture thereof having low work function. In particular, the second electrode 190 may be formed as a thin film by using lithium (Li), magnesium (Mg), aluminum (Al), aluminum-lithium (Al—Li), calcium (Ca), magnesium-indium (Mg—In), or magnesium-silver (Mg—Ag). Also, ITO or IZO may be used as metal for forming the second electrode 190. The second electrode 190 may be a reflective electrode or a transparent electrode.

Thus far, the OLED 10 has been described by referring to FIG. 1, but in other implementations, other structures of the OLED are possible.

As used herein, examples of the $C_1$-$C_{60}$ alkyl group may include a monovalent linear or branched aliphatic hydrocarbon group, such as a methyl group, an ethyl group, a propyl group, an isobutyl group, a sec-butyl group, a pentyl group, an iso-amyl group, a hexyl group, or the like. Examples of the substituted $C_1$-$C_{60}$ alkylene group include a divalent group that has the same structure as the $C_1$-$C_{60}$ alkyl group.

As used herein, a $C_1$-$C_{60}$ alkoxy group may denote a monovalent group having a formula of —$OA_{101}$ (here, $A_{101}$ is the $C_1$-$C_{60}$ alkyl group). Examples of the $C_1$-$C_{60}$ alkoxy group include a methoxy group, an ethoxy group, and an isopropyloxy group.

As used herein, the $C_2$-$C_{60}$ alkenyl group may have a structure including at least one carbon double bond in the middle or at an end of the $C_2$-$C_{60}$ alkyl group Examples of the $C_2$-$C_{60}$ alkenyl group include an ethenyl group, a propenyl group, and a butenyl group. As used herein, the $C_2$-$C_{60}$ alkenylene group may denote a divalent group that has the same structure as the $C_2$-$C_{60}$ alkenyl group.

As used herein, the $C_2$-$C_{60}$ alkynyl group may have a structure including at least one carbon triple bond in the middle or at an end of the $C_2$-$C_{60}$ alkyl group. Examples of the $C_2$-$C_{60}$ alkynyl group include an ethynyl group and a propynyl group. As used herein, the $C_2$-$C_{60}$ alkynylene group may denote a divalent group that has the same structure as the $C_2$-$C_{60}$ alkynyl group.

As used herein, the $C_3$-$C_{10}$ cycloalkyl group may denote a $C_3$-$C_{10}$ monovalent hydrocarbon monocyclic group. Examples of the $C_3$-$C_{10}$ cycloalkyl group may include a cyclopropyl group, a cyclobutyl group, a cyclopentyl group, a cyclohexyl group, and a cycloheptyl group. As used herein, the $C_3$-$C_{10}$ cycloalkylene group may denote a divalent group that has the same structure as the $C_3$-$C_{10}$ cycloalkyl group.

As used herein, the $C_3$-$C_{10}$ heterocycloalkyl group may denote a $C_3$-$C_{10}$ monovalent monocyclic group including at least one hetero atom of N, O, P, and S as a ring-forming atom. Examples of the $C_3$-$C_{10}$ heterocycloalkyl group include a tetrahydrofuranyl group and a tetrahydrothiophenyl group. As used herein, the $C_3$-$C_{10}$ heterocycloalkylene group denotes a divalent group that has the same structure with the $C_3$-$C_{10}$ heterocycloalkyl group.

As used herein, the $C_3$-$C_{10}$ cycloalkenyl group may denote a $C_3$-$C_{10}$ monocyclic group having at least one double bond in the ring while not losing its aromaticity. Examples of the $C_3$-$C_{10}$ cycloalkenyl group include a cyclopentyl group, a cyclohexenyl group, and a cycloheptenyl group. As used herein, the $C_3$-$C_{10}$ cycloalkenylene group may denote a divalent group that has the same structure as the $C_3$-$C_{10}$ cycloalkenyl group.

As used herein, the $C_3$-$C_{10}$ heterocycloalkenyl group may denote a $C_3$-$C_{10}$ monovalent monocyclic group including at least one hetero atom of N, O, P, and S as a ring-forming atom and at least one double bond in the ring Examples of the $C_3$-$C_{10}$ heterocycloalkenyl group include a 2,3-hydrofuranyl group and a 2,3-hydrothiophenyl group. As used herein, the $C_3$-$C_{10}$ heterocycloalkenylene group may denote a divalent group that has the same structure as the $C_3$-$C_{10}$ heterocycloalkenyl group.

As used herein, the $C_6$-$C_{60}$ aryl group may denote a monovalent group having a $C_6$-$C_{60}$ carbocyclic aromatic system, and the $C_6$-$C_{60}$ arylene group may denote a divalent group that has a $C_6$-$C_{60}$ carbocyclic aromatic system. Examples of the $C_6$-$C_{60}$ aryl group include a phenyl group, a naphthyl group, an anthracenyl group, a phenanthrenyl group, a pyrenyl group, and a chrysenyl group. As used herein, when the $C_6$-$C_{60}$ aryl group and the $C_6$-$C_{60}$ arylene group include at least two rings, the rings may be fused to each other.

As used herein, the $C_2$-$C_{60}$ heteroaryl group may denote a monovalent group including at least one hetero atom selected from N, O, P, and S as a ring-forming atom and having a $C_2$-$C_{60}$ carbocyclic aromatic system. The $C_2$-$C_{60}$ heteroarylene group may denote a divalent group including at least one hetero atom selected from N, O, P, and S as a ring-forming atom and having a $C_2$-$C_{60}$ carbocyclic aromatic system. Examples of the $C_2$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and a $C_2$-$C_{60}$ heteroarylene group include at least two rings, the rings may be fused to each other.

As used herein, the $C_6$-$C_{60}$ aryloxy group may denote —$OA_{102}$ (here, $A_{102}$ is the $C_6$-$C_{60}$ aryl group), and the $C_6$-$C_{60}$ arylthio group denotes —$SA_{103}$ (here, $A_{103}$ is the $C_6$-$C_{60}$ aryl group).

As used herein, the non-aromatic condensed polycyclic group may denote a monovalent group having at least two rings that are condensed to each other and non-aromaticity as a whole molecule. The non-aromatic condensed polycyclic group may include i) C only or ii) one hetero atom selected from N, O, P, and S as a ring-forming member. Examples of the non-aromatic condensed polycyclic group include a fluorenyl group and a carbazolyl group. As used herein, the divalent non-aromatic condensed polycyclic group may denote a divalent group that has the same structure as the non-aromatic condensed polycyclic group.

As used herein, the expression "Ph" denotes a phenyl group, the expression "Me" denotes a methyl group, the expression "Et" denotes an ethyl group, and the expression "ter-Bu" or "Bu$^t$" denotes a tert-butyl group.

Hereinafter, an OLED according to an embodiment will now be described in more detail with reference to the following examples. In the examples, the expression "B was used instead of A" indicates that an amount per mol of A and an amount per mol B are the same.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1

Synthesis of Compound 1

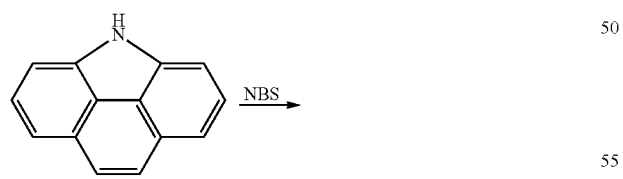

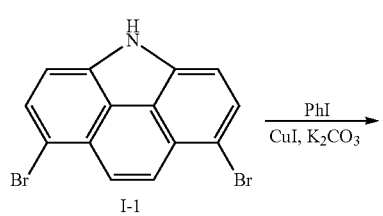

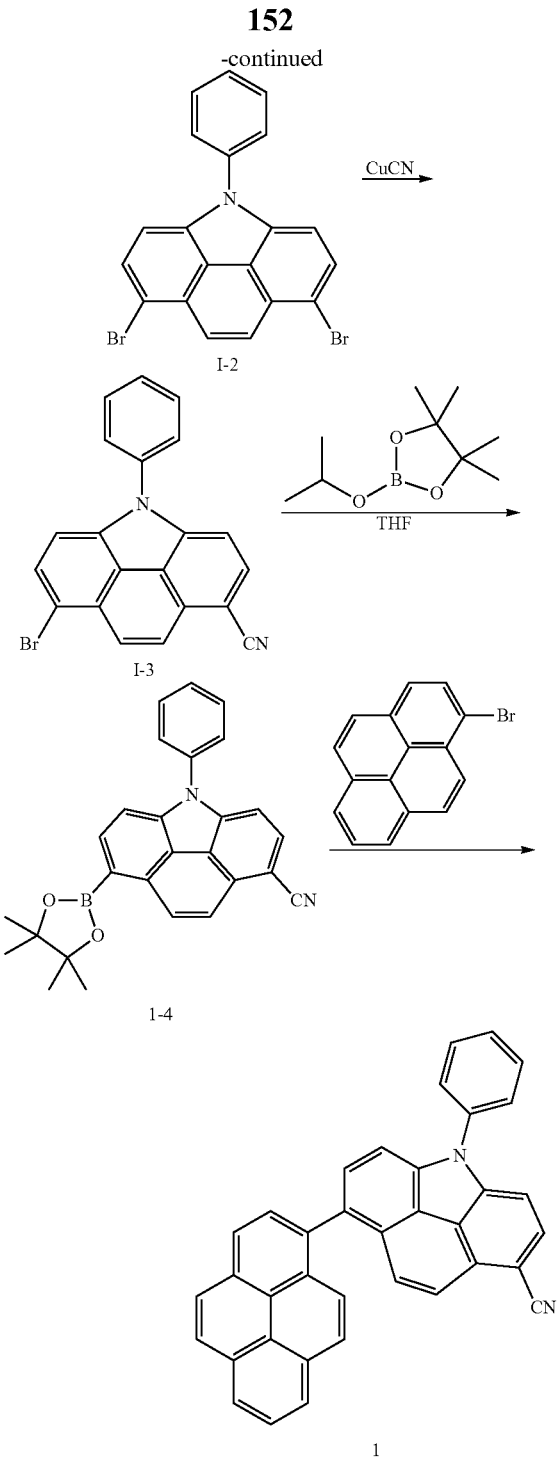

Synthesis of Intermediate I-1

9.55 g (50.0 mmol) of 6H-benzo[def]carbazole was completely dissolved in 250 mL of carbon tetrachloride (CCl$_4$), and 17.8 g (100.0 mmol) of N-bromosuccinimide was added thereto, and stirred at a temperature of 80° C. for 30 minutes. The resultant was cooled to room temperature and stirred for 30 minutes to precipitate a crystal. The crystal was collected by using a filter at a low pressure and washed with methanol to obtain 8.55 g of Intermediate I-1 (yield: 49%). The produced compound was confirmed by using LC-MS.

$C_{14}H_7Br_2N$: M$^+$ 346.9

Synthesis of Intermediate I-2

8.55 g (24.5 mmol) of Intermediate I-1, 6.0 g (29.4 mmol) of iodobenzene, 0.44 g (2.45 mmol) of 1,10-phenanthroline, 0.93 g (4.90 mmol) of CuI, and 10.2 g (73.5 mmol) of $K_2CO_3$ were dissolved in 100 mL of N,N-dimethylformamide (DMF) and stirred at a temperature of 80° C. for 24 hours. The reaction solution was cooled to room temperature and extracted with 100 mL of water. The collected supernatant was dried by using magnesium sulfate, and the solvent thereof was evaporated. The obtained residue was purified by using a silica gel column chromatography to obtain 8.23 g of Intermediate I-2 (yield: 79%). The produced compound was confirmed by using LC-MS.

$C_{20}H_{11}Br_2N$: $M^+$ 422.9

Synthesis of Intermediate I-3

8.23 g of Intermediate I-2 (19.3 mmol) and 2.57 g of CuCN (28.7 mmol) were dissolved in 70 mL of DMF and stirred at a temperature of 150° C. for 24 hours. The reaction solution was cooled to room temperature and 60 mL of ammonium hydroxide and 60 mL of water were added thereto, and the resultant was extracted with 50 mL of methylene chloride for 3 times. The collected supernatant was dried by using magnesium sulfate, and the solvent thereof was evaporated, and the residue obtained therefrom was purified by using a silica gel column chromatography to obtain 3.3 g of Intermediate I-3 (yield: 46%). The produced compound was confirmed by using LC-MS.

$C_{21}H_{11}BrN_2$: $M^+$ 370.0

Synthesis of Intermediate I-4

3.3 g of Intermediate I-3 (8.89 mmol) was dissolved in 60 mL of THF, and 3.9 mL of n-BuLi (9.78 mmol in 2.5 M hexane) was slowly and dropwisely added thereto at a temperature of −78° C. After stirring at the same temperature, 2.3 mL (11.6 mmol) of 2-isoproxy-4,4,5,5-tetramethyl-1,3,2-dioxaborolane was dropwisely added thereto, and stirred at room temperature for 24 hours. When the reaction was completed, 40 mL of water was added, and the resultant was extracted with 40 mL of ethylether for 3 times. The collected supernatant was dried by using magnesium sulfate, and the solvent was evaporated therefrom. The residue obtained therefrom was purified by using a silica gel column chromatography to obtain 2.83 g of Intermediate I-4 (yield: 76%). The produced compound was confirmed by using LC-MS.

$C_{27}H_{23}BN_2O_2$: $M^+$ 418.2

Synthesis of Compound 1

2.83 g (6.76 mmol) of Intermediate I-4, 1.90 g (6.76 mmol) of 1-bromopyrene, 0.39 g (0.34 mmol) of $Pd(PPh_3)_4$, and 2.80 g (20.3 mmol) of $K_2CO_3$ were dissolved in 60 mL of a mixture solution of $THF/H_2O$ (at a volume ratio of 2/1) and stirred at a temperature of 80° C. for 12 hours. The reaction solution was cooled to room temperature, and the resultant was extracted with 40 mL of water and 40 mL of ethylacetate for 3 times. The collected supernatant was dried by using magnesium sulfate, and the solvent was evaporated therefrom. The obtained residue was purified by using a silica gel column chromatography to obtain 2.70 g of Compound 1 (yield: 81%). The produced compound was confirmed by using MS/FAB and $^1H$ NMR ($CDCl_3$, 400 MHz).

$C_{37}H_{20}N_2$ cal. 492.16, found 492.21.

δ=8.21-8.19 (m, 1H), 8.13-8.12 (m, 1H), 8.11-8.10 (m, 1H), 8.09-8.08 (m, 2H), 8.06-8.05 (m, 2H), 8.02-7.99 (m, 2H), 7.87-7.85 (m, 1H), 7.71-7.69 (m, 1H), 7.66-7.64 (m, 1H), 7.55-7.49 (m, 4H), 7.47 (d, 1H), 7.42 (d, 1H), 7.40-7.36 (m, 2H)

Synthesis Example 2

Synthesis of Compound 3

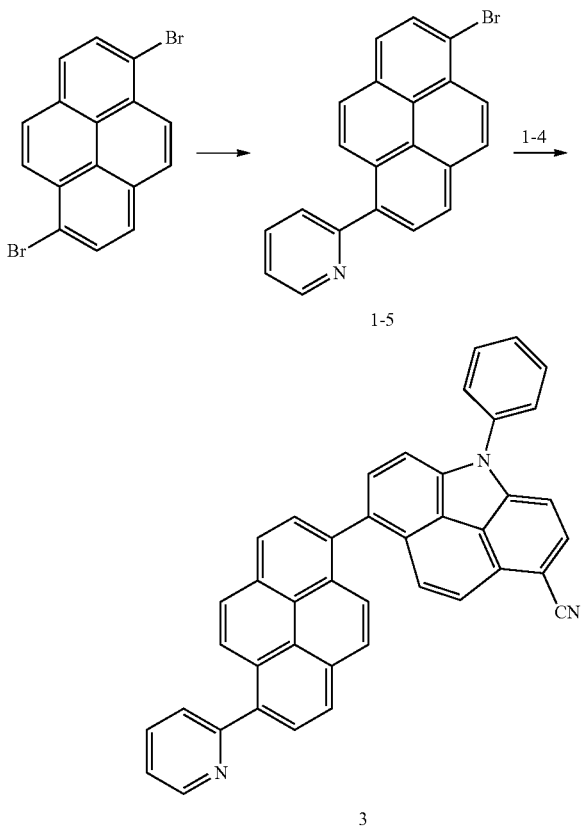

Synthesis of Intermediate I-5

5.40 g (15 mmol) of 1,6-dibromopyrene, 1.90 g (10 mmol) of 2-pyridineboronic acid, 0.58 g (0.5 mmol) of tetrakis(triphenylphsohpine)palladium ($Pd(PPh_3)_4$), and 4.15 g (30 mmol) of $K_2CO_3$ were dissolved in 60 mL of a mixture solution of $THF/H_2O$ (at a volume ration of 2/1) and stirred at a temperature of 70° C. for 5 hours. The reaction solution was cooled to room temperature, and 50 mL of water was added thereto and the resultant was extracted with 50 mL of ethylether for 3 times. The collected supernatant was dried by using magnesium sulfate, and the solvent was evaporated therefrom. The obtained residue was purified by using a silica gel column chromatography to obtain 2.26 g of Intermediate I-5 (yield: 63%). The produced compound was confirmed by using LC-MS.

$C_{21}H_{12}BrN$: $M^+$ 357.0

Synthesis of Compound 3

2.26 g (6.3 mmol) of Intermediate I-5, 2.64 g (6.3 mmol) of Intermediate I-4, 0.36 g (0.31 mmol) of Pd(PPh$_3$)$_4$, and 2.61 g (18.9 mmol) of K$_2$CO$_3$ were dissolved in 60 mL of a mixture solution of THF/H$_2$O (at a volume ratio of 2/1) and stirred at a temperature of 80° C. for 12 hours. The reaction solution was cooled to room temperature, and the resultant was extracted with 40 mL of water and 40 mL of ethylacetate for 3 times. The collected supernatant was dried by using magnesium sulfate, and the solvent was evaporated therefrom. The obtained residue was purified by using a silica gel column chromatography to obtain 2.80 g of Compound 3 (yield: 78%). The produced compound was confirmed by using MS/FAB and $^1$H NMR.

C$_{42}$H$_{23}$N$_3$ cal. 569.19, found 569.23.

δ=8.40-8.38 (m, 1H), 8.35 (d, 1H), 8.24 (d, 1H), 8.09-8.06 (m, 2H), 8.04-8.02 (m, 2H), 7.99-7.93 (m, 2H), 7.86-7.82 (tt, 1H), 7.76-7.73 (m, 1H), 7.71-7.66 (m, 3H), 7.55-7.48 (m, 4H), 7.46-7.41 (m, 2H), 7.40-7.35 (m, 2H), 7.25-7.22 (m, 1H)

Synthesis Example 3

Synthesis of Compound 13

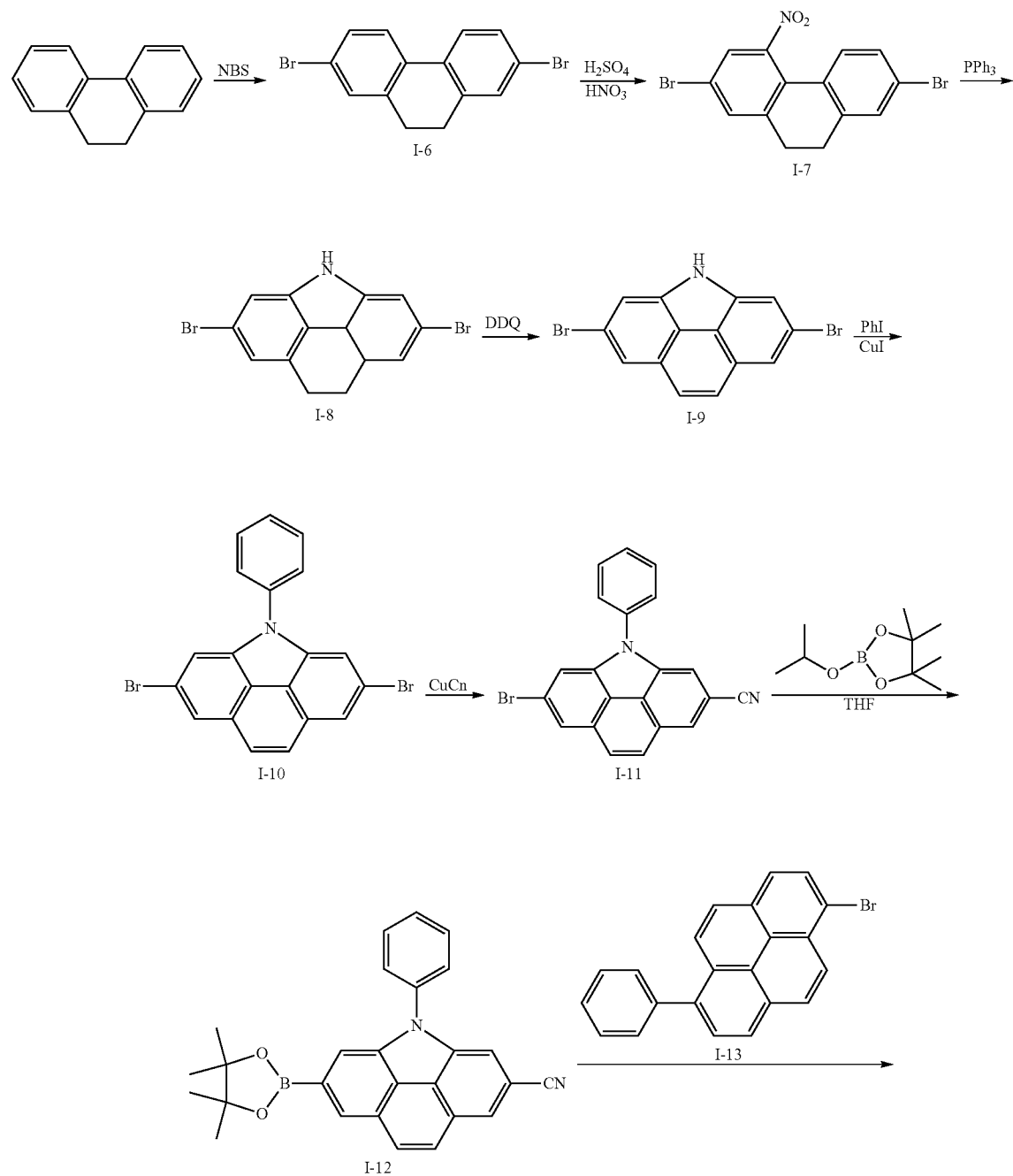

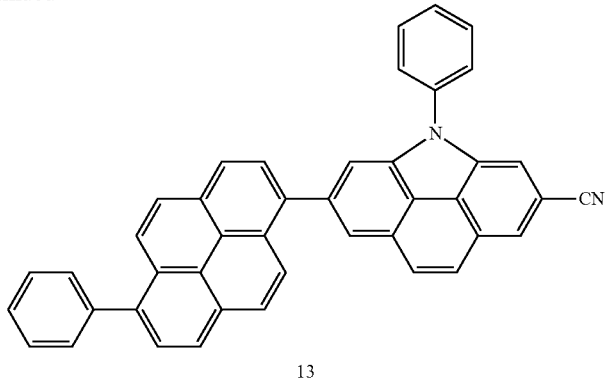

13

Synthesis of Intermediate I-6

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile and stirred at a temperature of 50° C. for 12 hours. The resultant was cooled to room temperature and stirred for 30 minutes to precipitate a crystal. The crystal was collected by using a filter at a low pressure and washed with methanol to obtain 8.4 g of Intermediate I-6 (yield: 45%), and a color of the crystal was gray. The produced compound was confirmed by using LC-MS.

$C_{14}H_{10}Br_2$: M$^+$ 335.9

Synthesis of Intermediate I-7

5.0 g (15.0 mmol) of Intermediate I-6 was completely dissolved in 50 mL of dichloromethane, 1.7 g (30.0 mmol) of nitric acid was added thereto at room temperature, and 1.5 g (15.0 mmol) of sulfuric acid was slowly and dropwisely added thereto and stirred at a temperature of 30° C. for 6 hours. After the reaction was completed, the resultant was cooled to room temperature, and 50 mL of methanol was added thereto and stirred for 2 hours to precipitate a crystal. The crystal collected by using a filter at a low pressure was washed with methanol, and thus 5.2 g of Intermediate I-7 (yield: 90%) was obtained. The produced compound was confirmed by using LC-MS.

$C_{14}H_9Br_2NO_2$: M$^+$ 380.9

Synthesis of Intermediate I-8

5.2 g (13.6 mmol) of Intermediate I-7 was dissolved in 30 mL of o-dichlorobenzene, and the solution was heated for complete dissolution. Then, 5.35 g (20.4 mmol) of triphenyl phosphine was added thereto and stirred at a temperature of 180° C. for 3 hours. The reaction solution was cooled to room temperature, and the solvent was evaporated. The residue obtained therefrom was purified by using a silica gel column chromatography to obtain 3.5 g of Intermediate I-8 (yield: 73%). The produced compound was confirmed by using LC-MS.

$C_{14}H_{11}Br_2N$: M$^+$ 350.9

Synthesis of Intermediate I-9

3.5 g (10.0 mmol) of Intermediate I-8 was dissolved in 100 mL of toluene in oxygen atmosphere, and 0.6 g (0.3 mmol) of 2,3-dichloro-5,6-a dicyano group-1,4-benzoquinone and 0.2 g (0.3 mmol) of NaNO$_2$ were added thereto, and stirred at a temperature of 110° C. for 6 hours. After the reaction was completed, the reaction solution was cooled to room temperature, and the solvent was evaporated. The residue obtained therefrom was purified by using a silica gel column chromatography to obtain 3.1 g of Intermediate I-9 (yield: 90%). The produced compound was confirmed by using LC-MS.

$C_{14}H_7Br_2N$: M$^+$ 346.9

Synthesis of Intermediate I-10

8.54 g of Intermediate I-10 (yield: 82%) was obtained in the same manner used in Synthesis of Intermediate I-2, except that Intermediate I-9 was used instead of Intermediate I-1 in the synthesis of Intermediate I-2. The produced compound was confirmed by using LC-MS.

$C_{20}H_{11}Br_2N$: M$^+$ 422.9

Synthesis of Intermediate I-11

3.21 g of Intermediate I-11 (yield: 43%) was obtained in the same manner used in Synthesis of Intermediate I-3, except that Intermediate I-10 was used instead of Intermediate I-2 in the synthesis of Intermediate I-3. The produced compound was confirmed by using LC-MS.

$C_{21}H_{11}BrN_2$: M$^+$ 370.0

Synthesis of Intermediate I-12

2.97 g of Intermediate I-12 (yield: 82%) was obtained in the same manner used in Synthesis of Intermediate I-4, except that Intermediate I-11 was used instead of Intermediate I-3 in the synthesis of Intermediate I-4. The produced compound was confirmed by using LC-MS.

$C_{27}H_{23}BN_2O_2$: M$^+$ 418.2

Synthesis of Compound 13

3.43 g of Compound 13 (yield: 85%) was obtained in the same manner used in Synthesis of Compound 1, except that Intermediate I-12 was used instead of Intermediate I-4, and Intermediate I-13 was used instead of 1-bromopyrene in the synthesis of Compound 1. The produced compound was confirmed by using MS/FAB and $^1$H NMR.

$C_{43}H_{24}N_2$ cal. 568.19, found 568.22.

δ=8.30-8.28 (m, 1H), 8.21-8.20 (m, 1H), 8.16-8.13 (m, 2H), 8.09-8.07 (m, 1H), 8.05-8.04 (m, 1H), 8.03-8.02 (m, 2H), 7.99-7.98 (m, 2H), 7.91-7.89 (m, 1H), 7.82-7.80 (m,

1H), 7.65-7.64 (m, 1H), 7.62-7.60 (m, 2H), 7.59-7.58 (m, 1H), 7.52-7.51 (m, 1H), 7.50-7.49 (m, 1H), 7.48-7.47 (m, 2H), 7.42-7.36 (m, 4H)

Synthesis Example 4

Synthesis of Compound 38

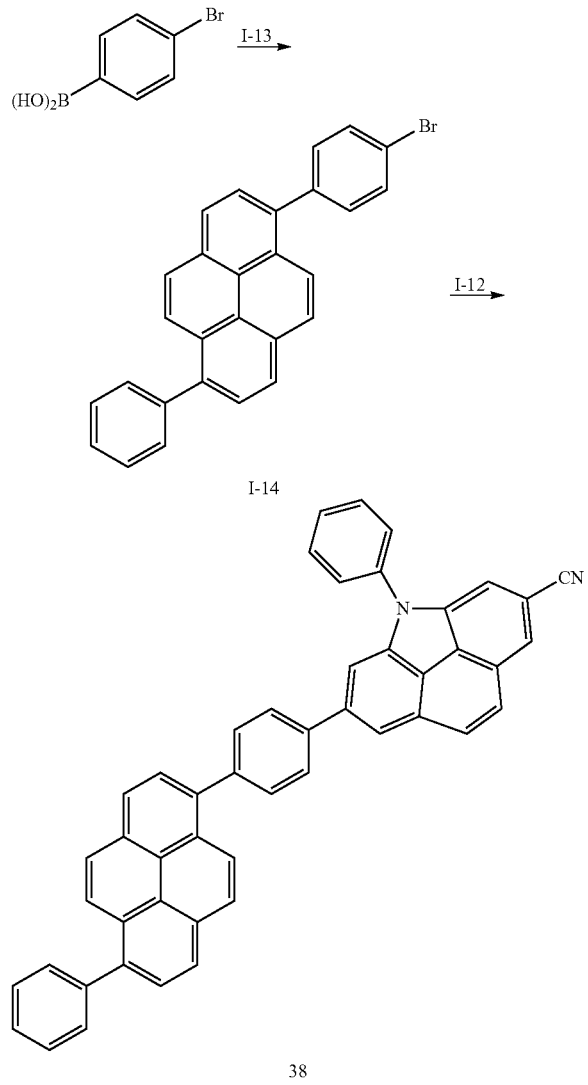

Synthesis of Intermediate I-14

2.0 g (10 mmol) of 4-bromophenylboronic acid, 3.57 g (10 mmol) of Intermediate I-13, 0.58 g (0.5 mmol) of Pd(PPh$_3$)$_4$, and 4.15 g (30 mmol) of K$_2$CO$_3$ were dissolved in 60 mL of a mixture solution of THF/H$_2$O (at a volume ratio of 2/1) and stirred at a temperature of 70° C. for 5 hours. The reaction solution was cooled to room temperature, 50 mL of water was added thereto, and the resultant was extracted with 50 mL of ethylether for 3 times. The collected supernatant was dried by using magnesium sulfate, and the solvent was evaporated therefrom. The obtained residue was purified by using a silica gel column chromatography to obtain 2.64 g of Intermediate I-14 (yield: 61%). The produced compound was confirmed by using LC-MS.

C$_{28}$H$_{17}$Br: M$^+$ 432.1

Synthesis of Compound 38

3.42 g of Compound 38 (yield: 87%) was obtained in the same manner used in Synthesis of Compound 1, except that Intermediate I-12 was used instead of Intermediate I-4, and Intermediate I-14 instead of 1-bromopyrene in the synthesis of Compound 1. The produced compound was confirmed by using MS/FAB and $^1$H NMR.

C$_{49}$H$_{28}$N$_2$ cal. 644.23, found 644.19.

δ=8.12-8.10 (m, 1H), 8.09-8.08 (m, 1H), 8.07-8.06 (m, 1H), 8.05-8.04 (m, 1H), 8.03-8.02 (m, 2H), 8.01-8.00 (m, 1H), 7.99-7.97 (m, 2H), 7.92-7.91 (m, 1H), 7.90-7.89 (m, 1H), 7.88-7.86 (m, 1H), 7.83-7.82 (m, 1H), 7.80-7.79 (m, 1H), 7.65-7.63 (m, 2H), 7.62-7.59 (m, 4H), 7.52-7.49 (m, 3H), 7.48-7.47 (m, 1H), 7.41-7.35 (m, 4H)

Synthesis Example 5

Synthesis of Compound 72

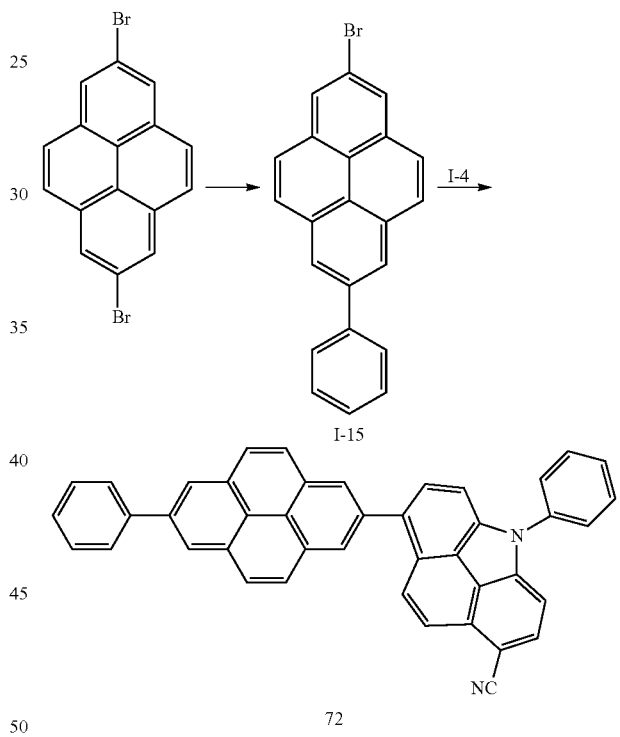

Synthesis of Intermediate I-15

2.39 g of Intermediate I-15 (yield: 67%) was obtained in the same manner used in Synthesis of Intermediate I-5, except that 2,7-dibromopyrene was used instead of 1,6-dibromopyrene, and phenylboronic acid instead of 2-pyridineboronic acid in the synthesis of Intermediate I-5. The produced compound was confirmed by using LC-MS.

C$_{22}$H$_{13}$Br: M$^+$ 356.0

Synthesis of Compound 72

3.08 g of Compound 72 (yield: 81%) was obtained in the same manner used in Synthesis of Compound 1, except that Intermediate I-15 was used instead of 1-bromopyrene, in the synthesis of Compound 1. The produced compound was confirmed by using MS/FAB and $^1$H NMR.

$C_{43}H_{24}N_2$ cal. 568.19, found 568.22.

δ=8.29-8.28 (m, 2H), 8.27-8.26 (m, 2H), 8.16 (d, 1H), 8.07 (d, 1H), 7.98-7.96 (m, 4H), 7.78-7.73 (m, 3H), 7.59-7.57 (m, 1H), 7.56-7.53 (m, 1H), 7.52-7.49 (m, 3H), 7.47-7.42 (m, 4H), 7.40-7.36 (m, 2H)

Synthesis Example 6

Synthesis of Compound 130

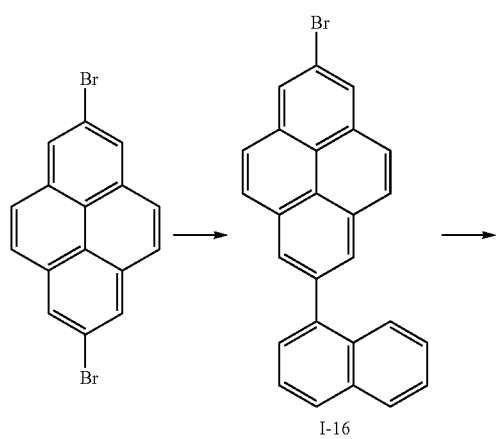

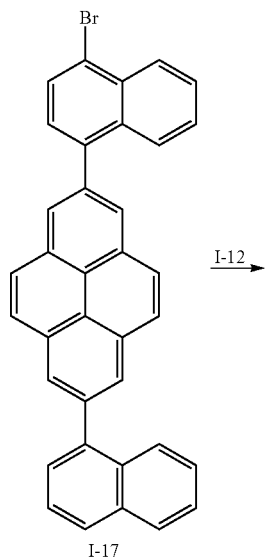

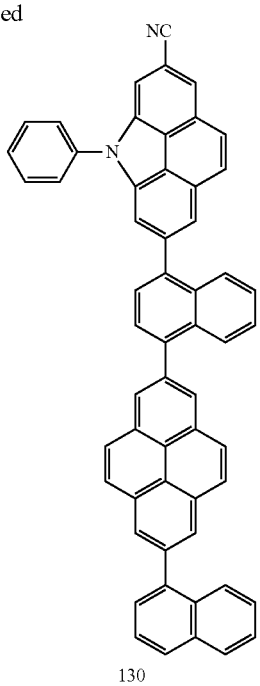

Synthesis of Intermediate I-16

2.65 g of Intermediate I-16 (yield: 65%) was obtained in the same manner used in Synthesis of Intermediate I-15, except that 1-naphthylboronic acid was used instead of phenylboronic acid, in the synthesis of Intermediate I-15. The produced compound was confirmed by using LC-MS.

$C_{26}H_{15}Br$: M$^+$ 406.0

Synthesis of Intermediate I-17

3.20 g of Intermediate I-17 (yield: 60%) was obtained in the same manner used in Synthesis of Intermediate I-14, except that 4-bromonaphthylboronic acid was used instead of 4-bromophenylboronic acid and Intermediate I-14 instead of Intermediate I-13, in the synthesis of Intermediate I-14. The produced compound was confirmed by using LC-MS.

$C_{36}H_{21}Br$: M$^+$ 532.1

Synthesis of Compound 130

3.84 g of Compound 130 (yield: 86%) was obtained in the same manner used in Synthesis of Compound 1, except that Intermediate I-12 was used instead of Intermediate I-4 and Intermediate I-17 instead of 1-bromopyrene, in the synthesis of Compound 1. The produced compound was confirmed by using MS/FAB and $^1$H NMR.

$C_{57}H_{32}N_2$ cal. 744.26, found 744.28.

δ=8.31-8.26 (m, 5H), 8.18-8.17 (m, 1H), 8.09-8.08 (m, 1H), 8.03-8.02 (m, 5H), 7.92-7.88 (m, 1H), 7.86-7.83 (m, 3H), 7.77-7.74 (m, 2H), 7.65-7.58 (m, 3H), 7.51-7.47 (m, 3H), 7.44-7.42 (m, 2H), 7.40-7.35 (m, 2H), 7.25-7.21 (m, 1H), 7.18-7.15 (m, 1H), 7.06-7.02 (m, 2H)

A synthesis method same with the synthesis pathways above and an appropriate intermediate material were used to synthesize additional compounds, and their $^1$H NMR and MS/FAB results are shown in Table 1.

Compounds other than those shown in Table 1 may be easily recognized to one of ordinary skill in the art in view of the synthesis method by referring to the synthesis pathways and the raw material.

TABLE 1

| Compound | ¹H NMR (CDCl₃, 400 MHz) | MS/FAB found | MS/FAB calc. |
|---|---|---|---|
| 1 | δ = 8.21-8.19 (m, 1H), 8.13-8.12 (m, 1H), 8.11-8.10 (m, 1H), 8.09-8.08 (m, 2H), 8.06-8.05 (m, 2H), 8.02-7.99 (m, 2H), 7.87-7.85 (m, 1H), 7.71-7.69 (m, 1H), 7.66-7.64 (m, 1H), 7.55-7.49 (m, 4H), 7.47 (d, 1H), 7.42 (d, 1H), 7.40-7.36 (m, 2H) | 492.21 | 492.16 |
| 3 | δ = 8.40-8.38 (m, 1H), 8.35 (d, 1H), 8.24 (d, 1H), 8.09-8.06 (m, 2H), 8.04-8.02 (m, 2H), 7.99-7.93 (m, 2H), 7.86-7.82 (tt, 1H), 7.76-7.73 (m, 1H), 7.71-7.66 (m, 3H), 7.55-7.48 (m, 4H), 7.46-7.41 (m, 2H), 7.40-7.35 (m, 2H), 7.25-7.22 (m, 1H) | 569.23 | 569.19 |
| 6 | δ = 8.41 (d, 1H), 8.27 (d, 1H), 8.19-8.16 (m, 2H), 8.12-8.10 (m, 1H), 8.08-8.05 (m, 2H), 8.02-8.01 (m, 1H), 7.99-7.96 (m, 1H), 7.92 (d, 1H), 7.81 (d, 1H), 7.79-7.74 (m, 2H), 7.73-7.70 (m, 2H), 7.66-7.64 (m, 1H), 7.55-7.51 (m, 4H), 7.50-7.47 (m, 3H), 7.43-7.35 (m, 4H) | 645.18 | 645.22 |
| 13 | δ = 8.30-8.28 (m, 1H), 8.21-8.20 (m, 1H), 8.16-8.13 (m, 2H), 8.09-8.07 (m, 1H), 8.05-8.04 (m, 1H), 8.03-8.02 (m, 2H), 7.99-7.98 (m, 2H), 7.91-7.89 (m, 1H), 7.82-7.80 (m, 1H), 7.65-7.64 (m, 1H), 7.62-7.60 (m, 2H), 7.59-7.58 (m, 1H), 7.52-7.51 (m, 1H), 7.50-7.49 (m, 1H), 7.48-7.47 (m, 2H), 7.42-7.36 (m, 4H) | 568.22 | 568.19 |
| 16 | δ = 8.32-8.30 (m, 1H), 8.21-8.20 (m, 1H), 8.15-8.12 (m, 3H), 8.08-8.06 (m, 1H), 8.04-8.03 (m, 2H), 8.01-7.99 (m, 1H), 7.92-7.91 (m, 1H), 7.90-7.88 (m, 3H), 7.84-7.82 (m, 2H), 7.76-7.74 (m, 1H), 7.64-7.61 (m, 1H), 7.60-7.57 (m, 3H), 7.56-7.53 (dd, 1H), 7.50-7.47 (m, 2H), 7.41-7.36 (m, 3H) | 618.25 | 618.21 |
| 22 | δ = 8.47-8.45 (d, 1H), 8.42-8.41 (m, 2H), 8.40-8.39 (m, 2H), 8.25-8.23 (m, 1H), 8.20-8.19 (m, 2H), 8.17-8.15 (m, 2H), 8.14-8.11 (m, 3H), 8.08-8.07 (m, 1H), 8.03 (d, 1H), 7.68-7.62 (m, 7H), 7.53-7.49 (m, 2H), 7.45 (t, 1H), 7.42-7.38 (m, 4H) | 723.21 | 723.24 |
| 25 | δ = 8.33-8.31 (m, 1H), 8.30-8.28 (m, 1H), 8.15-8.12 (m, 3H), 8.07-8.05 (m, 1H), 8.04-8.03 (m, 1H), 8.01-8.00 (m, 1H), 7.92-7.91 (m, 2H), 7.90-7.85 (m, 3H), 7.84-7.81 (m, 2H), 7.75-7.70 (m, 2H), 7.61-7.57 (m, 1H), 7.56-7.55 (m, 2H), 7.54-7.53 (m, 1H), 7.49-7.46 (m, 2H), 7.42 (d, 1H), 7.40-7.36 (m, 2H) | 618.18 | 618.21 |
| 29 | δ = 8.12-8.10 (m, 1H), 8.07 (d, 1H), 8.01-7.99 (m, 3H), 7.95-7.92 (m, 1H), 7.87-7.85 (m, 1H), 7.83-7.80 (m, 3H), 7.79-7.78 (m, 1H), 7.74-7.72 (m, 3H), 7.68-7.66 (m, 1H), 7.65-7.64 (m, 1H), 7.62-7.58 (m, 3H), 7.55-7.53 (m, 1H), 7.52-7.45 (m, 6H), 7.42 (d, 1H), 7.40-7.38 (m, 1H), 7.30-7.26 (tt, 1H), 7.04-7.00 (tt, 1H) | 694.27 | 694.24 |
| 32 | δ = 8.41 (d, 1H), 8.32-8.29 (m, 2H), 8.12-8.08 (m, 2H), 8.07-8.00 (m, 4H), 7.93-7.92 (m, 1H), 7.91-7.87 (m, 3H), 7.82-7.78 (m, 2H), 7.75-7.73 (m, 2H), 7.72-7.70 (m, 3H), 7.67-7.65 (m, 1H), 7.61-7.59 (m, 1H), 7.56-7.47 (m, 6H), 7.42 (d, 1H), 7.40-7.35 (m, 1H) | 722.21 | 722.25 |
| 38 | δ = 8.12-8.10 (m, 1H), 8.09-8.08 (m, 1H), 8.07-8.06 (m, 1H), 8.05-8.04 (m, 1H), 8.03-8.02 (m, 2H), 8.01-8.00 (m, 1H), 7.99-7.97 (m, 2H), 7.92-7.91 (m, 1H), 7.90-7.89 (m, 1H), 7.88-7.86 (m, 1H), 7.83-7.82 (m, 1H), 7.80-7.79 (m, 1H), 7.65-7.63 (m, 2H), 7.62-7.59 (m, 4H), 7.52-7.49 (m, 3H), 7.48-7.47 (m, 1H), 7.41-7.35 (m, 4H) | 644.19 | 644.23 |
| 42 | δ = 8.41 (d, 1H), 8.20-8.19 (m, 1H), 8.18-8.16 (m, 1H), 8.12-8.10 (m, 1H), 8.09-8.07 (m, 1H), 8.06-8.05 (m, 2H), 8.03-8.00 (m, 2H), 7.93-7.91 (m, 2H), 7.90-7.85 (m, 4H), 7.81 (d, 1H), 7.79-7.76 (m, 1H), 7.73-7.70 (m, 1H), 7.66-7.63 (m, 3H), 7.62-7.58 (m, 3H), 7.51-7.47 (m, 4H), 7.42-7.35 (m, 3H) | 725.22 | 721.25 |
| 45 | δ = 8.36-8.35 (dd, 1H), 8.34-8.33 (dd, 1H), 8.29 (d, 2H), 8.22 (t, 1H), 8.16-8.14 (m, 1H), 8.11-8.09 (m, 1H), 8.07-8.05 (m, 2H), 8.03-7.99 (m, 3H), 7.93-7.82 (m, 6H), 7.82-7.80 (m, 1H), 7.73-7.70 (m, 4H), 7.64-7.63 (m, 2H), 7.62-7.58 (m, 3H), 7.51-7.47 (m, 2H), 7.40-7.35 (m, 2H), 7.30-7.26 (m, 2H) | 798.33 | 798.28 |
| 49 | δ = 8.16-8.15 (m, 1H), 8.14-8.12 (m, 1H), 8.11-8.10 (m, 1H), 8.08-8.06 (m, 1H), 8.05-8.03 (m, 1H), 8.02-8.01 (m, 1H), 7.99-7.98 (m, 1H), 7.93-7.91 (m, 2H), 7.90-7.89 (m, 2H), 7.88-7.87 (m, 2H), 7.86-7.85 (m, 1H), 7.83-7.82 (m, 2H), 7.81-7.79 (m, 2H), 7.77-7.76 (m, 1H), 7.68-7.65 (m, 1H), 7.62-7.61 (m, 1H), 7.60-7.57 (m, 2H), 7.56-7.55 (m, 1H), 7.54-7.53 (m, 1H), 7.49-7.46 (m, 2H), 7.44-7.41 (m, 1H), 7.40-7.36 (m, 1H), 7.35-7.34 (dd, 1H) | 694.27 | 694.24 |

TABLE 1-continued

| Compound | $^1$H NMR (CDCl$_3$, 400 MHz) | MS/FAB found | MS/FAB calc. |
|---|---|---|---|
| 51 | δ = 8.19-8.18 (tt, 1H), 8.09-8.08 (m, 1H), 8.06-8.05 (m, 1H), 8.03-7.99 (m, 4H), 7.94-7.89 (m, 2H), 7.86-7.83 (m, 1H), 7.81-7.79 (m, 1H), 7.77-7.76 (m, 1H), 7.75-7.73 (m, 1H), 7.70-7.67 (m, 2H), 7.65-7.64 (m, 1H), 7.62-7.50 (m, 2H), 7.56-7.53 (m, 2H), 7.52-7.51 (m, 3H), 7.50-7.48 (m, 2H), 7.47-7.45 (m, 1H), 7.43-7.41 (m, 1H), 7.40-7.35 (m, 1H), 7.30-7.26 (m, 1H), 7.05-7.01 (m, 1H) | 694.27 | 694.24 |
| 55 | δ = 8.45-8.43 (m, 1H), 8.30-8.28 (m, 1H), 8.27-8.26 (m, 1H), 8.23-22 (m, 1H), 8.13-8.11 (m, 1H), 8.08-8.06 (m, 2H), 8.04-8.03 (m, 2H), 8.01-7.99 (m, 3H), 7.97-7.94 (m, 1H), 7.93-7.89 (m, 2H), 7.88-7.83 (m, 3H), 7.76-7.74 (m, 1H), 7.59-7.56 (m, 1H), 7.75-7.48 (m, 6H), 7.43-7.36 (m, 3H) | 695.21 | 695.24 |
| 61 | δ = 8.53 (d, 1H), 8.39 (d, 1H), 8.15-8.14 (m, 1H), 8.13-8.11 (m, 3H), 8.10-8.07 (m, 3H), 8.03-8.02 (m, 2H), 8.01-7.99 (m, 2H), 7.95-7.93 (dd, 1H), 7.64-7.58 (m, 4H), 7.50-7.47 (m, 2H), 7.45-7.43 (m, 1H), 7.40-7.35 (m, 2H) | 569.21 | 569.19 |
| 67 | δ = 8.40-8.39 (m, 1H), 8.33-8.31 (m, 3H), 8.30-8.28 (m, 2H), 8.23-8.21 (m, 3H), 8.17-8.16 (m, 1H), 8.11-8.07 (m, 4H), 8.03-8.00 (m, 3H), 7.97-7.93 (m, 3H), 7.85-7.83 (m, 1H), 7.76-7.74 (m, 1H), 7.64-7.59 (m, 3H), 7.53-7.52 (m, 1H), 7.51-7.47 (m, 5H), 7.43 (d, 1H), 7.40-7.35 (m, 2H), 7.31-7.27 (m, 2H) | 848.25 | 848.29 |
| 70 | δ = 8.47-8.45 (m, 1H), 8.31-8.29 (m, 1H), 8.23-8.21 (m, 2H), 8.20-8.19 (m, 1H), 8.13-8.11 (m, 1H), 8.10-8.09 (m, 1H), 8.08-8.06 (m, 2H), 8.05-8.04 (m, 1H), 8.03-8.00 (m, 2H), 7.96-7.89 (m, 3H), 7.86-7.85 (m, 1H), 7.84-7.81 (m, 2H), 7.79-7.75 (m, 2H), 7.66-7.64 (m, 1H), 7.58-7.53 (m, 2H), 7.49-7.46 (m, 2H), 7.44-7.43 (m, 1H), 7.41-7.35 (m, 3H) | 695.27 | 695.24 |
| 72 | δ = 8.29-8.28 (m, 2H), 8.27-8.26 (m, 2H), 8.16 (d, 1H), 8.07 (d, 1H), 7.98-7.96 (m, 4H), 7.78-7.73 (m, 3H), 7.59-7.57 (m, 1H), 7.56-7.53 (m, 1H), 7.52-7.49 (m, 3H), 7.47-7.42 (m, 4H), 7.40-7.36 (m, 2H) | 568.22 | 568.19 |
| 75 | δ = 8.31-8.30 (m, 2H), 8.27-8.26 (m, 2H), 8.24-8.23 (m, 1H), 8.17-8.15 (m, 1H), 8.07 (d, 1H), 8.02-8.01 (m, 1H), 8.00-7.98 (m, 4H), 7.97-7.95 (m, 1H), 7.94-7.92 (m, 1H), 7.87-7.85 (m, 1H), 7.76 (d, 1H), 7.62-7.59 (m, 1H), 7.58-7.57 (m, 1H), 7.56-7.53 (m, 2H), 7.52-7.47 (m, 4H), 7.42 (d, 1H), 7.40-7.35 (m, 1H) | 618.18 | 618.21 |
| 79 | δ = 8.39-8.37 (m, 2H), 8.29-8.27 (m, 3H), 8.25-8.24 (m, 2H), 8.20-8.19 (m, 2H), 8.14-8.13 (m, 1H), 8.07 (d, 1H), 8.02-7.99 (m, 2H), 7.78-7.75 (m, 1H), 7.73-7.70 (m, 4H), 7.59-7.57 (m, 1H), 7.54-7.48 (m, 5H), 7.43 (d, 1H), 7.40-7.37 (m, 1H), 7.31-7.28 (m, 2H) | 722.19 | 722.25 |
| 84 | δ = 8.56-8.54 (m, 1H), 8.42-8.40 (m, 1H), 8.29-8.28 (m, 2H), 8.20-8.19 (m, 1H), 8.17-8.16 (m, 2H), 8.09-8.08 (m, 1H), 8.06-8.03 (m, 2H), 8.01-7.99 (m, 4H), 7.64-7.58 (m, 3H), 7.50-7.43 (m, 4H), 7.41-7.35 (m, 2H) | 569.22 | 569.19 |
| 89 | δ = 8.56-8.54 (dd, 1H), 8.42-8.41 (m, 2H), 8.36-8.34 (m, 1H), 8.30-8.29 (m, 1H), 8.28-8.27 (m, 2H), 8.20-8.18 (dd, 1H), 8.12-8.10 (dd, 1H), 8.09-8.08 (m, 1H), 8.03 (d, 1H), 8.01-7.99 (m, 2H), 7.94-7.92 (m, 2H), 7.84-7.81 (m, 2H), 7.73-7.71 (m, 2H), 7.64-7.58 (m, 4H), 7.50-7.36 (m, 6H) | 695.22 | 695.24 |
| 100 | δ = 8.52-8.51 (m, 2H), 8.32-8.31 (m, 2H), 8.22-8.21 (m, 1H), 8.19-8.18 (m, 1H), 8.14-8.11 (m, 2H), 8.08-8.06 (m, 1H), 8.02-8.01 (m, 1H), 7.99-7.98 (m, 1H), 7.90-7.84 (m, 5H), 7.74-7.65 (m, 4H), 7.56-7.47 (m, 8H), 7.43-7.35 (m, 3H) | 721.24 | 721.25 |
| 106 | δ = 8.29-8.28 (m, 2H), 8.24-8.23 (m, 1H), 8.21-8.20 (m, 1H), 8.09-8.08 (m, 2H), 8.06-8.05 (m, 2H), 8.03-8.00 (m, 2H), 7.94-7.91 (m, 2H), 7.90-7.87 (m, 2H), 7.84-7.83 (m, 1H), 7.82-7.81 (m, 1H), 7.63-7.58 (m, 4H), 7.51-7.47 (m, 2H), 7.40-7.34 (m, 2H) | 568.20 | 568.19 |
| 116 | δ = 8.50-8.49 (m, 2H), 8.45-8.44 (m, 2H), 8.43-8.42 (m, 2H), 8.34-8.33 (m, 1H), 8.32-8.31 (m, 1H), 8.26-8.25 (m, 2H), 8.18-8.16 (m, 2H), 8.09-8.08 (m, 1H), 8.07-8.06 (m, 1H), 8.03 (d, 1H), 7.94-7.86 (m, 4H), 7.63-7.58 (m, 8H), 7.51-7.47 (m, 2H), 7.42-7.34 (m, 4H) | 799.28 | 799.27 |
| 121 | δ = 8.65-8.64 (dd, 1H), 8.42-8.41 (m, 2H), 8.28-8.27 (m, 2H), 8.19-8.14 (m, 3H), 8.11-8.06 (m, 2H), 8.01-7.99 (m, 2H), 7.96-7.94 (m, 1H), 7.78-7.74 (m, 3H), 7.68-7.66 (m, 1H), 7.60-7.57 (m, 1H), 7.54-7.38 (m, 9H) | 645.23 | 645.22 |
| 130 | δ = 8.31-8.26 (m, 5H), 8.18-8.17 (m, 1H), 8.09-8.08 (m, 1H), 8.03-8.02 (m, 5H), 7.92-7.88 (m, 1H), 7.86-7.83 (m, 3H), 7.77-7.74 (m, 2H), 7.65-7.58 (m, 3H), 7.51-7.47 (m, 3H), 7.44-7.42 (m, 2H), 7.40-7.35 (m, 2H), 7.25-7.21 (m, 1H), 7.18-7.15 (m, 1H), 7.06-7.02 (m, 2H) | 744.28 | 744.26 |

Example 1

A 15 Ω/cm$^2$ (1200 Å) ITO glass substrate (Corning), as an anode, was cut to a size of 50 mm×50 mm×0.7 mm, washed with ultrasonic waves in isopropyl alcohol and pure water for 5 minutes each, and then cleaned with UV for 30 minutes and exposed to ozone. The ITO glass substrate was mounted on a vacuum depositor.

2-TNATA was vacuum deposited on the ITO glass substrate to form a HIL having a thickness of 600 Å, and NPB was then deposited on the HIL to form a HTL having a thickness of 300 Å. Then, ADN (as a host) and DPAVBi (as a dopant) were co-deposited on the HTL at a weight ratio of 98:2 to form an EML having a thickness of 300 Å.

Compound 3 was deposited on the EML to form an ETL having a thickness of 300 Å, and LiF was deposited on the ETL to form an EIL having a thickness of 10 Å. Al was deposited on the EIL to form a cathode having a thickness of 3,000 Å, thereby completing manufacture of an OLED.

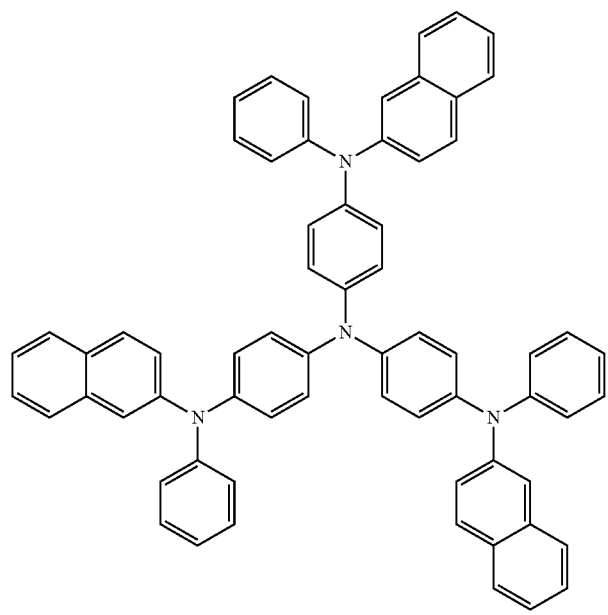

2-TNATA

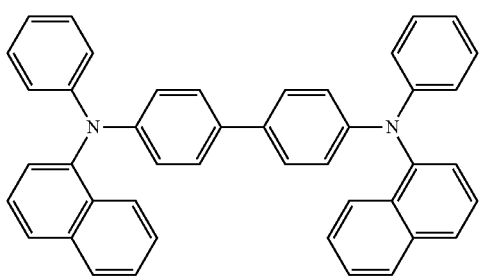

NPB

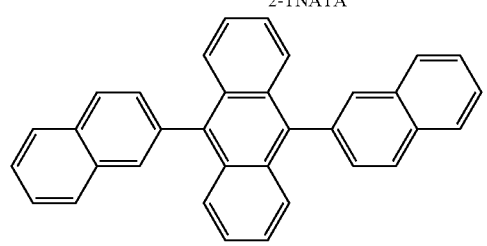

ADN

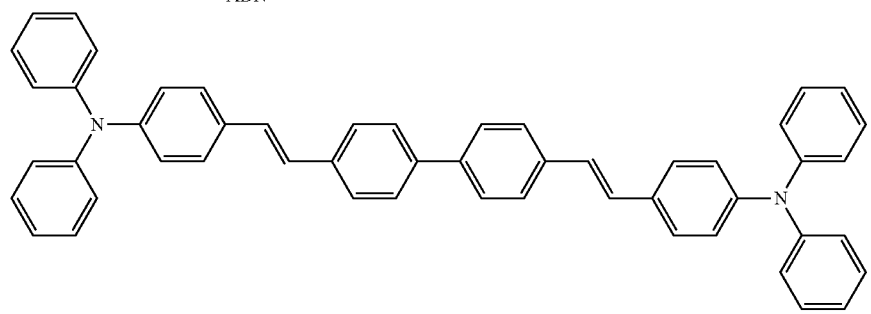

DPAVBi

Example 2

An OLED was manufactured in the same manner as in Example 1, except that Compound 16 was used instead of Compound 3 in the formation of the ETL.

Example 3

An OLED was manufactured in the same manner as in Example 1, except that Compound 38 was used instead of Compound 3 in the formation of the ETL.

Example 4

An OLED was manufactured in the same manner as in Example 1, except that Compound 51 was used instead of Compound 3 in the formation of the ETL.

Example 5

An OLED was manufactured in the same manner as in Example 1, except that Compound 72 was used instead of Compound 3 in the formation of the ETL.

Example 6

An OLED was manufactured in the same manner as in Example 1, except that Compound 89 was used instead of Compound 3 in the formation of the ETL.

Example 7

An OLED was manufactured in the same manner as in Example 1, except that Compound 130 was used instead of Compound 3 in the formation of the ETL.

Comparative Example 1

An OLED was manufactured in the same manner as in Example 1, except that Alq₃ was used instead of Compound 3 in the formation of the ETL.

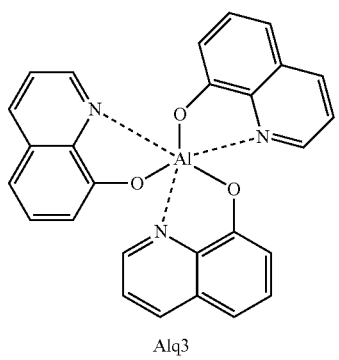

Alq3

Comparative Example 2

An OLED was manufactured in the same manner as in Example 1, except that Compound A was used instead of Compound 3 in the formation of the ETL.

<Compound A>

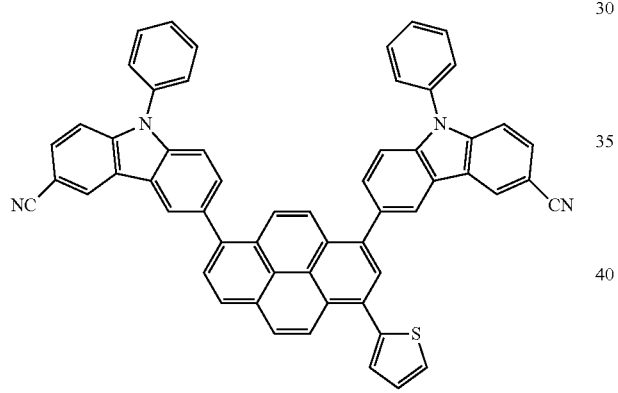

Comparative Example 3

An OLED was manufactured in the same manner as in Example 1, except that Compound B was used instead of Compound 3 in the formation of the ETL.

<Compound B>

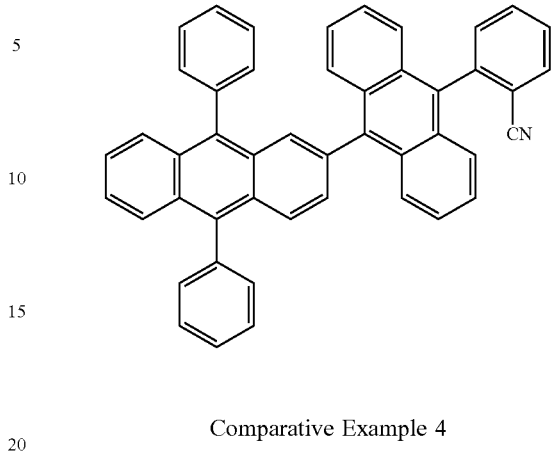

Comparative Example 4

An OLED was manufactured in the same manner as in Example 1, except that Compound C was used instead of Compound 3 in the formation of the ETL.

<Compound C>

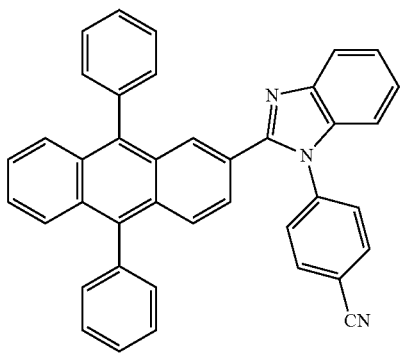 [SMILES: N#Cc1ccc(-n2c(-c3ccc4c(-c5ccccc5)c5ccccc5c(-c5ccccc5)c4c3)nc3ccccc32)cc1]

Evaluation Example 1

Driving voltage, current density, brightness, efficiency, and half-life of the OLEDs of Examples 1 to 7 and Comparative Examples 1 to 4 were evaluated using a current-voltmeter, Kethley SMU 236 and a brightness photometer, PR650, and the results are shown in Table 2 below. The half-life was time consumed for an OLED to have 50% reduced brightness compared to its initial brightness.

TABLE 2

|  | ETL | Driving voltage (V) | Current density (mA/cm²) | Brightness (cd/m²) | Efficiency (cd/A) | Color | Half-life (hr@ 100 mA/cm²) |
|---|---|---|---|---|---|---|---|
| Example 1 | Compound 3 | 5.52 | 50 | 3365 | 6.73 | Blue | 407 |
| Example 2 | Compound 16 | 5.26 | 50 | 3275 | 6.55 | Blue | 415 |
| Example 3 | Compound 38 | 5.38 | 50 | 3235 | 6.47 | Blue | 422 |
| Example 4 | Compound 51 | 5.61 | 50 | 3105 | 6.21 | Blue | 376 |
| Example 5 | Compound 72 | 5.18 | 50 | 3030 | 6.06 | Blue | 411 |
| Example 6 | Compound 89 | 5.31 | 50 | 3140 | 6.28 | Blue | 395 |
| Example 7 | Compound 130 | 5.26 | 50 | 3075 | 6.15 | Blue | 402 |
| Comparative Example 1 | Alq₃ | 7.35 | 50 | 2065 | 4.13 | Blue | 145 |

TABLE 2-continued

| | ETL | Driving voltage (V) | Current density (mA/cm$^2$) | Brightness (cd/m$^2$) | Efficiency (cd/A) | Color | Half-life (hr@ 100 mA/cm$^2$) |
|---|---|---|---|---|---|---|---|
| Comparative Example 2 | Compound A | 6.16 | 50 | 2770 | 5.54 | Blue | 324 |
| Comparative Example 3 | Compound B | 6.08 | 50 | 2555 | 5.11 | Blue | 228 |
| Comparative Example 4 | Compound C | 6.03 | 50 | 2640 | 5.28 | Blue | 263 |

Referring to Table 2, it was confirmed that the OLEDs of Examples 1 to 7 have better driving voltages, current densities, brightness, efficiency, and half-lives than the OLEDs of Comparative Examples 1 to 4.

As described above, according to the one or more of the above embodiments, an OLED including the pyrene-based compound may have high efficiency, low driving voltage, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:
1. A pyrene-based compound represented by Formula 1:

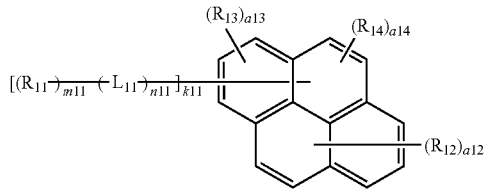

<Formula 1> wherein, in Formula 1,
$L_{11}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, and a substituted or unsubstituted non-aromatic condensed polycycle;
at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, and substituted non-aromatic condensed polycyclic group is selected from a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycycle; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycycle, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

n11 is an integer of 0 to 3;
m11 is an integer of 1 to 3;
$R_{11}$ is represented by one of Formulae 2-1 and 2-2;
k11 is an integer of 1 to 4;
$R_{12}$ to $R_{14}$ are each independently selected from
a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_1$-$C_{60}$ heteroaryl group, and a non-aromatic condensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycycle; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycycle, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a12 is an integer of 1 to 5;

a13 and a14 are each independently an integer of 1 to 3;

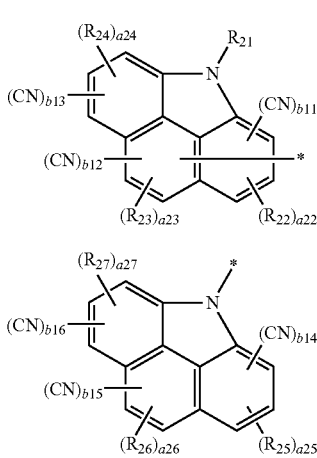

<Formula 2-1>

<Formula 2-2> wherein, in Formulae 2-1 and 2-2, $R_{21}$ to $R_{27}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a22 to a27 are each independently an integer of 0 to 3;

b11 to b16 are each independently an integer of 0 to 2;

the sum of b11, b12, and b13 is 1 or greater, and the sum of b14, b15, and b16 is 1 or greater; and

* is a binding site with $L_{11}$, or a pyrene ring in Formula 1.

2. The pyrene-based compound as claimed in claim 1, wherein $L_{11}$ is represented by Formulae 3-1 to 3-32:

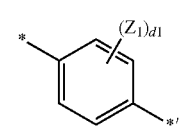

3-1

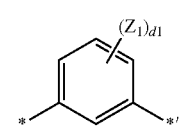

3-2

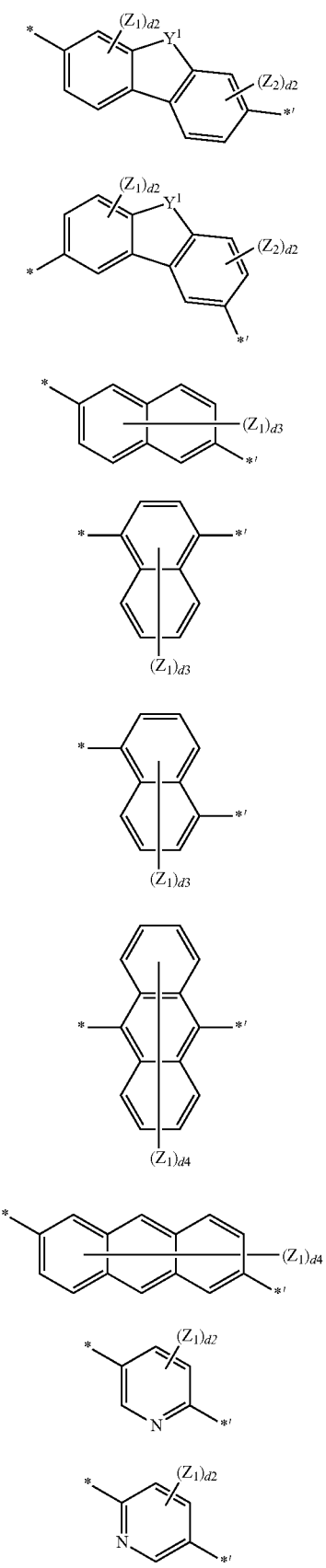
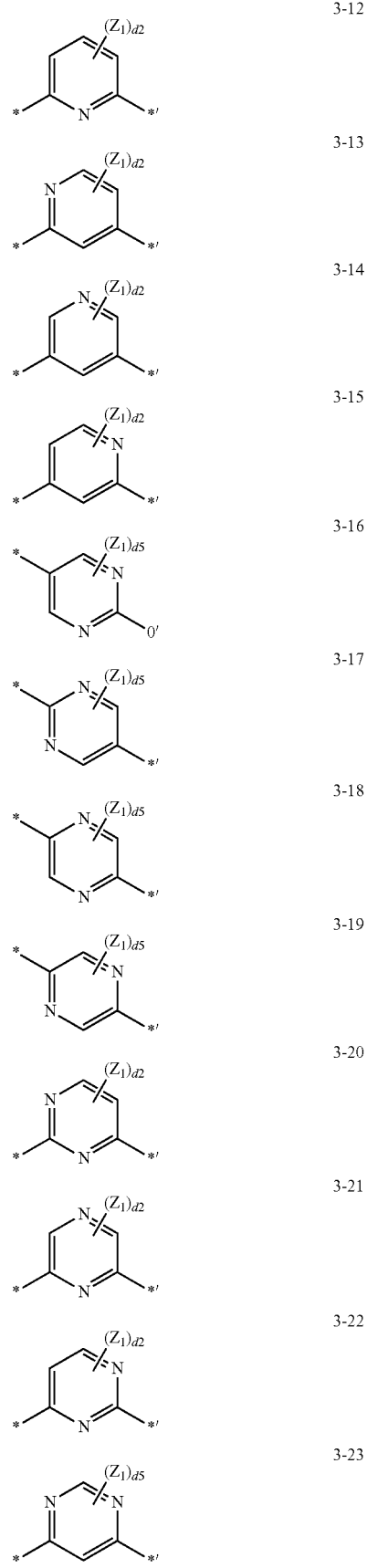

-continued

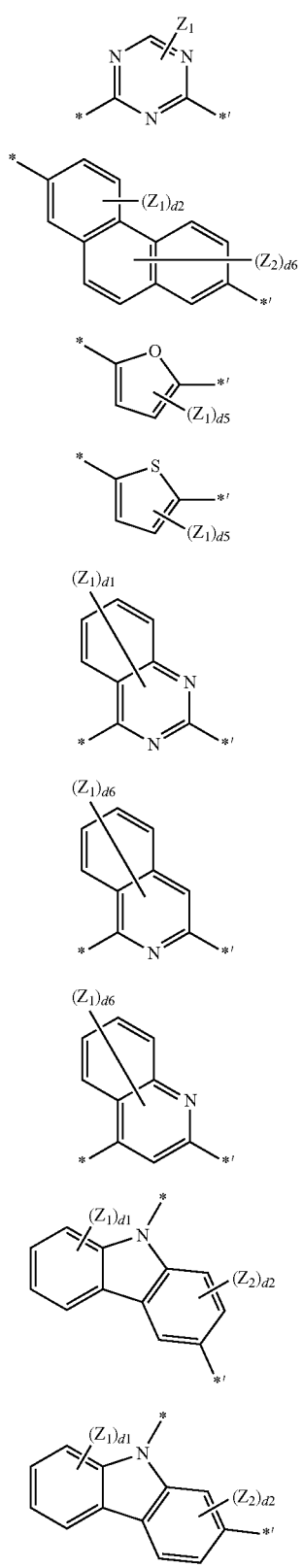

wherein, in Formulae 3-1 to 3-32,
* and *' represent a binding site with a pyrene ring, $R_{11}$ or another $L_{11}$ in Formula 1, $Y_1$ is selected from $C(Q_{31})(Q_{32})$, $N(Q_{33})$, an oxygen atom, a sulfur atom, and $Si(Q_{34})(Q_{35})$;

$Q_{31}$ to $Q_{35}$ are each independently selected from a hydrogen atom, a deuterium atom, a $C_1$-$C_{20}$ alkyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$Z_1$ and $Z_2$ are each independently selected from a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 is an integer of 1 to 4;
d2 is an integer of 1 to 3;
d3 is an integer of 1 to 6;
d4 is an integer of 1 to 8;
d5 is an integer of 1 or 2; and
d6 is an integer of 1 to 5.

3. The pyrene-based compound as claimed in claim 1, wherein $L_{11}$ is represented by Formulae 4-1 to 4-23:

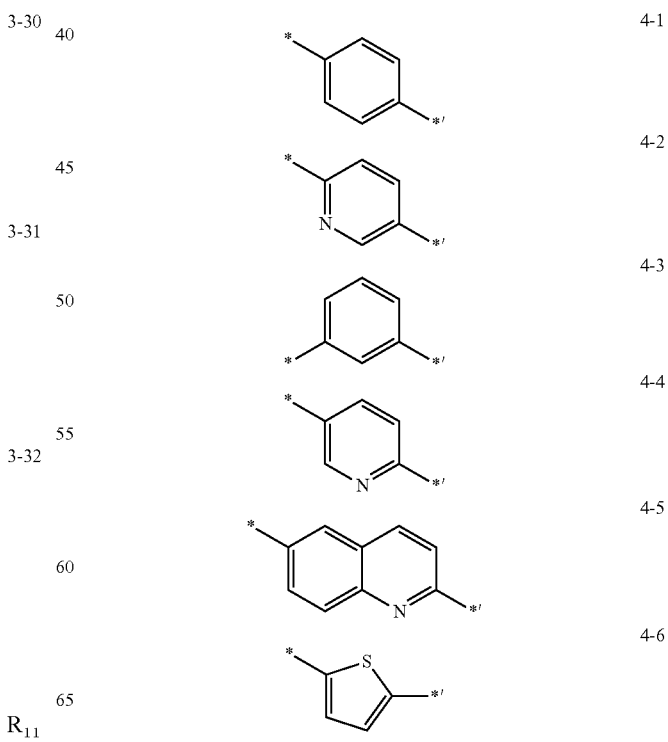

179
-continued
4-7
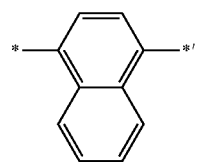
4-8
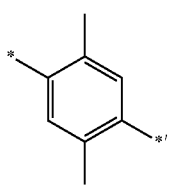
4-9
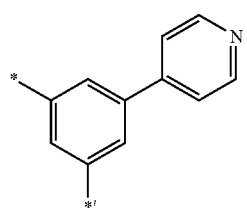
4-10
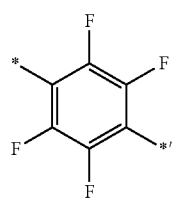
4-11
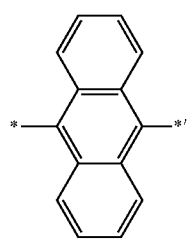
4-12
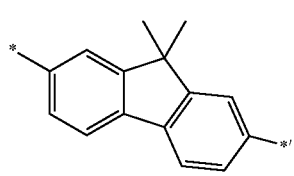
4-13
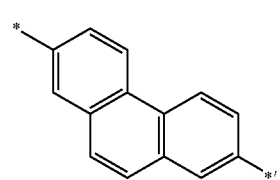
180
-continued
4-14
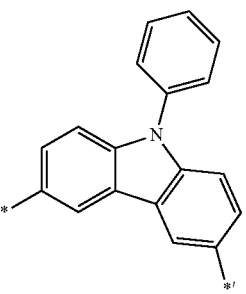
4-15
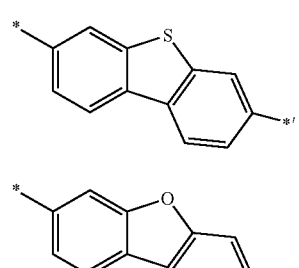
4-16
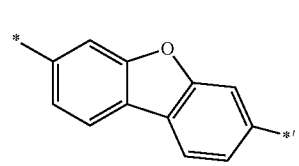
4-17
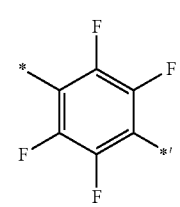
4-18
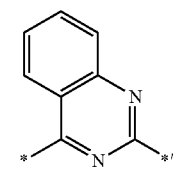
4-19
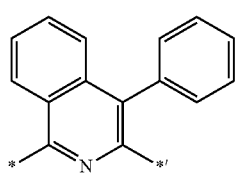
4-20
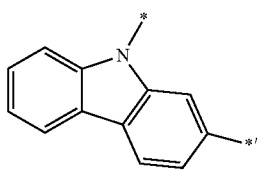
4-21

-continued 4-22

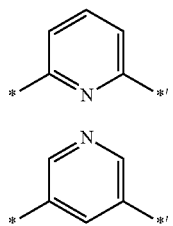

4-23 where * and *' represent a binding site with a pyrene ring, $R_{11}$ or another $L_{11}$ in Formula 1.

4. The pyrene-based compound as claimed in claim 1, wherein n11 and n12 each independently an integer of 0 or 1.

5. The pyrene-based compound as claimed in claim 1, wherein $R_{11}$ is represented by one of Formulae 2-1a and 2-2a:

<Formula 2-1a>
<Formula 2-2a>

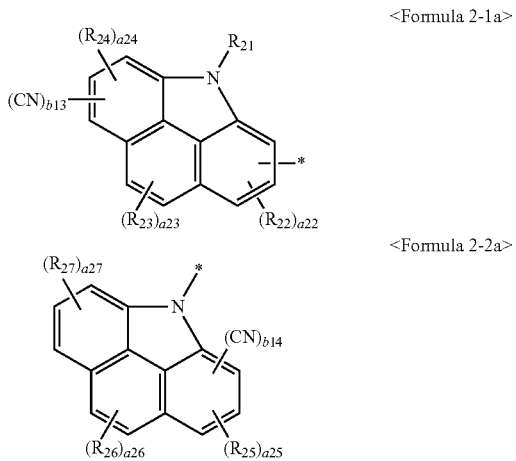

wherein, in Formulae 2-1a and 2-2a,
$R_{21}$ to $R_{27}$ are each independently selected from
a hydrogen atom, a deuterium atom, a halogen atom, a hydroxyl group, a cyano group, a nitro group, a $C_1$-$C_{60}$ alkyl group, and a $C_1$-$C_{60}$ alkoxy group;
a $C_1$-$C_{60}$ alkyl group and a $C_1$-$C_{60}$ alkoxy group, each substituted with at least one of a deuterium atom, a halogen atom, a hydroxyl group, a cyano group, a nitro group, a $C_6$-$C_{60}$ aryl group, a $C_2$-$C_{60}$ heteroaryl group, and a non-aromatic condensed polycyclic group;
a $C_6$-$C_{60}$ aryl group, a $C_2$-$C_{60}$ heteroaryl group, and a non-aromatic condensed polycyclic group; and
a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group;
a22 to a27 are each independently an integer of 0 to 3;
b13 and b14 are each independently an integer of 1 or 2; and
* is a binding site with $L_{11}$ or a pyrene ring in Formula 1.

6. The pyrene-based compound as claimed in claim 1, wherein $R_{11}$ is represented by one of Formula 2-1b:

<Formula 2-1b>

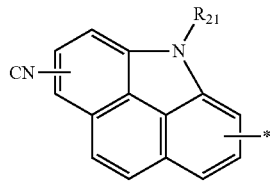

wherein, in Formula 2-1b,
$R_{21}$ is selected from
a $C_6$-$C_{60}$ aryl group, a $C_2$-$C_{60}$ heteroaryl group, and a non-aromatic condensed polycyclic group; and
a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group; and
* is a binding site with $L_{11}$ or a pyrene ring in Formula 1.

7. The pyrene-based compound as claimed in claim 1, wherein $R_{12}$ to $R_{14}$ are each independently selected from
a hydrogen atom, a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

8. The pyrene-based compound as claimed in claim 1, wherein $R_{12}$ to $R_{14}$ are each independently selected from a hydrogen atom, a deuterium atom, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, and a tert-butoxy group;

a phenyl group, a naphthyl group, a fluorenyl group, a benzofluorenyl group, an anthracenyl group, a pyrenyl group, a chrysenyl group, a pyridinyl group, a pyazinyl group, a pyrimidinyl group, a pyridazinyl group, a quinolinyl group, an isoquinolinyl group, a carbazolyl group, and a triazinyl group; and a phenyl group, a naphthyl group, a fluorenyl group, a benzofluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, and a triazinyl group, each substituted with at least one of a deuterium atom, a halogen atom, a cyano group, a nitro group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

9. The pyrene-based compound as claimed in claim 1, wherein $R_{12}$ is selected from a hydrogen atom, a deuterium atom, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, a tert-butoxy group, and one selected from Formulae 5-1 to 5-34;

5-1
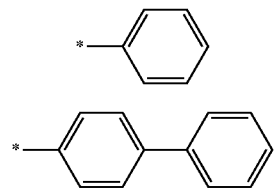

5-2
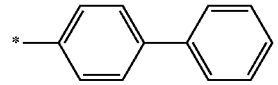

5-3
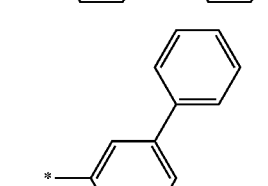

5-4
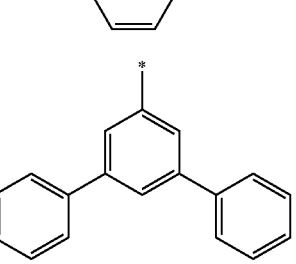

-continued 5-5
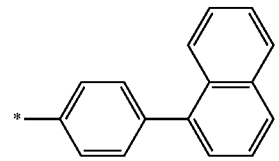

5-6
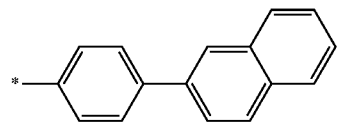

5-7
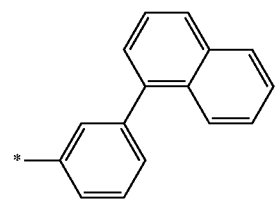

5-8
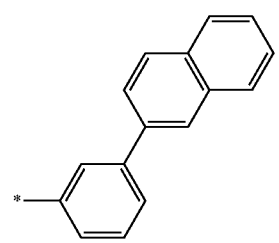

5-9
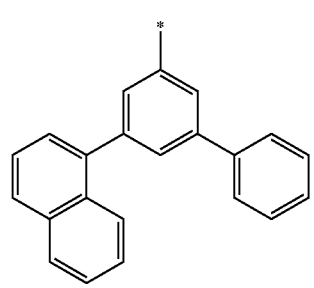

5-10
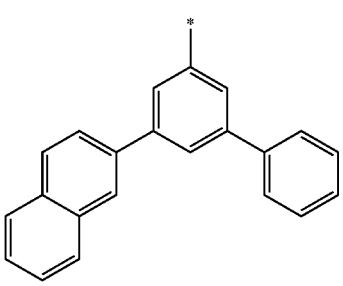

5-11
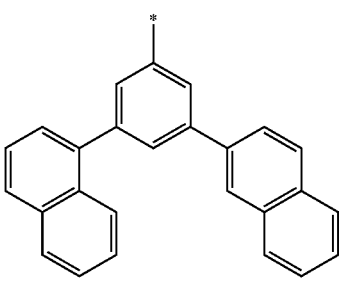

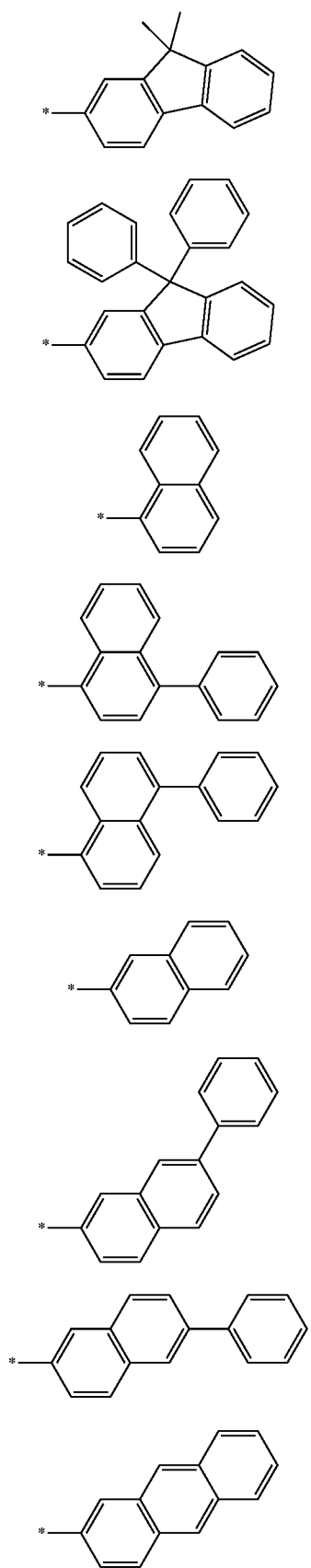
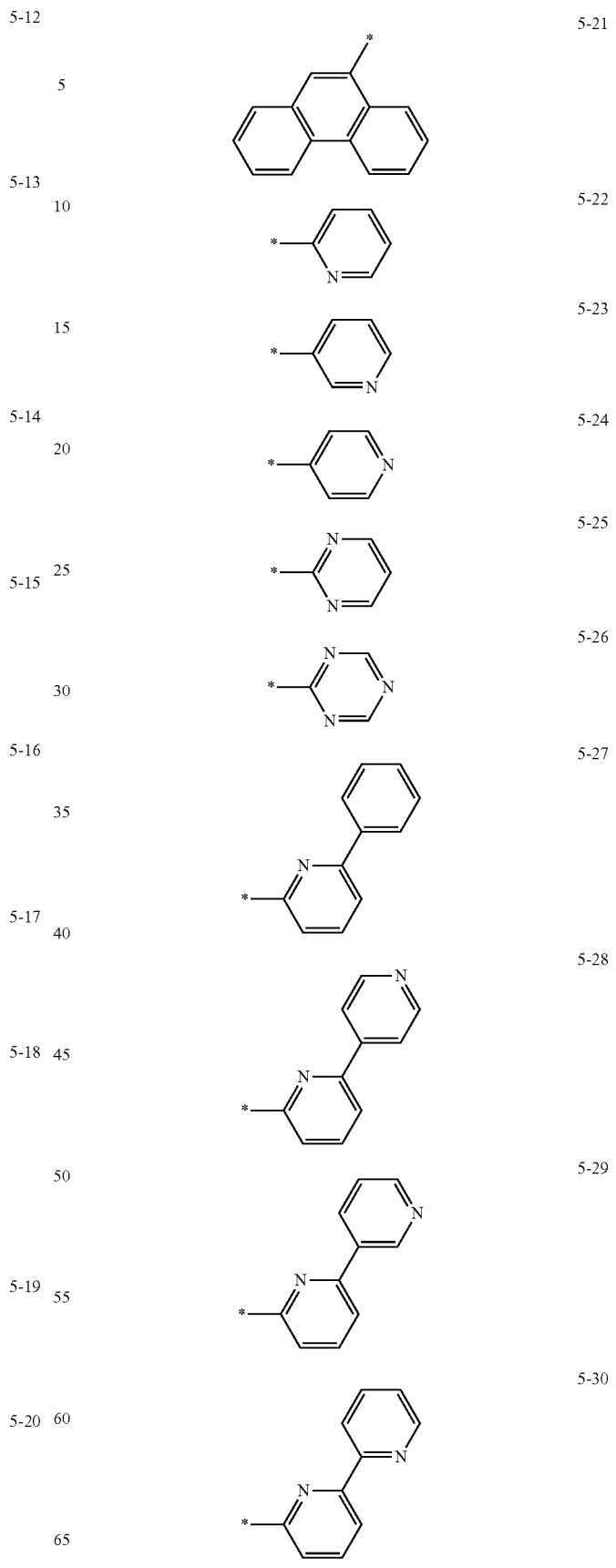

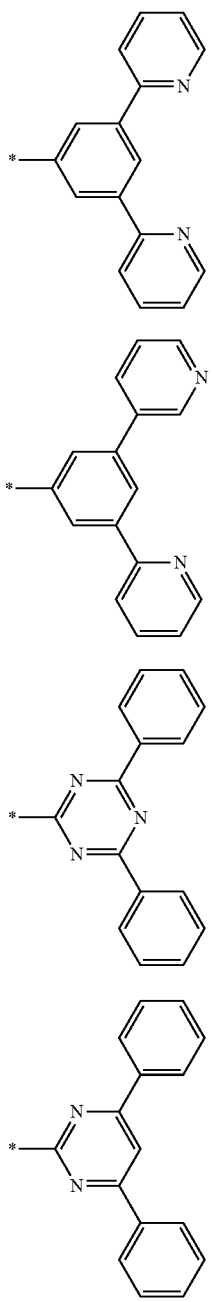

where * represents a binding site with a pyrene ring in Formula 1.

10. The pyrene-based compound as claimed in claim 1, wherein $R_{13}$ and $R_{14}$ are each independently selected from a hydrogen atom, a deuterium atom, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, and a tert-butoxy group.

11. The pyrene-based compound as claimed in claim 1, wherein a12 is 1.

12. The pyrene-based compound as claimed in claim 1 represented by one of Formulae 1-1 and 1-2:

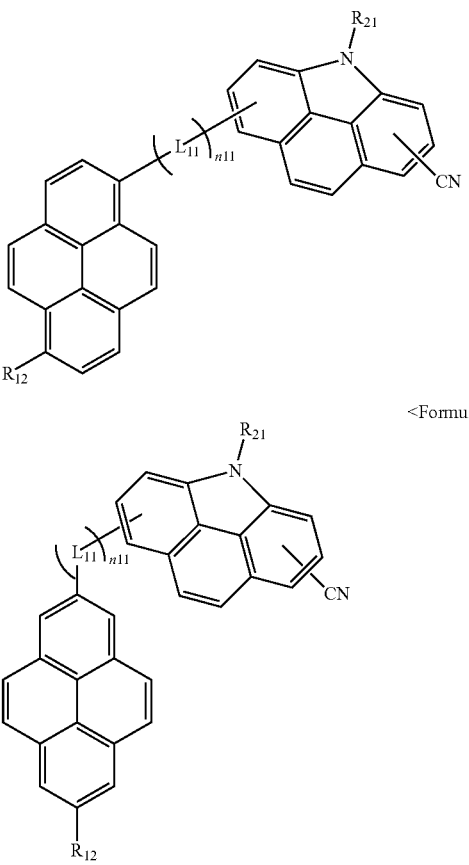

wherein, descriptions of $L_{11}$, n11, $R_{12}$, and $R_{21}$ are same as those described in claim 1.

13. The pyrene-based compound as claimed in claim 12, wherein $L_{11}$ is represented by one of Formulae 4-1 to 4-23; and n11 is an integer of 0 or 1:

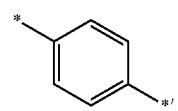

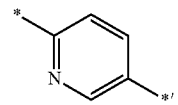

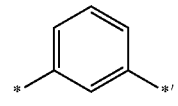

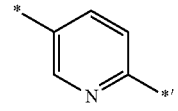

-continued
4-5
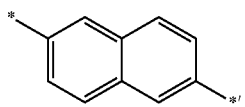
4-6
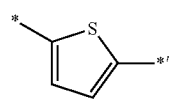
4-7
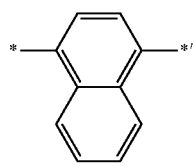
4-8
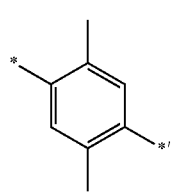
4-9
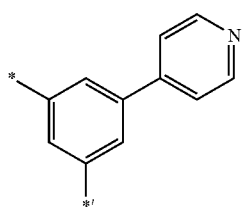
4-10
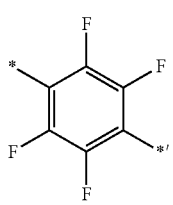
4-11
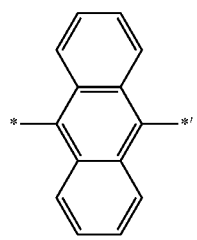
4-12
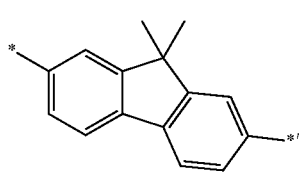
4-13
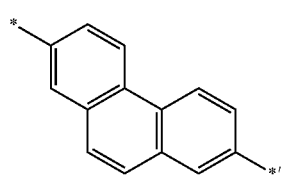
-continued
4-14
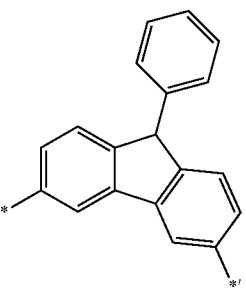
4-15
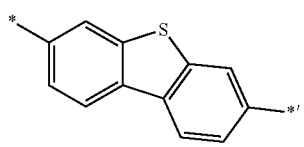
4-16
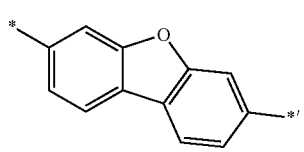
4-17
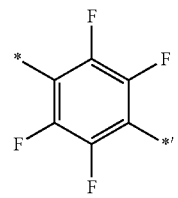
4-18
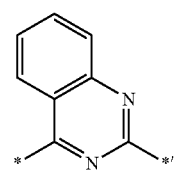
4-19
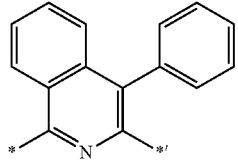
4-20
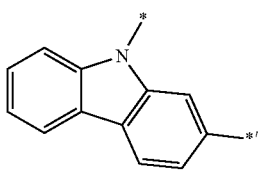
4-21
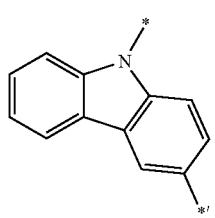

-continued

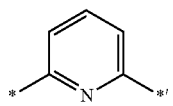
4-22

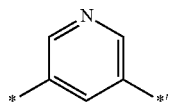
4-23 where * and *' represent a binding site with a pyrene ring, $R_{11}$ or another $L_{11}$ in Formula 1.

14. The pyrene-based compound as claimed in claim 12, wherein $R_{12}$ is selected from a hydrogen atom, a deuterium atom, a halogen atom, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, a tert-butoxy group, and Formulae 5-1 to 5-34:

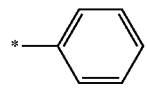
5-1

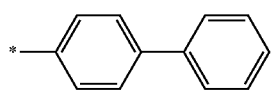
5-2

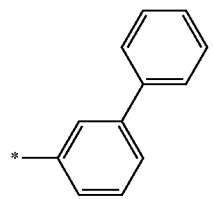
5-3

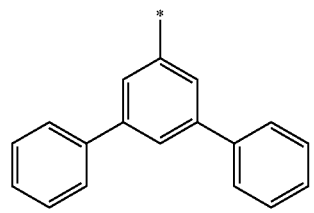
5-4

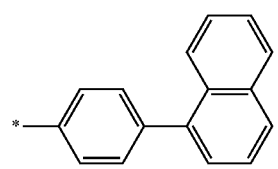
5-5

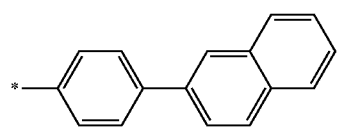
5-6

-continued

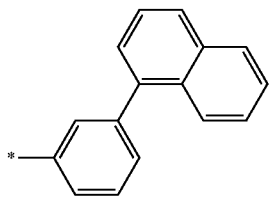
5-7

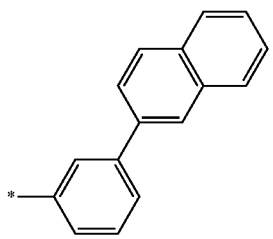
5-8

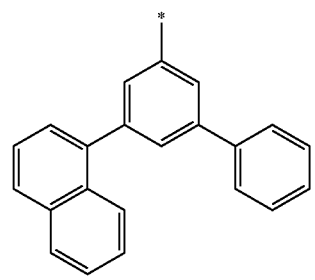
5-9

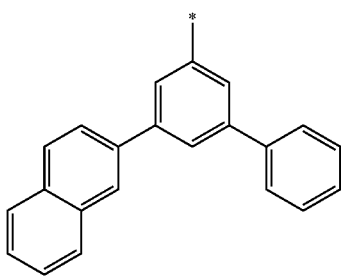
5-10

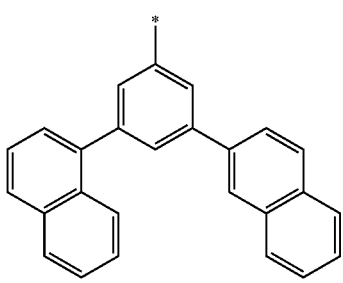
5-11

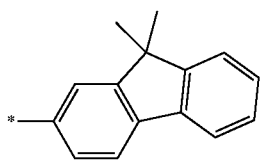
5-12

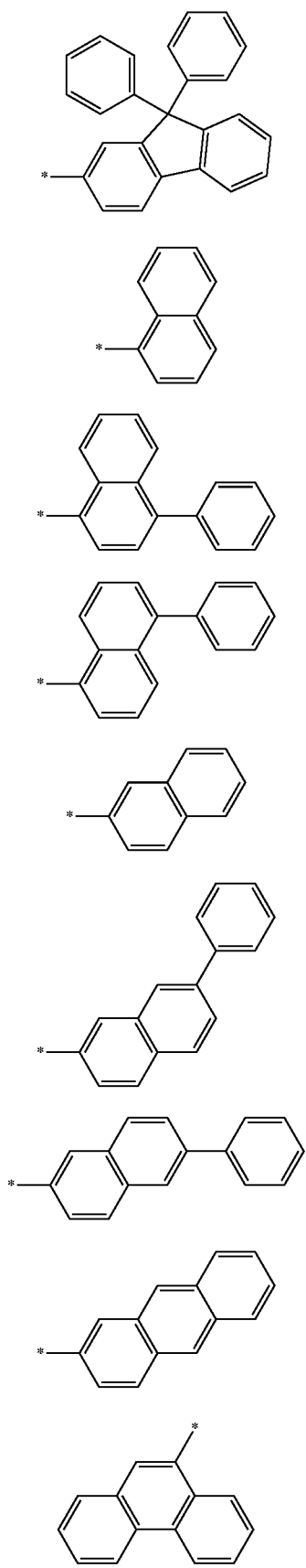
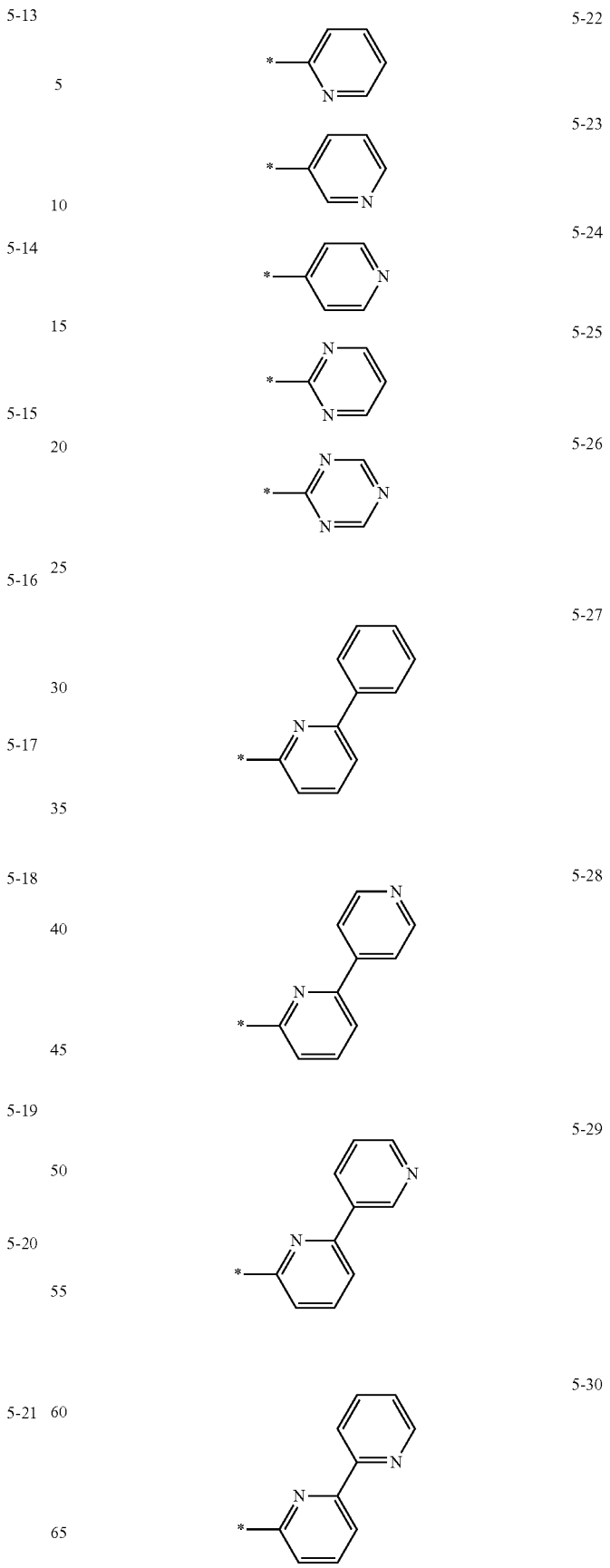

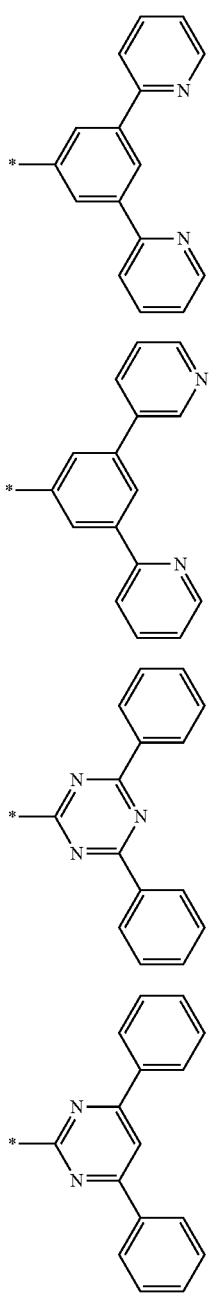

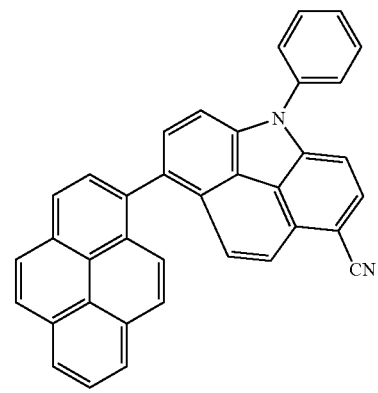

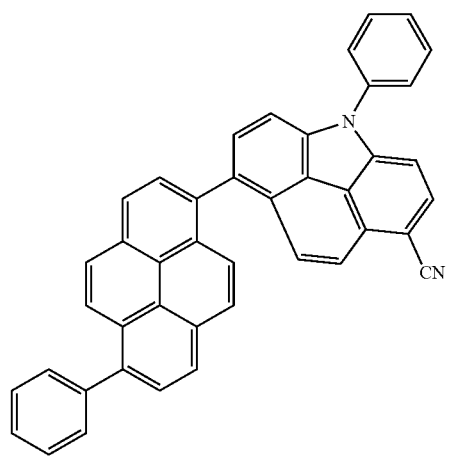

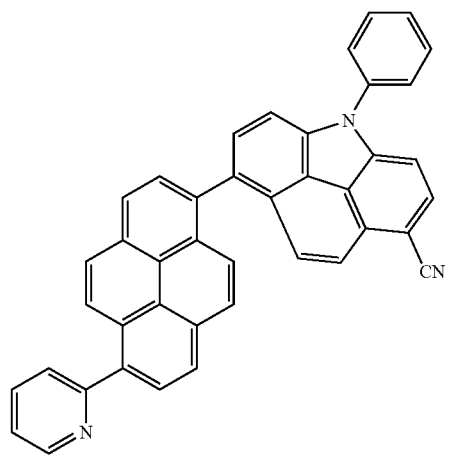

where * represents a binding site with a pyrene ring in Formula 1.

15. The pyrene-based compound as claimed in claim 12, wherein $R_{21}$ is selected from
   a $C_6$-$C_{60}$ aryl group, a $C_2$-$C_{60}$ heteroaryl group, and a non-aromatic condensed polycyclic group; and
   a $C_6$-$C_{60}$ aryl group, a $C_2$-$C_{60}$ heteroaryl group, and a non-aromatic condensed polycyclic group, each substituted with at least one of a deuterium atom, a halogen atom, a hydroxyl group, a cyano group, a nitro group, a $C_1$-$C_{60}$ alkyl group, a $C_1$-$C_{60}$ alkoxy group, a $C_6$-$C_{60}$ aryl group, a $C_2$-$C_{60}$ heteroaryl group, and a non-aromatic condensed polycyclic group.

16. The pyrene-based compound as claimed in claim 1, wherein the compound is one of Compounds 1 to 133:

197
-continued
198
-continued
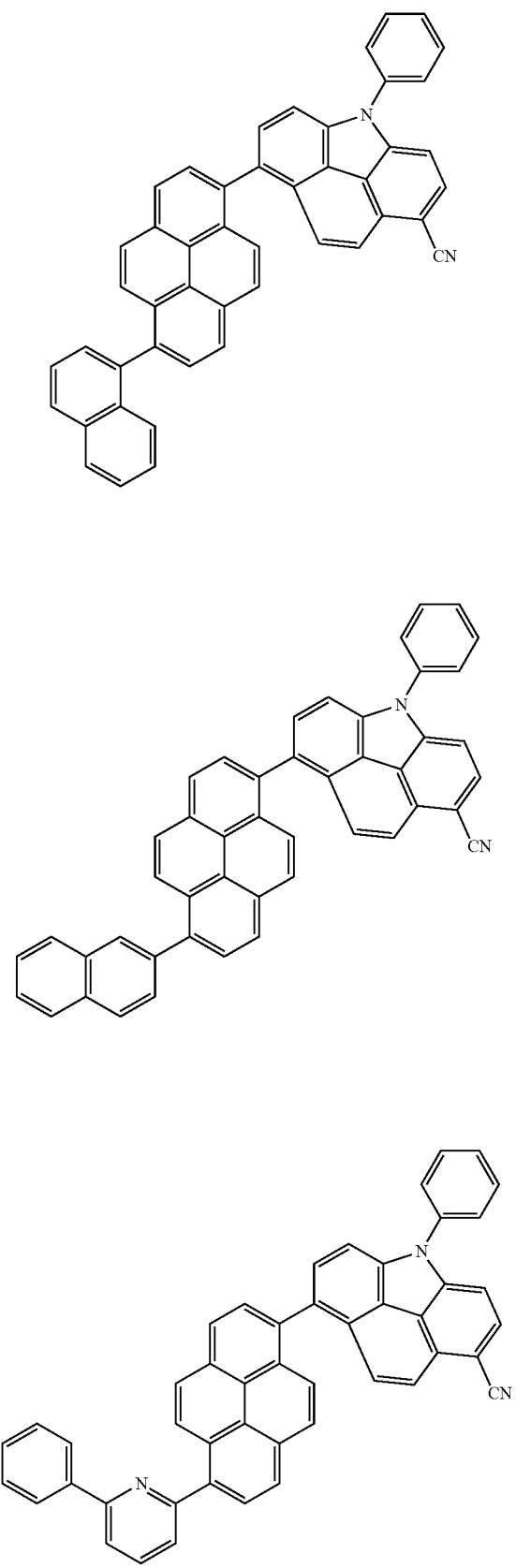
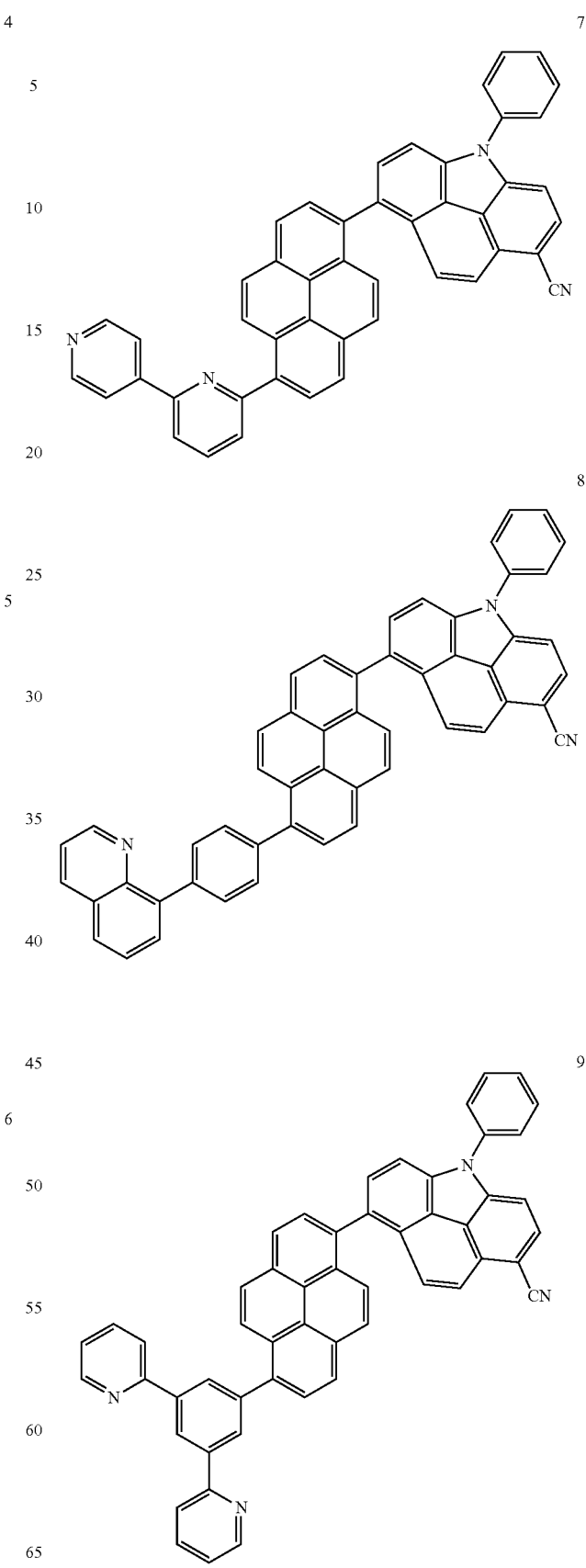

199
-continued
200
-continued
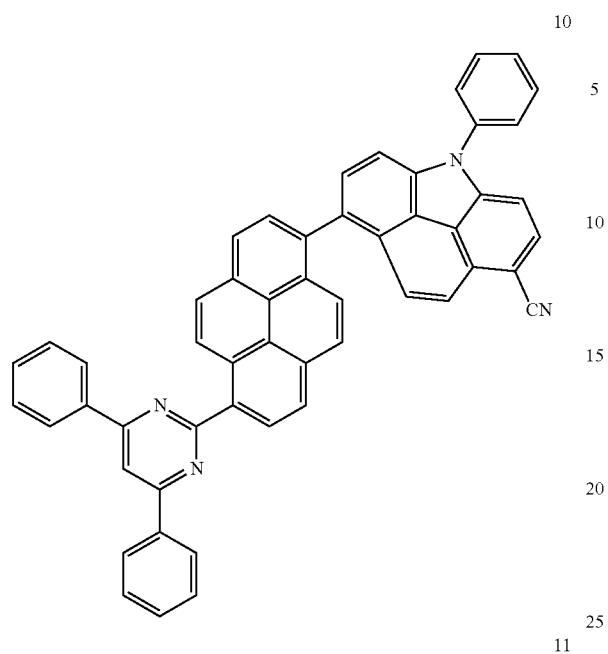
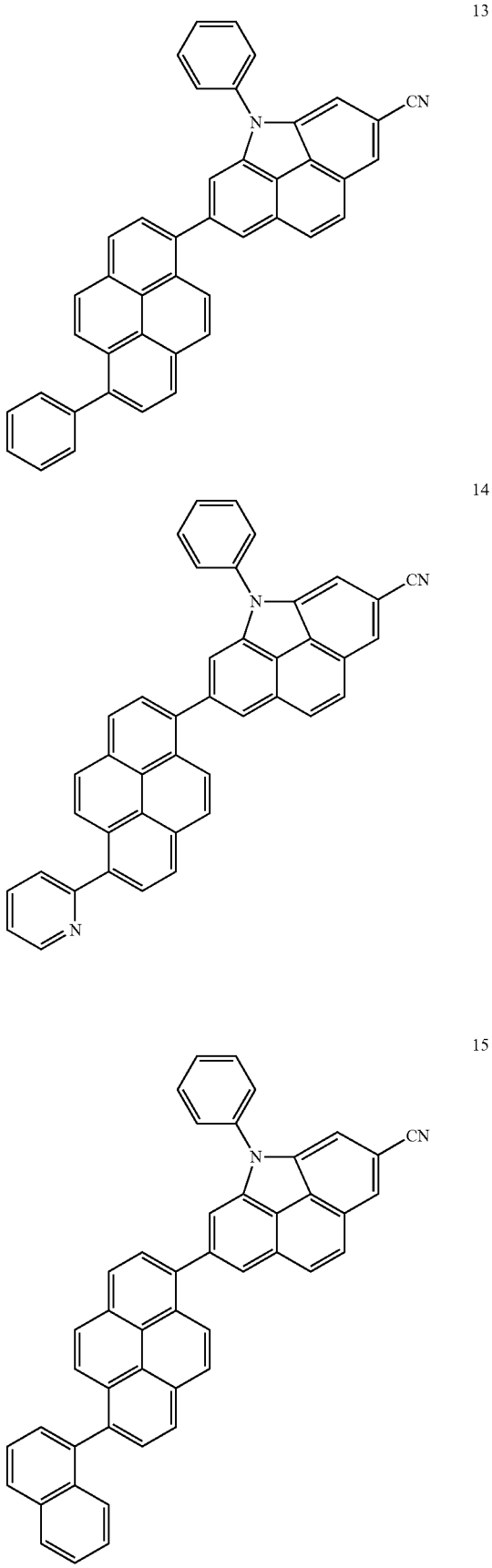

201
-continued
16
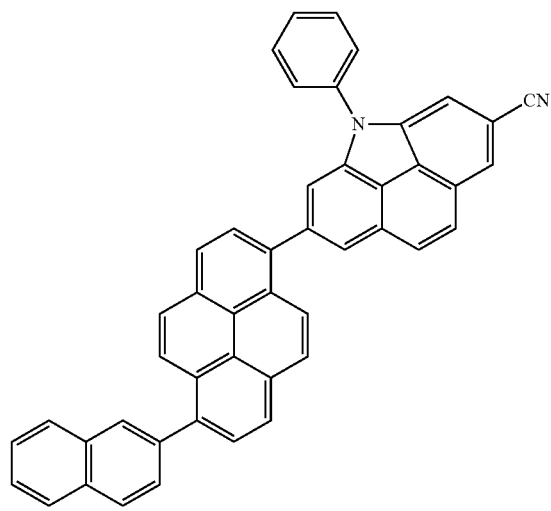
17
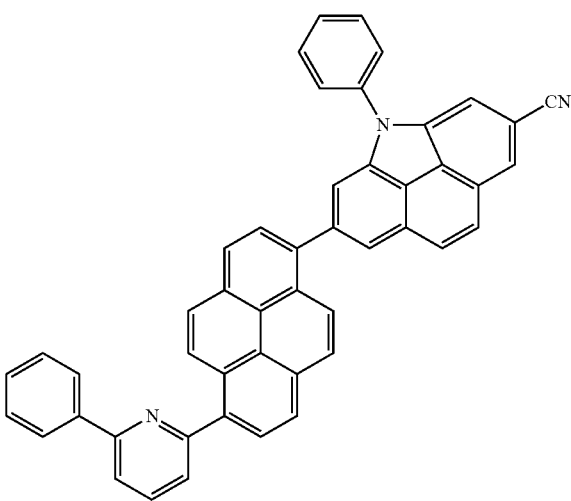
18
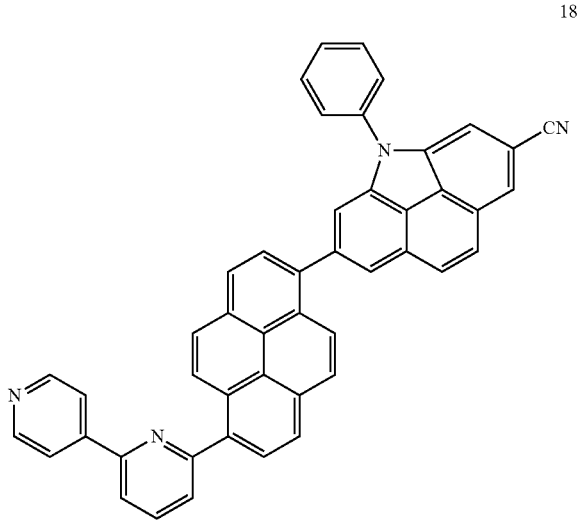
202
-continued
19
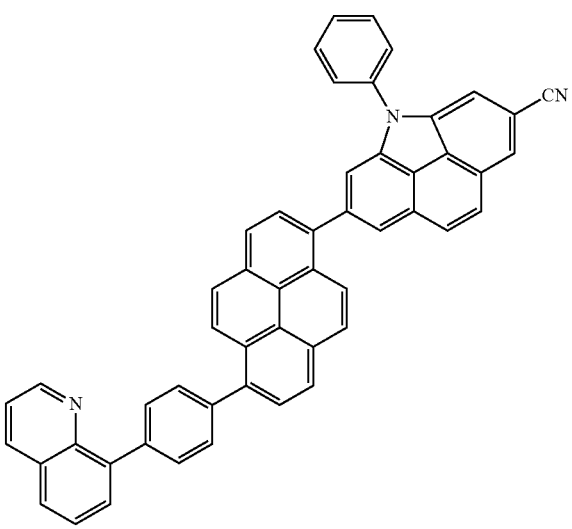
20
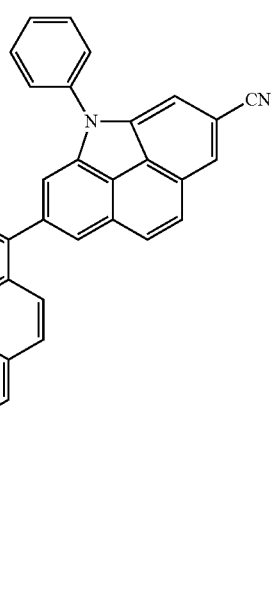

203
-continued
21
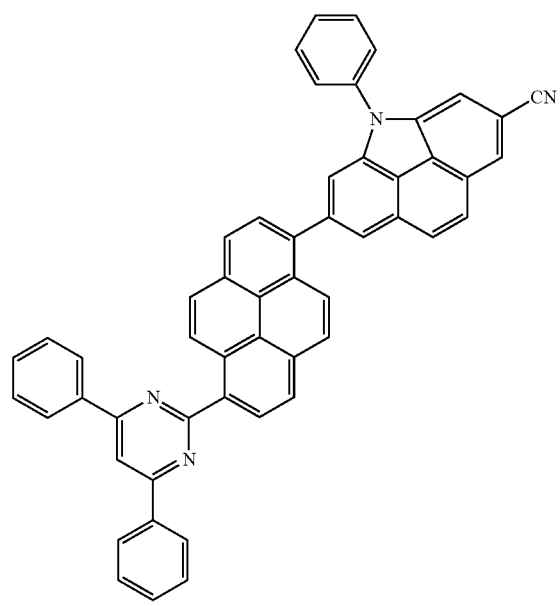
22
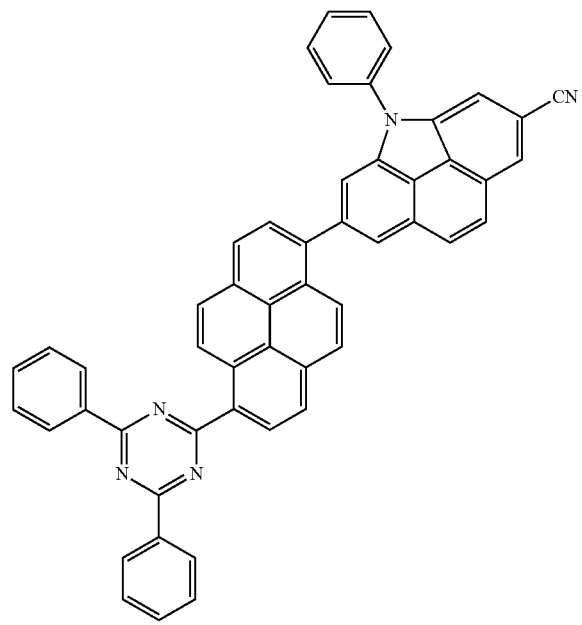
204
-continued
23
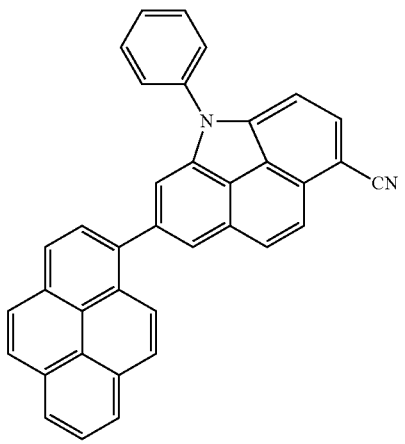
24
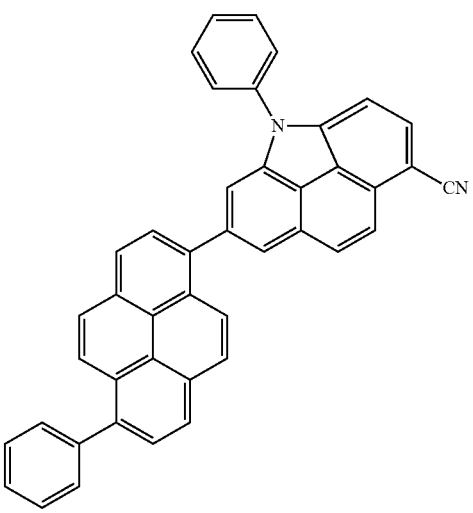
25
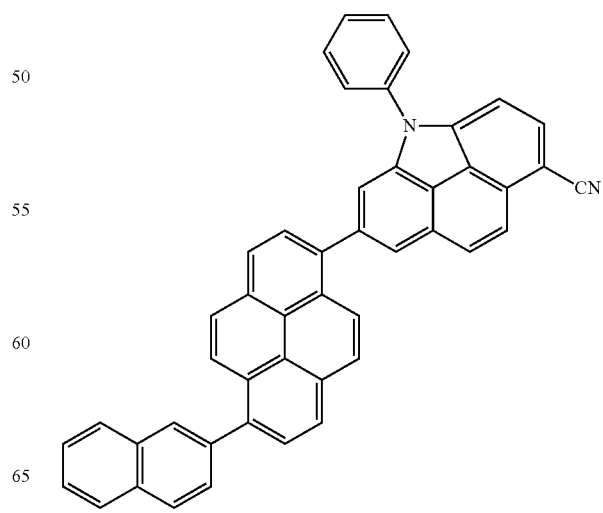

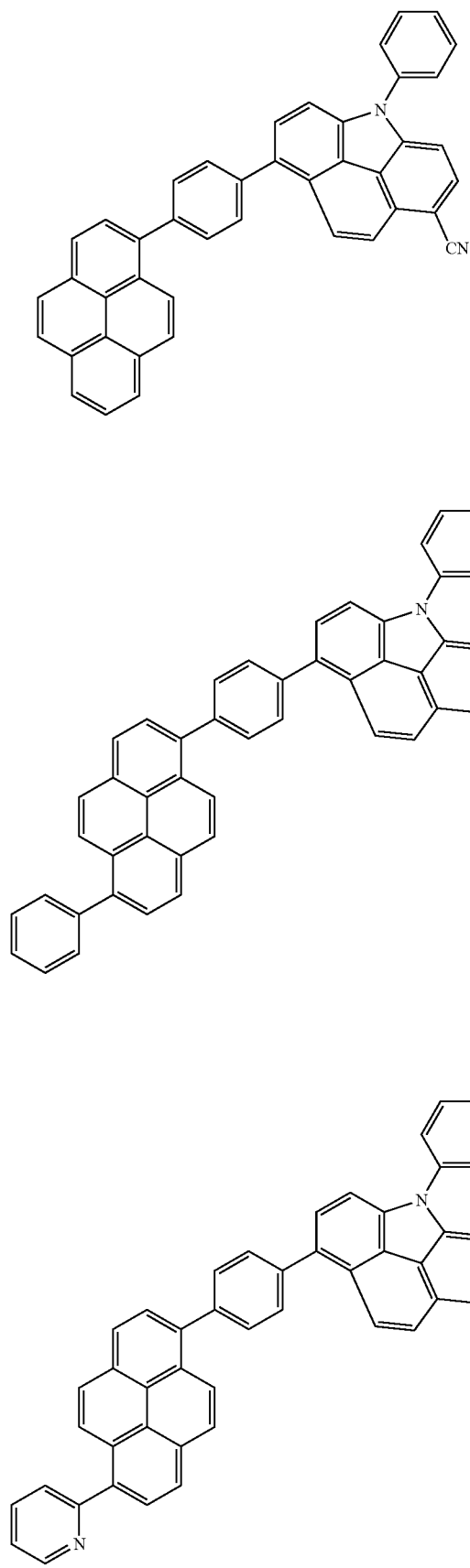
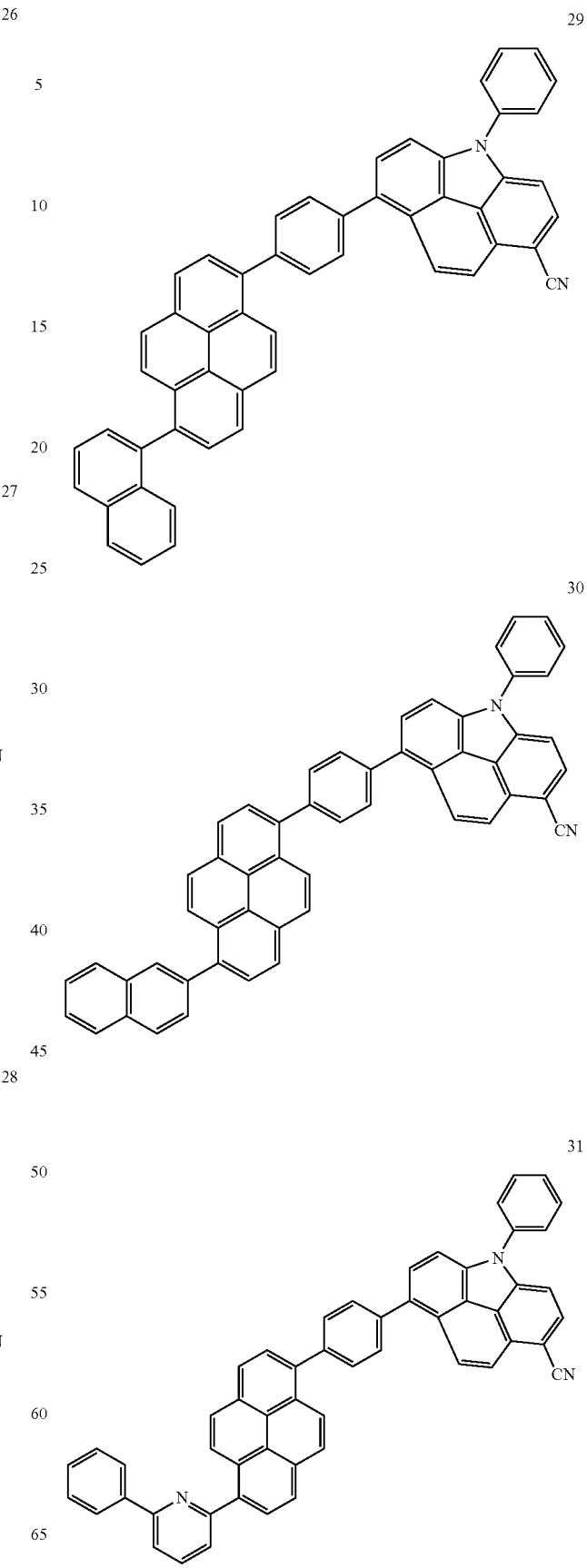

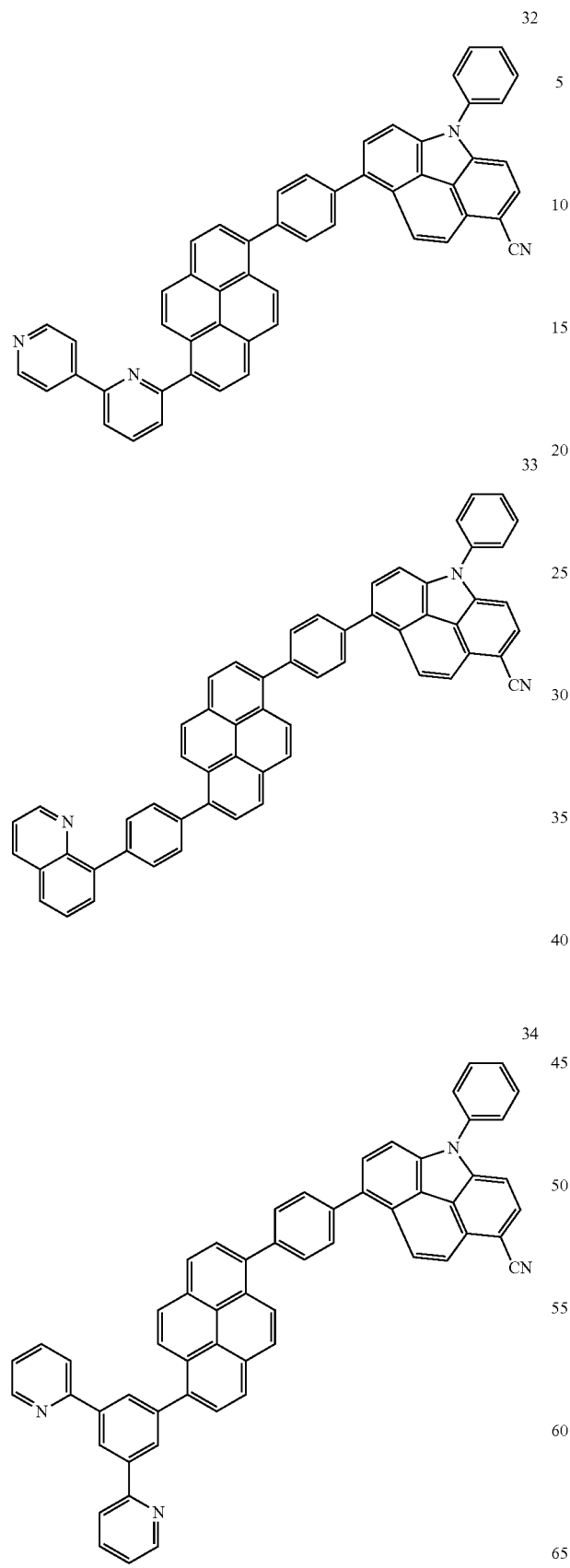
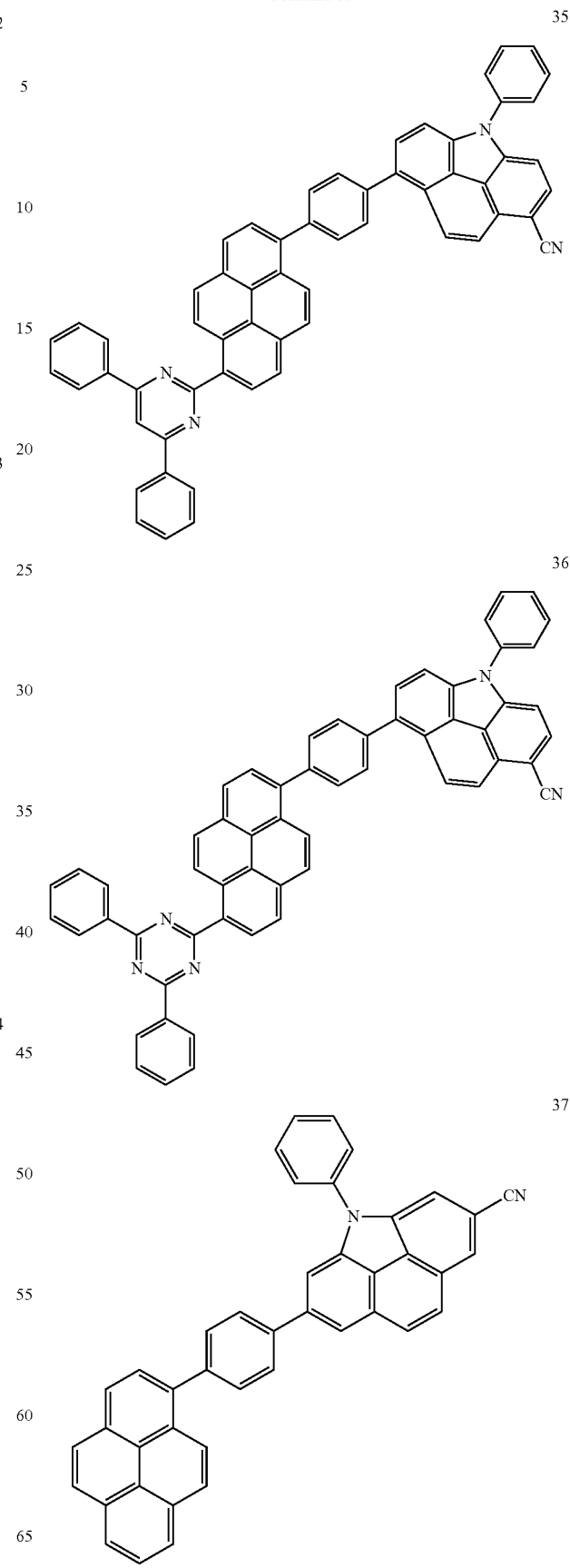

38
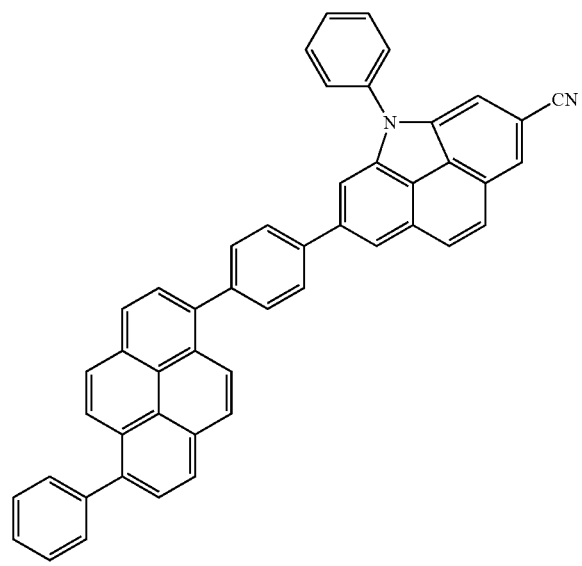
39
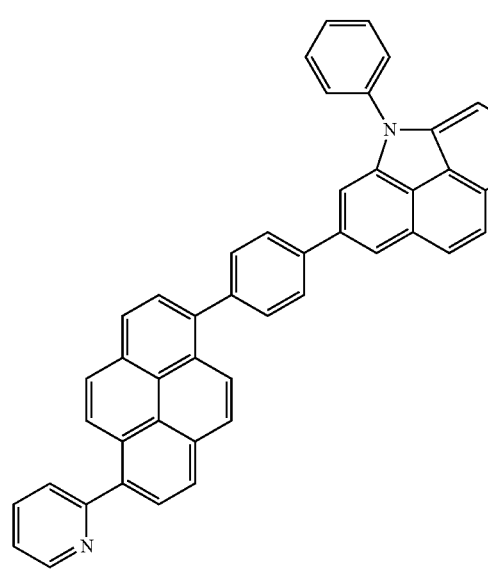
40
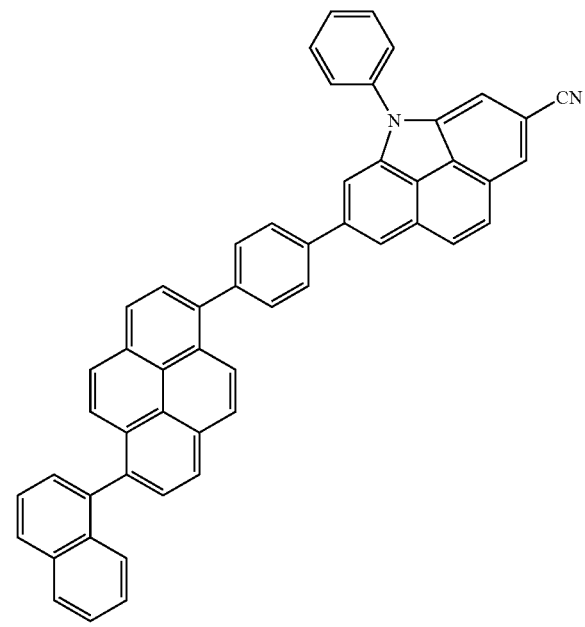
41
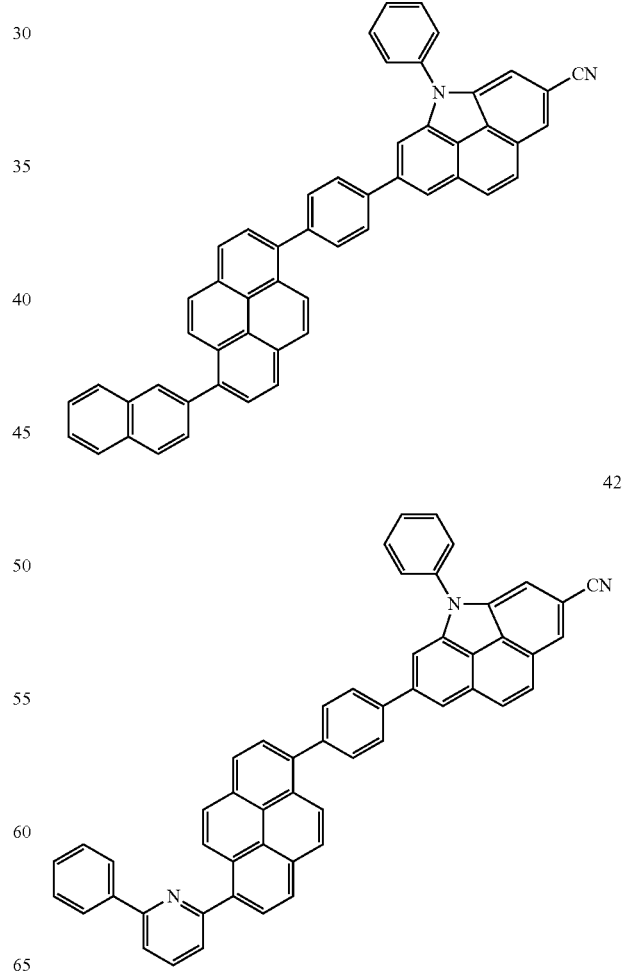
42

211
-continued
43
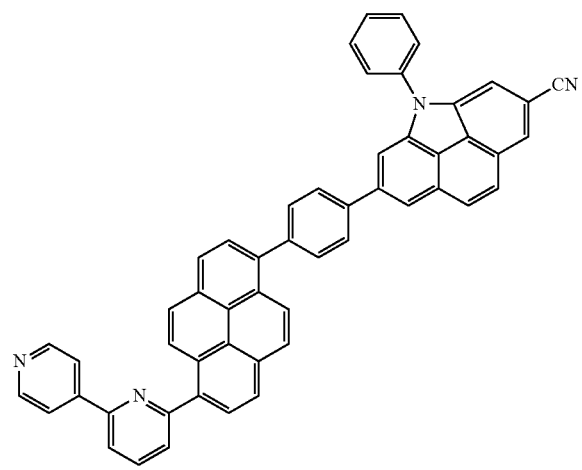
44
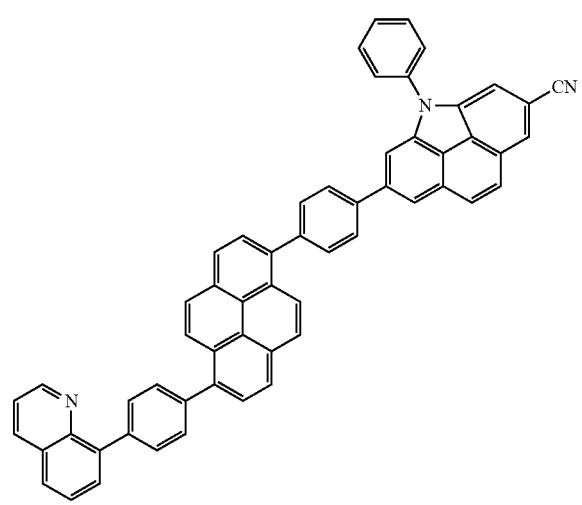
45
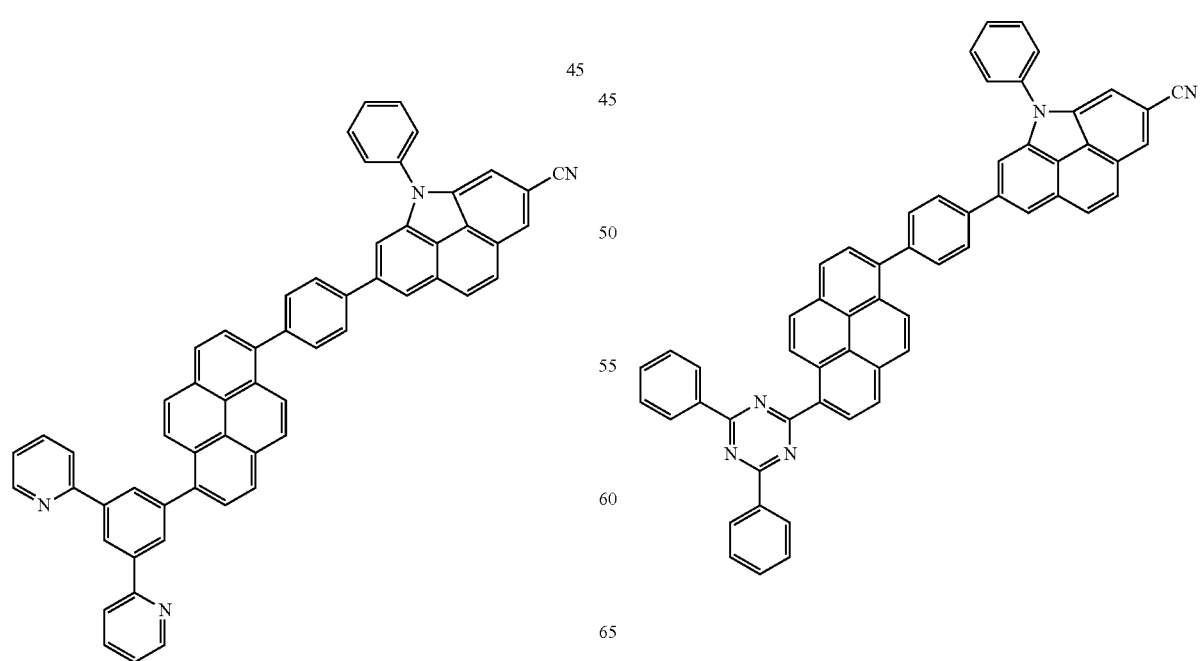
212
-continued
46
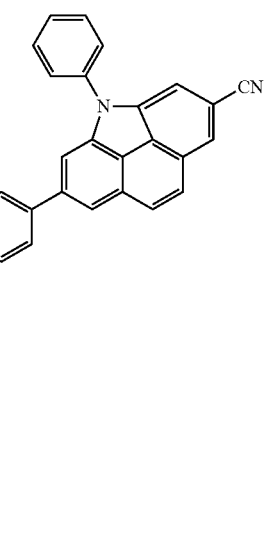
47
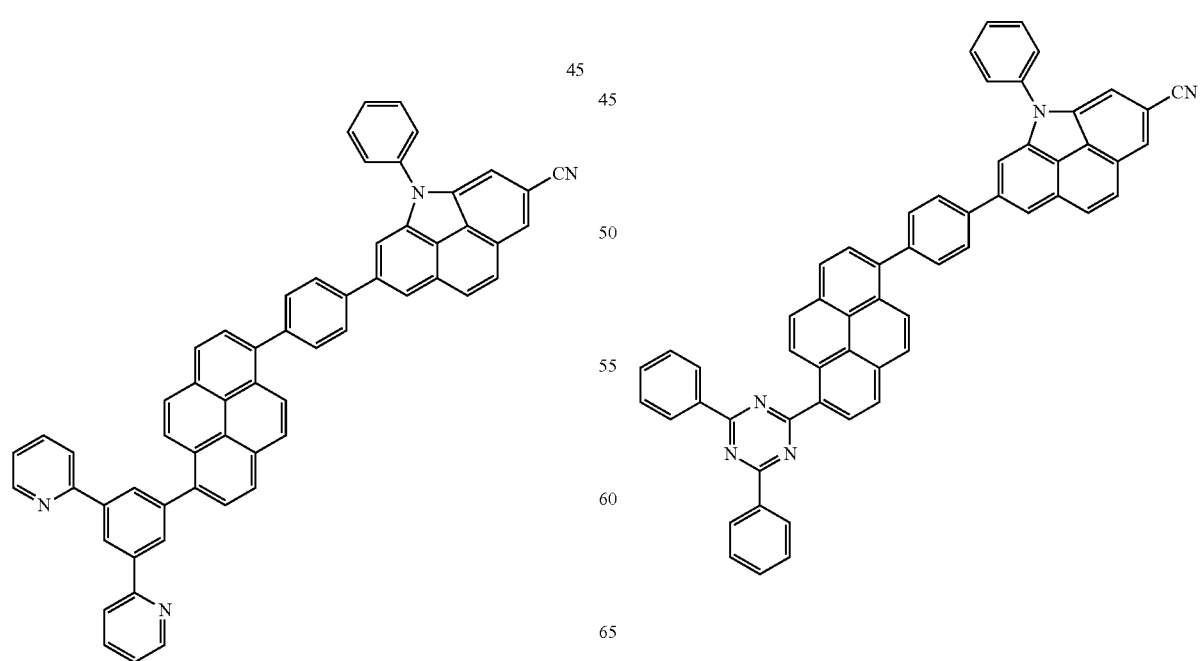

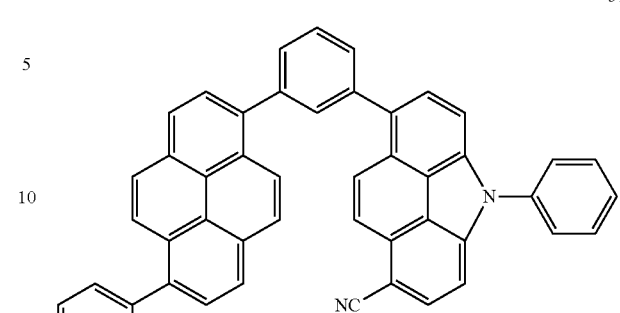
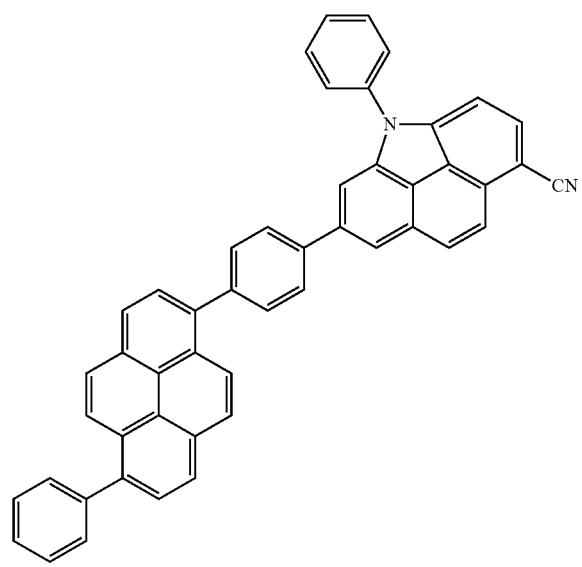
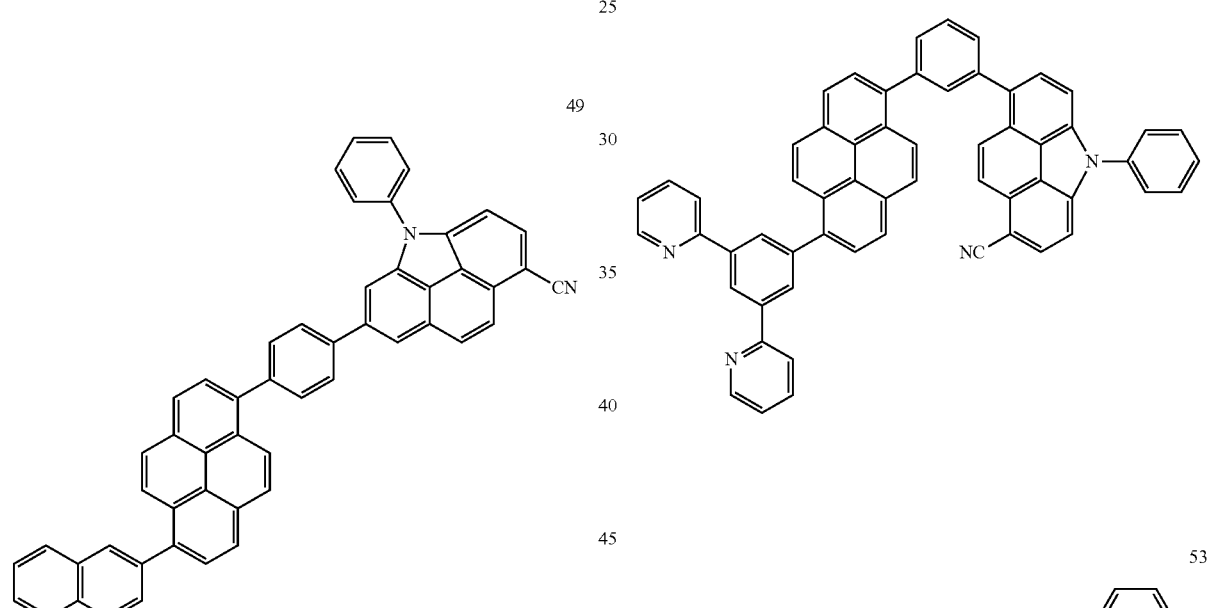
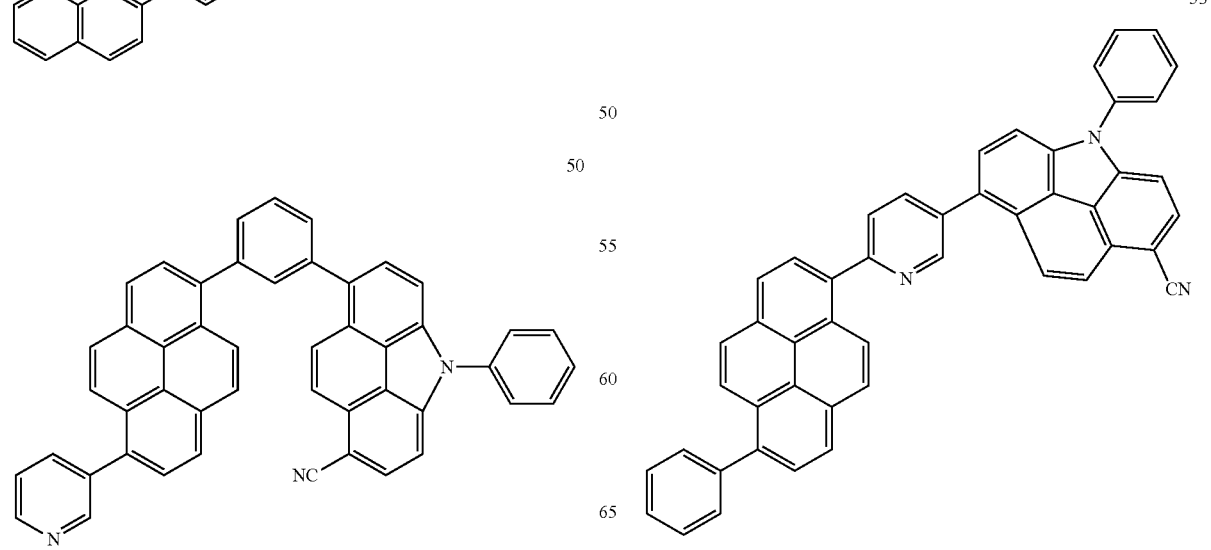

-continued
54
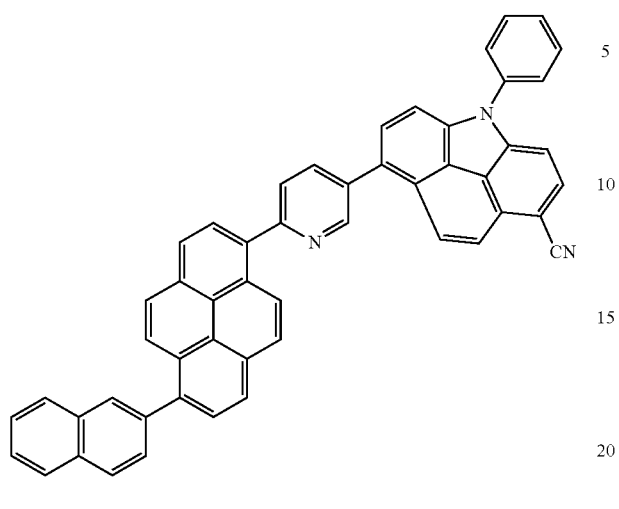
55
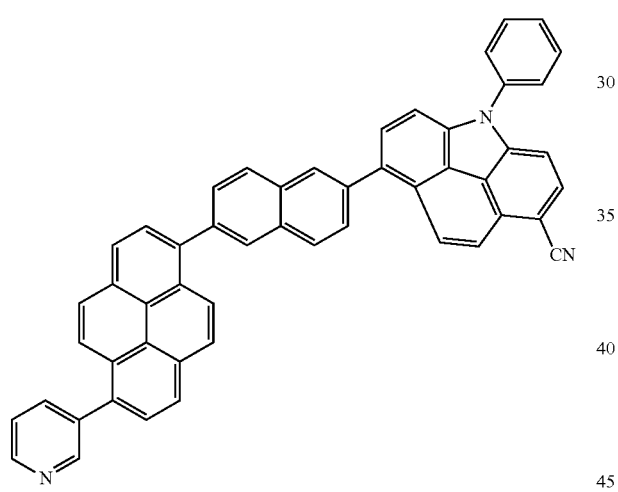
56
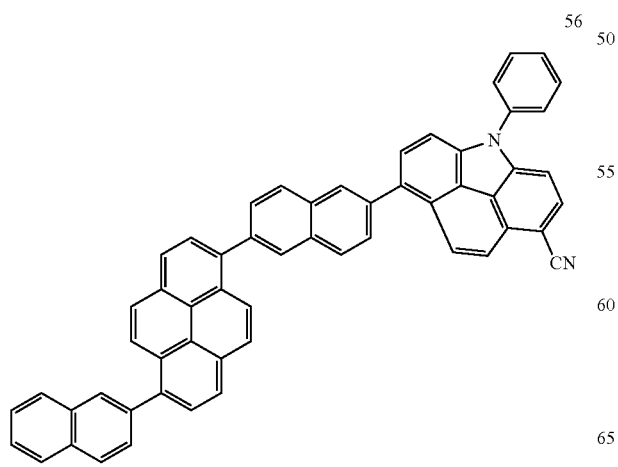
-continued
57
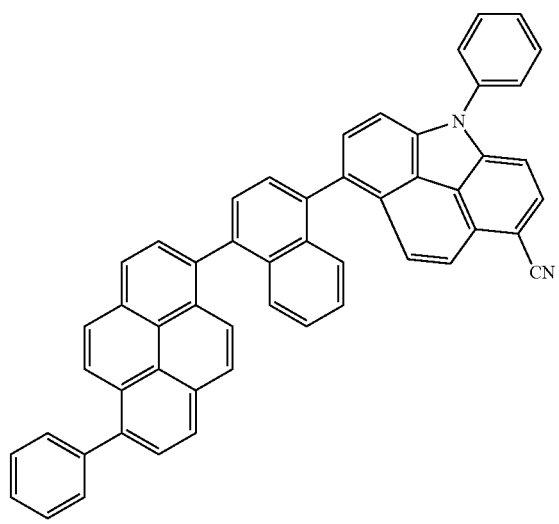
58
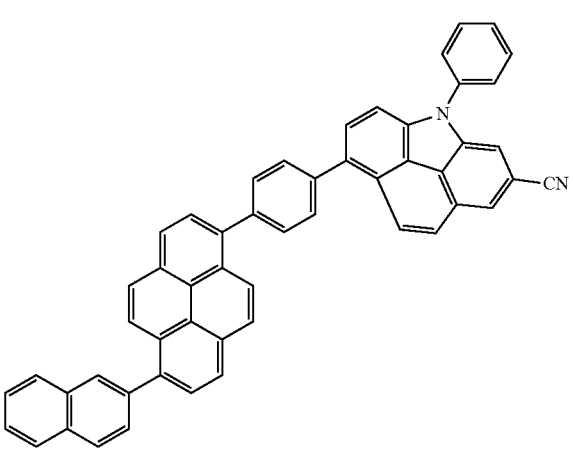
59

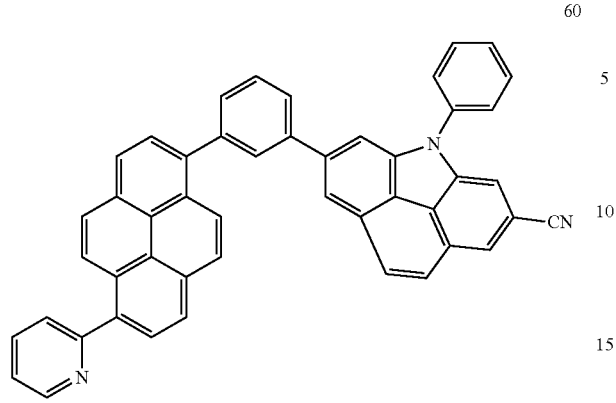
60
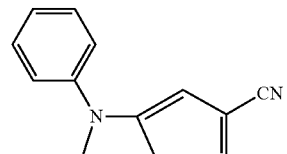
63
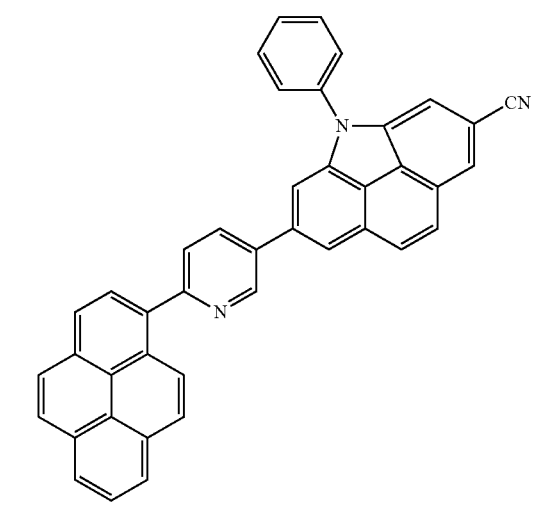
61
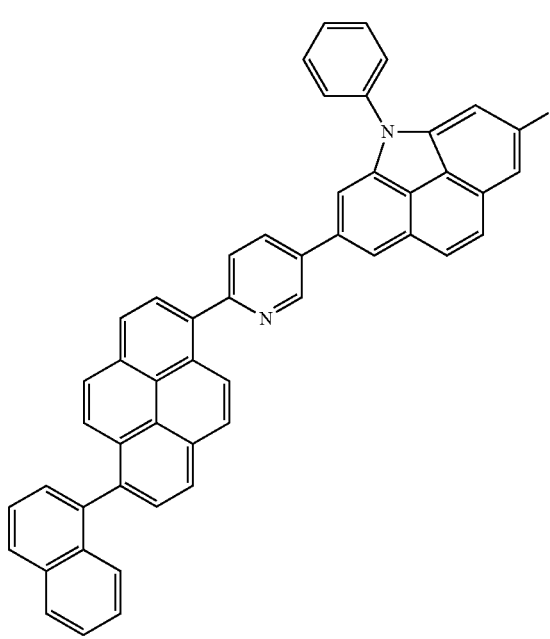
62
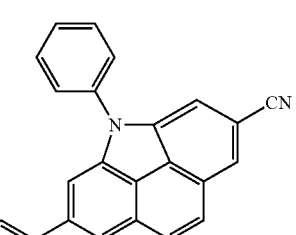
64

219
-continued
66
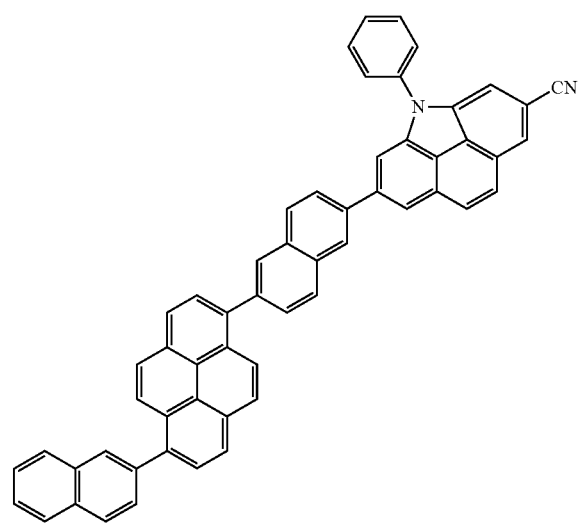
67
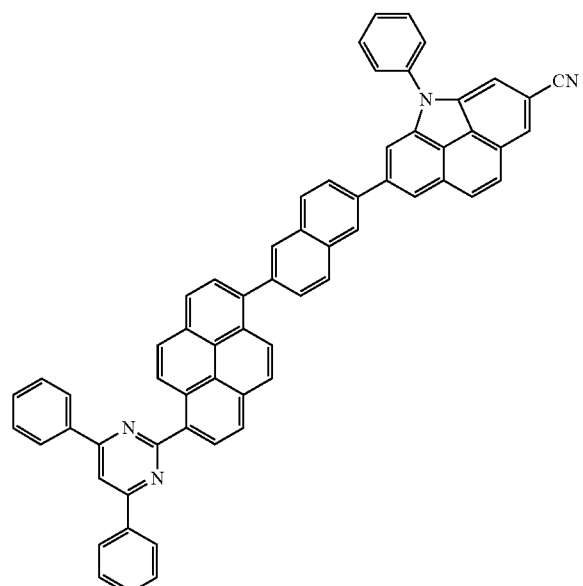
220
-continued
68
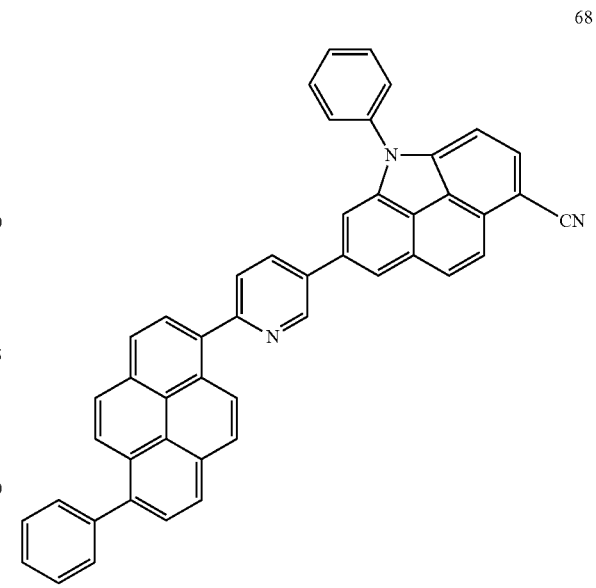
69
70
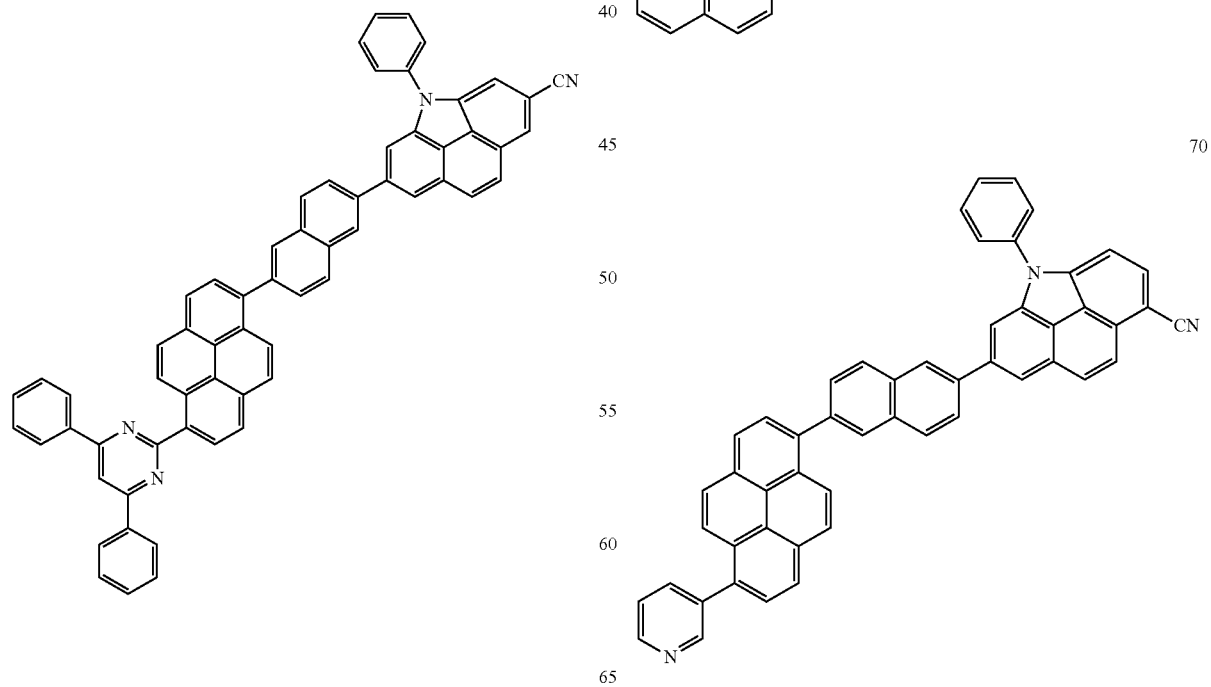

221
-continued
71
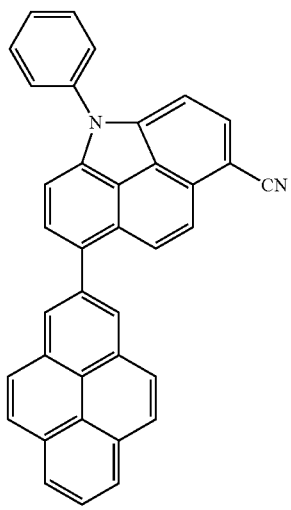
72
222
-continued
73
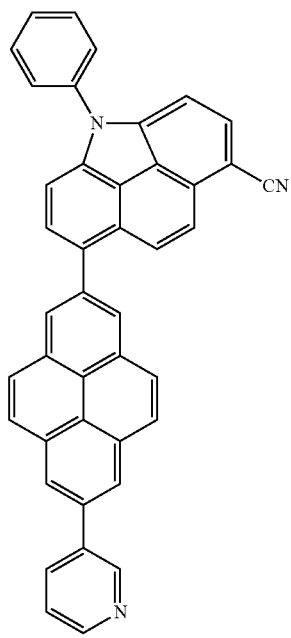
74

-continued
75
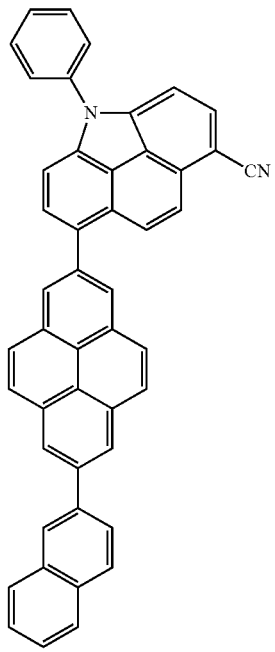
-continued
77
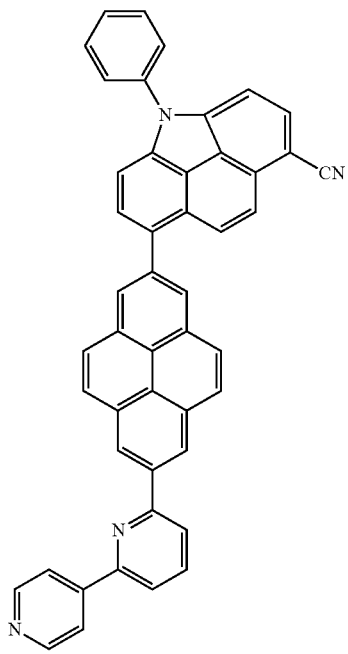
76
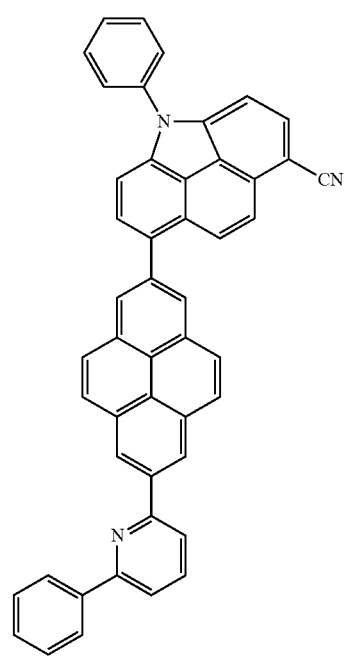
78
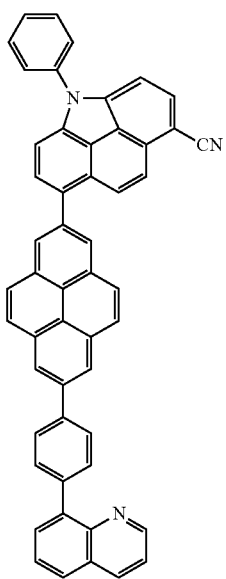

225
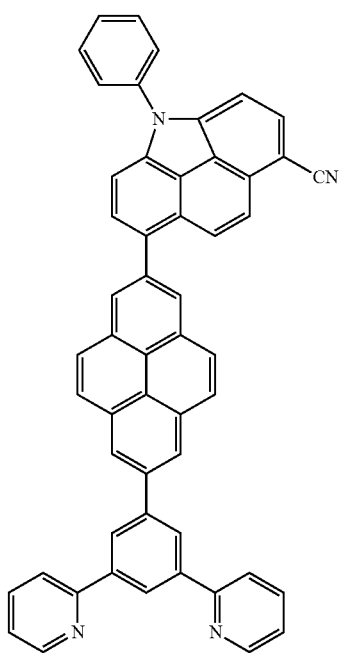
226
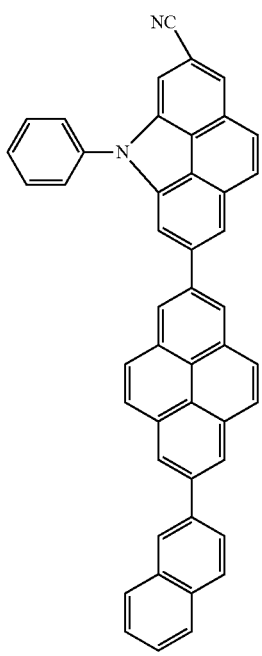
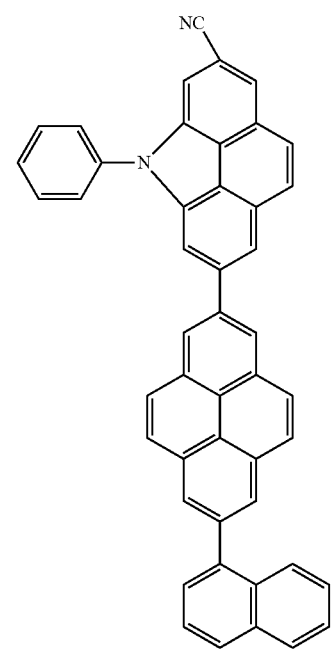
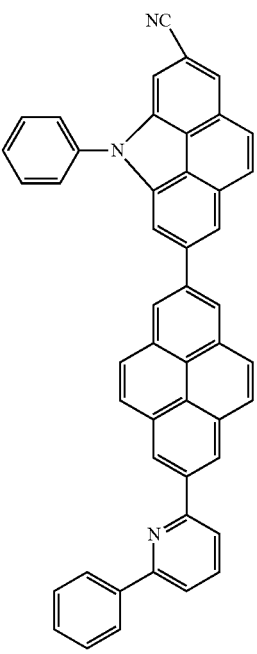

227
-continued
88
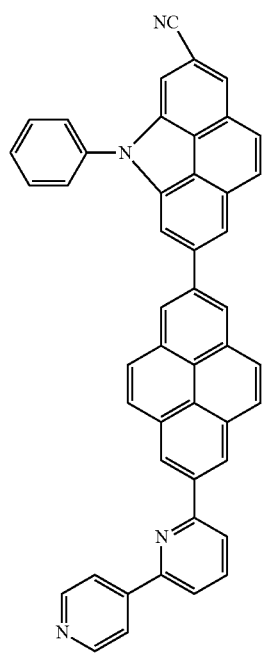
89
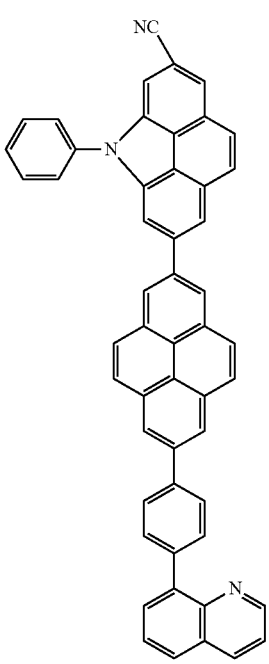
228
-continued
90
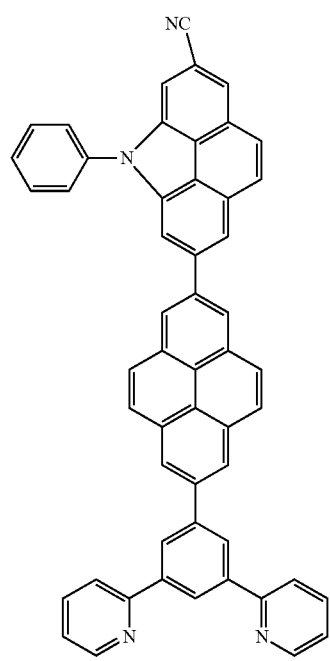
91
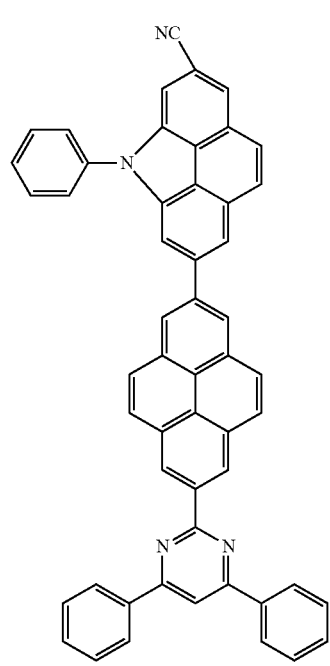

229
-continued
92
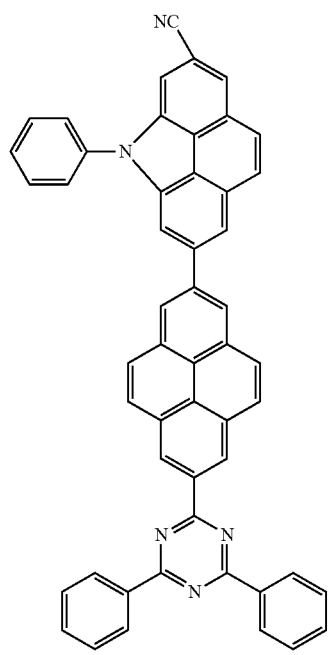
93
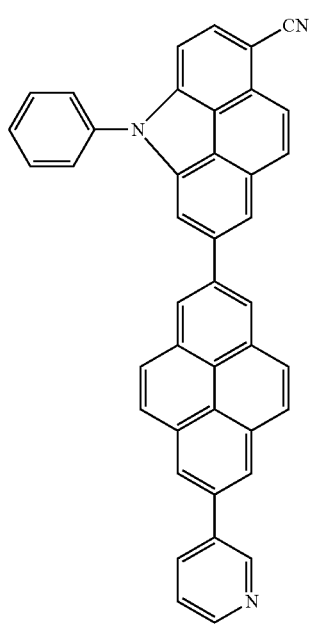
230
-continued
94
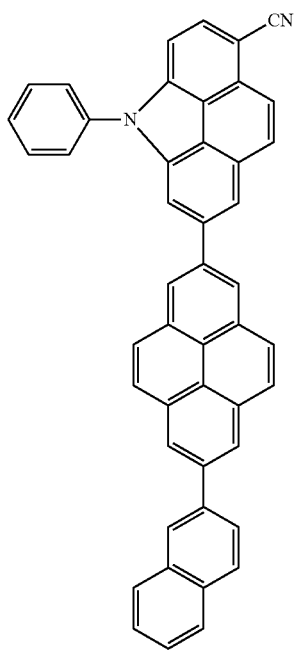
95
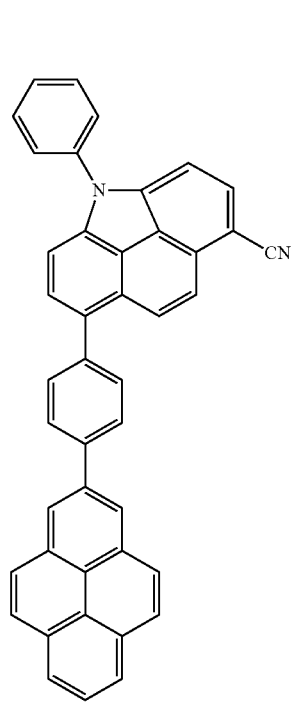

231
-continued
96
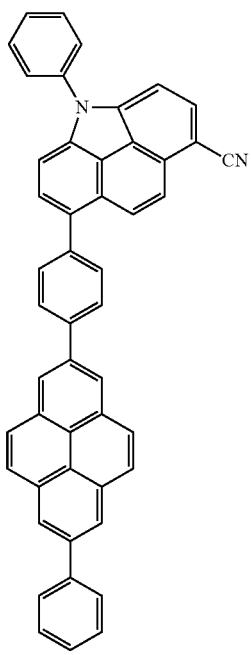
97
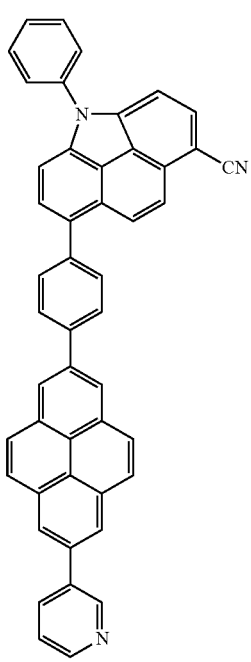
232
-continued
98
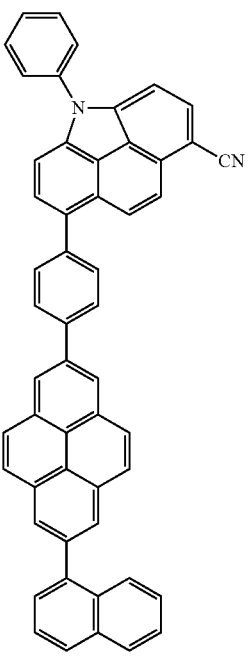
99
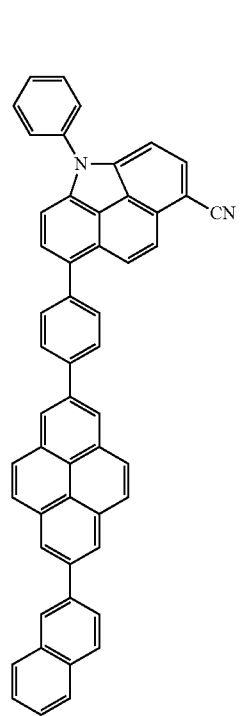

233
-continued
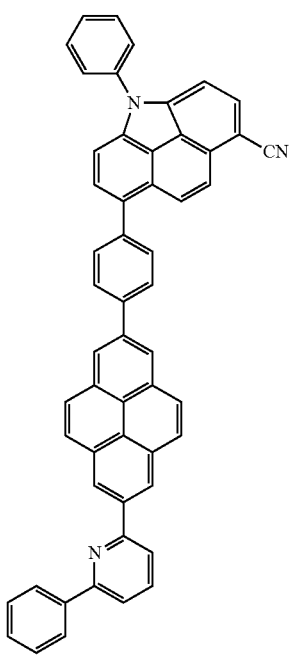
100
234
-continued
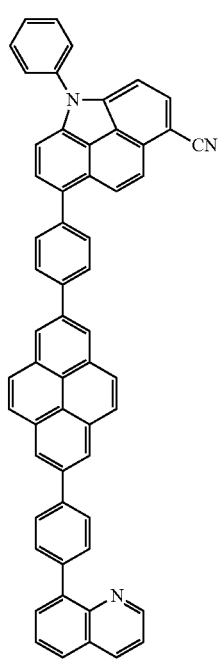
102
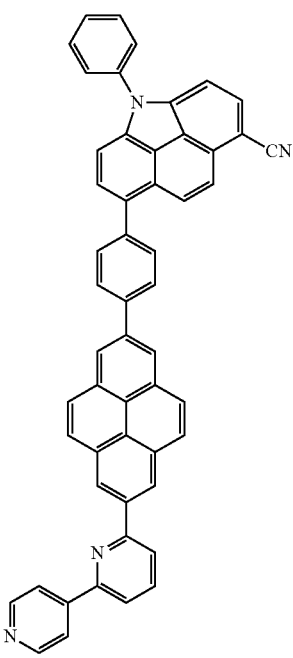
101
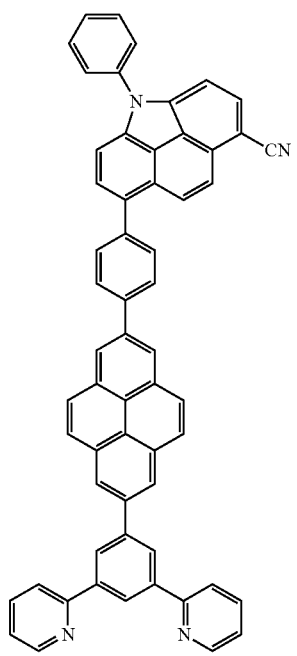
103

235
-continued
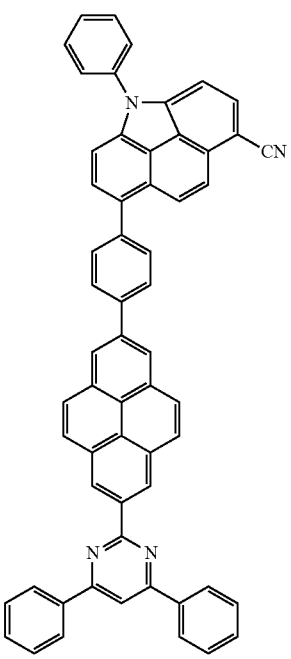
104
236
-continued
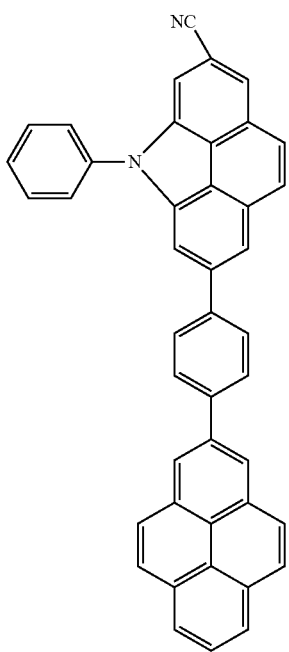
106
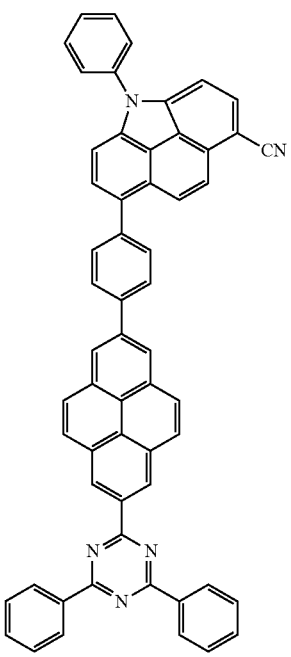
105
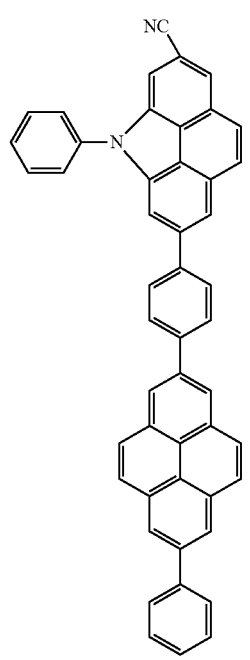
107

237
-continued
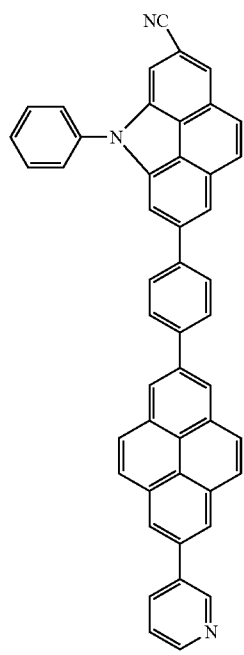
238
-continued
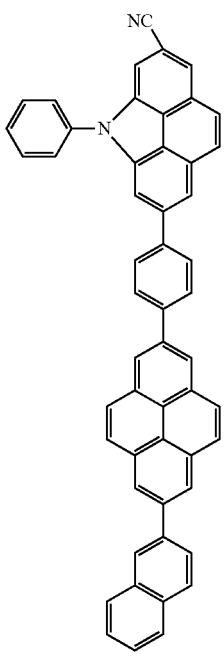

239
-continued
112
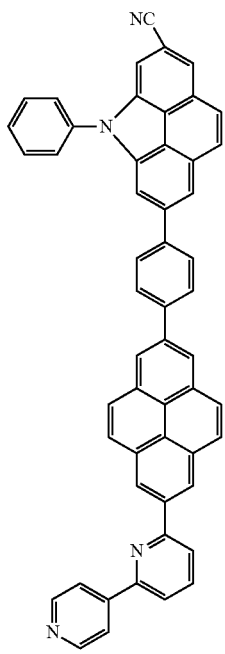
113
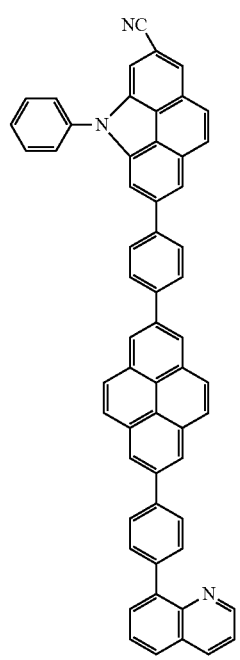
240
-continued
114
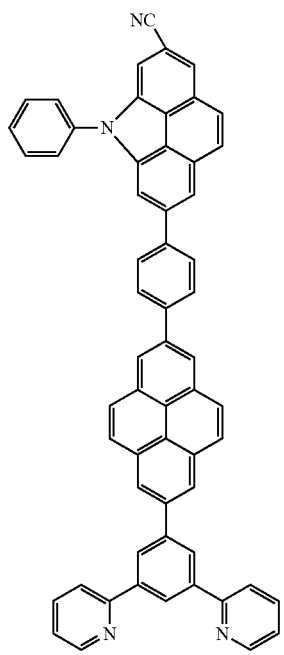
115
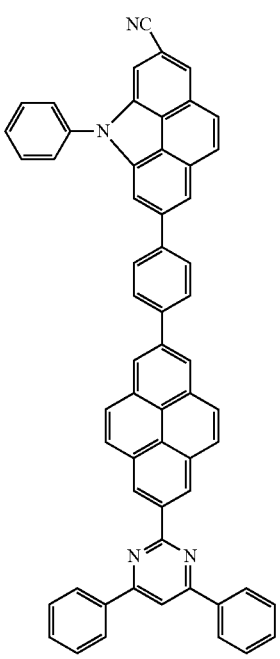

241
-continued
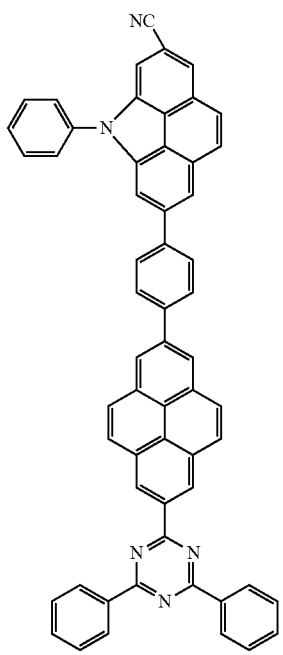
116
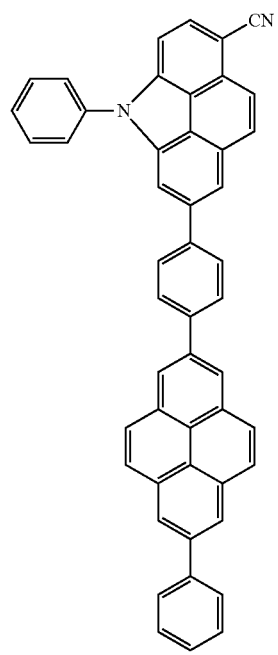
117
242
-continued
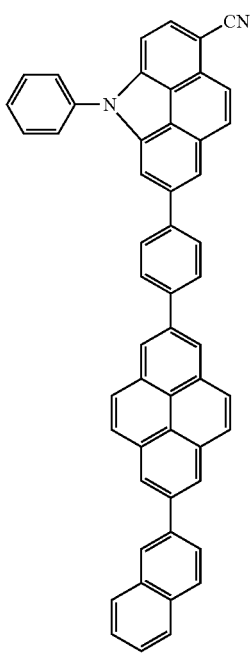
118
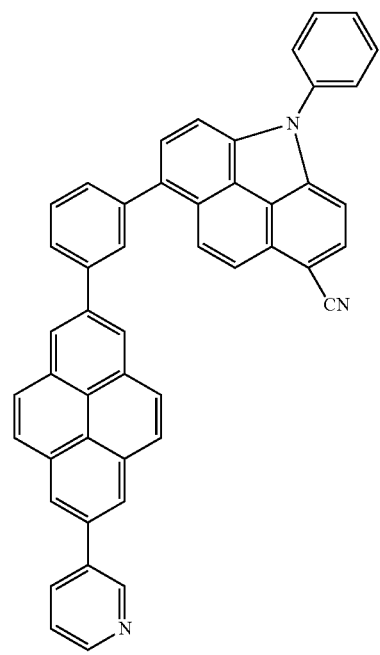
119

243
-continued
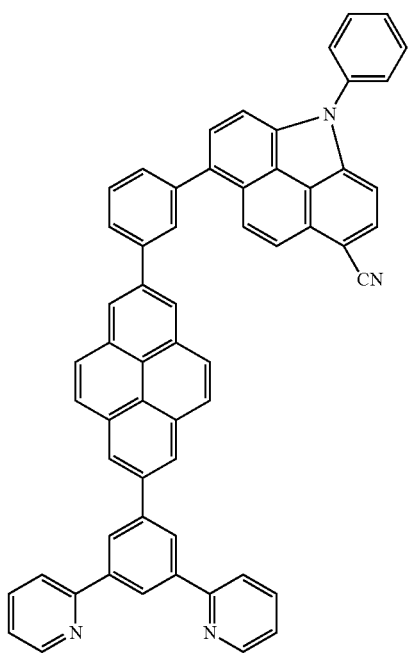
120
244
-continued
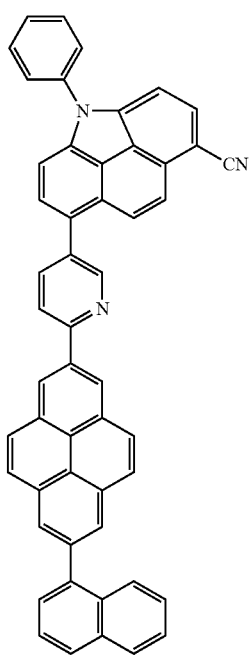
122
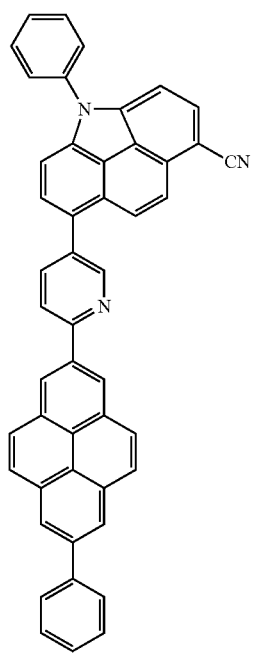
121
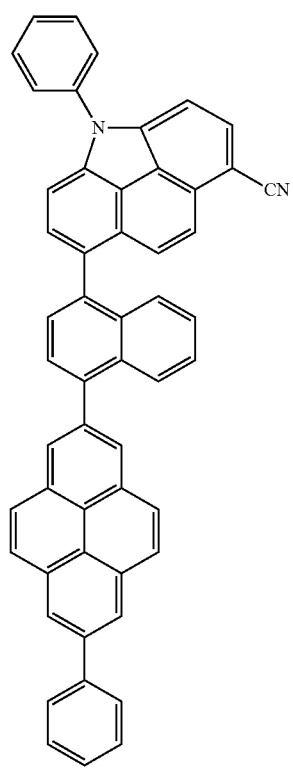
123

-continued
124
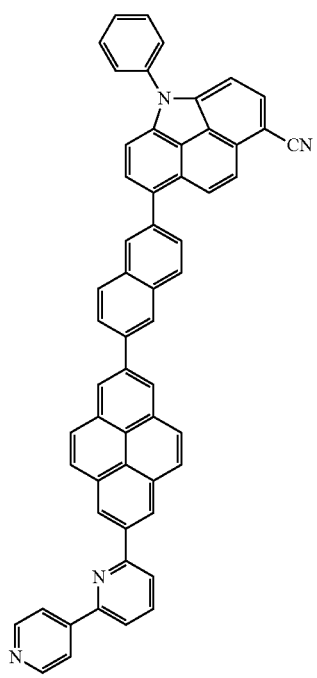
125
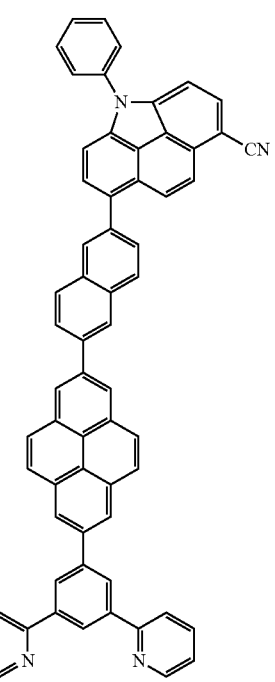
-continued
126
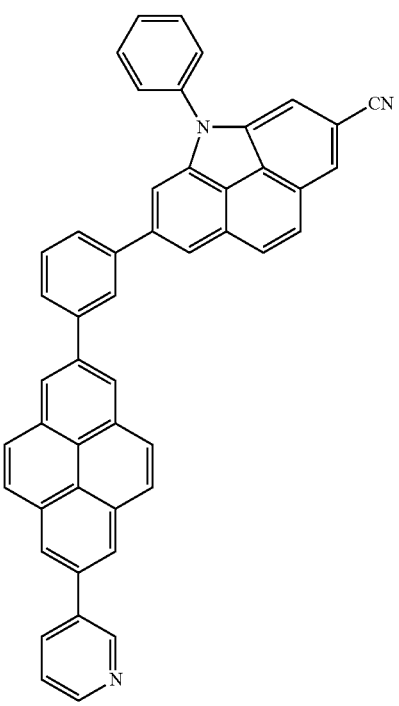
127
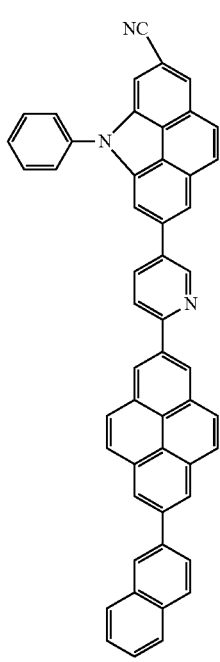

247
-continued
128
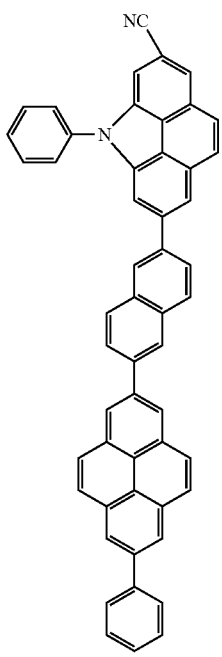
129
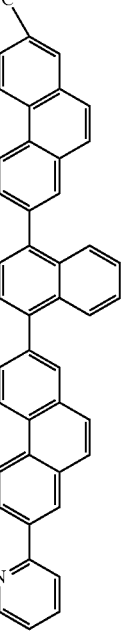
248
-continued
130
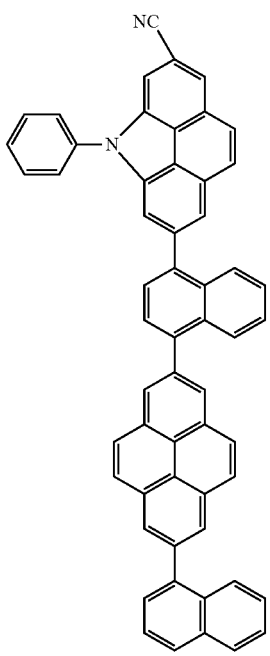
131
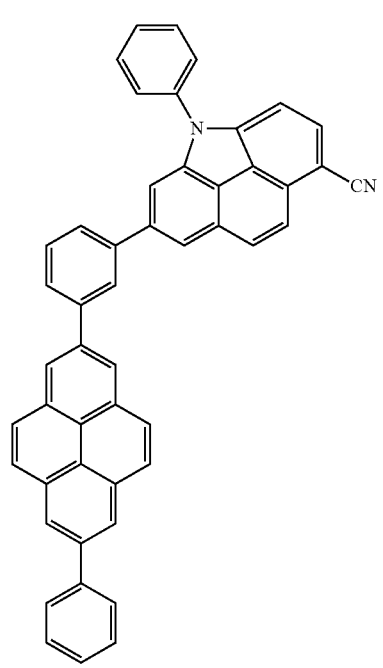

132

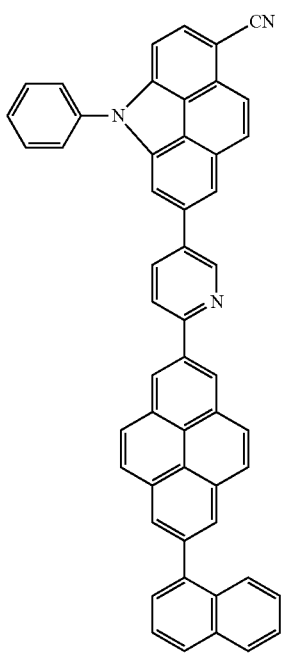

133

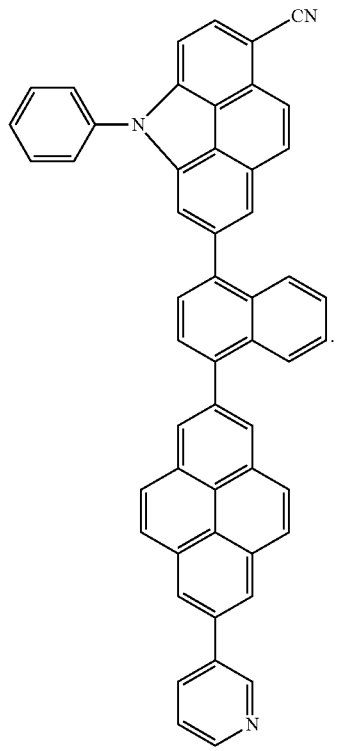

17. An organic light-emitting device (OLED), comprising a first electrode;
a second electrode facing the first electrode; and
an organic layer between the first electrode and the second electrode, the organic layer including an emission layer, wherein the organic layer includes the pyrene-based compound as claimed in claim 1.

18. The OLED as claimed in claim 17, wherein:
the organic layer includes an electron transport region between the emission layer and the second electrode, and
the electron transport region includes the pyrene-based compound of claim 1.

19. The OLED as claimed in claim 18, wherein:
the electron transport region includes an electron transport layer, and the electron transport layer includes the pyrene-based compound of claim 1.

20. The OLED as claimed in claim 17, wherein the organic layer includes a hole transport region disposed between the first electrode and the emission layer.

* * * * *